(12) United States Patent
Rein et al.

(10) Patent No.: US 8,455,035 B2
(45) Date of Patent: Jun. 4, 2013

(54) PLANT SEED OIL

(75) Inventors: Dietrich Rein, Berlin (DE); Toralf Senger, Heidelberg (DE); Jörg Bauer, Limburgerhof (DE)

(73) Assignee: BASF Plant Science GmbH, Ludwigshafen (DE)

( * ) Notice: Subject to any disclaimer, the term of this patent is extended or adjusted under 35 U.S.C. 154(b) by 253 days.

(21) Appl. No.: 12/989,108

(22) PCT Filed: Apr. 23, 2009

(86) PCT No.: PCT/EP2009/054916
§ 371 (c)(1),
(2), (4) Date: Oct. 22, 2010

(87) PCT Pub. No.: WO2009/130291
PCT Pub. Date: Oct. 29, 2009

(65) Prior Publication Data
US 2011/0039010 A1 Feb. 17, 2011

(30) Foreign Application Priority Data

Apr. 25, 2008 (EP) ..................................... 08155186

(51) Int. Cl.
*A23D 9/00* (2006.01)
(52) U.S. Cl.
USPC ............................ 426/601; 800/281; 554/157
(58) Field of Classification Search
USPC ....................................................... 426/601
See application file for complete search history.

(56) References Cited

U.S. PATENT DOCUMENTS

| | | | |
|---|---|---|---|
| 5,972,664 A | 10/1999 | Knutzon et al. | |
| 8,084,074 B2 * | 12/2011 | Kinney et al. | 426/601 |
| 2005/0132441 A1 | 6/2005 | Damude et al. | |
| 2007/0067870 A1 | 3/2007 | Knauf et al. | |
| 2007/0244192 A1 | 10/2007 | Metz | |
| 2008/0057495 A1 | 3/2008 | Ohyama | |
| 2008/0155705 A1 | 6/2008 | Zank et al. | |
| 2008/0220143 A1 * | 9/2008 | Kinney et al. | 426/590 |
| 2009/0172837 A1 | 7/2009 | Geiger et al. | |
| 2010/0088776 A1 | 4/2010 | Bauer et al. | |
| 2010/0192238 A1 | 7/2010 | Bauer et al. | |
| 2010/0199365 A1 | 8/2010 | Senger et al. | |

FOREIGN PATENT DOCUMENTS

| | | |
|---|---|---|
| CA | 2559360 A1 * | 9/2005 |
| DE | 102004062543 A1 | 7/2006 |
| WO | WO-2008/009600 A1 | 1/2008 |
| WO | WO-2008/022963 A2 | 2/2008 |
| WO | WO-2008/040787 A2 | 4/2008 |
| WO | WO-2008/043849 A2 | 4/2008 |
| WO | WO-2008/100545 A2 | 8/2008 |
| WO | WO-2009/016202 A2 | 2/2009 |
| WO | WO-2009/016208 A2 | 2/2009 |
| WO | WO-2009/077478 A2 | 6/2009 |
| WO | WO-2009/133145 A1 | 11/2009 |
| WO | WO-2009/147127 A1 | 12/2009 |
| WO | WO-2010/000708 A2 | 1/2010 |
| WO | WO-2010/007106 A1 | 1/2010 |
| WO | WO-2010/023202 A2 | 3/2010 |
| WO | WO-2010/066703 A2 | 6/2010 |

OTHER PUBLICATIONS

Innis, S. M., et al., "Plasma fatty acid responses, metabolic effects, and safety of microalgal and fungal oils rich in arachidonic and docosahexaenoic acids in healthy adults [1-3]", The American Journal of Clinical Nutrition, 1996, vol. 64, Issue 1, pp. 159-167.

Demmelmair, H., et al., "Metabolism of $U^{13}C$-labeled linoleic acid in lactating women", Journal of Lipid Research, 1998, vol. 39, Issue 7, pp. 1389-1396.

Wu, G., et al., "Stepwise engineering to produce high yields of very long-chain polyunsaturated fatty acids in plants", Nature Biotechnology, 2005, vol. 23, Issue 8, pp. 1013-1017.

Chen, R., et al., "Expression of DELTA6, DELTA5 desaturase and GLELO elongase genes from *Mortierella alpine* for production of arachidonic acid in soybean [*Glycine max* (L.) Merrill] seeds", Plant Science, 2006, vol. 170, Issue 2, pp. 399-406.

Koletzko, B., et al., "Long-chain polyunsaturated fatty acids in diets for infants: Choices for recommending and regulating bodies and for manufacturers of dietary products", Lipids, 1999, vol. 34, Issue 2, pp. 215-220.

Tahvonen, R. L. et al., "Black currant seed oil and fish oil supplements differ in their effect on fatty acid profiles of plasma lipids, and concentrations of serum total and lipoprotein lipids, plasma glucose and insulin", Journal of Nutritional Biochemistry, 2005, vol. 16, Issue 6, pp. 353-359.

Barre D. E., "Potential of evening primrose, borage, black currant, and fungal oils in human health", Annals of Nutrition and Metabolism, Kager, CH, 2001, vol. 45, Issue 2, pp. 47-57.

Napier, J.A., "Transgenic Plants as a Source of Fish Oils: Healthy Sustainable ang GM", J. Sci Food Agric, 2007, vol. 87, pp. 8-12.

* cited by examiner

*Primary Examiner* — Carolyn Paden
(74) *Attorney, Agent, or Firm* — Novak Druce Connolly Bove + Quigg LLP

(57) ABSTRACT

The invention relates to a plant seed oil, comprising arachidonic acid comprising approximately 7 to approximately 26 percent by weight of the total fatty acid content, the ratio of the percentages by weight of arachidonic acid to gamma-linolenic acid being approximately 1:1 to approximately 5:1 and the ratio of the percentages by weight of arachidonic acid to dihomo-gamma-linolenic acid being approximately 1:1 to approximately 5:1. The invention additionally relates to processes for the production of this plant seed oil and formulations and uses of the plant seed oil. In particular, the invention also makes available foodstuffs and baby food that contain the plant seed oil mentioned.

14 Claims, 10 Drawing Sheets

FIG. 7

| Ratios: | Australia | Canada | Chile | China | Japan | Mexico | Philippines | UK | USA | min | max |
|---|---|---|---|---|---|---|---|---|---|---|---|
| ARA/GLA | 2.2 | 2.3 | 2.8 | 3.3 | 3.1 | 2.8 | 3.9 | 2.1 | 2.6 | 2.1 | 3.9 |
| ARA/DGLA | 1.2 | 1.4 | 1.0 | 1.3 | 1.6 | 1.3 | 1.3 | 1.1 | 1.3 | 1.0 | 1.6 |
| ARA/SDA | 38.0 | 18.5 | 42.0 | 9.8 | 6.7 | 10.5 | 13.0 | 12.0 | 45.0 | 6.7 | 45.0 |
| ARA/EPA | 3.8 | 4.6 | 4.7 | 7.0 | 1.5 | 6.0 | 2.6 | 3.3 | 6.4 | 1.5 | 7.0 |
| LA/ALA | 11.8 | 9.4 | 15.6 | 7.4 | 9.5 | 15.3 | 18.4 | 8.6 | 14.1 | 7.4 | 18.4 |
| ARA/DHA | 3.9 | 7.2 | 2.7 | 5.8 | 1.3 | 4.0 | 0.6 | 5.1 | 6.2 | 0.6 | 7.2 |
| DHA/EPA | 2.3 | 2.1 | 4.8 | 5.0 | 3.8 | 3.7 | 4.9 | 2.2 | 2.4 | 2.1 | 5.0 |

Reference: Yuhas et al. 2006_Lipids 41:851-8

SEQUENCE LISTING

```
<160> NUMBER OF SEQ ID NOS: 34

<210> SEQ ID NO 1
<211> LENGTH: 873
<212> TYPE: DNA
<213> ORGANISM: Physcomitrella patens

<400> SEQUENCE: 1
atggaggtcg tggagagatt ctacggtgag ttggatggga aggtctcgca gggcgtgaat      60
gcattgctgg gtagttttgg ggtggagttg acggatacgc ccactaccaa aggcttgccc     120
ctcgttgaca gtcccacacc catcgtcctc ggtgtttctg tatacttgac tattgtcatt     180
ggagggcttt tgtggataaa ggccagggat ctgaaaccgc gcgcctcgga gccattttg      240 ctccaagctt tggtgcttgt gcacaacctg ttctgttttg cgctcagtct gtatatgtgc     300
gtgggcatcg cttatcaggc tattacctgg cggtactctc tctggggcaa tgcatacaat     360
cctaaacata aagagatggc gattctggta tacttgttct acatgtctaa gtacgtggaa     420
ttcatggata ccgttatcat gatactgaag cgcagcacca ggcaaataag cttcctccac     480
gtttatcatc attcttcaat ttccctcatt tggtgggcta ttgctcatca cgctcctggc     540
ggtgaagcat attggtctgc ggctctgaac tcaggagtgc atgttctcat gtatgcgtat     600
tacttcttgg ctgcctgcct tcgaagtagc ccaaagttaa aaaataagta ccttttttgg     660
```

```
ggcaggtact tgacacaatt ccaaatgttc cagtttatgc tgaacttagt gcaggcttac    720
tacgacatga aaacgaatgc gccatatcca caatggctga tcaagatttt gttctactac    780
atgatctcgt tgctgtttct tttcggcaat ttttacgtac aaaatacat caaaccctct    840 gacggaaagc aaaagggagc taaaactgag tga                                 873
```

<210> SEQ ID NO 2
<211> LENGTH: 290
<212> TYPE: PRT
<213> ORGANISM: Physcomitrella patens

<400> SEQUENCE: 2

```
Met Glu Val Val Glu Arg Phe Tyr Gly Glu Leu Asp Gly Lys Val Ser
1               5                   10                  15

Gln Gly Val Asn Ala Leu Leu Gly Ser Phe Gly Val Glu Leu Thr Asp
            20                  25                  30

Thr Pro Thr Thr Lys Gly Leu Pro Leu Val Asp Ser Pro Thr Pro Ile
        35                  40                  45

Val Leu Gly Val Ser Val Tyr Leu Thr Ile Val Ile Gly Gly Leu Leu
    50                  55                  60

Trp Ile Lys Ala Arg Asp Leu Lys Pro Arg Ala Ser Glu Pro Phe Leu
65                  70                  75                  80

Leu Gln Ala Leu Val Leu Val His Asn Leu Phe Cys Phe Ala Leu Ser
                85                  90                  95

Leu Tyr Met Cys Val Gly Ile Ala Tyr Gln Ala Ile Thr Trp Arg Tyr
            100                 105                 110

Ser Leu Trp Gly Asn Ala Tyr Asn Pro Lys His Lys Glu Met Ala Ile
        115                 120                 125

Leu Val Tyr Leu Phe Tyr Met Ser Lys Tyr Val Glu Phe Met Asp Thr
    130                 135                 140

Val Ile Met Ile Leu Lys Arg Ser Thr Arg Gln Ile Ser Phe Leu His
145                 150                 155                 160

Val Tyr His His Ser Ser Ile Ser Leu Ile Trp Trp Ala Ile Ala His
                165                 170                 175

His Ala Pro Gly Gly Glu Ala Tyr Trp Ser Ala Ala Leu Asn Ser Gly
            180                 185                 190

Val His Val Leu Met Tyr Ala Tyr Tyr Phe Leu Ala Ala Cys Leu Arg
        195                 200                 205

Ser Ser Pro Lys Leu Lys Asn Lys Tyr Leu Phe Trp Gly Arg Tyr Leu
    210                 215                 220

Thr Gln Phe Gln Met Phe Gln Phe Met Leu Asn Leu Val Gln Ala Tyr
225                 230                 235                 240

Tyr Asp Met Lys Thr Asn Ala Pro Tyr Pro Gln Trp Leu Ile Lys Ile
                245                 250                 255

Leu Phe Tyr Tyr Met Ile Ser Leu Leu Phe Leu Phe Gly Asn Phe Tyr
            260                 265                 270

Val Gln Lys Tyr Ile Lys Pro Ser Asp Gly Lys Gln Lys Gly Ala Lys
        275                 280                 285

Thr Glu
    290
```

<210> SEQ ID NO 3
<211> LENGTH: 819
<212> TYPE: DNA
<213> ORGANISM: Thalassiosira pseudonana

<400> SEQUENCE: 3

```
atggatgctt ataacgctgc tatggataag attggagctg ctatcatcga ttggagtgat    60
ccagatggaa agttcagagc tgatagggag gattggtggt tgtgcgattt cagatccgct   120
atcaccattg ctctcatcta catcgctttc gtgatcttgg atctgctgt gatgcaatct   180
ctcccagcta tggacccata ccctatcaag ttcctctaca acgtgtctca aatcttcctc   240
tgcgcttaca tgactgttga ggctggattc ctcgcttata ggaacggata caccgttatg   300
ccatgcaacc acttcaacgt gaacgatcca ccagttgcta acttgctctg gctcttctac   360
atctccaaag tgtgggattt ctgggatacc atcttcattg tgctcggaaa gaagtggaga   420
caactctctt tcttgcacgt gtaccaccac accaccatct tcctcttcta ctggttgaac   480
gctaacgtgc tctacgatgg agatatcttc ttgaccatcc tcctcaacgg attcattcac   540
accgtgatgt acacctacta cttcatctgc atgcacacca aggattctaa gaccggaaag   600
tctttgccaa tctggtggaa gtcatctttg accgctttcc aactcttgca attcaccatc   660
atgatgtccc aagctaccta cttggttttc cacggatgcg ataaggtttc cctcagaatc   720
accatcgtgt acttcgtgta cattctctcc cttttcttcc tcttcgctca gttcttcgtg   780
caatcctaca tggctccaaa gaagaagaag tccgcttga                         819
```

<210> SEQ ID NO 4
<211> LENGTH: 272
<212> TYPE: PRT
<213> ORGANISM: Thalassiosira pseudonana

<400> SEQUENCE: 4

```
Met Asp Ala Tyr Asn Ala Ala Met Asp Lys Ile Gly Ala Ala Ile Ile
 1               5                  10                  15

Asp Trp Ser Asp Pro Asp Gly Lys Phe Arg Ala Asp Arg Glu Asp Trp
            20                  25                  30

Trp Leu Cys Asp Phe Arg Ser Ala Ile Thr Ile Ala Leu Ile Tyr Ile
        35                  40                  45

Ala Phe Val Ile Leu Gly Ser Ala Val Met Gln Ser Leu Pro Ala Met
    50                  55                  60

Asp Pro Tyr Pro Ile Lys Phe Leu Tyr Asn Val Ser Gln Ile Phe Leu
65                  70                  75                  80

Cys Ala Tyr Met Thr Val Glu Ala Gly Phe Leu Ala Tyr Arg Asn Gly
                85                  90                  95

Tyr Thr Val Met Pro Cys Asn His Phe Asn Val Asn Asp Pro Pro Val
            100                 105                 110

Ala Asn Leu Leu Trp Leu Phe Tyr Ile Ser Lys Val Trp Asp Phe Trp
        115                 120                 125

Asp Thr Ile Phe Ile Val Leu Gly Lys Lys Trp Arg Gln Leu Ser Phe
    130                 135                 140

Leu His Val Tyr His His Thr Thr Ile Phe Leu Phe Tyr Trp Leu Asn
145                 150                 155                 160

Ala Asn Val Leu Tyr Asp Gly Asp Ile Phe Leu Thr Ile Leu Leu Asn
                165                 170                 175

Gly Phe Ile His Thr Val Met Tyr Thr Tyr Tyr Phe Ile Cys Met His
            180                 185                 190

Thr Lys Asp Ser Lys Thr Gly Lys Ser Leu Pro Ile Trp Trp Lys Ser
        195                 200                 205

Ser Leu Thr Ala Phe Gln Leu Leu Gln Phe Thr Ile Met Met Ser Gln
    210                 215                 220

Ala Thr Tyr Leu Val Phe His Gly Cys Asp Lys Val Ser Leu Arg Ile
```

```
                225                 230                 235                 240
Thr Ile Val Tyr Phe Val Tyr Ile Leu Ser Leu Phe Phe Leu Phe Ala
                    245                 250                 255
Gln Phe Phe Val Gln Ser Tyr Met Ala Pro Lys Lys Lys Ser Ala
                    260                 265                 270

<210> SEQ ID NO 5
<211> LENGTH: 1380
<212> TYPE: DNA
<213> ORGANISM: Pythium irregulare

<400> SEQUENCE: 5
atggtggacc tcaagcctgg agtgaagcgc ctggtgagct ggaaggagat ccgcgagcac      60
gcgacgcccg cgaccgcgtg gatcgtgatt caccacaagg tctacgacat ctccaagtgg     120
gactcgcacc cgggtggctc cgtgatgctc acgcaggccg gcgaggacgc cacggacgcc     180
ttcgcggtct tccacccgtc ctcggcgctc aagctgctcg agcagttcta cgtcggcgac     240
gtggacgaaa cctccaaggc cgagatcgag ggggagccgg cgagcgacga ggagcgcgcg     300
cgccgcgagc gcatcaacga gttcatcgcg tcctaccgcc gtctgcgcgt caaggtcaag     360
ggcatggggc tctacgacgc cagcgcgctc tactacgcgt ggaagctcgt gagcacgttc     420
ggcatcgcgg tgctctcgat ggcgatctgc ttcttcttca acagtttcgc catgtacatg     480
gtcgccggcg tgattatggg gctcttctac cagcagtccg gatggctggc gcacgacttc     540
ttgcacaacc aggtgtgcga gaaccgcacg ctcggcaacc ttatcggctg cctcgtgggc     600
aacgcctggc agggcttcag catgcagtgg tggaagaaca agcacaacct gcaccacgcg     660
gtgccgaacc tgcacagcgc caaggacgag ggcttcatcg cgacccggga catcgacacc     720
atgccgctgc tggcgtggtc taaggagatg gcgcgcaagg cgttcgagtc ggcgcacggc     780
ccgttcttca tccgcaacca ggcgttccta tactttccgc tgctgctgct cgcgcgcctg     840
agctggctcg cgcagtcgtt cttctacgtg ttcaccgagt tctcgttcgg catcttcgac     900
aaggtcgagt tcgacggacc ggagaaggcg ggtctgatcg tgcactacat ctggcagctc     960
gcgatcccgt acttctgcaa catgagcctg tttgagggcg tggcatactt cctcatgggc    1020
caggcgtcct gcggcttgct cctggcgctg tgttcagta ttggccacaa cggcatgtcg     1080
gtgtacgagc gcgaaaccaa gccggacttc tggcagctgc aggtgaccac gacgcgcaac    1140
atccgcgcgt cggtattcat ggactggttc accggtggct tgaactacca gatcgaccat    1200
cacctgttcc cgctcgtgcc gcgccacaac ttgccaaagg tcaacgtgct catcaagtcg    1260
ctatgcaagg agttcgacat cccgttccac gagaccggct tctgggaggg catctacgag    1320
gtcgtggacc acctggcgga catcagcaag gaatttatca ccgagttccc agcgatgtaa    1380

<210> SEQ ID NO 6
<211> LENGTH: 459
<212> TYPE: PRT
<213> ORGANISM: Pythium irregulare

<400> SEQUENCE: 6

Met Val Asp Leu Lys Pro Gly Val Lys Arg Leu Val Ser Trp Lys Glu
1               5                   10                  15

Ile Arg Glu His Ala Thr Pro Ala Thr Ala Trp Ile Val Ile His His
                20                  25                  30

Lys Val Tyr Asp Ile Ser Lys Trp Asp Ser His Pro Gly Gly Ser Val
            35                  40                  45

Met Leu Thr Gln Ala Gly Glu Asp Ala Thr Asp Ala Phe Ala Val Phe
```

```
                50                  55                  60
His Pro Ser Ser Ala Leu Lys Leu Leu Glu Gln Phe Tyr Val Gly Asp
 65                  70                  75                  80

Val Asp Glu Thr Ser Lys Ala Glu Ile Glu Gly Pro Ala Ser Asp
                 85                  90                  95

Glu Glu Arg Ala Arg Glu Arg Ile Asn Glu Phe Ile Ala Ser Tyr
                100                 105                 110

Arg Arg Leu Arg Val Lys Val Lys Gly Met Gly Leu Tyr Asp Ala Ser
                115                 120                 125

Ala Leu Tyr Tyr Ala Trp Lys Leu Val Ser Thr Phe Gly Ile Ala Val
130                 135                 140

Leu Ser Met Ala Ile Cys Phe Phe Asn Ser Phe Ala Met Tyr Met
145                 150                 155                 160

Val Ala Gly Val Ile Met Gly Leu Phe Tyr Gln Gln Ser Gly Trp Leu
                165                 170                 175

Ala His Asp Phe Leu His Asn Gln Val Cys Glu Asn Arg Thr Leu Gly
                180                 185                 190

Asn Leu Ile Gly Cys Leu Val Gly Asn Ala Trp Gln Gly Phe Ser Met
                195                 200                 205

Gln Trp Trp Lys Asn Lys His Asn Leu His His Ala Val Pro Asn Leu
210                 215                 220

His Ser Ala Lys Asp Glu Gly Phe Ile Gly Asp Pro Asp Ile Asp Thr
225                 230                 235                 240

Met Pro Leu Leu Ala Trp Ser Lys Glu Met Ala Arg Lys Ala Phe Glu
                245                 250                 255

Ser Ala His Gly Pro Phe Phe Ile Arg Asn Gln Ala Phe Leu Tyr Phe
                260                 265                 270

Pro Leu Leu Leu Ala Arg Leu Ser Trp Leu Ala Gln Ser Phe Phe
                275                 280                 285

Tyr Val Phe Thr Glu Phe Ser Phe Gly Ile Phe Asp Lys Val Glu Phe
                290                 295                 300

Asp Gly Pro Glu Lys Ala Gly Leu Ile Val His Tyr Ile Trp Gln Leu
305                 310                 315                 320

Ala Ile Pro Tyr Phe Cys Asn Met Ser Leu Phe Glu Gly Val Ala Tyr
                325                 330                 335

Phe Leu Met Gly Gln Ala Ser Cys Gly Leu Leu Leu Ala Leu Val Phe
                340                 345                 350

Ser Ile Gly His Asn Gly Met Ser Val Tyr Glu Arg Gly Thr Lys Pro
                355                 360                 365

Asp Phe Trp Gln Leu Gln Val Thr Thr Thr Arg Asn Ile Arg Ala Ser
370                 375                 380

Val Phe Met Asp Trp Phe Thr Gly Gly Leu Asn Tyr Gln Ile Asp His
385                 390                 395                 400

His Leu Phe Pro Leu Val Pro Arg His Asn Leu Pro Lys Val Asn Val
                405                 410                 415

Leu Ile Lys Ser Leu Cys Lys Glu Phe Asp Ile Pro Phe His Glu Thr
                420                 425                 430

Gly Phe Trp Glu Gly Ile Tyr Glu Val Val Asp His Leu Ala Asp Ile
                435                 440                 445

Ser Lys Glu Phe Ile Thr Glu Phe Pro Ala Met
450                 455

<210> SEQ ID NO 7
<211> LENGTH: 1371
```

```
<212> TYPE: DNA
<213> ORGANISM: Ostreococcus tauri

<400> SEQUENCE: 7
atgtgtgttg agaccgagaa caacgatgga atccctactg tggagatcgc tttcgatgga      60
gagagagaaa gagctgaggc taacgtgaag ttgtctgctg agaagatgga acctgctgct     120
ttggctaaga ccttcgctag aagatacgtg gttatcgagg gagttgagta cgatgtgacc     180
gatttcaaac atcctggagg aaccgtgatt ttctacgctc tctctaacac tggagctgat     240
gctactgagg ctttcaagga gttccaccac agatctagaa aggctaggaa ggctttggct     300
gctttgcctt ctagacctgc taagaccgct aaagtggatg atgctgagat gctccaggat     360
ttcgctaagt ggagaaagga gttggagagg gacggattct tcaagccttc tcctgctcat     420
gttgcttaca gattcgctga gttggctgct atgtacgctt gggaaccta cttgatgtac      480
gctagatacg ttgtgtcctc tgtgttggtt tacgcttgct tcttcggagc tagatgtgga     540
tgggttcaac atgagggagg acattcttct ttgaccggaa acatctggtg ggataagaga     600
atccaagctt tcactgctgg attcggattg gctggatctg agatatgtg aactccatg       660
cacaacaagc accatgctac tcctcaaaaa gtgaggcacg atatggattt ggataccact     720
cctgctgttg ctttcttcaa caccgctgtg gaggataata gacctagggg attctctaag     780
tactggctca gattgcaagc ttggaccttc attcctgtga cttctggatt ggtgttgctc     840
ttctggatgt tcttcctcca tccttctaag gctttgaagg gaggaaagta cgaggagctt     900
gtgtggatgt ggctgctca tgtgattaga acctggacca ttaaggctgt tactggattc     960
accgctatgc aatcctacgg actcttcttg gctacttctt gggtttccgg atgctacttg    1020
ttcgctcact tctctacttc tcacacccat ttggatgttg ttcctgctga tgagcatttg    1080
tcttgggtta ggtacgctgt ggatcacacc attgatatcg atccttctca gggatgggtt    1140
aactggttga tgggatactt gaactgccaa gtgattcatc acctcttccc ttctatgcct    1200
caattcagac aacctgaggt gtccagaaga ttcgttgctt cgctaagaa gtggaacctc     1260
aactacaagg tgatgactta tgctggagct tggaaggcta cttcgggaaa cctcgataat    1320
gtgggaaagc actactacgt gcacggacaa cattctggaa agaccgcttg a             1371

<210> SEQ ID NO 8
<211> LENGTH: 456
<212> TYPE: PRT
<213> ORGANISM: Ostreococcus tauri

<400> SEQUENCE: 8

Met Cys Val Glu Thr Glu Asn Asn Asp Gly Ile Pro Thr Val Glu Ile
1               5                   10                  15

Ala Phe Asp Gly Glu Arg Glu Arg Ala Glu Ala Asn Val Lys Leu Ser
            20                  25                  30

Ala Glu Lys Met Glu Pro Ala Ala Leu Ala Lys Thr Phe Ala Arg Arg
        35                  40                  45

Tyr Val Val Ile Glu Gly Val Glu Tyr Asp Val Thr Asp Phe Lys His
    50                  55                  60

Pro Gly Gly Thr Val Ile Phe Tyr Ala Leu Ser Asn Thr Gly Ala Asp
65                  70                  75                  80

Ala Thr Glu Ala Phe Lys Glu Phe His His Arg Ser Arg Lys Ala Arg
                85                  90                  95

Lys Ala Leu Ala Ala Leu Pro Ser Arg Pro Ala Lys Thr Ala Lys Val
            100                 105                 110
```

Asp Asp Ala Glu Met Leu Gln Asp Phe Ala Lys Trp Arg Lys Glu Leu
115                 120                 125

Glu Arg Asp Gly Phe Phe Lys Pro Ser Pro Ala His Val Ala Tyr Arg
130                 135                 140

Phe Ala Glu Leu Ala Ala Met Tyr Ala Leu Gly Thr Tyr Leu Met Tyr
145                 150                 155                 160

Ala Arg Tyr Val Val Ser Ser Val Leu Val Tyr Ala Cys Phe Phe Gly
                165                 170                 175

Ala Arg Cys Gly Trp Val Gln His Glu Gly Gly His Ser Ser Leu Thr
                180                 185                 190

Gly Asn Ile Trp Trp Asp Lys Arg Ile Gln Ala Phe Thr Ala Gly Phe
195                 200                 205

Gly Leu Ala Gly Ser Gly Asp Met Trp Asn Ser Met His Asn Lys His
210                 215                 220

His Ala Thr Pro Gln Lys Val Arg His Asp Met Asp Leu Asp Thr Thr
225                 230                 235                 240

Pro Ala Val Ala Phe Phe Asn Thr Ala Val Glu Asp Asn Arg Pro Arg
                245                 250                 255

Gly Phe Ser Lys Tyr Trp Leu Arg Leu Gln Ala Trp Thr Phe Ile Pro
                260                 265                 270

Val Thr Ser Gly Leu Val Leu Leu Phe Trp Met Phe Phe Leu His Pro
275                 280                 285

Ser Lys Ala Leu Lys Gly Gly Lys Tyr Glu Glu Leu Val Trp Met Leu
290                 295                 300

Ala Ala His Val Ile Arg Thr Trp Thr Ile Lys Ala Val Thr Gly Phe
305                 310                 315                 320

Thr Ala Met Gln Ser Tyr Gly Leu Phe Leu Ala Thr Ser Trp Val Ser
                325                 330                 335

Gly Cys Tyr Leu Phe Ala His Phe Ser Thr Ser His Thr His Leu Asp
                340                 345                 350

Val Val Pro Ala Asp Glu His Leu Ser Trp Val Arg Tyr Ala Val Asp
355                 360                 365

His Thr Ile Asp Ile Asp Pro Ser Gln Gly Trp Val Asn Trp Leu Met
370                 375                 380

Gly Tyr Leu Asn Cys Gln Val Ile His His Leu Phe Pro Ser Met Pro
385                 390                 395                 400

Gln Phe Arg Gln Pro Glu Val Ser Arg Arg Phe Val Ala Phe Ala Lys
                405                 410                 415

Lys Trp Asn Leu Asn Tyr Lys Val Met Thr Tyr Ala Gly Ala Trp Lys
                420                 425                 430

Ala Thr Leu Gly Asn Leu Asp Asn Val Gly Lys His Tyr Tyr Val His
435                 440                 445

Gly Gln His Ser Gly Lys Thr Ala
450                 455

<210> SEQ ID NO 9
<211> LENGTH: 1320
<212> TYPE: DNA
<213> ORGANISM: Thraustochytrium ssp.

<400> SEQUENCE: 9
atgggaaaag gatctgaggg aagatctgct gctagagaga tgactgctga ggctaacgga      60
gataagagaa agaccatcct cattgaggga gtgttgtacg atgctaccaa cttcaaacac     120
ccaggaggtt ccattattaa cttcctcacc gagggagaag ctggagttga tgctacccaa     180

```
gcttacagag agttccatca gagatccgga aaggctgata agtacctcaa gtccctccca    240
aagttggatg cttctaaggt ggagtctagg ttctctgcta aggagcaggc tagaagggac    300
gctatgacca gggattacgc tgctttcaga gaggagttgg ttgctgaggg atacttcgat    360
ccatctatcc cacacatgat ctacagagtg gtggagattg tggctttgtt cgctttgtct    420
ttctggttga tgtctaaggc ttctccaacc tctttggttt tgggagtggt gatgaacgga    480
atcgctcaag aagatgcgg atgggttatg cacgagatgg gacacggatc tttcactgga    540
gttatctggc tcgatgatag gatgtgcgag ttcttctacg agttggatg tggaatgtct    600 ggacactact ggaagaacca gcactctaag caccacgctg ctccaaacag attggagcac    660
gatgtggatt tgaacacctt gccactcgtt gctttcaacg agagagttgt gaggaaggtt    720
aagccaggat ctttgttggc tttgtggctc agagttcagg cttatttgtt cgctccagtg    780
tcttgcttgt tgatcggatt gggatggacc ttgtacttgc acccaagata tatgctcagg    840
accaagagac acatggagtt tgtgtggatc ttcgctagat atatcggatg gttctccttg    900
atgggagctt tgggatattc tcctggaact tctgtgggaa tgtacctctg ctctttcgga    960
cttggatgca tctacatctt cctccaattc gctgtgtctc acacccactt gccagttacc    1020
aacccagagg atcaattgca ctggcttgag tacgctgctg atcacaccgt gaacatctct    1080
accaagtctt ggttggttac ctggtggatg tctaacctca acttccaaat cgagcaccac    1140 tgttcccaa ccgctccaca attcaggttc aaggagatct ctccaagagt tgaggctctc    1200
ttcaagagac acaacctccc ttactacgat ttgccataca cctctgctgt ttctactacc    1260
ttcgctaacc tctactctgt tggacactct gttggagctg ataccaagaa gcaggattga   1320
```

<210> SEQ ID NO 10
<211> LENGTH: 439
<212> TYPE: PRT
<213> ORGANISM: Thraustochytrium ssp.

<400> SEQUENCE: 10

```
Met Gly Lys Gly Ser Glu Gly Arg Ser Ala Ala Arg Glu Met Thr Ala
1               5                   10                  15

Glu Ala Asn Gly Asp Lys Arg Lys Thr Ile Leu Ile Glu Gly Val Leu
                20                  25                  30

Tyr Asp Ala Thr Asn Phe Lys His Pro Gly Gly Ser Ile Ile Asn Phe
            35                  40                  45

Leu Thr Glu Gly Glu Ala Gly Val Asp Ala Thr Gln Ala Tyr Arg Glu
        50                  55                  60

Phe His Gln Arg Ser Gly Lys Ala Asp Lys Tyr Leu Lys Ser Leu Pro
65                  70                  75                  80

Lys Leu Asp Ala Ser Lys Val Glu Ser Arg Phe Ser Ala Lys Glu Gln
                85                  90                  95

Ala Arg Arg Asp Ala Met Thr Arg Asp Tyr Ala Ala Phe Arg Glu Glu
            100                 105                 110

Leu Val Ala Glu Gly Tyr Phe Asp Pro Ser Ile Pro His Met Ile Tyr
        115                 120                 125

Arg Val Val Glu Ile Val Ala Leu Phe Ala Leu Ser Phe Trp Leu Met
    130                 135                 140

Ser Lys Ala Ser Pro Thr Ser Leu Val Leu Gly Val Val Met Asn Gly
145                 150                 155                 160

Ile Ala Gln Gly Arg Cys Gly Trp Val Met His Glu Met Gly His Gly
                165                 170                 175

Ser Phe Thr Gly Val Ile Trp Leu Asp Asp Arg Met Cys Glu Phe Phe
```

```
                    180               185               190
Tyr Gly Val Gly Cys Gly Met Ser Gly His Tyr Trp Lys Asn Gln His
            195               200               205
Ser Lys His His Ala Ala Pro Asn Arg Leu Glu His Asp Val Asp Leu
        210               215               220
Asn Thr Leu Pro Leu Val Ala Phe Asn Glu Arg Val Val Arg Lys Val
225               230               235               240
Lys Pro Gly Ser Leu Leu Ala Leu Trp Leu Arg Val Gln Ala Tyr Leu
                245               250               255
Phe Ala Pro Val Ser Cys Leu Leu Ile Gly Leu Gly Trp Thr Leu Tyr
            260               265               270
Leu His Pro Arg Tyr Met Leu Arg Thr Lys Arg His Met Glu Phe Val
        275               280               285
Trp Ile Phe Ala Arg Tyr Ile Gly Trp Phe Ser Leu Met Gly Ala Leu
        290               295               300
Gly Tyr Ser Pro Gly Thr Ser Val Gly Met Tyr Leu Cys Ser Phe Gly
305               310               315               320
Leu Gly Cys Ile Tyr Ile Phe Leu Gln Phe Ala Val Ser His Thr His
                325               330               335
Leu Pro Val Thr Asn Pro Glu Asp Gln Leu His Trp Leu Glu Tyr Ala
            340               345               350
Ala Asp His Thr Val Asn Ile Ser Thr Lys Ser Trp Leu Val Thr Trp
        355               360               365
Trp Met Ser Asn Leu Asn Phe Gln Ile Glu His His Leu Phe Pro Thr
        370               375               380
Ala Pro Gln Phe Arg Phe Lys Glu Ile Ser Pro Arg Val Glu Ala Leu
385               390               395               400
Phe Lys Arg His Asn Leu Pro Tyr Tyr Asp Leu Pro Tyr Thr Ser Ala
                405               410               415
Val Ser Thr Thr Phe Ala Asn Leu Tyr Ser Val Gly His Ser Val Gly
            420               425               430
Ala Asp Thr Lys Lys Gln Asp
        435
```

<210> SEQ ID NO 11
<211> LENGTH: 1197
<212> TYPE: DNA
<213> ORGANISM: Phytophtora sojae

<400> SEQUENCE: 11

```
atggctattt tgaaccctga ggctgattct gctgctaacc tcgctactga ttctgaggct      60
aagcaaagac aattggctga ggctggatac actcatgttg agggtgctcc tgctcctttg     120
cctttggagt tgcctcattt tctctctcaga gatctcagag ctgctattcc taagcactgc    180
ttcgagagat ctttcgtgac ctccacctac tacatgatca agaacgtgtt gacttgcgct    240
gctttgttct acgctgctac cttcattgat agagctggag ctgctgctta tgttttgtgg    300
cctgtgtact ggttcttcca gggatcttac ttgactggag tgtgggttat cgctcatgag    360
tgtggacatc aggcttattg ctcttctgag gtggtgaaca acttgattgg actcgtgttg    420
cattctgctt tgttggtgcc ttaccactct tggagaatct ctcacagaaa gcaccattcc    480
aacactggat cttgcgagaa cgatgaggtt ttcgttcctg tgaccagatc tgtgttggct    540
tcttcttgga cgagaccttt ggaggattct cctctctacc aactctaccg tatcgtgtac    600
atgttggttg ttggatggat gcctggatac ctcttcttca acgctactgg acctactaag     660
```

```
tactggggaa agtctaggtc tcacttcaac ccttactccg ctatctatgc tgatagggag    720
agatggatga tcgtgctctc cgatattttc ttggtggcta tgttggctgt tttggctgct    780
ttggtgcaca ctttctcctt caacaccatg gtgaagttct acgtggtgcc ttacttcatt    840
gtgaacgctt acttggtgtt gattacctac ctccaacaca ccgataccta catccctcat    900
ttcagagagg gagagtggaa ttggttgaga ggagctttgt gcactgtgga tagatcattt    960
ggtccattcc tcgattctgt ggtgcataga atcgtggata cccatgtttg ccaccacatc   1020
ttctccaaga tgccttttcta tcattgcgag gaggctacca acgctattaa gcctctcctc   1080
ggaaagttct acttgaagga taccactcct gttcctgttg ctctctggag atcttacacc   1140
cattgcaagt tcgttgagga tgatggaaag gtggtgttct acaagaacaa gctctag      1197
```

<210> SEQ ID NO 12
<211> LENGTH: 398
<212> TYPE: PRT
<213> ORGANISM: Phytophtora sojae

<400> SEQUENCE: 12

```
Met Ala Ile Leu Asn Pro Glu Ala Asp Ser Ala Ala Asn Leu Ala Thr
1               5                  10                  15

Asp Ser Glu Ala Lys Gln Arg Gln Leu Ala Glu Ala Gly Tyr Thr His
            20                  25                  30

Val Glu Gly Ala Pro Ala Pro Leu Pro Leu Glu Leu Pro His Phe Ser
        35                  40                  45

Leu Arg Asp Leu Arg Ala Ala Ile Pro Lys His Cys Phe Glu Arg Ser
    50                  55                  60

Phe Val Thr Ser Thr Tyr Tyr Met Ile Lys Asn Val Leu Thr Cys Ala
65                  70                  75                  80

Ala Leu Phe Tyr Ala Ala Thr Phe Ile Asp Arg Ala Gly Ala Ala Ala
                85                  90                  95

Tyr Val Leu Trp Pro Val Tyr Trp Phe Gln Gly Ser Tyr Leu Thr
            100                 105                 110

Gly Val Trp Val Ile Ala His Glu Cys Gly His Gln Ala Tyr Cys Ser
        115                 120                 125

Ser Glu Val Val Asn Asn Leu Ile Gly Leu Val Leu His Ser Ala Leu
    130                 135                 140

Leu Val Pro Tyr His Ser Trp Arg Ile Ser His Arg Lys His His Ser
145                 150                 155                 160

Asn Thr Gly Ser Cys Glu Asn Asp Glu Val Phe Val Pro Val Thr Arg
                165                 170                 175

Ser Val Leu Ala Ser Ser Trp Asn Glu Thr Leu Glu Asp Ser Pro Leu
            180                 185                 190

Tyr Gln Leu Tyr Arg Ile Val Tyr Met Leu Val Val Gly Trp Met Pro
        195                 200                 205

Gly Tyr Leu Phe Phe Asn Ala Thr Gly Pro Thr Lys Tyr Trp Gly Lys
    210                 215                 220

Ser Arg Ser His Phe Asn Pro Tyr Ser Ala Ile Tyr Ala Asp Arg Glu
225                 230                 235                 240

Arg Trp Met Ile Val Leu Ser Asp Ile Phe Leu Val Ala Met Leu Ala
                245                 250                 255

Val Leu Ala Ala Leu Val His Thr Phe Ser Phe Asn Thr Met Val Lys
            260                 265                 270

Phe Tyr Val Val Pro Tyr Phe Ile Val Asn Ala Tyr Leu Val Leu Ile
        275                 280                 285
```

| Thr | Tyr | Leu | Gln | His | Thr | Asp | Thr | Tyr | Ile | Pro | His | Phe | Arg | Glu | Gly |
| | 290 | | | | | 295 | | | | | 300 | | | | |

| Glu | Trp | Asn | Trp | Leu | Arg | Gly | Ala | Leu | Cys | Thr | Val | Asp | Arg | Ser | Phe |
| 305 | | | | | 310 | | | | | 315 | | | | | 320 |

| Gly | Pro | Phe | Leu | Asp | Ser | Val | Val | His | Arg | Ile | Val | Asp | Thr | His | Val |
| | | | | 325 | | | | | 330 | | | | | 335 | |

| Cys | His | His | Ile | Phe | Ser | Lys | Met | Pro | Phe | Tyr | His | Cys | Glu | Glu | Ala |
| | | | 340 | | | | | 345 | | | | | 350 | | |

| Thr | Asn | Ala | Ile | Lys | Pro | Leu | Leu | Gly | Lys | Phe | Tyr | Leu | Lys | Asp | Thr |
| | | 355 | | | | | 360 | | | | | 365 | | | |

| Thr | Pro | Val | Pro | Val | Ala | Leu | Trp | Arg | Ser | Tyr | Thr | His | Cys | Lys | Phe |
| 370 | | | | | 375 | | | | | 380 | | | | | |

| Val | Glu | Asp | Asp | Gly | Lys | Val | Val | Phe | Tyr | Lys | Asn | Lys | Leu | | |
| 385 | | | | | 390 | | | | | 395 | | | | | |

<210> SEQ ID NO 13
<211> LENGTH: 1305
<212> TYPE: DNA
<213> ORGANISM: Thalassiosira pseudonana

<400> SEQUENCE: 13

```
atgggaaaag gaggaagatc tgtgactagg gctcaaactg ctgagaagtc tgctcacacc      60
attcaaacct tcaccgatgg aagatgggtt tccccttaca acccttggc taaggatgct     120
cctgagttgc cttctaaggg agagattaag gctgtgatcc ctaaggagtg cttcgagaga    180
tcttacctcc actccatgta cttcgtgttg agggatactg ttatggctgt tgcttgcgct    240
tacattgctc attctaccct ctccaccgat attccttctg agttgctctc tgtggatgct    300
ttgaagtggt tcttgggatg gaacacttac gctttctgga tgggatgcat tttgactgga    360
cattgggtgt tggctcatga gtgtggacat ggagctttct ctccatctca gaccttcaac    420
gatttctggg gattcatcat gcatcaagct gtgttggttc cttacttcgc ttggcaatac    480
tctcatgcta agcaccatag gaggaccaac aacatcatgg atggagagtc tcatgtgcct    540
aacatcgcta aggagatggg attgaacgag aagaacgaga gatctggagg atacgctgct    600
attcatgagg ctatcggaga tggacctttc gctatgttcc agatcttcgc tcatttggtg    660
attggatggc ctatctactt gatgggattc gcttctactg aaggcttgg acaagatgga    720
aaggagttgc aagctggaga gatcatcgat cactaccgtc cttggtctaa gatgttccct    780
accaagctca gattcaagat cgctttgtct accttgggag tgattgctgc ttgggttggg    840
ctttacttcg ctgctcaaga gtatggagtt ttgcctgtgg tgttgtggta tatcggacct    900
ttgatgtgga atcaggcttg gttggtgttg tacacctggt tgcaacacaa cgatccttct    960
gtgcctcaat acggatctga tgagtggact tgggttaagg gagcactttc cacaatcgat   1020
agaccttacg aatcttcga tttcttccac cacaagatcg gatctactca gtgtgctcat   1080
catctcttcc atgagatgcc tttctacaag gctgatgtgg ctaccgcttc tattaaggga   1140
ttcctcgagc taagggact ttacaactac gatcctaccc cttggtatgt tgctatgtgg   1200
agagttgcta gacttgcca ctacatcgag gatgttgatg gagttcagta ctacaagtcc   1260
ttggaggatg tgcctttgaa gaaggatgct aagaagtccg attga              1305
```

<210> SEQ ID NO 14
<211> LENGTH: 434
<212> TYPE: PRT
<213> ORGANISM: Thalassiosira pseudonana

<400> SEQUENCE: 14

```
Met Gly Lys Gly Gly Arg Ser Val Thr Arg Ala Gln Thr Ala Glu Lys
1               5                   10                  15

Ser Ala His Thr Ile Gln Thr Phe Thr Asp Gly Arg Trp Val Ser Pro
            20                  25                  30

Tyr Asn Pro Leu Ala Lys Asp Ala Pro Glu Leu Pro Ser Lys Gly Glu
                35                  40                  45

Ile Lys Ala Val Ile Pro Lys Glu Cys Phe Glu Arg Ser Tyr Leu His
    50                  55                  60

Ser Met Tyr Phe Val Leu Arg Asp Thr Val Met Ala Val Ala Cys Ala
65                  70                  75                  80

Tyr Ile Ala His Ser Thr Leu Ser Thr Asp Ile Pro Ser Glu Leu Leu
                85                  90                  95

Ser Val Asp Ala Leu Lys Trp Phe Leu Gly Trp Asn Thr Tyr Ala Phe
                100                 105                 110

Trp Met Gly Cys Ile Leu Thr Gly His Trp Val Leu Ala His Glu Cys
            115                 120                 125

Gly His Gly Ala Phe Ser Pro Ser Gln Thr Phe Asn Asp Phe Trp Gly
        130                 135                 140

Phe Ile Met His Gln Ala Val Leu Val Pro Tyr Phe Ala Trp Gln Tyr
145                 150                 155                 160

Ser His Ala Lys His His Arg Arg Thr Asn Asn Ile Met Asp Gly Glu
            165                 170                 175

Ser His Val Pro Asn Ile Ala Lys Glu Met Gly Leu Asn Glu Lys Asn
            180                 185                 190

Glu Arg Ser Gly Gly Tyr Ala Ala Ile His Glu Ala Ile Gly Asp Gly
        195                 200                 205

Pro Phe Ala Met Phe Gln Ile Phe Ala His Leu Val Ile Gly Trp Pro
    210                 215                 220

Ile Tyr Leu Met Gly Phe Ala Ser Thr Gly Arg Leu Gly Gln Asp Gly
225                 230                 235                 240

Lys Glu Leu Gln Ala Gly Glu Ile Ile Asp His Tyr Arg Pro Trp Ser
            245                 250                 255

Lys Met Phe Pro Thr Lys Leu Arg Phe Lys Ile Ala Leu Ser Thr Leu
            260                 265                 270

Gly Val Ile Ala Ala Trp Val Gly Leu Tyr Phe Ala Ala Gln Glu Tyr
        275                 280                 285

Gly Val Leu Pro Val Val Leu Trp Tyr Ile Gly Pro Leu Met Trp Asn
        290                 295                 300

Gln Ala Trp Leu Val Leu Tyr Thr Trp Leu Gln His Asn Asp Pro Ser
305                 310                 315                 320

Val Pro Gln Tyr Gly Ser Asp Glu Trp Thr Trp Val Lys Gly Ala Leu
                325                 330                 335

Ser Thr Ile Asp Arg Pro Tyr Gly Ile Phe Asp Phe Phe His His Lys
            340                 345                 350

Ile Gly Ser Thr His Val Ala His His Leu Phe His Glu Met Pro Phe
        355                 360                 365

Tyr Lys Ala Asp Val Ala Thr Ala Ser Ile Lys Gly Phe Leu Glu Pro
    370                 375                 380

Lys Gly Leu Tyr Asn Tyr Asp Pro Thr Pro Trp Tyr Val Ala Met Trp
385                 390                 395                 400

Arg Val Ala Lys Thr Cys His Tyr Ile Glu Asp Val Asp Gly Val Gln
                405                 410                 415

Tyr Tyr Lys Ser Leu Glu Asp Val Pro Leu Lys Lys Asp Ala Lys Lys
```

```
                        420            425           430
Ser Asp

<210> SEQ ID NO 15
<211> LENGTH: 24631
<212> TYPE: DNA
<213> ORGANISM: Artificial Sequence
<220> FEATURE:
<223> OTHER INFORMATION: binary T plasmid VC-LJB913-1qcz

<400> SEQUENCE: 15
acatacaaat ggacgaacgg ataaaccttt tcacgcccct ttaaatatcc gattattcta      60
ataaacgctc ttttctctta ggtttacccg ccaatatatc ctgtcaaaca ctgatagttt     120
aaactgaagg cgggaaacga caatcagatc tagtaggaaa cagctatgac catgattacg     180
ccaagcttat ttaaatcgta ccgtactagt aacggccgcc agtgtgctgg aattcgccct     240
taaaaaagat atcgattacg ccaagctatc aactttgtat agaaaagttg ccatgattac     300
gccaagcttg gcgcgccctg cagcaaattt acacattgcc actaaacgtc taaacccttg     360
taatttgttt ttgttttact atgtgtgtta tgtatttgat ttgcgataaa ttttttatatt    420
tggtactaaa tttataacac cttttatgct aacgtttgcc aacacttagc aatttgcaag     480
ttgattaatt gattctaaat tattttttgtc ttctaaatac atatactaat caactggaaa    540
tgtaaatatt tgctaatatt tctactatag gagaattaaa gtgagtgaat atggtaccac     600
aaggtttgga gatttaattg ttgcaatgct gcatggatgg catatacacc aaacattcaa     660
taattcttga ggataataat ggtaccacac aagatttgag gtgcatgaac gtcacgtgga     720
caaaaggttt agtaattttt caagacaaca atgttaccac acacaagttt tgaggtgcat     780
gcatggatgc cctgtggaaa gtttaaaaat attttggaaa tgatttgcat ggaagccatg     840
tgtaaaacca tgacatccac ttggaggatg caataatgaa gaaaactaca aatttacatg     900
caactagtta tgcatgtagt ctatataatg aggattttgc aatactttca ttcatacaca     960
ctcactaagt tttacacgat tataattttct tcatagccag taccatggaa gttgttgaga    1020
ggttctacgg agagttggat ggaaaggttt cccaaggagt gaacgctttg ttgggatctt     1080
tcggagttga gttgactgat accccaacta ctaagggatt gccactcgtt gattctccaa     1140
ctccaattgt gttgggagtg tctgtttact tgaccatcgt gatcggagga ttgctttgga     1200
tcaaggctag agatctcaag ccaagagctt ctgagccatt cttgttgcaa gctttggtgt     1260
tggtgcacaa cttgttctgc ttcgctttgt ctctttacat gtgcgtgggt atcgcttacc     1320
aagctatcac ctggagatat tccttgtggg gaaacgctta taacccaaag cacaaggaga    1380
tggctatcct cgtttacctc ttctacatgt ccaagtacgt ggagttcatg gataccgtga     1440
tcatgatcct caagagatcc accagacaga tttctttcct ccacgtgtac caccactctt    1500
ctatctccct tatctggtgg gctattgctc accgctcc aggaggagag gcttattgga     1560
gtgctgctct caactctgga gtgcacgtgt tgatgtacgc ttactacttc ttggctgctt     1620
gcttgagatc ttccccaaag ctcaagaaca agtacctctt ctggggaaga tacctcaccc    1680
aattccagat gttccagttc atgctcaact tggtgcaagc ttactacgat atgaaaacca     1740
acgctccata tccacaatgg ctcatcaaga tcctcttcta ctacatgatc ccctcttgt     1800
tcctcttcgg aaacttctac gtgcaaaagt acatcaagcc atccgatgga aagcaaaagg    1860
gagctaagac cgagtgatcg acaagctcga gtttctccat aataatgtgt gagtagttcc     1920
cagataaggg aattagggtt cctatagggt ttcgctcatg tgttgagcat ataagaaacc     1980
```

```
cttagtatgt atttgtattt gtaaaatact tctatcaata aaatttctaa ttcctaaaac    2040
caaaatccag tactaaaatc cagatccccc gaattaattc ggcgttaatt cagggccggc    2100
cgatctgtcg tctcaaactc attcatcaga accttcttga acttagttat ctcttgttca    2160
gagcttcctg ttagcaatat gtcatcaaca tataaacatg tcccagaagc cagaagatag    2220
aagttggatg atagaagtaa agtaatgtta ctggtggagt accacaatac aagttcatac    2280
aaactttatt gtccagaaac taacaaagtt gagttcagca tagatgaaag acaaaaagaa    2340
tatattaaat gacggctgca aaataaggag taatgaatac attgacctac ctactactag    2400
gctatttata cacaatatta gggtataata aaatattaaa ataccctcta tcagacttag    2460
tcaataagac attcctaaaa tataaattat ttccaacaat aatttgtctc aaataaaata    2520
tagaggtgca aaagttaaac taagagtgca aagtaaaatt ttgagagggc tcaaaattga    2580
atataataac aatattagtg tagtttaaga aaactcaggg gatgcagttg aactccctca    2640
actgtacgta gctcctcccc tggatgcagt gtaaagattt gaagatatat tttagtactt    2700
tggatattgt aggccagagg gtgttgaaga taaaggttca ggaactaaca cattcatcca    2760
caacttctat gtgtccatcg tcagtgaaat acatgccaaa tagggagtt aagaagagta     2820 gaaagggtca agatagtgat gtgcatcgtg atccttcata atgggagtgt ggtgagggct    2880
cgcatgggag tcatactaca aagagatcat gcataaaacc aactagaagt caactgtcaa    2940
gtatgacggc tgacaattaa ccgtccacca aatcttccag acatgtttac ttgtcccagt    3000
tttctgattt cttatatcca tacattgatg acattattga tgttggtggc gatggagatt    3060
ggggttttca tgctattaca gctttacttg gatggggtga agagtcatag cctttgattc    3120
agacgcagtt agatactcaa gttcatcaac accctcaatt gttttttaag ttgttttgtg    3180
acacgatctc tacagttaga aatgcgttac gagtagaaca cttggctgtg cagggtatag    3240
ataaatgaat gacgatttat gatatgggtt accctattgc ttctagatac aatgtcgtat    3300
ttgtctccct tccaaaagac ttaacatcac gttttttcct cttgccttat ctccacctat    3360
gtatacaagc aggcataaaa tcattgttgt tggttttgtc aacaacaatc attgagttta    3420
ggtaaagttg aaacttgatt gtccattacc tcttgtcact gactgttgaa gacagaattg    3480
tactgactgt atatatcaac atatgcgaga cgcgttaggc agtggaaaga cgtagttagg    3540
atgtcatcat aatttgtttc gtattttttat atgtagcaca gttttatat gtatatattt     3600 tatcgggtag ttttttatcg attcagttat ttgagaaaaa gtaatgcaga caaaaagtgg    3660
aaaagacaat ctgactgtac ataagaaatt tccaattttt gaaatttttt tataattatc    3720
agaaatttta aaatttccga taaaaacata catgtataga tcgaaaattt caaatttcta    3780
gtactttcaa atttcttgca gtaaagttg taatttttta aaaatttacg ataatttaca     3840
gtatttaaaa aaaatccaa tcttaaataa agggtataag aataaaagca ctcatgtgga    3900
gtggcaggtt tcgtcacacc ctaagaacat ccctaaatac accacatatg tataagtatt    3960
aagtgattga tgttaagtga aacgaaaata tttatatgtg aaatttaata ttcagcttac    4020
ttgattaaac tccatagtga cccaataagt gctaactttt actgtcttta cctttaaatg    4080
ttatattgat ttatttatgc atttcttttt cctgcatctc aatagtatat agggtatcaa    4140
atagtgatta tccaaactta ataagttag aggaaacacc aagatatgcc atatactctc     4200
aaatttgaca ctatgattca aagttgcact tgcataaaac ttattaattc aatagtaaaa    4260
ccaaacttgt gcgtgataca gttaaaatga ctaaactact aattaaggtc cctcccatta    4320
gtaaataagt tattttttta gaaaagaaa ataataaaaa gaatgacgag tctatctaaa     4380
```

```
tcatattaac aagtaataca tattgattca ttcgatggag gaggccaata attgtagtaa    4440
acaagcagtg ccgaggttaa tatatgctca agacagtaaa taatctaaat gaattaagac    4500
agtgatttgc aaagagtaga tgcagagaag agaactaaag atttgctgct acacgtatat    4560
aagaatagca acagatattc attctgtctc tttgtggaat atggatatct actaatcatc    4620
atctatctgt gaagaataaa agaagcggcc acaagcgcag cgtcgcacat atgatgtgta    4680
tcaaattagg actccatagc catgcatgct gaagaatgtc acacgttc tgtcacacgt    4740 gttactctct cactgttctc ctcttcctat aaatcaccgc gccacagctt ctccacttca    4800
ccacttcacc acttcactca caatccttca ttagttgttt actatcacag tcacaaccat    4860
ggttgatttg aagccaggag tgaagagatt ggtttcctgg aaggagatta gagagcacgc    4920
tactccagct actgcttgga ttgtgatcca ccacaaggtg tacgatatct ccaagtggga    4980
ttctcatcca ggtggaagtg tgatgttgac tcaggctgga gaggatgcta ctgatgcttt    5040
cgctgtgttc catccatctt ccgctttgaa gctcttggag cagttctacg taagtttctg    5100
cttctacctt tgatatatat ataataatta tcattaatta gtagtaatat aatatttcaa    5160
atattttttt caaaataaaa gaatgtagta tatagcaatt gcttttctgt agttataag    5220 tgtgtatatt ttaatttata acttttctaa tatatgacca aaatttgttg atgtgcaggt    5280
aggagatgtg gatgagactt ccaaggctga gattgaggga gaaccagctt ctgatgagga    5340
gagagctaga agagagagga tcaacgagtt catcgcttct tacagaaggc tcagggttaa    5400
ggttaaggga atgggactct acgatgcttc tgctctttac tacgcttgga agctcgtttc    5460
taccttcgga attgctgtgc tctctatggc tatctgcttc ttcttcaact ccttcgctat    5520
gtacatggtg gctggagtta ttatgggact cttctaccaa caatctggat ggcttgctca    5580
cgatttcttg cacaaccagg tgtgcgagaa cagaactttg ggaaacttga tcggatgcct    5640
tgttggaaat gcttggcagg gattctctat gcaatggtgg aagaacaagc acaacttgca    5700
ccacgctgtg ccaaacttgc actccgctaa ggatgaggga ttcatcggag atccagatat    5760
cgataccatg ccattgcttg cttggtctaa ggagatggct agaaaggctt tcgagtctgc    5820
tcacggacca ttcttcatca ggaaccaggc ttttcttgtac ttcccattgc tcttgttggc    5880
tagattgtct ggctcgctc agtctttctt ctacgtgttc accgagttct cattcggaat    5940
cttcgataag gtggagttcg atggaccaga aaaggctgga ttgatcgtgc actacatctg    6000
gcaactcgct attccatact tctgcaacat gtccttgttc gagggagttg cttacttctt    6060
gatgggacaa gcttcttgcg gattgctttt ggctctcgtg ttctctattg gacacaacgg    6120
aatgtctgtg tacgagagag agaccaagcc agatttctgg caattgcaag tgactaccac    6180
cagaaacatt agggcttccg tgttcatgga ttggttcacc ggaggactca actaccaaat    6240
cgatcaccac ttgttcccat ggtgccaag acacaacttg ccaaaggtga acgtgttgat    6300
caagtctctc tgcaaggagt tcgatatccc attccacgag actggattct gggagggaat    6360
ctacgaggtt gtggatcacc tcgctgatat ctctaaggag ttcatcactg agttcccagc    6420
tatgtgagat cctgcaatag aatgttgagg tgaccacttt ctgtaataaa ataattataa    6480
aataaattta gaattgctgt agtcaagaac atcagttcta aatattaat aaagttatgg    6540 cctttttgaca tatgtgtttc gataaaaaaa tcaaaataaa ttgagattta ttcgaaatac    6600
aatgaaagtt tgcagatatg agatatgttt ctacaaaata ataacttaaa actcaactat    6660
atgctaatgt ttttcttggt gtgtttcata gaaaattgta tccgtttctt agaaaatgct    6720
cgtaagttta aacttagcag atatttggtg tctaaatgtt tattttgtga tatgttcatg    6780
```

```
tttgaaatgg tggtttcgaa accagggaca acgttgggat ctgatagggt gtcaaagagt   6840
attatggatt gggacaattt cggtcatgag ttgcaaattc aagtatatcg ttcgattatg   6900
aaaattttcg aagaatatcc catttgagag agtctttacc tcattaatgt ttttagatta   6960
tgaaatttta tcatagttca tcgtagtctt tttggtgtaa aggctgtaaa aagaaattgt   7020
tcacttttgt tttcgtttat gtgaaggctg taaaagattg taaaagacta ttttggtgtt   7080
ttggataaaa tgatagtttt tatagattct tttgctttta gaagaaatac atttgaaatt   7140
ttttccatgt tgagtataaa ataccgaaat cgattgaaga tcatagaaat attttaactg   7200
aaaacaaatt tataactgat tcaattctct ccatttttat acctatttaa ccgtaatcga   7260
ttctaataga tgatcgattt tttatataat cctaattaac caacggcatg tattggataa   7320
ttaaccgatc aactctcacc cctaatagaa tcagtatttt ccttcgacgt taattgatcc   7380
tacactatgt aggtcatatc catcgtttta atttttggcc accattcaat tctgtcttgc   7440
ctttagggat gtgaatatga acggccaagg taagagaata aaataatccc aaattaaagc   7500
aagagaggcc aagtaagata atccaaatgt acacttgtca ttgccaaaat tagtaaaata   7560
ctcggcatat tgtattccca cacattatta aaataccgta tatgtattgg ctgcatttgc   7620
atgaataata ctacgtgtaa gcccaaaaga acccacgtgt agcccatgca aagttaacac   7680
tcacgacccc attcctcagt ctccactata taaacccacc atccccaatc tcaccaaacc   7740
caccacacaa ctcacaactc actctcacac cttaaagaac caatcaccac caaaaaacca   7800
tgggaaaagg atctgaggga agatctgctg ctagagagat gactgctgag gctaacggag   7860
ataagagaaa gaccatcctc attgagggag tgttgtacga tgctaccaac ttcaaacacc   7920
caggaggttc cattattaac ttcctcaccg agggagaagc tggagttgat gctacccaag   7980
cttacagaga gttccatcag agatccggaa aggctgataa gtacctcaag tccctcccaa   8040
agttggatgc ttctaaggtg gagtctaggt tctctgctaa ggagcaggct agaagggacg   8100
ctatgaccag ggattacgct gctttcagag aggagttggt tgctgaggga tacttcgatc   8160
catctatccc acacatgatc tacagagtgg tggagattgt ggctttgttc gctttgtctt   8220
tctggttgat gtctaaggct tctccaacct ctttggtttt gggagtggtg atgaacggaa   8280
tcgctcaagg aagatgcgga tgggttatgc acgagatggg acacggatct tcactggag   8340 ttatctggct cgatgatagg atgtgcgagt tcttctacgg agttggatgt ggaatgtctg   8400
gacactactg gaagaaccag cactctaagc accacgctgc tccaaacaga ttggagcacg   8460
atgtggattt gaacaccttg ccactcgttg ctttcaacga gagagttgtg aggaaggtta   8520
agccaggatc tttgttggct ttgtggctca gagttcaggc ttatttgttc gctccagtgt   8580
cttgcttgtt gatcggattg ggatggacct tgtacttgca cccaagatat atgctcagga   8640
ccaagagaca catggagttt gtgtggatct tcgctagata tatcggatgg ttctccttga   8700
tgggagcttt gggatattct cctggaactt ctgtgggaat gtacctctgc tctttcggac   8760
ttggatgcat ctacatcttc ctccaattcg ctgtgtctca cccacttg ccagttacca   8820 acccagagga tcaattgcac tggcttgagt acgctgctga tcacccgtg aacatctcta   8880 ccaagtcttg gttggttacc tggtggatgt ctaacctcaa cttccaaatc gagcaccact   8940
tgttcccaac cgctccacaa ttcaggttca aggagatctc tccaagagtt gaggctctct   9000
tcaagagaca caacctccct tactacgatt tgccatacac ctctgctgtt tctactacct   9060
tcgctaacct ctactctgtt ggacactctg ttggagctga taccaagaag caggattgac   9120
tgctttaatg agatatgcga gacgcctatg atcgcatgat atttgctttc aattctgttg   9180
```

```
tgcacgttgt aaaaaacctg agcatgtgta gctcagatcc ttaccgccgg tttcggttca    9240
ttctaatgaa tatatcaccc gttactatcg tattttatg aataatattc tccgttcaat     9300
ttactgattg tgtcgacgcg atcgcgtgcg cacgggcccc ctgcaggatt taaatcccgg    9360
gggtacccaa gtttgtacaa aaagcaggc tccatgatta cgccaagctt cccaattcga     9420
ggtaccctcg acggcccgga ctgtatccaa cttctgatct ttgaatctct ctgttccaac    9480
atgttctgaa ggagttctaa gacttttcag aaagcttgta acatgctttg tagactttct    9540
ttgaattact cttgcaaact ctgattgaac ctacgtgaaa actgctccag aagttctaac    9600
caaattccgt cttgggaagg cccaaaattt attgagtact tcagtttcat ggacgtgtct    9660
tcaaagattt ataacttgaa atcccatcat ttttaagaga agttctgttc cgcaatgtct    9720
tagatctcat tgaaatctac aactcttgtg tcagaagttc ttccagaatc aacttgcatc    9780
atggtgaaaa tctggccaga agttctgaac ttgtcatatt tcttaacagt tagaaaaatt    9840
tctaagtgtt tagaattttg acttttccaa agcaaacttg acttttgact ttcttaataa    9900
aacaaacttc atattctaac atgtcttgat gaaatgtgat tcttgaaatt tgatgttgat    9960
gcaaaagtca agtttgact tttcagtgtg caattgacca ttttgctctt gtgccaattc     10020
caaacctaaa ttgatgtatc agtgctgcaa acttgatgtc atggaagatc ttatgagaaa    10080
attcttgaag actgagagga aaattttgt agtacaacac aaagaatcct gttttcata     10140 gtcggactag acacattaac ataaaacacc acttcattcg aagagtgatt gaagaaggaa    10200
atgtgcagtt accttctgc agttcataag agcaacttac agacactttt actaaaatac     10260
tacaaagagg aagattttaa caacttagag aagtaatggg agttaaagag caacacatta    10320 aggggggagtg ttaaaattaa tgtgttgtaa ccaccactac ctttagtaag tattataaga   10380
aaattgtaat catcacatta taattattgt ccttatttaa aattatgata aagttgtatc    10440
attaagattg agaaaaccaa atagtcctcg tcttgatttt tgaattattg ttttctatgt    10500
tactttctct caagcctata taaaaacttt gtaatgctaa attgtatgct ggaaaaaaat    10560
gtgtaatgaa ttgaatagaa attatggtat ttcaaagtcc aaaatccatc aatagaaatt    10620
tagtacaaaa cgtaactcaa aaatattctc ttattttaaa ttttacaaca atataaaaat    10680
attctcttat tttaaatttt acaataatat aatttatcac ctgtcacctt tagaatacca    10740
ccaacaatat taatacttag atattttatt cttaataatt ttgagatctc tcaatatatc    10800
tgatatttat tttatatttg tgtcatattt tcttatgttt tagagttaac ccttatatct    10860
tggtcaaact agtaattcaa tatatgagtt tgtgaaggac acattgacat cttgaaacat    10920
tggttttaac cttgttggaa tgttaaaggt aataaaacat tcagaattat gaccatctat    10980
taatatactt cctttgtctt ttaaaaaagt gtgcatgaaa atgctctatg gtaagctaga    11040
gtgtcttgct ggcctgtgta tatcaattcc atttccagat ggtagaaact gccactacga    11100
ataattagtc ataagacacg tatgttaaca cacgtcccct tgcatgtttt ttgccatata    11160
ttccgtctct ttctttttct tcacgtataa aacaatgaac taattaatag agcgatcaag    11220
ctgaaccatg cgcgccacca tgtgtgttga gaccgagaac aacgatggaa tccctactgt    11280
ggagatcgct ttcgatggag agagagaaag agctgaggct aacgtgaagt tgtctgctga    11340
gaagatggaa cctgctgctt tggctaagac cttcgctaga agatacgtgg ttatcgaggg    11400
agttgagtac gatgtgaccg atttcaaaca tcctggagga accgtgattt tctacgctct    11460
ctctaacact ggagctgatg ctactgaggc tttcaaggag ttccaccaca gatctagaaa    11520
ggctaggaag gctttggctg ctttgccttc tagacctgct aagaccgcta aagtgggatga   11580
```

```
tgctgagatg ctccaggatt tcgctaagtg gagaaaggag ttggagaggg acggattctt    11640
caagccttct cctgctcatg ttgcttacag attcgctgag ttggctgcta tgtacgcttt    11700
gggaacctac ttgatgtacg ctagatacgt tgtgtcctct gtgttggttt acgcttgctt    11760
cttcggagct agatgtggat gggttcaaca tgagggagga cattcttctt tgaccggaaa    11820
catctggtgg gataagagaa tccaagcttt cactgctgga ttcggattgg ctggatctgg    11880
agatatgtgt aactccatgc acaacaagca ccatgctact cctcaaaaag tgaggcacga    11940
tatggatttg gataccactc ctgctgttgc tttcttcaac accgctgtgg aggataatag    12000
acctagggga ttctctaagt actggctcag attgcaagct tggaccttca ttcctgtgac    12060
ttctggattg gtgttgctct tctggatgtt cttcctccat ccttctaagg ctttgaaggg    12120
aggaaagtac gaggagcttg tgtggatgtt ggctgctcat gtgattagaa cctgaccat     12180 taaggctgtt actggattca ccgctatgca atcctacgga ctcttcttgg ctacttcttg    12240
ggtttccgga tgctacttgt tcgctcactt ctctacttct cacacccatt tggatgttgt    12300
tcctgctgat gagcatttgt cttgggttag gtacgctgtg gatcacacca ttgatatcga    12360
tccttctcag ggatgggtta actggttgat gggatacttg aactgccaag tgattcatca    12420
cctcttccct tctatgcctc aattcagaca acctgaggtg tccagaagat tcgttgcttt    12480
cgctaagaag tggaacctca actacaaggt gatgacttat gctggagctt ggaaggctac    12540
tttgggaaac ctcgataatg tgggaaagca ctactacgtg cacggacaac attctggaaa    12600
gaccgcttga taattaatta aggccgcctc gaccgtaccc cctgcagata gactatacta    12660
tgttttagcc tgcctgctgg ctagctacta tgttatgtta tgttgtaaaa taaacacctg    12720
ctaaggtata tctatctata ttttagcatg gctttctcaa taaattgtct ttccttatcg    12780
tttactatct tatacctaat aatgaaataa taatatcaca tatgaggaac ggggcaggtt    12840
taggcatata tatacgagtg tagggcggag tgggggggat cggggggtacc acccagcttt    12900 cttgtacaaa gtggccatga ttacgccaag ctctccaccg cggtggcggc cgctctagcc    12960
caagctttaa ggatgaccta cccattcttg agacaaatgt tacattttag tatcagagta    13020
aaatgtgtac ctataactca aattcgattg acatgtatcc attcaacata aaattaaacc    13080
agcctgcacc tgcatccaca tttcaagtat tttcaaaccg ttcggctcct atccaccggg    13140
tgtaacaaga cggattccga atttggaaga ttttgactca aattcccaat ttatattgac    13200
cgtgactaaa tcaactttaa cttctataat tctgattaag ctcccaattt atattcccaa    13260
cggcactacc tccaaaattt atagactctc atccccttt aaaccaactt agtaaacgtt     13320 tttttttaa tttttatgaag ttaagttttt accttgtttt taaaaagaat cgttcataag    13380
atgccatgcc agaacattag ctacacgtta cacatagcat gcagccgcgg agaattgttt    13440
ttcttcgcca cttgtcactc ccttcaaaca cctaagagct tctctctcac agcacacaca    13500
tacaatcaca tgcgtgcatg cattattaca cgtgatcgcc atgcaaatct cctttatagc    13560
ctataaatta actcatcggc ttcactcttt actcaaacca aaactcatca atacaaacaa    13620
gattaaaaac ataaggcgcg ccggatccgc catggctatt ttgaaccctg aggctgattc    13680
tgctgctaac ctcgctactg attctgaggc taagcaaaga caattggctg aggctggata    13740
cactcatgtt gagggtgctc ctgctccttt gcctttggag ttgcctcatt tctctctcag    13800
agatctcaga gctgctattc ctaagcactg cttcgagaga tctttcgtga cctccaccta    13860
ctacatgatc aagaacgtgt tgacttgcgc tgctttgttc tacgctgcta ccttcattga    13920
tagagctgga gctgctgctt atgttttgtg gcctgtgtac tggttcttcc agggatctta    13980
```

```
cttgactgga gtgtgggtta tcgctcatga gtgtggacat caggcttatt gctcttctga   14040
ggtggtgaac aacttgattg gactcgtgtt gcattctgct ttgttggtgc cttaccactc   14100
ttggagaatc tctcacagaa agcaccattc caacactgga tcttgcgaga acgatgaggt   14160
tttcgttcct gtgaccagat ctgtgttggc ttcttcttgg aacgagacct tggaggattc   14220
tcctctctac caactctacc gtatcgtgta catgttggtt gttggatgga tgcctggata   14280
cctcttcttc aacgctactg gacctactaa gtactgggga aagtctaggt ctcacttcaa   14340
cccttactcc gctatctatg ctgataggga gagatggatg atcgtgctct ccgatatttt   14400
cttggtggct atgttggctg ttttggctgc tttggtgcac actttctcct tcaacaccat   14460
ggtgaagttc tacgtggtgc cttacttcat tgtgaacgct tacttggtgt tgattaccta   14520
cctccaacac accgatacct acatccctca tttcagagag ggagagtgga attggttgag   14580
aggagctttg tgcactgtgg atagatcatt tggtccattc ctcgattctg tggtgcatag   14640
aatcgtggat acccatgttt gccaccacat cttctccaag atgcctttct atcattgcga   14700
ggaggctacc aacgctatta agcctctcct cggaaagttc tacttgaagg ataccactcc   14760
tgttcctgtt gctctctgga gatcttacac ccattgcaag ttcgttgagg atgatggaaa   14820
ggtggtgttc tacaagaaca agctctagtt aattaaggcc gcctcgagca tgcatctaga   14880
gggcccgcta gcgttaaccc tgctttaatg agatatgcga gacgcctatg atcgcatgat   14940
atttgctttc aattctgttg tgcacgttgt aaaaaacctg agcatgtgta gctcagatcc   15000
ttaccgccgg tttcggttca ttctaatgaa tatatcaccc gttactatcg tattttatg   15060 aataatattc tccgttcaat ttactgattg tccgtcgagc atatgctaga ggatccccgg   15120
gtacccaact ttattataca tagttgataa ttcactggcc ggatatcttt tttaagggcg   15180
aattctgcag atatccatca cactggcggc cgctcgaggt accatcgttc aaacatttgg   15240
caataaagtt tcttaagatt gaatcctgtt gccggtcttg cgatgattat catataattt   15300
ctgttgaatt acgttaagca tgtaataatt aacatgtaat gcatgacgtt atttatgaga   15360
tgggttttta tgattagagt cccgcaatta tacatttaat acgcgataga aaacaaaata   15420
tagcgcgcaa actaggataa attatcgcgc gcggtgtcat ctatgttact agatcgggca   15480
ttaccctgtt atccctagag gggaaaattc gaatccaaaa attacggata tgaatatagg   15540
catatccgta tccgaattat ccgtttgaca gctagcaacg attgtacaat tgcttcttta   15600
aaaaaggaag aaagaaagaa agaaaagaat caacatcagc gttaacaaac ggccccgtta   15660
cggcccaaac ggtcatatag agtaacgcgc ttaagcgttg aaagactcct atcgaaatac   15720
gtaaccgcaa acgtgtcata gtcagatccc ctcttccttc accgcctcaa acacaaaaat   15780
aatcttctac agcctatata tacaaccccc ccttctatct ctcctttctc acaattcatc   15840
atctttcttt ctctaccccc aattttaaga atcctctct tctcctcttc attttcaagg   15900
taaatctctc tctctctctc tctctctgtt attccttgtt ttaattaggt atgtattatt   15960
gctagtttgt taatctgctt atcttatgta tgccttatgt gaatatcttt atcttgttca   16020
tctcatccgt ttagaagcta taaatttgtt gatttgactg tgtatctaca cgtggttatg   16080
tttatatcta atcagatatg aatttcttca tattgttgcg tttgtgtgta ccaatccgaa   16140
atcgttgatt ttttcatttt aatcgtgtag ctaattgtac gtatacatat ggatctacgt   16200
atcaattgtt catctgtttg tgtttgtatg tatacagatc tgaaaacatc acttctctca   16260
tctgattgtg ttgttacata catagatata gatctgttat atcatttttt ttattaattg   16320
tgtatatata tatgtgcata gatctggatt acatgattgt gattatttac atgattttgt   16380
```

```
tatttacgta tgtatatatg tagatctgga cttttttggag ttgttgactt gattgtattt    16440
gtgtgtgtat atgtgtgttc tgatcttgat atgttatgta tgtgcagctg aaccatggcg    16500
gcggcaacaa caacaacaac aacatcttct tcgatctcct tctccaccaa accatctcct    16560
tcctcctcca aatcaccatt accaatctcc agattctccc tcccattctc cctaaacccc    16620
aacaaatcat cctcctcctc ccgccgccgc ggtatcaaat ccagctctcc ctcctccatc    16680
tccgccgtgc tcaacacaac caccaatgtc acaccactc cctctccaac caaacctacc     16740
aaacccgaaa cattcatctc ccgattcgct ccagatcaac cccgcaaagg cgctgatatc    16800
ctcgtcgaag ctttagaacg tcaaggcgta gaaaccgtat tcgcttaccc tggaggtaca    16860
tcaatggaga ttcaccaagc cttaacccgc tcttcctcaa tccgtaacgt ccttcctcgt    16920
cacgaacaag gaggtgtatt cgcagcagaa ggatacgctc gatcctcagg taaaccaggt    16980
atctgtatag ccacttcagg tcccggagct acaaatctcg ttagcggatt agccgatgcg    17040
ttgttagata gtgttcctct tgtagcaatc acaggacaag tccctcgtcg tatgattggt    17100
acagatgcgt ttcaagagac tccgattgtt gaggtaacgc gttcgattac gaagcataac    17160
tatcttgtga tggatgttga agatatccct aggattattg aggaagcttt ctttttagct    17220
acttctggta gacctggacc tgttttggtt gatgttccta aagatattca acaacagctt    17280
gcgattccta attgggaaca ggctatgaga ttacctggtt atatgtctag gatgcctaaa    17340
cctccggaag attctcattt ggagcagatt gttaggttga tttctgagtc taagaagcct    17400
gtgttgtatg ttggtggtgg ttgtttgaat tctagcgatg aattgggtag gtttgttgag    17460
cttacgggga tccctgttgc gagtacgttg atggggctgg gatcttatcc ttgtgatgat    17520
gagttgtcgt tacatatgct tggaatgcat gggactgtgt atgcaaatta cgctgtggag    17580
catagtgatt tgttgttggc gtttggggta aggtttgatg atcgtgtcac gggtaagctt    17640
gaggcttttg ctagtagggc taagattgtt catattgata ttgactcggc tgagattggg    17700
aagaataaga ctcctcatgt gtctgtgtgt ggtgatgtta agctggcttt gcaagggatg    17760
aataaggttc ttgagaaccg agcggaggag cttaagcttg attttggagt ttggaggaat    17820
gagttgaacg tacagaaaca gaagtttccg ttgagcttta agacgtttgg ggaagctatt    17880
cctccacagt atgcgattaa ggtccttgat gagttgactg atggaaaagc cataataagt    17940
actggtgtcg gcaacatca aatgtgggcg gcgcagttct acaattacaa gaaaccaagg    18000
cagtggctat catcaggagg ccttggagct atgggatttg gacttcctgc tgcgattgga    18060
gcgtctgttc taaccctga tgcgatagtt gtggatattg acggagatgg aagctttata    18120
atgaatgtgc aagagctagc cactattcgt gtagagaatc ttccagtgaa ggtactttta    18180
ttaaacaacc agcatcttgg catggttatg caatgggaag atcggttcta caaagctaac    18240
cgagctcaca catttctcgg ggatccggct caggaggacg agatattccc gaacatgttg    18300
ctgtttgcag cagcttgcgg gattccagcg gcgagggtga caaagaaagc agatctccga    18360
gaagctattc agacaatgct ggatacacca ggaccttacc tgttggatgt gatttgtccg    18420
caccaagaac atgtgttgcc gatgatcccg aatggtggca cttttcaacga tgtcataacg    18480 gaaggagatg gccggattaa atactgatag ggataacagg gtaatttccc gacccaagct    18540
ctagatcttg ctgcgttcgg atattttcgt ggagttcccg ccacagaccc ggatgatccc    18600
cgatcgttca aacatttggc aataaagttt cttaagattg aatcctgttg ccggtcttgc    18660
gatgattatc atataaattc tgttgaatta cgttaagcat gtaataatta acatgtaatg    18720
catgacgtta tttatgagat gggttttttat gattagagtc ccgcaattat acatttaata    18780
```

```
cgcgatagaa aacaaaatat agcgcgcaaa ctaggataaa ttatcgcgcg cggtgtcatc    18840
tatgttacta gatcgggcct cctgtcaagc tctgcttggt aataattgtc attagattgt    18900
ttttatgcat agatgcactc gaaatcagcc aattttagac aagtatcaaa cggatgttaa    18960
ttcagtacat taaagacgtc cgcaatgtgt tattaagttg tctaagcgtc aatttgttta    19020
caccacaata tatcctgcca ccagccagcc aacagctccc cgaccggcag ctcggcacaa    19080
aatcaccacg cgttaccacc acgcggccg gccgcatggt gttgaccgtg ttcgccggca    19140
ttgccgagtt cgagcgttcc ctaatcatcg accgcacccg gagcgggcgc gaggccgcca    19200
aggcccgagg cgtgaagttt ggccccgcc ctaccctcac cccggcacag atcgcgcacg    19260
cccgcgagct gatcgaccag gaaggccgca ccgtgaaaga ggcggctgca ctgcttggcg    19320
tgcatcgctc gaccctgtac cgcgcacttg agcgcagcga ggaagtgacg cccaccgagg    19380
ccaggcggcg cggtgccttc cgtgaggacg cattgaccga ggccgacgcc ctggcggccg    19440
ccgagaatga acgccaagag gaacaagcat gaaaccgcac caggacggcc aggacgaacc    19500
gtttttcatt accgaagaga tcgaggcgga gatgatcgcg gccgggtacg tgttcgagcc    19560
gcccgcgcac gtctcaaccg tgcggctgca tgaaatcctg gccggtttgt ctgatgccaa    19620
gctggcggcc tggccggcca gcttggccgc tgaagaaacc gagcgccgcc gtctaaaaag    19680
gtgatgtgta tttgagtaaa acagcttgcg tcatgcggtc gctgcgtata tgatgcgatg    19740
agtaaataaa caaatacgca aggggaacgc atgaaggtta tcgctgtact taaccagaaa    19800
ggcgggtcag gcaagacgac catcgcaacc catctagccc gcgccctgca actcgccggg    19860
gccgatgttc tgttagtcga ttccgatccc cagggcagtg cccgcgattg ggcggccgtg    19920
cgggaagatc aaccgctaac cgttgtcggc atcgaccgcc cgacgattga ccgcgacgtg    19980
aaggccatcg gccggcgcga cttcgtagtg atcgacggag cgccccaggc ggcggacttg    20040
gctgtgtccg cgatcaaggc agccgacttc gtgctgattc cggtgcagcc aagcccttac    20100
gacatatggg ccaccgccga cctggtggag ctggttaagc agcgcattga ggtcacggat    20160
ggaaggctac aagcggcctt tgtcgtgtcg cgggcgatca aaggcacgcg catcggcggt    20220
gaggttgccg aggcgctggc cgggtacgag ctgcccattc ttgagtcccg tatcacgcag    20280
cgcgtgagct acccaggcac tgccgccgcc ggcacaaccg ttcttgaatc agaacccgag    20340
ggcgacgctg cccgcgaggt ccaggcgctg gccgctgaaa ttaaatcaaa actcatttga    20400
gttaatgagg taaagagaaa atgagcaaaa gcacaaacac gctaagtgcc ggccgtccga    20460
gcgcacgcag cagcaaggct gcaacgttgg ccagcctggc agacacgcca gccatgaagc    20520
gggtcaactt tcagttgccg gcggaggatc acaccaagct gaagatgtac gcggtacgcc    20580
aaggcaagac cattaccgag ctgctatctg aatacatcgc gcagctacca gagtaaatga    20640
gcaaatgaat aaatgagtag atgaatttta gcggctaaag gaggcggcat ggaaaatcaa    20700
gaacaaccag gcaccgacgc cgtggaatgc cccatgtgtg gaggaacggg cggttggcca    20760
ggcgtaagcg gctgggttgt ctgccggccc tgcaatggca ctggaacccc caagcccgag    20820
gaatcggcgt gagcggtcgc aaaccatccg gcccggtaca aatcggcgcg gcgctgggtg    20880
atgacctggt ggagaagttg aaggccgcgc aggccgccca gcggcaacgc atcgaggcag    20940
aagcacgccc cggtgaatcg tggcaagcgg ccgctgatcg aatccgcaaa gaatcccggc    21000
aaccgccggc agccggtgcg ccgtcgatta ggaagccgcc caagggcgac gagcaaccag    21060
attttttcgt tccgatgctc tatgacgtgg gcacccgcga tagtcgcagc atcatggacg    21120
tggccgtttt ccgtctgtcg aagcgtgacc gacgagctgg cgaggtgatc cgctacgagc    21180
```

```
ttccagacgg gcacgtagag gtttccgcag ggccggccgg catggccagt gtgtgggatt      21240
acgacctggt actgatggcg gtttcccatc taaccgaatc catgaaccga taccgggaag      21300
ggaagggaga caagcccggc cgcgtgttcc gtccacacgt tgcggacgta ctcaagttct      21360
gccggcgagc cgatggcgga aagcagaaag acgacctggt agaaacctgc attcggttaa      21420
acaccacgca cgttgccatg cagcgtacga agaaggccaa gaacggccgc ctggtgacgg      21480
tatccgaggg tgaagccttg attagccgct acaagatcgt aaagagcgaa accgggcggc      21540
cggagtacat cgagatcgag ctagctgatt ggatgtaccg cgagatcaca gaaggcaaga      21600
acccggacgt gctgacggtt cacccccgatt acttttttgat cgatcccggc atcggccgtt      21660
ttctctaccg cctggcacgc cgcgccgcag gcaaggcaga agccagatgg ttgttcaaga      21720
cgatctacga acgcagtggc agcgccgag agttcaagaa gttctgtttc accgtgcgca      21780
agctgatcgg gtcaaatgac ctgccggagt acgatttgaa ggaggaggcg gggcaggctg      21840
gcccgatcct agtcatgcgc taccgcaacc tgatcgaggg cgaagcatcc gccggttcct      21900
aatgtacgga gcagatgcta gggcaaattg ccctagcagg ggaaaaaggt cgaaaaggtc      21960
tctttcctgt ggatagcacg tacattggga acccaaagcc gtacattggg aaccggaacc      22020
cgtacattgg gaacccaaag ccgtacattg ggaaccggtc acacatgtaa gtgactgata      22080
taaaagagaa aaaaggcgat ttttccgcct aaaactcttt aaaacttatt aaaactctta      22140
aaacccgcct ggcctgtgca taactgtctg gccagcgcac agccgaagag ctgcaaaaag      22200
cgcctaccct tcggtcgctg cgctcccctac gccccgccgc ttcgcgtcgg cctatcgcgg      22260
ccgctggccg ctcaaaaatg gctggcctac ggccaggcaa tctaccaggg cgcggacaag      22320
ccgcgccgtc gccactcgac cgccggcgcc cacatcaagg cacctgcct cgcgcgtttc      22380 ggtgatgacg gtgaaaacct ctgacacatg cagctcccgg gacggtcac agcttgtctg      22440 taagcggatg ccgggagcag acaagcccgt cagggcgcgt cagcgggtgt tggcgggtgt      22500
cggggcgcag ccatgaccca gtcacgtagc gatagcggag tgtatactgg cttaactatg      22560
cggcatcaga gcagattgta ctgagagtgc accatatgcg gtgtgaaata ccgcacagat      22620
gcgtaaggag aaaataccgc atcaggcgct cttccgcttc ctcgctcact gactcgctgc      22680
gctcggtcgt tcggctgcgg cgagcggtat cagctcactc aaaggcggta atacggttat      22740
ccacagaatc aggggataac gcaggaaaga acatgtgagc aaaaggccag caaaaggcca      22800
ggaaccgtaa aaaggccgcg ttgctggcgt ttttccatag gctccgcccc cctgacgagc      22860
atcacaaaaa tcgacgctca gtcagaggt ggcgaaaccc gacaggacta taaagatacc      22920
aggcgtttcc ccctggaagc tccctcgtgc gctctcctgt tccgaccctg ccgcttaccg      22980
gatacctgtc cgcctttctc ccttcgggaa gcgtggcgct ttctcatagc tcacgctgta      23040
ggtatctcag ttcggtgtag gtcgttcgct ccaagctggg ctgtgtgcac gaaccccccg      23100
ttcagcccga ccgctgcgcc ttatccggta actatcgtct tgagtccaac ccggtaagac      23160
acgacttatc gccactggca gcagccactg gtaacaggat tagcagagcg aggtatgtag      23220
gcggtgctac agagttcttg aagtggtggc ctaactacgg ctacactaga aggacagtat      23280
ttggtatctg cgctctgctg aagccagtta ccttcggaaa aagagttggt agctcttgat      23340
ccggcaaaca aaccaccgct ggtagcggtg gtttttttgt ttgcaagcag cagattacgc      23400
gcagaaaaaa aggatctcaa gaagatcctt tgatcttttc tacggggtct gacgctcagt      23460
ggaacgaaaa ctcacgttaa gggattttgg tcatgcatga tatatctccc aatttgtgta      23520
gggcttatta tgcacgctta aaaataataa aagcagactt gacctgatag tttggctgtg      23580
```

| | |
|---|---|
| agcaattatg tgcttagtgc atctaacgct tgagttaagc cgcgccgcga agcggcgtcg | 23640 |
| gcttgaacga atttctagct agacattatt tgccgactac cttggtgatc tcgcctttca | 23700 |
| cgtagtggac aaattcttcc aactgatctg cgcgcgaggc caagcgatct tcttcttgtc | 23760 |
| caagataagc ctgtctagct tcaagtatga cgggctgata ctgggccggc aggcgctcca | 23820 |
| ttgcccagtc ggcagcgaca tccttcggcg cgattttgcc ggttactgcg ctgtaccaaa | 23880 |
| tgcgggacaa cgtaagcact acatttcgct catcgccagc ccagtcgggc ggcgagttcc | 23940 |
| atagcgttaa ggtttcattt agcgcctcaa atagatcctg ttcaggaacc ggatcaaaga | 24000 |
| gttcctccgc cgctggacct accaaggcaa cgctatgttc tcttgctttt gtcagcaaga | 24060 |
| tagccagatc aatgtcgatc gtggctggct cgaagatacc tgcaagaatg tcattgcgct | 24120 |
| gccattctcc aaattgcagt tcgcgcttag ctggataacg ccacggaatg atgtcgtcgt | 24180 |
| gcacaacaat ggtgacttct acagcgcgga gaatctcgct ctctccaggg gaagccgaag | 24240 |
| tttccaaaag gtcgttgatc aaagctcgcc gcgttgtttc atcaagcctt acggtcaccg | 24300 |
| taaccagcaa atcaatatca ctgtgtggct tcaggccgcc atccactgcg gagccgtaca | 24360 |
| aatgtacggc cagcaacgtc ggttcgagat ggcgctcgat gacgcaact acctctgata | 24420 |
| gttgagtcga tacttcggcg atcaccgctt cccccatgat gtttaacttt gttttagggc | 24480 |
| gactgccctg ctgcgtaaca tcgttgctgc tccataacat caaacatcga cccacggcgt | 24540 |
| aacgcgcttg ctgcttggat gcccgaggca tagactgtac cccaaaaaaa cagtcataac | 24600 |
| aagccatgaa accgccact gcgttccatg g | 24631 |

<210> SEQ ID NO 16
<211> LENGTH: 24356
<212> TYPE: DNA
<213> ORGANISM: Artificial Sequence
<220> FEATURE:
<223> OTHER INFORMATION: binary T plasmid VC-LJB1327-1qcz

<400> SEQUENCE: 16

| | |
|---|---|
| gtgattttgt gccgagctgc cggtcgggga gctgttggct ggctggtggc aggatatatt | 60 |
| gtggtgtaaa caaattgacg cttagacaac ttaataacac attgcggacg tctttaatgt | 120 |
| actgaattta gttactgatc actgattaag tactgcgatc gcctcgacat attgttttg | 180 |
| tttcacataa atgtcgtttt ggattattca tgtaatattt taaactaaag tacaattttt | 240 |
| gactacttta gtttactagt taagctttta ttttttgac taaccattga atgatgaaga | 300 |
| gatcaacgca tcatatttac aacttacata gtcttttgga agtgtaaatt gctaatacta | 360 |
| cctaaaatat atctataatt aactaatatt ttttcgtcaa ttataataga tcaattaaaa | 420 |
| ggctatcaaa aggaaaaaaa tgaaatccac atcctgccat cataacctca tgctggaaaa | 480 |
| agaaatgaaa aaatataaaa aatttctttt gtttattaaa tttacaactt taatactagt | 540 |
| ttcttttcta tttttaaaa gcttttgtca cttacttaaa aaaaaaaac tttttgaaat | 600 |
| attcctactt ccaatgtctg attagtgctt ctggatttcc ttttggatc atgtgaatcc | 660 |
| taaatcagaa aaattcatat aatacccaat tcagtatatt ttcatacttc aatttacaag | 720 |
| agttctctat gttttagct tctttctttt aagccaaatg ttttaagcat cttttataca | 780 |
| ttaaaataat ttagtgttga gttgagattt tttttttttt ttttggatt tacttgttca | 840 |
| aaatctgaaa aaatgtttac agaaggttaa aatgaaccaa aaggcatatc aagctagatt | 900 |
| ttgaattacc ctatttcatc gtatacacaa aactgataat gtggacacag ttgattttac | 960 |
| ttctcgatga catcgtagtt ttatttaatt tggaaaccac ggcccatatg agcacatttc | 1020 |

```
aattaaaaac caatggtaag agcattttcc atgcaagatt cgagagatat taacccagtg      1080
actgttaaaa cagcttagaa ccctaataac gaatttcaat tactcaattt accattcgca      1140
tttcgcaata accaaactga gccagtcaca aggagtaaac cgaaccggat tatttattta      1200
taaaatgaaa gaaaggaaac caaacaacaa cagcagtagt agtctgacgt aaaccaaaaa      1260
gcaggcagat caacaactaa aagaaactca aattaccaaa acaaacagga aattgcaaac      1320
taagtttttt taccatatgc atacaaagac cataaaaggt tctgataatc accggtttca      1380
tctcgtcgag attaccctgt tatccctatc agtatttaat ccggccatct ccttccgtta      1440
tgacatcgtt gaaagtgcca ccattcggga tcatcggcaa cacatgttct tggtgcggac      1500
aaatcacatc caacaggtaa ggtcctggtg tatccagcat tgtctgaata gcttctcgga      1560
gatctgcttt ctttgtcacc ctcgccgctg aatcccgca agctgctgca aacagcaaca       1620
tgttcgggaa tatctcgtcc tcctgagccg atccccgag aaatgtgtga gctcggttag       1680
ctttgtagaa ccgatcttcc cattgcataa ccatgccaag atgctggttg tttaataaaa      1740
gtaccttcac tggaagattc tctacacgaa tagtggctag ctcttgcaca ttcattataa      1800
agcttccatc tccgtcaata tccacaacta tcgcatcagg gttagcaaca gacgctccaa      1860
tcgcagcagg aagtccaaat cccatagctc caaggcctcc tgatgatagc cactgccttg      1920
gtttcttgta attgtagaac tgcgccgccc acatttgatg ttgcccgaca ccagtactta      1980
ttatggcttt tccatcagtc aactcatcaa ggaccttaat cgcatactgt ggaggaatag      2040
cttccccaaa cgtcttaaag ctcaacggaa acttctgttt ctgtacgttc aactcattcc      2100
tccaaactcc aaaatcaagc ttaagctcct ccgctcggtt ctcaagaacc ttattcatcc      2160
cttgcaaagc cagcttaaca tcaccacaca cagacacatg aggagtctta ttcttcccaa      2220
tctcagccga gtcaatatca atatgaacaa tcttagccct actagcaaaa gcctcaagct      2280
tacccgtgac acgatcatca aaccttaccc caaacgccaa caacaaatca ctatgctcca      2340
cagcgtaatt tgcatacaca gtcccatgca ttccaagcat atgtaacgac aactcatcat      2400
cacaaggata agatcccagc cccatcaacg tactcgcaac agggatcccc gtaagctcaa      2460
caaacctacc caattcatcg ctagaattca acaaccacc accaacatac aacacaggct       2520
tcttagactc agaaatcaac ctaacaatct gctccaaatg agaatcttcc ggaggtttag      2580
gcatcctaga catataacca ggtaatctca tagcctgttc ccaattagga atcgcaagct      2640
gttgttgaat atctttagga acatcaacca aaacaggtcc aggtctacca gaagtagcta      2700
aaaagaaagc ttcctcaata atcctaggga tatcttcaac atccatcaca agatagttat      2760
gcttcgtaat cgaacgcgtt acctcaacaa tcggagtctc ttgaaacgca tctgtaccaa      2820
tcatacgacg agggacttgt cctgtgattg ctacaagagg aacactatct aacaacgcat      2880
cggctaatcc gctaacgaga tttgtagctc cgggacctga agtggctata cagataccctg      2940 gtttacctga ggatcgagcg tatccttctg ctgcgaatac acctccttgt tcgtgacgag      3000
gaaggacgtt acgattgag gaagagcggg ttaaggcttg gtgaatctcc attgatgtac       3060
ctccagggta agcgaatacg gtttctacgc cttgacgttc taaagcttcg acgaggatat      3120
cagcgccttt gcggggttga tctggagcga atcgggagat gaatgtttcg ggtttggtag      3180
gtttggttgg agagggagtg gttgtgacat tggtggttgt gttgagcacg gcggagatgg      3240
aggagggaga gctggatttg ataccgcggc ggcgggagga ggaggatgat tgttggggt       3300 ttagggagaa tggagggag aatctggaga ttggtaatgg tgatttggag gaggaaggag       3360
atggtttggt ggagaaggag atcgaagaag atgttgttgt tgttgttgtt gccgccgcca      3420
```

```
tggttcagct gcacatacat aacatatcaa gatcagaaca cacatataca cacacaaata   3480
caatcaagtc aacaactcca aaaagtccag atctacatat atacatacgt aaataacaaa   3540
atcatgtaaa taatcacaat catgtaatcc agatctatgc acatatatat atacacaatt   3600
aataaaaaaa atgatataac agatctatat ctatgtatgt aacaacacaa tcagatgaga   3660
gaagtgatgt tttcagatct gtatacatac aaacacaaac agatgaacaa ttgatacgta   3720
gatccatatg tatacgtaca attagctaca cgattaaatg aaaaaaatca acgatttcgg   3780
attggtacac acaaacgcaa caatatgaag aaattcatat ctgattagat ataaacataa   3840
ccacgtgtag atacacagtc aaatcaacaa atttatagct tctaaacgga tgagatgaac   3900
aagataaaga tattcacata aggcatacat aagataagca gattaacaaa ctagcaataa   3960
tacataccta attaaaacaa ggaataacag agagagagag agagagagag atttaccttg   4020
aaaatgaaga ggagaagaga ggatttctta aaattggggg tagagaaaga aagatgatga   4080
attgtgagaa aggagagata gaagggggg ttgtatatat aggctgtaga agattatttt   4140
tgtgtttgag gcggtgaagg aagaggggat ctgactatga cacgtttgcg gttacgtatt   4200
tcgataggag tctttcaacg cttaacgccg ttactctata tgaccgtttg ggccgtaacg   4260
gggccgtttg ttaacgctga tgttgattct tttctttctt tctttcttcc ttttttaaag   4320
aagcaattgt acaatcgttg ctagctgtca aacggataat tcggatacgg atatgcctat   4380
attcatatcc gtaattttg gattcgaatt ttcccctcta gggataacag ggtaatggat   4440
ctatattgtt tttgtttcac ataaatgtcg ttttggatta ttcatgtaat atttttaaact   4500 aaagtacaat ttttgactac tttagtttac tagttaagct tttattttt tgactaacca   4560 ttgaatgatg aagagatcaa cgcatcatat ttacaactta catagtcttt tggaagtgta   4620
aattgctaat actacctaaa atatatctat aattaactaa tatttttcg tcaattataa   4680 tagatcaatt aaaaggctat caaaaggaaa aaaatgaaat ccacatcctg ccatcataac   4740
ctcatgctgg aaaaagaaat gaaaaaatat aaaaaatttc ttttgtttat taaatttaca   4800
actttaatac tagtttcttt tctatttttt aaaagctttt gtcacttact taaaaaaaaa   4860 aaacttttg aaatattcct acttccaatg tctgattagt gcttctggat ttccttttg    4920 gatcatgtga atcctaaatc agaaaaattc atataatacc caattcagta tattttcata   4980
cttcaattta caagagttct ctatgttttt agcttctttc ttttaagcca aatgttttaa   5040
gcatctttta tacattaaaa taatttagtg ttgagttgag attttttttt ttttttttg    5100 gatttacttg ttcaaaatct gaaaaatgt tacagaagg ttaaaatgaa ccaaaaggca    5160
tatcaagcta gattttgaat taccctattt catcgtatac acaaaactga taatgtggac   5220
acagttgatt ttacttctcg atgacatcgt agttttattt aatttggaaa ccacggccca   5280
tatgagcaca tttcaattaa aaaccaatgg taagagcatt ttccatgcaa gattcgagag   5340
atattaaccc agtgactgtt aaaacagctt agaaccctaa taacgaattt caattactca   5400
atttaccatt cgcatttcgc aataaccaaa ctgagccagt cacaaggagt aaaccgaacc   5460
ggattattta tttataaaat gaagaaaagg aaaccaaaca acaacagcag tagtagtctg   5520
acgtaaacca aaaagcaggc agatcaacaa ctaaagaaa ctcaaattac caaaacaaac    5580
aggaaattgc aaactaagtt tttttaccat atgcatacaa agaccataaa aggttctgat   5640
aatcaccggt ttcatctcag atccgcgatc gccaattgac gcgtactagt gtacaagctt   5700
gcggccgcga attcggtaca tccgccagt gaattatcaa ctatgtataa taaagttggg    5760
taccggccta ttaggccacg gtccgtacag tgtttaaacg attgacctgc aggatacaag   5820
```

```
tgcgcacaga ctagcggccg ctaatcccgg gaattaccgg tagtaggcgc cattgatgca    5880
tgttgtcaat caattggcaa gtcataaaat gcattaaaaa atattttcat actcaactac    5940
aaatccatga gtataactat aattataaag caatgattag aatctgacaa ggattctgga    6000
aaattacata aaggaaagtt cataaatgtc taaaacacaa gaggcatac ttgtattcag     6060 taacatttgc agcttttcta ggtctgaaaa tatatttgtt gcctagtgaa taagcataat    6120
ggtacaacta caagtgtttt actcctcata ttaacttcgg tcattagagg ccacgatttg    6180
acacattttt actcaaaaca aaatgtttgc atatctctta taatttcaaa ttcaacacac    6240
aacaaataag agaaaaaaca aataatatta atttgagaat gaacaaaagg accatatcat    6300
tcattaactc ttctccatcc atttccattt cacagttcga tagcgaaaac cgaataaaaa    6360
acacagtaaa ttacaagcac aacaaatggt acaagaaaaa cagttttccc aatgccataa    6420
tactcgaacc aatcaattat taattaacta gagcttgttc ttgtagaaca ccacctttcc    6480
atcatcctca acgaacttgc aatgggtgta agatctccag agagcaacag gaacaggagt    6540
ggtatccttc aagtagaact ttccgaggag aggcttaata gcgttggtag cctcctcgca    6600
atgatagaaa ggcatcttgg agaagatgtg gtggcaaaca tgggtatcca cgattctatg    6660
caccacagaa tcgaggaatg gaccaaatga tctatccaca gtgcacaaag ctcctctcaa    6720
ccaattccac tctccctctc tgaaatgagg gatgtaggta tcggtgtgtt ggaggtaggt    6780
aatcaacacc aagtaagcgt tcacaatgaa gtaaggcacc acgtagaact tcaccatggt    6840
gttgaaggag aaagtgtgca ccaaagcagc caaaacagcc aacatagcca ccaagaaaat    6900
atcggagagc acgatcatcc atctctccct atcagcatag atagcggagt aagggttgaa    6960
gtgagaccta gactttcccc agtacttagt aggtccagta gcgttgaaga agaggtatcc    7020
aggcatccat ccaacaacca acatgtacac gatacggtag agttggtaga gaggagaatc    7080
ctccaaggtc tcgttccaag aagaagccaa cacagatctg gtcacaggaa cgaaaacctc    7140
atcgttctcg caagatccag tgttggaatg gtgctttctg tgagagattc tccaagagtg    7200
gtaaggcacc aacaaagcag aatgcaacac gagtccaatc aagttgttca ccacctcaga    7260
agagcaataa gcctgatgtc cacactcatg agcgataacc cacactccag tcaagtaaga    7320
tccctggaag aaccagtaca caggccacaa acataagca gcagctccag ctctatcaat     7380
gaaggtagca gcgtagaaca aagcagcgca agtcaacacg ttcttgatca tgtagtaggt    7440
ggaggtcacg aaagatctct cgaagcagtg cttaggaata gcagctctga gatctctgag    7500
agagaaatga ggcaactcca aaggcaaagg agcaggagca ccctcaacat gagtgtatcc    7560
agcctcagcc aattgtcttt gcttagcctc agaatcagta gcgaggttag cagcagaatc    7620
agcctcaggg ttcaaaatag ccatggcgga tccggcgcgc atggtgtttt taatcttgtt    7680
tgtattgatg agttttggtt tgagtaaaga gtgaagccga tgagttaatt tataggctat    7740
aaaggagatt tgcatggcga tcacgtgtaa taatgcatgc acgcatgtga ttgtatgtgt    7800
gtgctgtgag agagaagctc ttaggtgttt gaagggagtg acaagtggcg aagaaaaaca    7860
attctccgcg gctgcatgct atgtgtaacg tgtagctaat gttctggcat ggcatcttat    7920
gaacgattct tttaaaaac aaggtaaaaa cttaacttca taaaattaaa aaaaaacgt     7980 ttactaagtt ggtttaaaag gggatgagag tctataaatt ttggaggtag tgccgttggg    8040
aatataaatt gggagcttaa tcagaattat agaagttaaa gttgatttag tcacggtcaa    8100
tataaattgg gaatttgagt caaaatcttc caaattcgga atccgtcttg ttacacccgg    8160
tggataggag ccgaacggtt tgaaaatact tgaaatgtgg atgcaggtgc aggctggttt    8220
```

```
aattttatgt tgaatggata catgtcaatc gaatttgagt tataggtaca cattttactc    8280
tgatactaaa atgtaacatt tgtctcaaga atgggtaggt catccttatg gccggcctag    8340
tagatttaaa ttggccttag tggccaagct tggcgtaatc atggccactt tgtacaagaa    8400
agctgggtgg taccggccta ttaggccacg gtccgtacag tgtttgccat cggtttcatt    8460
cggtttgatg cgatattccc cttttgtcac ttttaagttc ggttttaaag tcacttttcc    8520
atacagatga gagtattagc attttcataa gctcaatacg ttttcaaat atatcaactt     8580
ttacatttga ttcggtttca attcttgatc aaaagcaagg attgaagaat tcggttctct    8640
attccaatcc gactagtaaa taaatcgtcg tactaaacca ctctatatag aacaaacttc    8700
tttttattaa tacaaggcct acacctagtg caccacatca tcaccatacg ttacaaacgt    8760
aattatttt gtttacacgt acgtaaaaac attaatatca tacaatactt gcatgtacgt     8820
tatatagtag gcttttgtta ttatctttgc ggccggggat cctctaggtc gaccagatct    8880
gatatctgcg gccttaatta acatcaagcg gacttcttct tctttggagc catgtaggat    8940
tgcacgaaga actgagcgaa gaggaagaaa agggagagaa tgtacacgaa gtacacgatg    9000
gtgattctga gggaaacctt atcgcatccg tggaaaacca agtaggtagc ttgggacatc    9060
atgatggtga attgcaagag ttggaaagcg gtcaaagatg acttccacca gattggcaaa    9120
gactttccgg tcttagaatc cttggtgtgc atgcagatga agtagtaggt gtacatcacg    9180
gtgtgaatga atccgttgag gaggatggtc aagaagatat ctccatcgta gagcacgtta    9240
gcgttcaacc agtagaagag gaagatggtg gtgtggtggt acacgtgcaa gaaagagagt    9300
tgtctccact tctttccgag cacaatgaag atggtatccc agaaatccca cactttggag    9360
atgtagaaga gccagagcaa gttagcaact ggtggatcgt tcacgttgaa gtggttgcat    9420
ggcataacgg tgtatccgtt cctataagcg aggaatccag cctcaacagt catgtaagcg    9480
cagaggaaga tttgagacac gttgtagagg aacttgatag ggtatgggtc catagctggg    9540
agagattgca tcacagcaga tcccaagatc acgaaagcga tgtagatgag agcaatggtg    9600
atagcggatc tgaaatcgca caaccaccaa tcctccctat cagctctgaa ctttccatct    9660
ggatcactcc aatcgatgat agcagctcca atcttatcca tagcagcgtt ataagcatcc    9720
atggtagggc gcgccgattt atgataaaaa tgtcggtttc tttgtggatg ggatgggaaa    9780
gttggggagg gttgggcaaa ggtctaatat aggaggtggg tggagtggtg ttctactatc    9840
cttgcatgaa gagaacgtgg ccctgagtct tgcgtacgtg gcggctccag aattggccaa    9900
catcttattc caaggttaca aacagcctgc catgcatttt gatttttttt accatgggaa    9960
tttggacttt tgttagatat aacatttcgt cacatataat cacacgtacg ctaccacatt   10020
tgtattctta cctttttaca agttgattat aataagtaac ttggatagat tatttttat    10080
tataagtaaa ttggatagat attttttttc tttgaacaaa gtaagttata aattaaacta   10140
atgaaaattc ggttctatta tatctatccc aagtacatgc aaaatttaac ggttcacaaa   10200
atttgattgc aaatgcaatc caggattttg gtattctaac tatttattca aaattcattc   10260
actataagtt gaaattatcc ggttaaaaag gcctgttgac gggaatgggt atacccgaaa   10320
ccagtgatta tcggatagcg agtgggatgg atttagtagt atccgcctcg atacctaccc   10380
gacgggtaac ccagcattat actatgtcat gttcctcaac atattctatc ttaattttaa   10440
ttttcaatt gttagatcta attccaactc tgtaataaaa gtcatgtcgg tgaaatttgt    10500
gttcttgaat atatttttct ttttattttc ctacaaatat ggaaatttat gaatatgtgt   10560
ttcttaaaat tgcatccaat atgaaaatat taacattttt gttttgttta tcaaataaaa   10620
```

```
aatatatatt tagtaatcag gttttacccg attaaacggg taaatctgaa acccgctaac   10680
ggacgggtac ggtttaaaat tccggtctgg tttatgtaaa cgggtgggta cgtgtaaaac   10740
ccgacgacta gatgggtggg taatagatat gtttaacctg tacccatacc catccattgc   10800
tatccttgtt agaaactaaa tatgtaattc attctaaata atctataatt aaataaaaaa   10860
aattgtcaat ttatattcaa caaaatgcac aaatcttaca gtgaaatccc accctaagag   10920
tctcggtcga accactggtt caaccgaaga atcttatttg ggtctcagct gataccaacc   10980
ccttggtagt caccatctgg cggagggact ctcctgacc tgtcgagcat caacttcact   11040
ctttcaatac ctttactgac tctttgtctc ctaagcactg tttctaactt gtcaatccgc   11100
actaccatgt gctaaacatg aaagtataga gaccattcct tgtagtactg cttaggagat   11160
gtaactaatc gagcggctag ctcaactttg caacttccat cttgttgcta aactatggtt   11220
cctcggtttc ttgtctcctc ttgactcatg ttctcaccaa tatataatac taatcaaaga   11280
gtactaccaa gaccttagtc aactttttat attatgtcat ccctcatcat gatgacggtt   11340
ttgacaagtt tgattactat gcccctctag cactttttc tcttaacctc catcaagagt   11400
tctttcctag ctctttgtct gaagcatact atgcttgtag tagtccctat gtcctgcccg   11460
tgtggccggc ctaacctgca ggatacaagt gcgcacagac tagcggccgc taatcccggg   11520
aattaccggt agtaggcgcc ccccactccg ccctacactc gtatatatat gcctaaacct   11580
gcccccgttcc tcatatgtga tattattatt tcattattag gtataagata gtaaacgata   11640
aggaaagaca atttattgag aaagccatgc taaaatatag atagatatac cttagcaggt   11700
gtttatttta caacataaca taacatagta gctagccagc aggcaggcta aaacatagta   11760
tagtctatct gcagggggta cggtcgaggc ggccttaatt aatcaagcgg tctttccaga   11820
gtgttgtccg tgcacgtagt agtgcttttcc cacattatcg aggtttccca aagtagcctt   11880
ccaagctcca gcataagtca tcaccttgta gttgaggttc cacttcttag cgaaagcaac   11940
gaatcttctg gacacctcag gttgtctgaa ttgaggcata gaagggaaga ggtggtgaat   12000
cacttggcag ttcaagtatc ccatcaacca gttaacccat ccctgagaag gatcgatatc   12060
aatggtgtga tccacagcgt acctaaccca agacaagtgc tcatcagcag gaacaacatc   12120
caagtgggtg tgagaagtag agaagtgagc gaacaagtag catccggaaa cccaagaagt   12180
agccaagaag agtccgtagg attgcatagc ggtgaatcca gtaacagcct taatggtcca   12240
ggttctaatc acgtgagcag ccaacatcca cacaagctcc tcgtactttc ctcccttcaa   12300
agccttagaa gggtggagga agaacatcca gaagagcaac accaatccag aagtcacagg   12360
aatgaaggtc caagcttgca atctgagcca gtacttagag aatcccctag gtctattatc   12420
ctccacagcg gtgttgaaga aagcaacagc aggagtggta tccaaatcca tatcgtgcct   12480
cacttttga ggagtagcgt ggtgcttgtt gtgcatggag ttccacatat ctccagatcc   12540
agccaatccg aatccagcag tgaaagcttg gattctctta tcccaccaga tgtttccggt   12600
caaagaagag tgtcctccct cgtgttgaac ccatccacat ctagctccga agaagcaagc   12660
gtaaaccaac acagaggaca caacgtatct agcgtacatc aagtaggttc ccaaagcgta   12720
catagcagcc aactcagcga atctgtaagc aacatgagca ggagaaggct tgaagaatcc   12780
gtccctctcc aactcctttc tccacttagc gaaatcctgg agcatctcag catcatccac   12840
tttagcggtc ttagcaggtc tagaaggcaa agcagccaaa gccttcctag cctttctaga   12900
tctgtggtgg aactccttga aagcctcagt agcatcagct ccagtgttag agagagcgta   12960
gaaaatcacg gttcctccag gatgtttgaa atcggtcaca tcgtactcaa ctccctcgat   13020
```

```
aaccacgtat cttctagcga aggtcttagc caaagcagca ggttccatct tctcagcaga    13080
caacttcacg ttagcctcag ctcttttctct ctctccatcg aaagcgatct ccacagtagg   13140
gattccatcg ttgttctcgg tctcaacaca catggtaggg ttcagcttga tcgctctatt    13200
aattagttca ttgttttata cgtgaagaaa aagaaagaga cggaatatat ggcaaaaaac    13260
atgcaagggg acgtgtgtta acatacgtgt cttatgacta attattcgta gtggcagttt    13320
ctaccatctg gaaatggaat tgatatacac aggccagcaa gacactctag cttaccatag    13380
agcattttca tgcacacttt tttaaaagac aaaggaagta tattaataga tggtcataat    13440
tctgaatgtt ttattacctt taacattcca acaaggttaa aaccaatgtt tcaagatgtc    13500
aatgtgtcct tcacaaactc atatattgaa ttactagttt gaccaagata taagggttaa    13560
ctctaaaaca taagaaaata tgacacaaat ataaaataaa tatcagatat attgagagat    13620
ctcaaaatta ttaagaataa aatatctaag tattaatatt gttggtggta ttctaaaggt    13680
gacaggtgat aaattatatt attgtaaaat ttaaataaag agaatatttt tatattgttg    13740
taaaatttaa aataagagaa tatttttgag ttacgtttg tactaaattt ctattgatgg     13800
attttggact ttgaaatacc ataatttcta ttcaattcat tacacatttt tttccagcat    13860
acaatttagc attacaaagt ttttatatag gcttgaagaa aagtaacata gaaaacaata    13920
attcaaaaat caagacgagg actatttggt tttctcaatc ttaatgatac aactttatca    13980
taattttaaa taaggacaat aattataatg tgatgattac aattttctta taatacttac    14040
taaaggtagt ggtggttaca acacattaat tttaacactc cccttaatg tgttgctctt     14100 taactcccat tacttctcta agttgttaaa atcttcctct ttgtagtatt ttagtaaaag    14160
tgtctgtaag ttgctcttat gaactgcaga aaggtaactg cacatttcct tcttcaatca    14220
ctcttcgaat gaagtggtgt tttatgttaa tgtgtctagt ccgactatga aaaacaggat    14280
tctttgtgtt gtactacaaa attttttcctc tcagtcttca agaattttct cataagatct   14340
tccatgacat caagtttgca gcactgatac atcaatttag gtttggaatt ggcacaagag    14400
caaaatggtc aattgcacac tgaaaagtca aactttgact tttgcatcaa catcaaattt    14460
caagaatcac atttcatcaa gacatgttag aatatgaagt ttgttttatt aagaaagtca    14520
aaagtcaagt ttgctttgga aaagtcaaaa ttctaaacac ttagaaattt ttctaactgt    14580
taagaaatat gacaagttca gaacttctgg ccagatttc accatgatgc aagttgattc     14640
tggaagaact tctgacacaa gagttgtaga tttcaatgag atctaagaca ttgcggaaca    14700
gaacttctct taaaaatgat gggatttcaa gttataaatc tttgaagaca cgtccatgaa    14760
actgaagtac tcaataaatt ttgggccttc ccaagacgga atttggttag aacttctgga    14820
gcagttttca cgtaggttca atcagagttt gcaaagagtaa ttcaaagaaa gtctacaaag   14880
catgttacaa gctttctgaa aagtcttaga actccttcag aacatgttgg aacagagaga    14940
ttcaaagatc agaagttgga tacagtccgg gccgtcgatg gccggcctag tagatttaaa    15000
ttggccttag tggccaagct tggcgtaatc atggagcctg ctttttttgta caaacttggg   15060 tacccccggg atttaaatcc tgcagggggc ccgtgcgcac gcgatcgcgt cgacacaatc    15120
agtaaattga acggagaata ttattcataa aaatacgata gtaacgggtg atatattcat    15180
tagaatgaac cgaaaccggc ggtaaggatc tgagctacac atgctcaggt ttttacaac     15240 gtgcacaaca gaattgaaag caaatatcat gcgatcatag gcgtctcgca tatctcatta    15300
aagcagtcaa tcctgcttct tggtatcagc tccaacagag tgtccaacag agtagaggtt    15360
agcgaaggta gtagaaacag cagaggtgta tggcaaatcg tagtaaggga ggttgtgtct    15420
```

```
cttgaagaga gcctcaactc ttggagagat ctccttgaac ctgaattgtg gagcggttgg    15480
gaacaagtgg tgctcgattt ggaagttgag gttagacatc caccaggtaa ccaaccaaga    15540
cttggtagag atgttcacgg tgtgatcagc agcgtactca agccagtgca attgatcctc    15600
tgggttggta actggcaagt gggtgtgaga cacagcgaat ggaggaaga tgtagatgca     15660 tccaagtccg aaagagcaga ggtacattcc cacagaagtt ccaggagaat atcccaaagc    15720
tcccatcaag gagaaccatc cgatatatct agcgaagatc cacacaaact ccatgtgtct    15780
cttggtcctg agcatatatc ttgggtgcaa gtacaaggtc catcccaatc cgatcaacaa    15840
gcaagacact ggagcgaaca aataagcctg aactctgagc cacaaagcca caaagatcc     15900 tggcttaacc ttcctcacaa ctctctcgtt gaaagcaacg agtggcaagg tgttcaaatc    15960
cacatcgtgc tccaatctgt ttggagcagc gtggtgctta gagtgctggt tcttccagta    16020
gtgtccagac attccacatc caactccgta gaagaactcg cacatcctat catcgagcca    16080
gataactcca gtgaaagatc cgtgtcccat tcgtgcata acccatccgc atcttccttg      16140
agcgattccg ttcatcacca ctcccaaaac caaagaggtt ggagaagcct tagacatcaa    16200
ccagaaagac aaagcgaaca aagccacaat ctccaccact ctgtagatca tgtgtgggat    16260
agatggatcg aagtatccct cagcaaccaa ctcctctctg aaagcagcgt aatccctggt    16320
catagcgtcc cttctagcct gctccttagc agagaaccta gactccaccct tagaagcatc   16380 caactttggg agggacttga ggtacttatc agcctttccg gatctctgat ggaactctct    16440
gtaagcttgg gtagcatcaa ctccagcttc ccctcggtg aggaagttaa taatggaacc      16500
tcctgggtgt ttgaagttgg tagcatcgta caacactccc tcaatgagga tggtctttct    16560
cttatctccg ttagcctcag cagtcatctc tctagcagca gatcttccct cagatccttt    16620
tcccatggtt ttttggtggt gattggttct ttaaggtgtg agagtgagtt gtgagttgtg    16680
tggtgggttt ggtgagattg gggatggtgg gtttatatag tggagactga ggaatggggt    16740
cgtgagtgtt aactttgcat gggctacacg tgggttcttt tgggcttaca cgtagtatta    16800
ttcatgcaaa tgcagccaat acatatacgg tatttaata atgtgtggga atacaatatg     16860
ccgagtattt tactaatttt ggcaatgaca agtgtacatt tggattatct tacttggcct    16920
ctcttgcttt aatttggatt atttttattc tcttaccttg gccgttcata ttcacatccc    16980
taaaggcaag acagaattga atggtggcca aaaattaaaa cgatggatat gacctacata    17040
gtgtaggatc aattaacgtc gaaggaaaat actgattcta ttaggggtga gagttgatcg    17100
gttaattatc caatacatgc cgttggttaa ttaggattat ataaaaaatc gatcatctat    17160
tagaatcgat tacggttaaa taggtataaa aatggagaga attgaatcag ttataaattt    17220
gttttcagtt aaaatatttc tatgatcttc aatcgatttc ggtatttat actcaacatg     17280 gaaaaaattt caaatgtatt tcttctaaaa gcaaagaat ctataaaac tatcatttta      17340 tccaaaacac caaaatagtc ttttacaatc ttttacagcc ttcacataaa cgaaaacaaa    17400
agtgaacaat ttctttttac agcctttaca ccaaaaagac tacgatgaac tatgataaaa    17460
tttcataatc taaaaacatt aatgaggtaa agactctctc aaatgggata ttcttcgaaa    17520
attttcataa tcgaacgata tacttgaatt tgcaactcat gaccgaaatt gtcccaatcc    17580
ataatactct ttgacacccct atcagatccc aacgttgtcc ctggtttcga accaccatt    17640 tcaaacatga acatatcaca aaataaacat ttagacacca aatatctgct aagtttccct    17700
gaattaacgc cgaattaatt cggggggatct ggattttagt actggatttt ggttttagga    17760
attagaaatt ttattgatag aagtattta caaatacaaa tacatactaa gggtttctta     17820
```

```
tatgctcaac acatgagcga aaccctatag gaaccctaat tcccttatct gggaactact    17880
cacacattat tatggagaaa ctcgagcttg tcgatcactc ggtcttagct cccttttgct    17940
ttccatcgga tggcttgatg tacttttgca cgtagaagtt tccgaagagg aacaagaggg    18000
agatcatgta gtagaagagg atcttgatga gccattgtgg atatggagcg ttggttttca    18060
tatcgtagta agcttgcacc aagttgagca tgaactggaa catctggaat tgggtgaggt    18120
atcttcccca gaagaggtac ttgttcttga gctttggggga agatctcaag caagcagcca   18180
agaagtagta agcgtacatc aacacgtgca ctccagagtt gagagcagca ctccaataag    18240
cctctcctcc tggagcgtgg tgagcaatag cccaccagat aagggagata gaagagtggt    18300
ggtacacgtg gaggaaagaa atctgtctgg tggatctctt gaggatcatg atcacggtat    18360
ccatgaactc cacgtacttg gacatgtaga agaggtaaac gaggatagcc atctccttgt    18420
gctttgggtt ataagcgttt ccccacaagg aatatctcca ggtgatagct tggtaagcga    18480
tacccacgca catgtaaaga gacaaagcga agcagaacaa gttgtgcacc aacaccaaag    18540
cttgcaacaa gaatggctca gaagctcttg gcttgagatc tctagccttg atccaaagca    18600
atcctccgat cacgatggtc aagtaaacag acactcccaa cacaattgga gttggagaat    18660
caacgagtgg caatccctta gtagttgggg tatcagtcaa ctcaactccg aaagatccca    18720
acaaagcgtt cactccttgg gaaacctttc catccaactc tccgtagaac ctctcaacaa    18780
cttccatggt actggctatg aagaaattat aatcgtgtaa aacttagtga gtgtgtatga    18840
atgaaagtat tgcaaaatcc tcattatata gactacatgc ataactagtt gcatgtaaat    18900
ttgtagtttt cttcattatt gcatcctcca agtggatgtc atggttttac acatggcttc    18960
catgcaaatc atttccaaaa tattttaaaa cttccacag gcatccatg catgcacctc      19020
aaaacttgtg tgtggtaaca ttgttgtctt gaaaaattac taaaccttt gtccacgtga     19080
cgttcatgca cctcaaatct tgtgtggtac cattattatc ctcaagaatt attgaatgtt    19140
tggtgtatat gccatccatg cagcattgca acaattaaat ctccaaacct tgtggtacca    19200
tattcactca cttaattct cctatagtag aaatattagc aaatatttac atttccagtt     19260
gattagtata tgtatttaga agacaaaaat aatttagaat caattaatca acttgcaaat    19320
tgctaagtgt tggcaaacgt tagcataaaa ggtgttataa atttagtacc aaatataaaa    19380
atttatcgca aatcaaatac ataacacaca tagtaaaaca aaaacaaatt acaagggttt    19440
agacgtttag tggcaatgtg taaatttgct gcagggcgcg ccaagcttgg cgtaatcatg    19500
gcaacttttc tatacaaagt tgatagcttg gcgtaatcga tgtaccgata tcaatttaaa    19560
ttggccggcc gagctccctg caggggggccc ggcgcgcctc tagattaatt aaaggcctta   19620
gttactaatc agtgatcaga ttgtcgtttc ccgccttcag tttaaactat cagtgtttga    19680
caggatatat tggcgggtaa acctaagaga aaagagcgtt tattagaata atcggatatt    19740
taaaagggcg tgaaaaggtt tatccgttcg tccatttgta tgtcaatatc catgataagt    19800
cgcgctgtat gtgtttgttt gaatattcat ggaacgcagt ggcggttttc atggcttgtt    19860
atgactgttt ttttgggta cagtctatgc ctcgggcatc caagcagcaa gcgcgttacg     19920
ccgtgggtcg atgtttgatg ttatggagca gcaacgatgt tacgcagcag ggcagtcgcc    19980
ctaaaacaaa gttaaacatc atgggtgaag cggtcatcgc cgaggtgtcc acccagctgt    20040
cggaagtcgt gggtgtcatc gagcgccacc tcgaaccgac cctcctcgcc gtgcatctgt    20100
atggtagcgc cgttgacggc ggccttaagc cccattcgga catcgacctg cttgtcaccg    20160
ttaccgtccg tctcgacgag accacgcgcc gcgcgcttat caacgacctt ctggaaacgt    20220
```

```
ccgcctcccc cggcgagagc gaaatcctgc gcgcggttga ggtgacgatt gtggtgcacg    20280
atgacatcat ccccctggcgc tatccggcca aacgcgaact ccagttcggc gaatggcagc    20340
gtaatgatat tctggcgggt atctttgaac cggccaccat cgacattgat ctggcgatcc    20400
tgctcaccaa ggcccgggag catagcgtgg ccctcgtcgg ccccgcggcc gaggaacttt    20460
tcgacccggt gccggaacag gatctgttcg aagcactgaa cgagacgctg accctgtgga    20520
actccccgcc ggattgggcg ggcgatgagc gcaatgtggt ccttacgctg agccggattt    20580
ggtactcggc ggttaccggc aagatcgcgc cgaaggatgt cgccgccgac tgggcgatgg    20640
agcgccttcc ggcgcaatac cagcccgtga tcctcgaagc gcgccaagcc tatctgggcc    20700
aagaagaaga ccgtctcgcg tcccgggccg accagctcga agaatttgtc cactatgtca    20760
agggcgagat cacgaaggtc gttggcaaat aatgtctagc tagaaattcg ttcaagccga    20820
cgccgcttcg cggcgcggct taactcaagc gttagatgca ctaagcacat aattgctcac    20880
agccaaacta tcgatgagtt gaaggacccc gtagaaaaga tcaaaggatc ttcttgagat    20940
cctttttttc tgcgcgtaat ctgctgcttg caaacaaaaa aaccaccgct accagcggtg    21000
gtttgtttgc cggatcaaga gctaccaact ctttttccga aggtaactgg cttcagcaga    21060
gcgcagatac caaatactgt ccttctagtg tagccgtagt taggccacca cttcaagaac    21120
tctgtagcac cgcctacata cctcgctctg ctaatcctgt taccagtggc tgctgccagt    21180
ggcgataagt cgtgtcttac cgggttggac tcaagacgat agttaccgga taaggcgcag    21240
cggtcgggct gaacggggggt tcgtgcaca cagcccagct tggagcgaac gacctacacc    21300
gaactgagat acctacagcg tgagctatga gaaagcgcca cgcttcccga agggagaaag    21360
gcggacaggt atccggtaag cggcagggtc ggaacaggag agcgcacgag ggagcttcca    21420
gggggaaacg cctggtatct ttatagtcct gtcgggtttc gccacctctg acttgagcgt    21480
cgatttttgt gatgctcgtc agggggggcgg agcctatgga aaaacgccag caacgcggcc    21540
ttttacggt tcctggcctt ttgctggcct tttgctcaca tgttctttcc tgcgttatcc    21600
cctgattctg tggataaccg tattaccgcc tttgagtgag ctgataccgc tcgccgcagc    21660
cgaacgaccg agcgcagcga gtcagtgagc gaggaagcgg aagagcgcct gatgcggtat    21720
tttctcctta cgcatctgtg cggtatttca caccgcatag gccgcgatag gccgacgcga    21780
agcggcgggg cgtagggagc gcagcgaccg aagggtaggc gcttttgca gctcttcggc    21840
tgtgcgctgg ccagacagtt atgcacaggc caggcgggtt ttaagagttt taataagttt    21900
taaagagttt taggcggaaa aatcgccttt tttctctttt atatcagtca cttacatgtg    21960
tgaccggttc ccaatgtacg gctttgggtt cccaatgtac gggttccggt tcccaatgta    22020
cggctttggg ttcccaatgt acgtgctatc cacaggaaag agaccttttc gacctttttc    22080
ccctgctagg gcaatttgcc ctagcatctg ctccgtacat taggaaccgg cggatgcttc    22140
gccctcgatc aggttgcggt agcgcatgac taggatcggg ccagcctgcc ccgcctcctc    22200
cttcaaatcg tactccggca ggtcatttga cccgatcagc ttgcgcacgg tgaaacagaa    22260
cttcttgaac tctccggcgc tgccactgcg ttcgtagatc gtcttgaaca accatctggc    22320
ttctgccttg cctgcggcgc ggcgtgccag gcggtagaga aaacggccga tgccggggtc    22380
gatcaaaaag taatcggggt gaaccgtcag cacgtccggg ttcttgcctt ctgtgatctc    22440
gcggtacatc caatcagcaa gctcgatctc gatgtactcc ggccgccgg tttcgctctt    22500
tacgatcttg tagcggctaa tcaaggcttc accctcggat accgtcacca ggcggccgtt    22560
cttggccttc ttggtacgct gcatggcaac gtgcgtggtg tttaaccgaa tgcaggtttc    22620
```

```
taccaggtcg tctttctgct ttccgccatc ggctcgccgg cagaacttga gtacgtccgc   22680
aacgtgtgga cggaacacgc ggccgggctt gtctcccttc ccttcccggt atcggttcat   22740
ggattcggtt agatgggaaa ccgccatcag taccaggtcg taatcccaca cactggccat   22800
gccggcgggg cctgcggaaa cctctacgtg cccgtctgga agctcgtagc ggatcacctc   22860
gccagctcgt cggtcacgct tcgacagacg gaaaacggcc acgtccatga tgctgcgact   22920
atcgcgggtg cccacgtcat agagcatcgg aacgaaaaaa tctggttgct cgtcgccctt   22980
gggcggcttc ctaatcgacg gcgcaccggc tgccggcggt tgccgggatt ctttgcggat   23040
tcgatcagcg gccccttgcc acgattcacc ggggcgtgct tctgcctcga tgcgttgccg   23100
ctgggcggcc tgcgcggcct tcaacttctc caccaggtca tcacccagcg ccgcgccgat   23160
ttgtaccggg ccgatggtt tgcgaccgct cacgccgatt cctcgggctt ggggggttcca   23220 gtgccattgc agggccggca gacaacccag ccgcttacgc ctggccaacc gccgttcct   23280 ccacacatgg ggcattccac ggcgtcggtg cctggttgtt cttgattttc catgccgcct   23340
cctttagccg ctaaaattca tctactcatt tattcatttg ctcatttact ctggtagctg   23400
cgcgatgtat tcagatagca gctcggtaat ggtcttgcct tggcgtaccg cgtacatctt   23460
cagcttggtg tgatcctccg ccggcaactg aaagttgacc cgcttcatgg ctggcgtgtc   23520
tgccaggctg gccaacgttg cagccttgct gctgcgtgcg ctcggacggc cggcacttag   23580
cgtgtttgtg cttttgctca ttttctcttt acctcattaa ctcaaatgag ttttgattta   23640
atttcagcgg ccagcgcctg gacctcgcgg gcagcgtcgc cctcgggttc tgattcaaga   23700
acggttgtgc cggcggcggc agtgcctggg tagctcacgc gctgcgtgat acgggactca   23760
agaatgggca gctcgtaccc ggccagcgcc tcggcaacct caccgccgat gcgcgtgcct   23820
ttgatcgccc gcgacacgac aaaggccgct tgtagccttc catccgtgac ctcaatgcgc   23880
tgcttaacca gctccaccag gtcggcggtg gcccaaatgt cgtaagggct tggctgcacc   23940
ggaatcagca cgaagtcggc tgccttgatc gcggacacag ccaagtccgc cgcctggggc   24000
gctccgtcga tcactacgaa gtcgcgccgg ccgatggcct tcacgtcgcg gtcaatcgtc   24060
gggcggtcga tgccgacaac ggttagcggt tgatcttccc gcacggccgc ccaatcgcgg   24120
gcactgccct ggggatcgga atcgactaac agaacatcgg ccccggcgag ttgcagggcg   24180
cgggctagat gggttgcgat ggtcgtcttg cctgacccgc ttttctggtt aagtacagcg   24240
ataaccttca tgcgttcccc ttgcgtattt gtttatttac tcatcgcatc atatacgcag   24300
cgaccgcatg acgcaagctg ttttactcaa atacacatca ccttttttaga tgatca       24356
```

<210> SEQ ID NO 17
<211> LENGTH: 23990
<212> TYPE: DNA
<213> ORGANISM: Artificial Sequence
<220> FEATURE:
<223> OTHER INFORMATION: binary T plasmid VC-LJB1328-1qcz

<400> SEQUENCE: 17

```
gacatacaaa tggacgaacg gataaacctt ttcacgccct tttaaatatc cgattattct     60
aataaacgct cttttctctt aggtttaccc gccaatatat cctgtcaaac actgatagtt    120
taaactgaag gcgggaaacg acaatctgat cactgattag taactaaggc ctttaattaa    180
tctagaggcg cgccgggccc cctgcaggga gctcggccgg ccaatttaaa ttgatatcgg    240
tacatcgatt acgccaagct atcaactttg tatagaaaag ttgccatgat tacgccaagc    300
ttggccacta aggccaattt cgcgccctgc agcaaattta cacattgcca ctaaacgtct    360
```

```
aaacccttgt aatttgtttt tgttttacta tgtgtgttat gtatttgatt tgcgataaat    420
ttttatattt ggtactaaat ttataacacc tttatgcta acgttgcca acacttagca     480 atttgcaagt tgattaattg attctaaatt attttgtct tctaaataca tatactaatc    540
aactggaaat gtaaatattt gctaatattt ctactatagg agaattaaag tgagtgaata   600
tggtaccaca aggtttggag atttaattgt tgcaatgctg catggatggc atatacacca   660
aacattcaat aattcttgag gataataatg gtaccacaca agatttgagg tgcatgaacg   720
tcacgtggac aaaaggttta gtaatttttc aagacaacaa tgttaccaca cacaagtttt   780
gaggtgcatg catggatgcc ctgtggaaag tttaaaaata ttttggaaat gatttgcatg   840
gaagccatgt gtaaaaccat gacatccact tggaggatgc aataatgaag aaaactacaa   900
atttacatgc aactagttat gcatgtagtc tatataatga ggattttgca atactttcat   960
tcatacacac tcactaagtt ttacacgatt ataatttctt catagccagt accatggaag   1020
ttgttgagag gttctacgga gagttggatg gaaaggtttc ccaaggagtg aacgctttgt   1080
tgggatcttt cggagttgag ttgactgata ccccaactac taagggattg ccactcgttg   1140
attctccaac tccaattgtg ttgggagtgt ctgtttactt gaccatcgtg atcggaggat   1200
tgctttggat caaggctaga gatctcaagc caagagcttc tgagccattc ttgttgcaag   1260
ctttggtgtt ggtgcacaac ttgttctgct tcgctttgtc tctttacatg tgcgtgggta   1320
tcgcttacca agctatcacc tggagatatt ccttgtgggg aaacgcttat aacccaaagc   1380
acaaggagat ggctatcctc gtttacctct tctacatgtc caagtacgtg gagttcatgg   1440
ataccgtgat catgatcctc aagagatcca ccagacagat ttctttcctc cacgtgtacc   1500
accactcttc tatctccctt atctggtggg ctattgctca ccacgctcca ggaggagagg   1560
cttattggag tgctgctctc aactctggag tgcacgtgtt gatgtacgct tactacttct   1620
tggctgcttg cttgagatct tccccaaagc tcaagaacaa gtacctcttc tggggaagat   1680
acctcaccca attccagatg ttccagttca tgctcaactt ggtgcaagct tactacgata   1740
tgaaaaccaa cgctccatat ccacaatggc tcatcaagat cctcttctac tacatgatct   1800
ccctcttgtt cctcttcgga aacttctacg tgcaaaagta catcaagcca tccgatggaa   1860
agcaaaaggg agctaagacc gagtgatcga caagctcgag tttctccata ataatgtgtg   1920
agtagttccc agataaggga attagggttc ctataggggt tcgctcatgt gttgagcata   1980
taagaaaccc ttagtatgta tttgtatttg taaaatactt ctatcaataa aatttctaat   2040
tcctaaaacc aaaatccagt actaaaatcc agatcccccg aattaattcg gcgttaattc   2100
agggccggcc aaagtaggcg cctactaccg gtaattcccg ggattagcgg ccgctagtct   2160
gtgcgcactt gtatcctgca ggttaggccg gccataagga tgacctaccc attcttgaga   2220
caaatgttac attttagtat cagagtaaaa tgtgtaccta taactcaaat tcgattgaca   2280
tgtatccatt caacataaaa ttaaaccagc ctgcacctgc atccacattt caagtatttt   2340
caaaccgttc ggctcctatc caccgggtgt aacaagacgg attccgaatt tggaagattt   2400
tgactcaaat tcccaatttta tattgaccgt gactaaatca actttaactt ctataattct   2460
gattaagctc ccaatttata ttcccaacgg cactacctcc aaaatttata gactctcatc   2520
cccttttaaa ccaacttagt aaacgttttt tttttaattt tatgaagtta agttttacc    2580 ttgtttttaa aaagaatcgt tcataagatg ccatgccaga acattagcta cacgttacac   2640
atagcatgca gccgcggaga attgttttc ttcgccactt gtcactccct tcaaacacct    2700
aagagcttct ctctcacagc acacacatac aatcacatgc gtgcatgcat tattacacgt   2760
```

-continued

```
gatcgccatg caaatctcct ttatagccta taaattaact catcggcttc actctttact    2820
caaaccaaaa ctcatcaata caaacaagat taaaaacacc atgggaaaag gatctgaggg    2880
aagatctgct gctagagaga tgactgctga ggctaacgga gataagagaa agaccatcct    2940
cattgaggga gtgttgtacg atgctaccaa cttcaaacac ccaggaggtt ccattattaa    3000
cttcctcacc gagggagaag ctggagttga tgctacccaa gcttacagag agttccatca    3060
gagatccgga aaggctgata agtacctcaa gtccctccca aagttggatg cttctaaggt    3120
ggagtctagg ttctctgcta aggagcaggc tagaagggac gctatgacca gggattacgc    3180
tgctttcaga gaggagttgg ttgctgaggg atacttcgat ccatctatcc cacacatgat    3240
ctacagagtg gtggagattg tggctttgtt cgctttgtct ttctggttga tgtctaaggc    3300
ttctccaacc tctttggttt tgggagtggt gatgaacgga atcgctcaag gaagatgcgg    3360
atgggttatg cacgagatgg gacacggatc tttcactgga gttatctggc tcgatgatag    3420
gatgtgcgag ttcttctacg gagttggatg tggaatgtct ggacactact ggaagaacca    3480
gcactctaag caccacgctg ctccaaacag attggagcac gatgtggatt tgaacaccct    3540
gccactcgtt gctttcaacg agagagttgt gaggaaggtt aagccaggat ctttgttggc    3600
tttgtggctc agagttcagg cttatttgtt cgctccagtg tcttgcttgt tgatcggatt    3660
gggatggacc ttgtacttgc acccaagata tatgctcagg accaagagac acatggagtt    3720
tgtgtggatc ttcgctagat atatcggatg gttctccttg atgggagctt tgggatattc    3780
tcctggaact tctgtgggaa tgtacctctg ctctttcgga cttggatgca tctacatctt    3840
cctccaattc gctgtgtctc acacccactt gccagttacc aacccagagg atcaattgca    3900
ctggcttgag tacgctgctg atcacaccgt gaacatctct accaagtctt ggttggttac    3960
ctggtggatg tctaacctca acttccaaat cgagcaccac ttgttcccaa ccgctccaca    4020
attcaggttc aaggagatct ctccaagagt tgaggctctc ttcaagagac acaacctccc    4080
ttactacgat ttgccataca cctctgctgt ttctactacc ttcgctaacc tctactctgt    4140
tggacactct gttggagctg ataccaagaa gcaggattga ctgctttaat gagatatgcg    4200
agacgcctat gatcgcatga tatttgcttt caattctgtt gtgcacgttg taaaaaacct    4260
gagcatgtgt agctcagatc cttaccgccg gtttcggttc attctaatga atatatcacc    4320
cgttactatc gtatttttat gaataatatt ctccgttcaa tttactgatt gtgtcgacgc    4380
gatcgcgtgc gcctaccggt atcggtccga ttgcggccgc ttaaagggcg aattctgcag    4440
ataaacactg tacggaccgt ggcctaatag gccgtaccc aagtttgtac aaaaaagcag    4500
gctccatgat tacgccaagc ttggccacta aggccaattt aaatctacta ggccggccat    4560
cgacggcccg gactgtatcc aacttctgat ctttgaatct ctctgttcca acatgttctg    4620
aaggagttct aagactttc agaaagcttg taacatgctt tgtagacttt ctttgaatta    4680
ctcttgcaaa ctctgattga acctacgtga aaactgctcc agaagttcta accaaattcc    4740
gtcttgggaa ggcccaaaat ttattgagta cttcagtttc atggacgtgt cttcaaagat    4800
ttataacttg aaatcccatc attttaaga gaagttctgt ccgcaatgt cttagatctc    4860 attgaaatct acaactcttg tgtcagaagt tcttccagaa tcaacttgca tcatggtgaa    4920
aatctggcca gaagttctga acttgtcata tttcttaaca gttagaaaaa tttctaagtg    4980
tttagaattt tgactttcc aaagcaaact tgactttga ctttcttaat aaaacaaact    5040
tcatattcta acatgtcttg atgaaatgtg attcttgaaa tttgatgttg atgcaaaagt    5100
caaagtttga cttttcagtg tgcaattgac cattttgctc ttgtgccaat tccaaaccta    5160
```

```
aattgatgta tcagtgctgc aaacttgatg tcatggaaga tcttatgaga aaattcttga   5220
agactgagag gaaaaatttt gtagtacaac acaaagaatc ctgtttttca tagtcggact   5280
agacacatta acataaaaca ccacttcatt cgaagagtga ttgaagaagg aaatgtgcag   5340
ttacctttct gcagttcata agagcaactt acagacactt ttactaaaat actacaaaga   5400
ggaagatttt aacaacttag agaagtaatg ggagttaaag agcaacacat taaggggag    5460 tgttaaaatt aatgtgttgt aaccaccact acctttagta agtattataa gaaaattgta   5520
atcatcacat tataattatt gtccttattt aaaattatga taaagttgta tcattaagat   5580
tgagaaaacc aaatagtcct cgtcttgatt tttgaattat tgttttctat gttacttttc   5640
ttcaagccta tataaaaact ttgtaatgct aaattgtatg ctggaaaaaa atgtgtaatg   5700
aattgaatag aaattatggt atttcaaagt ccaaaatcca tcaatagaaa tttagtacaa   5760
aacgtaactc aaaaatattc tcttatttta aattttacaa caatataaaa atattctctt   5820 atttttaaatt ttacaataat ataatttatc acctgtcacc tttagaatac caccaacaat   5880
attaatactt agatatttta ttcttaataa ttttgagatc tctcaatata tctgatattt   5940 atttatatt tgtgtcatat tttcttatgt tttagagtta acccttatat cttggtcaaa    6000
ctagtaattc aatatatgag tttgtgaagg acacattgac atcttgaaac attggttta    6060 accttgttgg aatgttaaag gtaataaaac attcagaatt atgaccatct attaatatac   6120
ttcctttgtc ttttaaaaaa gtgtgcatga aaatgctcta tggtaagcta gagtgtcttg   6180
ctggcctgtg tatatcaatt ccatttccag atggtagaaa ctgccactac gaataattag   6240
tcataagaca cgtatgttaa cacacgtccc cttgcatgtt ttttgccata tattccgtct   6300 cttctttt cttcacgtat aaaacaatga actaattaat agagcgatca agctgaaccc    6360
taccatgtgt gttgagaccg agaacaacga tggaatccct actgtggaga tcgctttcga   6420
tggagagaga gaaagagctg aggctaacgt gaagttgtct gctgagaaga tggaacctgc   6480
tgctttggct aagaccttcg ctagaagata cgtggttatc gagggagttg agtacgatgt   6540
gaccgatttc aaacatcctg gaggaaccgt gattttctac gctctctcta acactggagc   6600
tgatgctact gaggctttca aggagttcca ccacagatct agaaaggcta ggaaggcttt   6660
ggctgctttg ccttctagac ctgctaagac cgctaaagtg gatgatgctg agatgctcca   6720
ggatttcgct aagtggagaa aggagttgga gagggacgga ttcttcaagc cttctcctgc   6780
tcatgttgct tacagattcg ctgagttggc tgctatgtac gctttgggaa cctacttgat   6840
gtacgctaga tacgttgtgt cctctgtgtt ggtttacgct tgcttcttcg gagctagatg   6900
tggatgggtt caacacgagg gaggacactc ttctttgacc ggaaacatct ggtgggataa   6960
gagaatccaa gctttcactg ctggattcgg attggctgga tctggagata tgtggaactc   7020
catgcacaac aagcaccacg ctactcctca aaaagtgagg cacgatatgg atttggatac   7080
cactcctgct gttgctttct tcaacaccgc tgtgaggat aatagaccta ggggattctc    7140
taagtactgg ctcagattgc aagcttggac cttcattcct gtgacttctg gattggtgtt   7200
gctcttctgg atgttcttcc tccacccttc taaggctttg aagggaggaa agtacgagga   7260
gcttgtgtgg atgttggctg ctcacgtgat tagaacctgg accattaagg ctgttactgg   7320
attcaccgct atgcaatcct acggactctt cttggctact tcttgggttt ccggatgcta   7380
cttgttcgct cacttctcta cttctcacac ccacttggat gttgttcctg ctgatgagca   7440
cttgtcttgg gttaggtacg ctgtggatca caccattgat atcgatcctt ctcagggatg   7500
ggttaactgg ttgatgggat acttgaactg ccaagtgatt caccacctct tcccttctat   7560
```

```
gcctcaattc agacaacctg aggtgtccag aagattcgtt gctttcgcta agaagtggaa    7620
cctcaactac aaggtgatga cttatgctgg agcttggaag gctactttgg gaaacctcga    7680
taatgtggga aagcactact acgtgcacgg acaacactct ggaaagaccg cttgattaat    7740
taaggccgcc tcgaccgtac ccctgcaga tagactatac tatgttttag cctgcctgct     7800
ggctagctac tatgttatgt tatgttgtaa aataaacacc tgctaaggta tatctatcta    7860
tattttagca tggcttttctc aataaattgt cttttccttat cgtttactat cttatacct a   7920 ataatgaaat aataatatca catatgagga acggggcagg tttaggcata tatatacgag    7980
tgtagggcgg agtgggggc gcctactacc ggtaattccc gggattagcg ccgctagtc      8040 tgtgcgcact tgtatcctgc aggttaggcc ggccatcgac ggcccggact gtatccaact    8100
tctgatcttt gaatctctct gttccaacat gttctgaagg agttctaaga cttttcagaa    8160
agcttgtaac atgctttgta gactttcttt gaattactct tgcaaactct gattgaacct    8220
acgtgaaaac tgctccagaa gttctaacca aattccgtct gggaaggcc caaaatttat     8280 tgagtacttc agtttcatgg acgtgtcttc aaagattat aacttgaaat cccatcattt     8340
ttaagagaag ttctgttccg caatgtctta gatctcattg aaatctacaa ctcttgtgtc    8400
agaagttctt ccagaatcaa cttgcatcat ggtgaaaatc tggccagaag ttctgaactt    8460
gtcatatttc ttaacagtta gaaaaatttc taagtgttta gaattttgac ttttccaaag    8520
caaacttgac ttttgacttt cttaataaaa caaacttcat attctaacat gtcttgatga    8580
aatgtgattc ttgaaatttg atgttgatgc aaaagtcaaa gtttgacttt tcagtgtgca    8640
attgaccatt ttgctcttgt gccaattcca aacctaaatt gatgtatcag tgctgcaaac    8700
ttgatgtcat ggaagatctt atgagaaaat tcttgaagac tgagaggaaa aattttgtag    8760
tacaacacaa agaatcctgt ttttcatagt cggactagac acattaacat aaaacaccac    8820
ttcattcgaa gagtgattga agaaggaaat gtgcagttac ctttctgcag ttcataagag    8880
caacttacag acacttttac taaaatacta caaagaggaa gattttaaca acttagagaa    8940
gtaatgggag ttaaagagca acacattaag ggggagtgtt aaaattaatg tgttgtaacc    9000
accactacct ttagtaagta ttataagaaa attgtaatca tcacattata attattgtcc    9060
ttatttaaaa ttatgataaa gttgtatcat taagattgag aaaaccaaat agtcctcgtc    9120
ttgatttttg aattattgtt ttctatgtta cttttcttca agcctatata aaaactttgt    9180
aatgctaaat tgtatgctgg aaaaaaatgt gtaatgaatt gaatagaaat tatggtatt t   9240 caaagtccaa aatccatcaa tagaaattta gtacaaaacg taactcaaaa atattctctt    9300
attttaaatt ttacaacaat ataaaaatat tctcttatt taaatttac aataatataa     9360 tttatcacct gtcaccttta gaataccacc aacaatatta atacttagat attttattct    9420
taataatttt gagatctctc aatatatctg atatttattt tatatttgtg tcatattttc    9480
ttatgtttta gagttaaccc ttatatcttg gtcaaactag taattcaata tatgagtttg    9540
tgaaggacac attgacatct tgaaacattg gttttaacct tgttggaatg ttaaaggtaa    9600
taaaacattc agaattatga ccatctatta atatacttcc tttgtctttt aaaaaagtgt    9660
gcatgaaaat gctctatggt aagctagagt gtcttgctgg cctgtgtata tcaattccat    9720
ttccagatgg tagaaactgc cactacgaat aattagtcat aagacacgta tgttaacaca    9780
cgtccccttg catgtttttt gccatatatt ccgtctcttt cttttcttc acgtataaaa     9840 caatgaacta attaatagag cgatcaagct gaaccatgga tgcttataac gctgctatgg    9900
ataagattgg agctgctatc atcgattgga gtgatccaga tggaaagttc agagctgata    9960
```

```
gggaggattg gtggttgtgc gatttcagat ccgctatcac cattgctctc atctacatcg   10020
ctttcgtgat cttgggatct gctgtgatgc aatctctccc agctatggac ccatacccta   10080
tcaagttcct ctacaacgtg tctcaaatct tcctctgcgc ttacatgact gttgaggctg   10140
gattcctcgc ttataggaac ggatacaccg ttatgccatg caaccacttc aacgtgaacg   10200
atccaccagt tgctaacttg ctctggctct tctacatctc caaagtgtgg gatttctggg   10260
ataccatctt cattgtgctc ggaaagaagt ggagacaact ctctttcttg cacgtgtacc   10320
accacaccac catcttcctc ttctactggt tgaacgctaa cgtgctctac gatggagata   10380
tcttcttgac catcctcctc aacggattca ttcacaccgt gatgtacacc tactacttca   10440
tctgcatgca caccaaggat tctaagaccg aaagtctttt gccaatctgg tggaagtcat   10500
ctttgaccgt tttccaactc ttgcaattca ccatcatgat gtcccaagct acctacttgg   10560
ttttccacgg atgcgataag gtttccctca gaatcaccat cgtgtacttc gtgtacattc   10620
tctcccttt  cttcctcttc gctcagttct tcgtgcaatc ctacatggct ccaaagaaga   10680
agaagtccgc ttgaccccta tcgattaatt aaggccgcct cgaccgtacc ccctgcagat   10740
agactatact atgtttagc  ctgcctgctg gctagctact atgttatgtt atgttgtaaa   10800
ataaacacct gctaaggtat atctatctat attttagcat ggctttctca ataaattgtc   10860
tttccttatc gttactatc  ttatacctaa taatgaaata ataatatcac atatgaggaa   10920
cggggcaggt ttaggcatat atatacgagt gtagggcgga gtgggggca  aacactgtac   10980
ggaccgtggc ctaataggcc ggtaccaccc agctttcttg tacaaagtgg ccatgattac   11040
gccaagctct ccaccgcggt ggcggccgct ctagcccaag ctttaaggat gacctaccca   11100
ttcttgagac aaatgttaca ttttagtatc agagtaaaat gtgtacctat aactcaaatt   11160
cgattgacat gtatccattc aacataaaat taaaccagcc tgcacctgca tccacatttc   11220
aagtattttc aaaccgttcg gctcctatcc accgggtgta acaagacgga ttccgaattt   11280
ggaagatttt gactcaaatt cccaatttat attgaccgtg actaaatcaa cttaacttc    11340
tataattctg attaagctcc caatttatat tcccaacggc actacctcca aaatttatag   11400
actctcatcc ccttttaaac caacttagta aacgtttttt ttttaatttt atgaagttaa   11460
gtttttacct tgttttaaa  aagaatcgtt cataagatgc catgccagaa cattagctac   11520
acgttacaca tagcatgcag ccgcggagaa ttgttttct  tcgccacttg tcactccctt   11580
caaacaccta agagcttctc tctcacagca cacacataca atcacatgcg tgcatgcatt   11640
attacacgtg atcgccatgc aaatctcctt tatagcctat aaattaactc atcggcttca   11700
ctctttactc aaaccaaaac tcatcaatac aaacaagatt aaaaacataa ggcgcgccgg   11760
atccgccatg ggaaaggag  gaagatctgt gactagggct caaactgctg agaagtctgc   11820
tcacaccatt caaaccttca ccgatggaag atgggtttcc ccttacaacc ctttggctaa   11880
ggatgctcct gagttgcctt ctaagggaga gattaaggct gtgatcccta aggagtgctt   11940
cgagagatct tacctccact ccatgtactt cgtgttgagg gatactgtta ggctgttgc    12000
ttgcgcttac attgctcatt ctaccctctc caccgatatt ccttctgagt tgctctctgt   12060
ggatgctttg aagtggttct tgggatggaa cacttacgct ttctggatgg gatgcatttt   12120
gactggacat tgggtgttgg ctcatgagtg tggacatgga gctttctctc catctcagac   12180
cttcaacgat ttctggggat tcatcatgca tcaagctgtg ttggttcctt acttcgcttg   12240
gcaatactct catgctaagc accataggag gaccaacaac atcatggatg agagtctca   12300
tgtgcctaac atcgctaagg agatgggatt gaacgagaag aacgagagat ctggaggata   12360
```

```
cgctgctatt catgaggcta tcggagatgg acctttcgct atgttccaga tcttcgctca   12420
tttggtgatt ggatggccta tctacttgat gggattcgct tctactggaa ggcttggaca   12480
agatggaaag gagttgcaag ctggagagat catcgatcac taccgtcctt ggtctaagat   12540
gttccctacc aagctcagat tcaagatcgc tttgtctacc ttgggagtga ttgctgcttg   12600
ggttgggctt tacttcgctg ctcaagagta tggagttttg cctgtggtgt tgtggtatat   12660
cggacctttg atgtggaatc aggcttggtt ggtgttgtac acctggttgc aacacaacga   12720
tccttctgtg cctcaatacg gatctgatga gtggacttgg gttaagggag cactttccac   12780
aatcgataga ccttacggaa tcttcgattt cttccaccac aagatcggat ctactcatgt   12840
ggctcatcat ctcttccatg agatgccttt ctacaaggct gatgtggcta ccgcttctat   12900
taagggattc ctcgagccta agggacttta caactacgat cctacccctt ggtatgttgc   12960
tatgtggaga gttgctaaga cttgccacta catcgaggat gttgatggag ttcagtacta   13020
caagtccttg gaggatgtgc ctttgaagaa ggatgctaag aagtccgatt gatagttaat   13080
taataattga ttggttcgag tattatggca ttgggaaaac tgttttttctt gtaccatttg   13140 ttgtgcttgt aatttactgt gttttttatt cggttttcgc tatcgaactg tgaaatggaa   13200
atggatggag aagagttaat gaatgatatg gtccttttgt tcattctcaa attaatatta   13260
tttgtttttt ctcttatttg ttgtgtgttg aatttgaaat tataagagat atgcaaacat   13320
tttgttttga gtaaaaatgt gtcaaatcgt ggcctctaat gaccgaagtt aatatgagga   13380
gtaaaacact tgtagttgta ccattatgct tattcactag gcaacaaata tatttcaga   13440 cctagaaaag ctgcaaatgt tactgaatac aagtatgtcc tcttgtgttt tagacattta   13500 tgaacttttcc tttatgtaat tttccagaat ccttgtcaga ttctaatcat tgctttataa   13560
ttatagttat actcatggat ttgtagttga gtatgaaaat attttttaat gcattttatg   13620
acttgccaat tgattgacaa catgcatcaa tggcggtacc caactttatt atacatagtt   13680
gataattcac tggccggatg taccgaattc gcggccgcaa gcttgtacac tagtacgcgt   13740
caattggcga tcgcggatct gagatgaaac cggtgattat cagaaccttt tatggtcttt   13800
gtatgcatat ggtaaaaaaa cttagtttgc aatttcctgt ttgttttggt aatttgagtt   13860
tcttttagtt gttgatctgc ctgcttttg gtttacgtca gactactact gctgttgttg   13920
tttggtttcc tttctttcat tttataaata aataatccgg ttcggtttac tccttgtgac   13980
tggctcagtt tggttattgc gaaatgcgaa tggtaaattg agtaattgaa attcgttatt   14040
agggttctaa gctgttttaa cagtcactgg gttaatatct ctcgaatctt gcatggaaaa   14100
tgctcttacc attggttttt aattgaaatg tgctcatatg ggccgtggtt tccaaattaa   14160
ataaaactac gatgtcatcg agaagtaaaa tcaactgtgt ccacattatc agttttgtgt   14220
atacgatgaa ataggtaat tcaaaatcta gcttgatatg cctttggtt cattttaacc   14280 ttctgtaaac atttttcag attttgaaca agtaaatcca aaaaaaaaa aaaaaatct   14340 caactcaaca ctaaattatt ttaatgtata aaagatgctt aaaacatttg gcttaaaaga   14400
aagaagctaa aaacatagag aactcttgta aattgaagta tgaaaatata ctgaattggg   14460
tattatatga atttttctga tttaggattc acatgatcca aaaaggaaat ccagaagcac   14520
taatcagaca ttggaagtag gaatatttca aaaagttttt ttttttttaag taagtgcaaa   14580 aagcttttaa aaaatagaaa agaaactagt attaaagttg taaattttaat aaacaaaaga   14640 aatttttat atttttcat ttcttttccc agcatgaggt tatgatggca ggatgtggat   14700 ttcattttttt tccttttgat agccttttaa ttgatctatt ataattgacg aaaaaatatt   14760
```

```
agttaattat agatatattt taggtagtat tagcaattta cacttccaaa agactatgta    14820
agttgtaaat atgatgcgtt gatctcttca tcattcaatg gttagtcaaa aaaataaaag    14880
cttaactagt aaactaaagt agtcaaaaat tgtactttag tttaaaatat tacatgaata   14940
atccaaaacg acatttatgt gaaacaaaaa caatatagat ccattaccct gttatcccta    15000
gaggggaaaa ttcgaatcca aaaattacgg atatgaatat aggcatatcc gtatccgaat    15060
tatccgtttg acagctagca acgattgtac aattgcttct ttaaaaaagg aagaaagaaa    15120
gaaagaaaag aatcaacatc agcgttaaca aacggcccg ttacggccca aacggtcata     15180
tagagtaacg gcgttaagcg ttgaaagact cctatcgaaa tacgtaaccg caaacgtgtc    15240
atagtcagat cccctcttcc ttcaccgcct caaacacaaa aataatcttc tacagcctat    15300
atatacaacc ccccttcta tctctccttt ctcacaattc atcatctttc tttctctacc     15360
cccaatttta agaaatcctc tcttctcctc ttcattttca aggtaaatct ctctctctct    15420
ctctctctct gttattcctt gttttaatta ggtatgtatt attgctagtt tgttaatctg    15480
cttatcttat gtatgcctta tgtgaatatc tttatcttgt tcatctcatc cgtttagaag    15540
ctataaattt gttgatttga ctgtgtatct acacgtggtt atgtttatat ctaatcagat    15600
atgaatttct tcatattgtt gcgtttgtgt gtaccaatcc gaaatcgttg attttttca     15660
tttaatcgtg tagctaattg tacgtataca tatggatcta cgtatcaatt gttcatctgt   15720
ttgtgtttgt atgtatacag atctgaaaac atcacttctc tcatctgatt gtgttgttac   15780
atacatagat atagatctgt tatatcattt tttttattaa ttgtgtatat atatatgtgc    15840
atagatctgg attacatgat tgtgattatt tacatgattt tgttatttac gtatgtatat   15900
atgtagatct ggactttttg gagttgttga cttgattgta tttgtgtgtg tatatgtgtg   15960
ttctgatctt gatatgttat gtatgtgcag ctgaaccatg gcggcggcaa caacaacaac   16020
aacaacatct tcttcgatct ccttctccac caaaccatct ccttcctcct ccaaatcacc    16080
attaccaatc tccagattct ccctcccatt ctccctaaac cccaacaaat catcctcctc    16140
ctcccgccgc cgcggtatca aatccagctc tccctcctcc atctccgccg tgctcaacac    16200
aaccaccaat gtcacaacca ctccctctcc aaccaaacct accaaacccg aaacattcat    16260
ctcccgattc gctccagatc aaccccgcaa aggcgctgat atcctcgtcg aagctttaga    16320
acgtcaaggc gtagaaaccg tattcgctta ccctggaggt acatcaatgg agattcacca    16380
agccttaacc cgctcttcct caatccgtaa cgtccttcct cgtcacgaac aaggaggtgt    16440
attcgcagca gaaggatacg ctcgatcctc aggtaaacca ggtatctgta tagccacttc    16500
aggtcccgga gctacaaatc tcgttagcgg attagccgat gcgttgttag atagtgttcc    16560
tcttgtagca atcacaggac aagtccctcg tcgtatgatt ggtacagatg cgtttcaaga    16620
gactccgatt gttgaggtaa cgcgttcgat tacgaagcat aactatcttg tgatggatgt    16680
tgaagatatc cctaggatta ttgaggaagc tttcttttta gctacttctg gtagacctgg    16740
acctgttttg gttgatgttc ctaaagatat tcaacaacag cttgcgattc ctaattggga    16800
acaggctatg agattacctg gttatatgtc taggatgcct aaacctccgg aagattctca    16860
tttggagcag attgttaggt tgatttctga gtctaagaag cctgtgttgt atgttggtgg    16920
tggttgtttg aattctagcg atgaattggg taggtttgtt gagcttacgg ggatccctgt    16980
tgcgagtacg ttgatggggc tgggatctta tccttgtgat gatgagttgt cgttacatat    17040
gcttggaatg catgggactg tgtatgcaaa ttacgctgtg gagcatagtg atttgttgtt    17100
ggcgtttggg gtaaggtttg atgatcgtgt cacgggtaag cttgaggctt ttgctagtag    17160
```

```
ggctaagatt gttcatattg atattgactc ggctgagatt gggaagaata agactcctca   17220
tgtgtctgtg tgtggtgatg ttaagctggc tttgcaaggg atgaataagg ttcttgagaa   17280
ccgagcggag gagcttaagc ttgattttgg agtttggagg aatgagttga acgtacagaa   17340
acagaagttt ccgttgagct ttaagacgtt tggggaagct attcctccac agtatgcgat   17400
taaggtcctt gatgagttga ctgatggaaa agccataata agtactggtg tcgggcaaca   17460
tcaaatgtgg gcggcgcagt tctacaatta caagaaacca aggcagtggc tatcatcagg   17520
aggccttgga gctatgggat ttggacttcc tgctgcgatt ggagcgtctg ttgctaaccc   17580
tgatgcgata gttgtggata ttgacggaga tggaagcttt ataatgaatg tgcaagagct   17640
agccactatt cgtgtagaga atcttccagt gaaggtactt ttattaaaca accagcatct   17700
tggcatggtt atgcaatggg aagatcggtt ctacaaagct aaccgagctc acacatttct   17760
cggggatccg gctcaggagg acgagatatt cccgaacatg ttgctgtttg cagcagcttg   17820
cgggattcca gcggcgaggg tgacaaagaa agcagatctc cgagaagcta ttcagacaat   17880
gctggataca ccaggacctt acctgttgga tgtgatttgt ccgcaccaag aacatgtgtt   17940
gccgatgatc ccgaatggtg gcactttcaa cgatgtcata acggaaggag atggccggat   18000
taaatactga tagggataac agggtaatct cgacgagatg aaaccggtga ttatcagaac   18060
cttttatggt ctttgtatgc atatggtaaa aaaacttagt ttgcaatttc ctgtttgttt   18120
tggtaatttg agtttctttt agttgttgat ctgcctgctt tttggtttac gtcagactac   18180
tactgctgtt gttgtttggt ttcctttctt tcatttata aataataat ccggttcggt   18240 ttactccttg tgactggctc agtttggtta ttgcgaaatg cgaatggtaa attgagtaat   18300
tgaaattcgt tattagggtt ctaagctgtt ttaacagtca ctgggttaat atctctcgaa   18360
tcttgcatgg aaaatgctct taccattggt tttaattga aatgtgctca tatgggccgt   18420
ggtttccaaa ttaaataaaa ctacgatgtc atcgagaagt aaaatcaact gtgtccacat   18480
tatcagtttt gtgtatacga tgaaataggg taattcaaaa tctagcttga tatgccttt   18540 ggttcatttt aaccttctgt aaacatttt tcagattttg aacaagtaaa tccaaaaaaa   18600
aaaaaaaaaa atctcaactc aacactaaat tattttaatg tataaagat gcttaaaaca   18660 tttggcttaa aagaagaag ctaaaaacat agagaactct tgtaaattga agtatgaaaa   18720
tatactgaat tgggtattat atgaattttt ctgatttagg attcacatga tccaaaaagg   18780
aaatccagaa gcactaatca gacattggaa gtaggaatat ttcaaaaagt ttttttttt   18840 taagtaagtg acaaaagctt ttaaaaaata gaaaagaaac tagtattaaa gttgtaaatt   18900
taataaacaa agaaattttt ttatatttt tcatttcttt ttccagcatg aggttatgat   18960
ggcaggatgt ggatttcatt ttttccttt tgatagcctt taattgatc tattataatt   19020 gacgaaaaaa tattagttaa ttatagatat attttaggta gtattagcaa tttacacttc   19080
caaaagacta tgtaagttgt aaatatgatg cgttgatctc ttcatcattc aatggttagt   19140
caaaaaaata aaagcttaac tagtaaacta aagtagtcaa aaattgtact ttagtttaaa   19200
atattacatg aataatccaa aacgacattt atgtgaaaca aaacaatat gtcgaggcga   19260 tcgcagtact taatcagtga tcagtaacta aattcagtac attaaagacg tccgcaatgt   19320
gttattaagt tgtctaagcg tcaatttgtt tacaccacaa tatatcctgc caccagccag   19380
ccaacagctc cccgaccggc agctcggcac aaaatcactg atcatctaaa aaggtgatgt   19440
gtatttgagt aaaacagctt gcgtcatgcg gtcgctgcgt atatgatgcg atgagtaaat   19500
aaacaaatac gcaagggaa cgcatgaagg ttatcgctgt acttaaccag aaaggcgggt   19560
```

```
caggcaagac gaccatcgca acccatctag cccgcgccct gcaactcgcc ggggccgatg    19620
ttctgttagt cgattccgat ccccagggca gtgcccgcga ttgggcggcc gtgcgggaag    19680
atcaaccgct aaccgttgtc ggcatcgacc gcccgacgat tgaccgcgac gtgaaggcca    19740
tcggccggcg cgacttcgta gtgatcgacg gagcgcccca ggcggcggac ttggctgtgt    19800
ccgcgatcaa ggcagccgac ttcgtgctga ttccggtgca gccaagccct tacgacattt    19860
gggccaccgc cgacctggtg gagctggtta agcagcgcat tgaggtcacg gatggaaggc    19920
tacaagcggc ctttgtcgtg tcgcgggcga tcaaaggcac gcgcatcggc ggtgaggttg    19980
ccgaggcgct ggccgggtac gagctgccca ttcttgagtc ccgtatcacg cagcgcgtga    20040
gctacccagg cactgccgcc gccggcacaa ccgttcttga atcagaaccc gagggcgacg    20100
ctgcccgcga ggtccaggcg ctggccgctg aaattaaatc aaaactcatt tgagttaatg    20160
aggtaaagag aaaatgagca aaagcacaaa cacgctaagt gccggccgtc cgagcgcacg    20220
cagcagcaag gctgcaacgt tggccagcct ggcagacacg ccagccatga agcgggtcaa    20280
ctttcagttg ccggcggagg atcacaccaa gctgaagatg tacgcggtac gccaaggcaa    20340
gaccattacc gagctgctat ctgaatacat cgcgcagcta ccagagtaaa tgagcaaatg    20400
aataaatgag tagatgaatt ttagcggcta aaggaggcgg catggaaaat caagaacaac    20460
caggcaccga cgccgtggaa tgccccatgt gtggaggaac gggcggttgg ccaggcgtaa    20520
gcggctgggt tgtctgccgg ccctgcaatg gcactggaac ccccaagccc gaggaatcgg    20580
cgtgagcggc cgcaaaccat ccggcccggt acaaatcggc gcggcgctgg gtgatgacct    20640
ggtggagaag ttgaaggccg cgcaggccgc ccagcggcaa cgcatcgagg cagaagcacg    20700
ccccggtgaa tcgtggcaag gggccgctga tcgaatccgc aaagaatccc ggcaaccgcc    20760
ggcagccggt gcgccgtcga ttaggaagcc gcccaagggc gacgagcaac cagatttttt    20820
cgttccgatg ctctatgacg tgggcacccg cgatagtcgc agcatcatgg acgtggccgt    20880
tttccgtctg tcgaagcgtg accgacgagc tggcgaggtg atccgctacg agcttccaga    20940
cgggcacgta gaggttttccg caggccccgc cggcatggcc agtgtgtggg attacgacct    21000
ggtactgatg gcggtttccc atctaaccga atccatgaac cgataccggg aagggaaggg    21060
agacaagccc ggccgcgtgt tccgtccaca cgttgcggac gtactcaagt tctgccggcg    21120
agccgatggc ggaaagcaga aagacgacct ggtagaaacc tgcattcggt taaacaccac    21180
gcacgttgcc atgcagcgta ccaagaaggc caagaacggc cgcctggtga cggtatccga    21240
gggtgaagcc ttgattagcc gctacaagat cgtaaagagc gaaaccgggc ggccggagta    21300
catcgagatc gagcttgctg attggatgta ccgcgagatc acagaaggca agaacccgga    21360
cgtgctgacg gttcaccccg attacttttt gatcgacccc ggcatcggcc gttttctcta    21420
ccgcctggca cgccgcgccg caggcaaggc agaagccaga tggttgttca agacgatcta    21480
cgaacgcagt ggcagcgccg gagagttcaa gaagttctgt ttcaccgtgc gcaagctgat    21540
cgggtcaaat gacctgccgg agtacgattt gaaggaggag gcggggcagg ctggcccgat    21600
cctagtcatg cgctaccgca acctgatcga gggcgaagca tccgccggtt cctaatgtac    21660
ggagcagatg ctagggcaaa ttgccctagc aggggaaaaa ggtcgaaaag gtctctttcc    21720
tgtggatagc acgtacattg ggaacccaaa gccgtacatt gggaaccgga acccgtacat    21780
tgggaaccca aagccgtaca ttgggaaccg gtcacacatg taagtgactg atataaaaga    21840 gaaaaaggc gatttttccg cctaaaactc tttaaaactt attaaaactc ttaaaacccg    21900
cctggcctgt gcataactgt ctggccagcg cacagccgaa gagctgcaaa aagcgcctac    21960
```

```
ccttcggtcg ctgcgctccc tacgccccgc cgcttcgcgt cggcctatcg cggcctatgc    22020
ggtgtgaaat accgcacaga tgcgtaagga gaaataccg catcaggcgc tcttccgctt     22080
cctcgctcac tgactcgctg cgctcggtcg ttcggctgcg gcgagcggta tcagctcact    22140
caaaggcggt aatacggtta ccacagaat caggggataa cgcaggaaag aacatgtgag     22200
caaaaggcca gcaaaaggcc aggaaccgta aaaaggccgc gttgctggcg ttttttccata   22260 ggctccgccc cctgacgag catcacaaaa atcgacgctc aagtcagagg tggcgaaacc    22320
cgacaggact ataaagatac caggcgtttc ccctggaag ctccctcgtg cgctctcctg     22380
ttccgaccct gccgcttacc ggatacgtgt ccgcctttct cccttcggga agcgtggcgc   22440
tttctcatag ctcacgctgt aggtatctca gttcggtgta ggtcgttcgc tccaagctgg    22500
gctgtgtgca cgaacccccc gttcagcccg accgctgcgc cttatccggt aactatcgtc    22560
ttgagtccaa cccggtaaga cacgacttat cgccactggc agcagccact ggtaacagga    22620
ttagcagagc gaggtatgta ggcggtgcta cagagttctt gaagtggtgg cctaactacg    22680
gctacactag aaggacagta tttggtatct gcgctctgct gaagccagtt accttcggaa    22740
aaagagttgg tagctcttga tccggcaaac aaaccaccgc tggtagcggt ggttttttg     22800 tttgcaagca gcagattacg cgcagaaaaa aaggatctca agaagatcct tgatcttttt    22860
ctacggggtc cttcaactca tcgatagttt ggctgtgagc aattatgtgc ttagtgcatc    22920
taacgcttga gttaagccgc gccgcgaagc ggcgtcggct tgaacgaatt tctagctaga    22980
cattatttgc caacgacctt cgtgatctcg cccttgacat agtggacaaa ttcttcgagc   23040
tggtcggccc gggacgcgag acggtcttct tcttggccca gataggcttg gcgcgcttcg    23100
aggatcacgg gctggtattg cgccggaagg cgctccatcg cccagtcggc ggcgacatcc    23160
ttcggcgcga tcttgccggt aaccgccgag taccaaatcc ggctcagcgt aaggaccaca    23220
ttgcgctcat cgcccgccca atccggcggg gagttccaca gggtcagcgt ctcgttcagt    23280
gcttcgaaca gatcctgttc cggcaccggg tcgaaaagtt cctcggccgc ggggccgacg    23340
agggccacgc tatgctcccg ggccttggtg agcaggatcg ccagatcaat gtcgatggtg    23400
gccggttcaa agatacccgc cagaatatca ttacgctgcc attcgccgaa ctggagttcg    23460
cgtttggccg gatagcgcca ggggatgatg tcatcgtgca ccacaatcgt cacctcaacc    23520
gcgcgcagga tttcgctctc gccggggag gcggacgttt ccagaaggtc gttgataagc    23580
gcgcggcgcg tggtctcgtc gagacggacg gtaacggtga caagcaggtc gatgtccgaa    23640
tggggcttaa ggccgccgtc aacggcgcta ccatacagat gcacggcgag gagggtcggt    23700
tcgaggtggc gctcgatgac acccacgact tccgacagct gggtggacac ctcggcgatg    23760
accgcttcac ccatgatgtt taactttgtt tagggcgac tgccctgctg cgtaacatcg     23820
ttgctgctcc ataacatcaa acatcgaccc acggcgtaac gcgcttgctg cttggatgcc    23880
cgaggcatag actgtacccc aaaaaaacag tcataacaag ccatgaaaac cgccactgcg    23940
ttccatgaat attcaaacaa acacatacag cgcgacttat catggatatt               23990
```

<210> SEQ ID NO 18
<211> LENGTH: 903
<212> TYPE: DNA
<213> ORGANISM: Ostreococcus tauri

<400> SEQUENCE: 18

```
atgtctgctt ctggagcttt gttgcctgct attgctttcg ctgcttacgc ttacgctacc    60
tacgcttatg ctttcgagtg gtctcatgct aacggaatcg ataacgtgga tgctagagag    120
```

-continued

```
tggattggag ctttgtctttt gagactccct gcaattgcta ccaccatgta cctcttgttc      180
tgccttgtgg gacctagatt gatggctaag agggaggctt ttgatcctaa gggattcatg      240
ctcgcttaca acgcttacca aaccgctttc aacgttgtgg tgctcggaat gttcgctaga      300
gagatctctg gattgggaca acctgttggg ggatctacta tgccttggag cgataggaag      360
tccttcaaga ttttgttggg agtgtggctc cactacaaca ataagtacct cgagttgttg      420
gatactgtgt tcatggtggc taggaaaaag accaagcagc tctctttctt gcacgtgtac      480
caccacgctt tgttgatttg gcttggtgg cttgtttgtc acctcatggc taccaacgat      540
tgcatcgatg cttatttcgg agctgcttgc aactcttttca tccacatcgt gatgtactcc      600
tactacctca tgtctgcttt gggaattaga tgcccttgga agagatatat cacccaggct      660
cagatgttgc aattcgtgat cgtgttcgct cacgctgttt tcgtgctcag acaaaagcac      720
tgccctgtta ctttgccttg gcacaaatg ttcgtgatga caaatatgtt ggtgctcttc      780
ggaaacttct acctcaaggc ttactctaac aagtctaggg gagatggagc ttcttctgtt      840
aagcctgctg agactactag agcaccttct gtgagaagaa ccaggtccag gaagatcgat      900
tga                                                                    903
```

<210> SEQ ID NO 19
<211> LENGTH: 300
<212> TYPE: PRT
<213> ORGANISM: Ostreococcus tauri

<400> SEQUENCE: 19

```
Met Ser Ala Ser Gly Ala Leu Leu Pro Ala Ile Ala Phe Ala Ala Tyr
 1               5                  10                  15

Ala Tyr Ala Thr Tyr Ala Tyr Ala Phe Glu Trp Ser His Ala Asn Gly
            20                  25                  30

Ile Asp Asn Val Asp Ala Arg Glu Trp Ile Gly Ala Leu Ser Leu Arg
        35                  40                  45

Leu Pro Ala Ile Ala Thr Thr Met Tyr Leu Leu Phe Cys Leu Val Gly
    50                  55                  60

Pro Arg Leu Met Ala Lys Arg Glu Ala Phe Asp Pro Lys Gly Phe Met
65                  70                  75                  80

Leu Ala Tyr Asn Ala Tyr Gln Thr Ala Phe Asn Val Val Leu Gly
                85                  90                  95

Met Phe Ala Arg Glu Ile Ser Gly Leu Gly Gln Pro Val Trp Gly Ser
            100                 105                 110

Thr Met Pro Trp Ser Asp Arg Lys Ser Phe Lys Ile Leu Leu Gly Val
        115                 120                 125

Trp Leu His Tyr Asn Asn Lys Tyr Leu Glu Leu Asp Thr Val Phe
    130                 135                 140

Met Val Ala Arg Lys Lys Thr Lys Gln Leu Ser Phe Leu His Val Tyr
145                 150                 155                 160

His His Ala Leu Leu Ile Trp Ala Trp Trp Leu Val Cys His Leu Met
                165                 170                 175

Ala Thr Asn Asp Cys Ile Asp Ala Tyr Phe Gly Ala Ala Cys Asn Ser
            180                 185                 190

Phe Ile His Ile Val Met Tyr Ser Tyr Tyr Leu Met Ser Ala Leu Gly
        195                 200                 205

Ile Arg Cys Pro Trp Lys Arg Tyr Ile Thr Gln Ala Gln Met Leu Gln
    210                 215                 220

Phe Val Ile Val Phe Ala His Ala Val Phe Val Leu Arg Gln Lys His
225                 230                 235                 240
```

```
Cys Pro Val Thr Leu Pro Trp Ala Gln Met Phe Val Met Thr Asn Met
            245                 250                 255

Leu Val Leu Phe Gly Asn Phe Tyr Leu Lys Ala Tyr Ser Asn Lys Ser
            260                 265                 270

Arg Gly Asp Gly Ala Ser Ser Val Lys Pro Ala Glu Thr Thr Arg Ala
            275                 280                 285

Pro Ser Val Arg Arg Thr Arg Ser Arg Lys Ile Asp
            290                 295                 300

<210> SEQ ID NO 20
<211> LENGTH: 1560
<212> TYPE: DNA
<213> ORGANISM: Thraustochytrium ssp.

<400> SEQUENCE: 20
atgactgttg gatacgatga ggagatccca ttcgagcaag ttagggctca taacaagcca      60
gatgatgctt ggtgtgctat tcatggacac gtgtacgatg ttaccaagtt cgcttctgtt     120
catccaggag agatattat cttgctcgct gctggaaagg aagctactgt gctctacgag      180
acctaccatt tagaggagt gtctgatgct gtgctcagaa agtacagaat cggaaagttg      240
ccagatggac aaggaggagc taacgagaag gagaagagaa ccttgtctgg attgtcctct     300
gcttcttact acacctggaa ctccgatttc tacagagtga tgaggagag agttgtggct      360 agattgaagg agagaggaaa ggctagaaga ggaggatacg agttgtggat caaggctttc     420
ttgctccttg ttggattctg gtcctctctt tactggatgt gcaccctcga tccatctttc     480
ggagctatct tggctgctat gtctttggga gtgttcgctg cttttgttgg aacctgcatc     540
caacacgatg gaaaccacgg agctttcgct caatctagat gggttaacaa ggtggcagga     600
tggactttgg atatgatcgg agcttctgga atgacttggg agttccaaca cgtgttggga     660
caccacccat acactaactt gatcgaggag gagaacggat gcaaaaggt gtccggaaag     720 aagatggata ccaagttggc tgatcaagag tctgatccag atgtgttctc cacctaccca     780
atgatgagat tgcacccatg gcaccagaag agatggtatc acaggttcca gcacatctac     840
ggaccattca tcttcggatt catgaccatc aacaaggtgg tgactcaaga tgttggagtg     900
gtgttgagaa agaggctctt ccaaatcgat gctgagtgca gatatgcttc cccaatgtac     960
gttgctaggt tctggatcat gaaggctttg accgtgttgt acatggttgc tctcccatgt    1020
tatatgcaag gaccatggca cggattgaag ctcttcgcta tcgctcactt cacttgcgga    1080
gaggttttgg ctaccatgtt catcgtgaac acacattatcg agggagtgtc ttacgcttct    1140
aaggatgctg ttaagggaac tatggctcca ccaaagacta tgcacggagt gaccccaatg    1200
aacaacacta gaaaggaggt tgaggctgag gcttctaagt ctggagctgt ggttaagtct    1260
gtgccattgg atgattgggc tgctgttcaa tgccaaacct ctgtgaactg gtctgttgga    1320
tcttggttct ggaaccactt ctctggagga ctcaaccacc aaatcgagca ccactcttc    1380 ccaggattgt ctcacgagac ctactaccac atccaagatg tggttcaatc tacctgtgct    1440
gagtacggag ttccatacca acacgagcca tctttgtgga ctgcttactg gaagatgctc    1500
gaacacttga acaattggg aaacgaggag actcacgagt catggcaaag agctgcttga    1560

<210> SEQ ID NO 21
<211> LENGTH: 519
<212> TYPE: PRT
<213> ORGANISM: Thraustochytrium ssp.

<400> SEQUENCE: 21
```

-continued

```
Met Thr Val Gly Tyr Asp Glu Glu Ile Pro Phe Glu Gln Val Arg Ala
1               5                   10                  15

His Asn Lys Pro Asp Asp Ala Trp Cys Ala Ile His Gly His Val Tyr
            20                  25                  30

Asp Val Thr Lys Phe Ala Ser Val His Pro Gly Gly Asp Ile Ile Leu
                35                  40                  45

Leu Ala Ala Gly Lys Glu Ala Thr Val Leu Tyr Glu Thr Tyr His Val
        50                  55                  60

Arg Gly Val Ser Asp Ala Val Leu Arg Lys Tyr Arg Ile Gly Lys Leu
65                  70                  75                  80

Pro Asp Gly Gln Gly Gly Ala Asn Glu Lys Glu Lys Arg Thr Leu Ser
                85                  90                  95

Gly Leu Ser Ser Ala Ser Tyr Tyr Thr Trp Asn Ser Asp Phe Tyr Arg
                100                 105                 110

Val Met Arg Glu Arg Val Val Ala Arg Leu Lys Glu Arg Gly Lys Ala
            115                 120                 125

Arg Arg Gly Gly Tyr Glu Leu Trp Ile Lys Ala Phe Leu Leu Leu Val
130                 135                 140

Gly Phe Trp Ser Ser Leu Tyr Trp Met Cys Thr Leu Asp Pro Ser Phe
145                 150                 155                 160

Gly Ala Ile Leu Ala Ala Met Ser Leu Gly Val Phe Ala Ala Phe Val
                165                 170                 175

Gly Thr Cys Ile Gln His Asp Gly Asn His Gly Ala Phe Ala Gln Ser
                180                 185                 190

Arg Trp Val Asn Lys Val Ala Gly Trp Thr Leu Asp Met Ile Gly Ala
            195                 200                 205

Ser Gly Met Thr Trp Glu Phe Gln His Val Leu Gly His His Pro Tyr
            210                 215                 220

Thr Asn Leu Ile Glu Glu Glu Asn Gly Leu Gln Lys Val Ser Gly Lys
225                 230                 235                 240

Lys Met Asp Thr Lys Leu Ala Asp Gln Glu Ser Asp Pro Asp Val Phe
                245                 250                 255

Ser Thr Tyr Pro Met Met Arg Leu His Pro Trp His Gln Lys Arg Trp
                260                 265                 270

Tyr His Arg Phe Gln His Ile Tyr Gly Pro Phe Ile Phe Gly Phe Met
            275                 280                 285

Thr Ile Asn Lys Val Val Thr Gln Asp Val Gly Val Val Leu Arg Lys
            290                 295                 300

Arg Leu Phe Gln Ile Asp Ala Glu Cys Arg Tyr Ala Ser Pro Met Tyr
305                 310                 315                 320

Val Ala Arg Phe Trp Ile Met Lys Ala Leu Thr Val Leu Tyr Met Val
                325                 330                 335

Ala Leu Pro Cys Tyr Met Gln Gly Pro Trp His Gly Leu Lys Leu Phe
                340                 345                 350

Ala Ile Ala His Phe Thr Cys Gly Glu Val Leu Ala Thr Met Phe Ile
            355                 360                 365

Val Asn His Ile Ile Glu Gly Val Ser Tyr Ala Ser Lys Asp Ala Val
            370                 375                 380

Lys Gly Thr Met Ala Pro Pro Lys Thr Met His Gly Val Thr Pro Met
385                 390                 395                 400

Asn Asn Thr Arg Lys Glu Val Glu Ala Glu Ala Ser Lys Ser Gly Ala
                405                 410                 415

Val Val Lys Ser Val Pro Leu Asp Asp Trp Ala Ala Val Gln Cys Gln
```

```
                     420                 425                 430
Thr Ser Val Asn Trp Ser Val Gly Ser Trp Phe Trp Asn His Phe Ser
        435                 440                 445
Gly Gly Leu Asn His Gln Ile Glu His His Leu Phe Pro Gly Leu Ser
        450                 455                 460
His Glu Thr Tyr Tyr His Ile Gln Asp Val Val Gln Ser Thr Cys Ala
465                 470                 475                 480
Glu Tyr Gly Val Pro Tyr Gln His Glu Pro Ser Leu Trp Thr Ala Tyr
                485                 490                 495
Trp Lys Met Leu Glu His Leu Arg Gln Leu Gly Asn Glu Thr His
                500                 505                 510
Glu Ser Trp Gln Arg Ala Ala
        515

<210> SEQ ID NO 22
<211> LENGTH: 684
<212> TYPE: DNA
<213> ORGANISM: Vicia faba

<400> SEQUENCE: 22
ctgcagcaaa tttacacatt gccactaaac gtctaaaccc ttgtaatttg tttttgtttt      60
actatgtgtg ttatgtattt gatttgcgat aaattttat atttggtact aaatttataa     120
caccttttat gctaacgttt gccaacactt agcaatttgc aagttgatta attgattcta    180 aattatttt gtcttctaaa tacatatact aatcaactgg aaatgtaaat atttgctaat     240
atttctacta taggagaatt aaagtgagtg aatatggtac cacaaggttt ggagatttaa    300
ttgttgcaat gctgcatgga tggcatatac accaaacatt caataattct tgaggataat    360
aatggtacca cacaagattt gaggtgcatg aacgtcacgt ggacaaaagg tttagtaatt    420
tttcaagaca acaatgttac cacacacaag ttttgaggtg catgcatgga tgccctgtgg    480
aaagtttaaa aatattttgg aaatgatttg catggaagcc atgtgtaaaa ccatgacatc    540
cacttggagg atgcaataat gaagaaaact acaaatttac atgcaactag ttatgcatgt    600
agtctatata atgaggattt tgcaaatactt tcattcatac acactcacta agttttacac    660
gattataatt tcttcatagc cagt                                            684

<210> SEQ ID NO 23
<211> LENGTH: 175
<212> TYPE: DNA
<213> ORGANISM: Cauliflower mosaic virus

<400> SEQUENCE: 23
tttctccata taatgtgtg agtagttccc agataaggga attagggttc ctatagggtt      60
tcgctcatgt gttgagcata taagaaaccc ttagtatgta tttgtatttg taaaatactt    120
ctatcaataa aatttctaat tcctaaaacc aaaatccagt actaaaatcc agatc          175

<210> SEQ ID NO 24
<211> LENGTH: 2754
<212> TYPE: DNA
<213> ORGANISM: Vicia faba

<400> SEQUENCE: 24
gatctgtcgt ctcaaactca ttcatcagaa ccttcttgaa cttagttatc tcttgttcag      60
agcttcctgt tagcaatatg tcatcaacat ataacatgt cccagaagcc agaagataga     120
agttggatga tagaagtaaa gtaatgttac tggtggagta ccacaataca agttcataca    180
```

```
aacttta ttg tccagaaact aacaaagttg agttcagcat agatgaaaga caaaaagaat    240
atattaaatg acggctgcaa aataaggagt aatgaataca ttgacctacc tactactagg    300
ctatttatac acaatattag ggtataataa aatattaaaa taccctctat cagacttagt    360
caataagaca ttcctaaaat ataaattatt ccaacaata atttgtctca aataaaatat     420
agaggtgcaa aagttaaact aagagtgcaa agtaaaattt tgagagggct caaaattgaa    480
tataataaca atattagtgt agtttaagaa aactcagggg atgcagttga actccctcaa    540
ctgtacgtag ctcctcccct ggatgcagtg taaagatttg aagatatatt ttagtacttt    600
ggatattgta ggccagaggg tgttgaagat aaaggttcag gaactaacac attcatccac    660
aacttctatg tgtccatcgt cagtgaaata catgccaaat aggggagtta agaagagtag    720
aaagggtcaa gatagtgatg tgcatcgtga tccttcataa tgggagtgtg gtgagggctc    780
gcatgggagt catactacaa agagatcatg cataaaacca actagaagtc aactgtcaag    840
tatgacggct gacaattaac cgtccaccaa atcttccaga catgtttact tgtcccagtt    900
ttctgatttc ttatatccat acattgatga cattattgat gttggtggcg atggagattg    960
gggttttcat gctattacag ctttacttgg atggggtgaa gagtcatagc ctttgattca   1020
gacgcagtta gatactcaag ttcatcaaca ccctcaattg ttttttaagt tgttttgtga   1080
cacgatctct acagttagaa atgcgttacg agtagaacac ttggctgtgc agggtataga   1140
taaatgaatg acgatttatg atatgggtta ccctattgct tctagataca atgtcgtatt   1200
tgtctccctt ccaaaagact taacatcacg ttttttcctc ttgccttatc tccacctatg   1260
tatacaagca ggcataaaat cattgttgtt ggttttgtca acaacaatca ttgagtttag   1320
gtaaagttga aacttgattg tccattacct cttgtcactg actgttgaag acagaattgt   1380
actgactgta tatatcaaca tatgcgagac gcgttaggca gtggaaagac gtagttagga   1440
tgtcatcata atttgtttcg tattttata tgtagcacag ttttatatg tatatatttt    1500 atcgggtagt ttttatcga ttcagttatt tgagaaaaag taatgcagac aaaaagtgga   1560
aaagacaatc tgactgtaca taagaaattt ccaattttg aaatttttt ataattatca    1620 gaaattttaa aatttccgat aaaaacatac atgtatagat cgaaaatttc aaatttctag   1680
tactttcaaa tttcttgcag taaaagttgt aattttttaa aaatttacga taatttacag   1740
tatttaaaaa aaaatccaat cttaaataaa gggtataaga ataaaagcac tcatgtggag   1800
tggcaggttt cgtcacaccc taagaacatc cctaaataca ccacatatgt ataagtatta   1860
agtgattgat gttaagtgaa acgaaaatat ttatatgtga aatttaatat tcagcttact   1920
tgattaaact ccatagtgac ccaataagtg ctaactttta ctgtctttac ctttaaatgt   1980
tatattgatt tatttatgca tttctttttc ctgcatctca atagtatata gggtatcaaa   2040
tagtgattat ccaaacttaa ataagttaga ggaaacacca agatatgcca tatactctca   2100
aatttgacac tatgattcaa agttgcactt gcataaaact tattaattca atagtaaaac   2160
caaacttgtg cgtgatacag ttaaaatgac taaactacta attaaggtcc ctcccattag   2220
taaataagtt attttttttag aaaaagaaaa taataaaaag aatgacgagt ctatctaaat   2280
catattaaca agtaatacat attgattcat tcgatggagg aggccaataa ttgtagtaaa   2340
caagcagtgc cgaggttaat atatgctcaa gacagtaaat aatctaaatg aattaagaca   2400
gtgatttgca aagagtagat gcagagaaga gaactaaaga tttgctgcta cacgtatata   2460
agaatagcaa cagatattca ttctgtctct ttgtggaata tggatatcta ctaatcatca   2520
tctatctgtg aagaataaaa gaagcggcca caagcgcagc gtcgcacata tgatgtgtat   2580
```

| | |
|---|---|
| caaattagga ctccatagcc atgcatgctg aagaatgtca cacacgttct gtcacacgtg | 2640 |
| ttactctctc actgttctcc tcttcctata aatcaccgcg ccacagcttc tccacttcac | 2700 |
| cacttcacca cttcactcac aatccttcat tagttgttta ctatcacagt caca | 2754 |

<210> SEQ ID NO 25
<211> LENGTH: 297
<212> TYPE: DNA
<213> ORGANISM: Vicia faba

<400> SEQUENCE: 25

| | |
|---|---|
| atcctgcaat agaatgttga ggtgaccact ttctgtaata aaataattat aaaataaatt | 60 |
| tagaattgct gtagtcaaga acatcagttc taaaatatta ataaagttat ggccttttga | 120 |
| catatgtgtt tcgataaaaa aatcaaaata aattgagatt tattcgaaat acaatgaaag | 180 |
| tttgcagata tgagatatgt ttctacaaaa taataactta aaactcaact atatgctaat | 240 |
| gttttcttg gtgtgtttca tagaaaattg tatccgtttc ttagaaaatg ctcgtaa | 297 |

<210> SEQ ID NO 26
<211> LENGTH: 1039
<212> TYPE: DNA
<213> ORGANISM: Linum usitatissimum

<400> SEQUENCE: 26

| | |
|---|---|
| ttagcagata tttggtgtct aaatgtttat tttgtgatat gttcatgttt gaaatggtgg | 60 |
| tttcgaaacc agggacaacg ttgggatctg atagggtgtc aaagagtatt atggattggg | 120 |
| acaatttcgg tcatgagttg caaattcaag tatatcgttc gattatgaaa attttcgaag | 180 |
| aatatcccat ttgagagagt ctttacctca ttaatgtttt tagattatga aattttatca | 240 |
| tagttcatcg tagtcttttt ggtgtaaagg ctgtaaaaag aaattgttca cttttgtttt | 300 |
| cgtttatgtg aaggctgtaa aagattgtaa aagactattt tggtgttttg gataaaatga | 360 |
| tagtttttat agattctttt gcttttagaa gaaatacatt tgaaatttt tccatgttga | 420 |
| gtataaaata ccgaaatcga ttgaagatca tagaaatatt ttaactgaaa acaaatttat | 480 |
| aactgattca attctctcca tttttatacc tatttaaccg taatcgattc taatagatga | 540 |
| tcgatttttt atataatcct aattaaccaa cggcatgtat tggataatta accgatcaac | 600 |
| tctcaccct aatagaatca gtattttcct tcgacgttaa ttgatcctac actatgtagg | 660 |
| tcatatccat cgttttaatt tttggccacc attcaattct gtcttgcctt tagggatgtg | 720 |
| aatatgaacg gccaaggtaa gagaataaaa ataatccaaa ttaaagcaag agaggccaag | 780 |
| taagataatc caaatgtaca cttgtcattg ccaaaattag taaaatactc ggcatattgt | 840 |
| attcccacac attattaaaa taccgtatat gtattggctg catttgcatg aataatacta | 900 |
| cgtgtaagcc caaagaaacc cacgtgtagc ccatgcaaag ttaacactca cgaccccatt | 960 |
| cctcagtctc cactatataa acccaccatc cccaatctca ccaaacccac cacacaactc | 1020 |
| acaactcact ctcacaccct | 1039 |

<210> SEQ ID NO 27
<211> LENGTH: 192
<212> TYPE: DNA
<213> ORGANISM: Agrobacterium tumefaciens

<400> SEQUENCE: 27

| | |
|---|---|
| ctgctttaat gagatatgcg agacgcctat gatcgcatga tatttgcttt caattctgtt | 60 |
| gtgcacgttg taaaaaacct gagcatgtgt agctcagatc cttaccgccg gtttcggttc | 120 |

-continued

```
attctaatga atatatcacc cgttactatc gtattttat gaataatatt ctccgttcaa    180
tttactgatt gt                                                       192

<210> SEQ ID NO 28
<211> LENGTH: 1799
<212> TYPE: DNA
<213> ORGANISM: Vicia faba

<400> SEQUENCE: 28
tcgacggccc ggactgtatc caacttctga tctttgaatc tctctgttcc aacatgttct     60
gaaggagttc taagactttt cagaaagctt gtaacatgct tgtagacttt tctttgaatt    120
actcttgcaa actctgattg aacctacgtg aaaactgctc cagaagttct aaccaaattc    180
cgtcttggga aggcccaaaa tttattgagt acttcagttt catggacgtg tcttcaaaga    240
tttataactt gaaatcccat cattttaag agaagttctg ttccgcaatg tcttagatct    300
cattgaaatc tacaactctt gtgtcagaag ttcttccaga atcaacttgc atcatggtga    360
aaatctggcc agaagttctg aacttgtcat atttcttaac agttagaaaa atttctaagt    420
gtttagaatt ttgactttc caaagcaaac ttgactttg actttcttaa taaaacaaac     480
ttcatattct aacatgtctt gatgaaatgt gattcttgaa atttgatgtt gatgcaaaag    540
tcaaagtttg acttttcagt gtgcaattga ccattttgct cttgtgccaa ttccaaacct    600
aaattgatgt atcagtgctg caaacttgat gtcatggaag atcttatgag aaaattcttg    660
aagactgaga ggaaaaattt tgtagtacaa cacaaagaat cctgttttc atagtcggac    720 tagacacatt aacataaaac accacttcat tcgaagagtg attgaagaag gaaatgtgca    780 gttaccttc tgcagttcat aagagcaact tacagacact tttactaaaa tactacaaag    840
aggaagattt taacaactta gagaagtaat gggagttaaa gagcaacaca ttaagggga    900 gtgttaaaat taatgtgttg taaccaccac tacctttagt aagtattata agaaaattgt    960
aatcatcaca ttataattat tgtccttatt taaaattatg ataaagttgt atcattaaga   1020
ttgagaaaac caaatagtcc tcgtcttgat ttttgaatta ttgttttcta tgttactttt   1080
cttcaagcct atataaaaac tttgtaatgc taaattgtat gctggaaaaa aatgtgtaat   1140
gaattgaata gaaattatgg tatttcaaag tccaaaatcc atcaatagaa atttagtaca   1200
aaacgtaact caaaaatatt ctcttatttt aaatttaca acaatataa aatattctct    1260 tattttaaat tttacaataa tataattat cacctgtcac ctttagaata ccaccaacaa    1320
tattaatact tagatatttt attcttaata attttgagat ctctcaatat atctgatatt   1380 tatttttatat ttgtgtcata ttttcttatg ttttagagtt aaccctttata tcttggtcaa   1440 actagtaatt caatatatga gtttgtgaag gacacattga catcttgaaa cattggtttt   1500
aaccttgttg gaatgttaaa ggtaataaaa cattcagaat tatgaccatc tattaatata   1560
cttcctttgt cttttaaaaa agtgtgcatg aaaatgctct atggtaagct agagtgtctt   1620
gctggcctgt gtatatcaat tccatttcca gatggtagaa actgccacta cgaataatta   1680
gtcataagac acgtatgtta acacacgtcc ccttgcatgt ttttgccat atattccgtc   1740 tctttctttt tcttcacgta taaaacaatg aactaattaa tagagcgatc aagctgaac    1799

<210> SEQ ID NO 29
<211> LENGTH: 235
<212> TYPE: DNA
<213> ORGANISM: Brassica napus

<400> SEQUENCE: 29
```

-continued

```
cctgcagata gactatacta tgttttagcc tgcctgctgg ctagctacta tgttatgtta    60
tgttgtaaaa taaacacctg ctaaggtata tctatctata ttttagcatg gctttctcaa   120
taaattgtct ttccttatcg tttactatct tatacctaat aatgaaataa taatatcaca   180
tatgaggaac ggggcaggtt taggcatata tatacgagtg tagggcggag tgggg        235
```

<210> SEQ ID NO 30
<211> LENGTH: 664
<212> TYPE: DNA
<213> ORGANISM: Brassica napus

<400> SEQUENCE: 30

```
taaggatgac ctacccattc ttgagacaaa tgttacattt tagtatcaga gtaaaatgtg    60
tacctataac tcaaattcga ttgacatgta tccattcaac ataaaattaa accagcctgc   120
acctgcatcc acatttcaag tattttcaaa ccgttcggct cctatccacc gggtgtaaca   180
agacggattc cgaatttgga agattttgac tcaaattccc aatttatatt gaccgtgact   240
aaatcaactt taacttctat aattctgatt aagctcccaa tttatattcc caacggcact   300
acctccaaaa tttatagact ctcatcccct tttaaaccaa cttagtaaac gttttttttt   360
taattttatg aagttaagtt tttaccttgt ttttaaaaag aatcgttcat aagatgccat   420
gccagaacat tagctacacg ttacacatag catgcagccg cggagaattg tttttcttcg   480
ccacttgtca ctcccttcaa acacctaaga gcttctctct cacagcacac acatacaatc   540
acatgcgtgc atgcattatt acacgtgatc gccatgcaaa tctcctttat agcctataaa   600
ttaactcatc ggcttcactc tttactcaaa ccaaaactca tcaatacaaa caagattaaa   660
aaca                                                                664
```

<210> SEQ ID NO 31
<211> LENGTH: 199
<212> TYPE: DNA
<213> ORGANISM: Agrobacterium tumefaciens

<400> SEQUENCE: 31

```
aaccctgctt taatgagata tgcgagacgc ctatgatcgc atgatatttg ctttcaattc    60
tgttgtgcac gttgtaaaaa acctgagcat gtgtagctca gatccttacc gccggtttcg   120
gttcattcta atgaatatat cacccgttac tatcgtattt ttatgaataa tattctccgt   180
tcaatttact gattgtccg                                                199
```

<210> SEQ ID NO 32
<211> LENGTH: 558
<212> TYPE: DNA
<213> ORGANISM: Pisum sativum

<400> SEQUENCE: 32

```
gttcgagtat tatggcattg ggaaaactgt ttttcttgta ccatttgttg tgcttgtaat    60
ttactgtgtt ttttattcgg ttttcgctat cgaactgtga atggaaatg gatggagaag    120 agttaatgaa tgatatggtc cttttgttca ttctcaaatt aatattattt gttttttctc   180
ttatttgttg tgtgttgaat tgaaattat aagagatatg caaacatttt gttttgagta   240
aaaatgtgtc aaatcgtggc ctctaatgac cgaagttaat atgaggagta aaacacttgt   300
agttgtacca ttatgcttat tcactaggca acaaatatat tttcagacct agaaaagctg   360
caaatgttac tgaatacaag tatgtcctct tgtgttttag acatttatga actttccttt   420
atgtaatttt ccagaatcct tgtcagattc taatcattgc tttataatta tagttatact   480
```

```
catggatttg tagttgagta tgaaaatatt ttttaatgca ttttatgact tgccaattga    540
ttgacaacat gcatcaat                                                 558

<210> SEQ ID NO 33
<211> LENGTH: 1727
<212> TYPE: DNA
<213> ORGANISM: Linum usitatissimum

<400> SEQUENCE: 33
cacgggcagg acatagggac tactacaagc atagtatgct tcagacaaag agctaggaaa    60
gaactcttga tggaggttaa gagaaaaaag tgctagaggg gcatagtaat caaacttgtc   120
aaaaccgtca tcatgatgag ggatgacata atataaaaag ttgactaagg tcttggtagt   180
actctttgat tagtattata tattggtgag aacatgagtc aagaggagac aagaaaccga   240
ggaaccatag tttagcaaca agatggaagt tgcaaagttg agctagccgc tcgattagtt   300
acatctccta agcagtacta caaggaatgg tctctatact ttcatgttta gcacatggta   360
gtgcggattg acaagttaga aacagtgctt aggagacaaa gagtcagtaa aggtattgaa   420
agagtgaagt tgatgctcga caggtcagga gaagtccctc cgccagatgg tgactaccaa   480
ggggttggta tcagctgaga cccaaataag attcttcggt tgaaccagtg gttcgaccga   540
gactcttagg gtgggatttc actgtaagat ttgtgcattt tgttgaatat aaattgacaa   600
ttttttttat ttaattatag attatttaga atgaattaca tatttagttt ctaacaagga   660
tagcaatgga tgggtatggg tacaggttaa acatatctat tacccaccca tctagtcgtc   720
gggttttaca cgtacccacc cgtttacata aaccagaccg gaattttaaa ccgtacccgt   780
ccgttagcgg gtttcagatt tacccgttta atcgggtaaa acctgattac taaatatata   840 tttttattt gataaacaaa acaaaaatgt taatattttc atattggatg caattttaag   900
aaacacatat tcataaattt ccatatttgt aggaaaataa aagaaaaat atattcaaga   960 acacaaattt caccgacatg acttttatta cagagttgga attagatcta acaattgaaa  1020
aattaaaatt aagatagaat atgttgagga acatgacata gtataatgct gggttacccg  1080
tcgggtaggt atcgaggcgg atactactaa atccatccca ctcgctatcc gataatcact  1140
ggtttcgggt atacccattc ccgtcaacag gcctttttaa ccggataatt tcaacttata  1200
gtgaatgaat tttgaataaa tagttagaat accaaaatcc tggattgcat ttgcaatcaa  1260
attttgtgaa ccgttaaatt ttgcatgtac ttgggataga tataatagaa ccgaattttc  1320
attagtttaa tttataactt actttgttca aagaaaaaaa atatctatcc aatttactta  1380
taataaaaaa taatctatcc aagttactta ttataatcaa cttgtaaaaa ggtaagaata  1440
caaatgtggt agcgtacgtg tgattatatg tgacgaaatg ttatatctaa caaagtccaa  1500
aattcccatg gtaaaaaaaa tcaaaatgca tggcaggctg tttgtaacct tggaataaga  1560
tgttggccaa ttctggagcc gccacgtacg caagactcag ggccacgttc tcttcatgca  1620
aggatagtag aacaccactc cacccacctc ctatattaga cctttgccca accctcccca  1680
actttcccat cccatccaca aagaaaccga cattttttatc ataaatc               1727

<210> SEQ ID NO 34
<211> LENGTH: 400
<212> TYPE: DNA
<213> ORGANISM: Arabidopsis thaliana

<400> SEQUENCE: 34
aaagataata acaaaagcct actatataac gtacatgcaa gtattgtatg atattaatgt    60
```

```
-continued ttttacgtac gtgtaaacaa aaataattac gtttgtaacg tatggtgatg atgtggtgca      120
ctaggtgtag gccttgtatt aataaaaaga agtttgttct atatagagtg gtttagtacg      180
acgatttatt tactagtcgg attggaatag agaaccgaat tcttcaatcc ttgcttttga      240
tcaagaattg aaaccgaatc aaatgtaaaa gttgatatat ttgaaaaacg tattgagctt      300
atgaaaatgc taatactctc atctgtatgg aaaagtgact ttaaaaccga acttaaaagt      360
gacaaaaggg gaatatcgca tcaaaccgaa tgaaaccgat                            400
```

PLANT SEED OIL

RELATED APPLICATIONS

This application is a national stage application (under 35 U.S.C. §371) of PCT/EP2009/054916, filed Apr. 23, 2009, which claims benefit of European application 08155186.3, filed Apr. 25, 2008.

SUBMISSION OF SEQUENCE LISTING

The Sequence Listing associated with this application is filed in electronic format via EFS-Web and hereby incorporated by reference into the specification in its entirety. The name of the text file containing the Sequence Listing is Sequence Listing_13987_00130_US. The size of the text file is 154 KB, and the text file was created on Oct. 21, 2010.

BACKGROUND OF THE INVENTION

The invention relates to a plant seed oil, comprising arachidonic acid comprising approximately 7 to approximately 26 percent by weight of the total fatty acid content, the ratio of the percentages by weight of arachidonic acid to gamma-linolenic acid being approximately 1:1 to approximately 5:1 and the ratio of the percentages by weight of arachidonic acid to dihomo-gamma-linolenic acid being approximately 1:1 to approximately 5:1. The invention furthermore relates to processes for the production of this plant seed oil and also formulations and uses of the plant seed oil. In particular, the invention also makes foodstuffs and baby food available that comprise the plant seed oil mentioned.

Arachidonic acid (ARA) is a long-chain, polyunsaturated fatty acid of the omega-6 (n-6) class (C20:4 5,8,11,14-eicosatetraenoic acid). Below, polyunsaturated fatty acids are designated as PUFA, PUFAs, LCPUFA or LCPUFAs (poly unsaturated fatty acids, PUFA; long chain poly unsaturated fatty acids, LCPUFA).

ARA is the most frequently occurring C20-PUFA in human blood plasma (Siguel and Schaefer (1988) Aging and nutritional requirements of essential fatty acids. In: Dietary Fat Requirements in Health and Development (Beare-Rogers, ed.) pp 163-189, American Oil Chemist's Society, Champaign, Ill.). It is especially present in organ, muscle and blood tissue, where it fulfills an important function as a structural lipid that is predominantly associated with phospholipids in blood, liver, muscles and other important organ systems. In addition to its principal function as a structural lipid, ARA also serves as a direct precursor for a series of circulating eicosanoids such as prostaglandin E2 (PGE2), prostacyclin 12 (PGI2), thromboxane A2 (TxA2) and the leukotrienes B4 (LTB4) and C4 (LTC4). These eicosanoids influence growth control, the inflammatory defense reaction, blood rheology, vascular tone, the leukocyte function and platelet activation (Calder 2006, Prostaglandins Leukot Essent Fatty Acids. 75:197-202; Roland et al. 2004, Mini Rev Med Chem. 4:659-68).

Human breast milk in all stages of lactation comprises a considerable proportion of ARA. This amounts to approximately 0.2 to 1.0% of the total content of fatty acids (Brenna et al. 2007 AJCN 85:1457). The concentration depends on the lactation stage, on the nutritional state of the mother and on environmental conditions. Therefore organizations such as the "World Association of Perinatal Medicine", the "Early Nutrition Academy", the "Child Health Foundation", the "World Health Organization", the "British Nutrition Foundation", the "European Society of Paediatric Gastroenterology and Nutrition", and the "International Society for the Study of Fatty Acids and Lipids", in cases in which breast-feeding is not an option, recommend the use of baby food that is supplemented, inter alia, with ARA (Koletzko et al. 2008, J Perinat Med. 2008;36:5-14; Diersen-Schade et al. 2005 Lipid Technology 17:225). ARA is meanwhile also being added by more and more manufacturers of infant food in order to match this with the breast milk. Interestingly, the concentration of ARA in the breast milk in general varies less than that of docosahexaenoic acid (DHA, 0.1 to more than 1.0% of the total content of fatty acids) (Diersen-Schade 2005 LipTech 17:225; Innis 2007 ProcNutrSoc 66:397; Brenna et al. 2007 AJCN 85:1457), which points to a more exact physiological regulation, in order that the ARA content necessary for the infant food is available.

The potential health advantages that ARA offers for infants in the pre-, pen- and postnatal stages lie in the encouragement of brain development and functions and also in an improved development of the eyes (Diersen-Schade et al. 2005 Lipid Technology 17:225). The agreeing recommendations and practical guidelines for health care that are recommended by the "World Association of Perinatal Medicine", the "Early Nutrition Academy" and the "Child Health Foundation" underline the importance of an adequate intake of ARA with baby food (Koletzko et al. 2008, J Perinat Med. 2008; 36:5-14). In particular the fetus and the newborn child should receive LC-PUFA in adequate amount in order to support optimum visual and cognitive development. It is assumed that for the newborn child up to the age of approximately two years advantages result on account of nutritional supplementation with ARA.

From May 2001, infant food supplemented by ARA was no longer a niche product, because ARA evolved in the highly developed countries to be an almost obligatory constituent of infant milk. This development was also supported in that the US "Food and Drug Administration" (FDA) had given a positive assessment to Martek's GRAS classification with regard to the use of DHASCO® (DHA, *Crypthecodinium cohnii*) and ARASCO® (ARA, *Mortierella alpina*) oil mixtures in infant foods. The abbreviation "GRAS" designates here the classification "Generally Recognized as Safe", i.e. as safe for use in foodstuffs. The addition of ARA to the infant milk and thus also to the ARA market was on the one hand expedited by Martek's exertion of influence and on the other hand by the fact that the potential health advantages of ARA for the development of infants were increasingly recognized.

Apart from ARA, DHA (docosahexaenoic acid) is also an important fatty acid that should be added to infant food. DHA occurs in human breast milk, and it is assumed that the development of the brain, the nerve tissue and the eyes of the growing infant is supported. It was demonstrated that the addition of DHA in effective concentrations both in the case of infants born at the calculated term and in the case of infants born too early improves the cognitive development of visual acuity.

In addition to ARA and DHA, breast milk comprises still further high-grade unsaturated fatty acids, which are less researched, but also play a great role for the development of the infant. These fatty acids are, for example, gamma-linolenic acid (GLA, 0.1-0.2% of the total content of fatty acids), dihomo-gamma-linolenic acid (DGLA, 0.2-0.4% of the total content of fatty acids), stearidonic acid (SDA, up to 0.1% of the total content of fatty acids) and eicosapentaenoic acid (EPA, 0.05-0.3% of the total content of fatty acids) (Yuhas et al. 2006 Lipids 41:851-8). In order to match the substitute food as well as possible with the breast milk, it is important to integrate these high-grade unsaturated fatty acids into the lipid content of the infant food.

The role of the high-grade unsaturated n-6-fatty acids GLA and DGLA is currently being investigated. The presence of GLA and DGLA in the breast milk supports the fact that, independently of ARA, they are important for the development of the nursing infant. Research shows that the n-6 fatty acids of the infant compete with one another in the physiological integration into the human tissue lipids (Al et al. 2008, Am J Clin Nutr 71:285S-91S). It is therefore important that a balanced fatty acid pattern is made possible in the case of expectant and nursing mothers (Geppert et al. 2008, Br. J. Nutrition 99: 360-9).

The potential advantages of the early additional administration of GLA include a reduced total IgE value in the first year of life in the case of infants who suffer from atopic dermatitis or atopic eczema, a frequent hereditary skin disorder (Demmelmair H., Feldl F., Horvath I. et al. Influence of formulas with borage oil or borage oil plus fish oil on the arachidonic acid status in premature infants, Lipids 2001; 36:555-66. Kitz R., Rose M A., Schonborn H., Zielen S., Bohles H J. Impact of early dietary gamma-linolenic acid supplementation on atopic eczema in infancy. Pediatr. Allergy Immunol. 2006, 17:112-7). The tendency is also seen that by the additional administration of GLA in children with a high familial risk of atopic dermatitis the disorder can be kept under control in late infancy (van Gool et al. 2003, Am J Clin Nutr 77:943). Although the frequency of atopic eczema cannot be influenced or decreased by GLA supplied the food (Kritz et al. 2006), the total IgE value in the case of children who suffer from atopic eczema appears to decrease as a result of the additional administration of GLA in the first year of life (Kritz et al. 2006). DGLA is a precursor in the synthesis of prostaglandin El (PGE1) and also the series 3 prostaglandins (Das 2008, Lipids in Health and Disease 7:9). Other advantages of DGLA supplementation in baby milk were also shown. For example, DGLA influences cytokine production in human Peripheral Blood Mononuclear Cells independently of cyclooxygenase activation (Dooper et al. 2003 Immunology 110:348-57). This points to a reinforcement of the immune function by DGLA, which is also of importance for the newborn child. Moreover, an increase in the concentration of DGLA and ARA in the newborn child food decreases the risk of HIV virus transmission between mother and child (Villamor et al. 2007 Am J Clin Nutr 86:682-689).

There is thus a need for baby food that allows the baby an adequate intake of long-chain polyunsaturated fatty acids in order to support the optimum development of the baby.

SUMMARY OF THE INVENTION

This technical problem is solved by a plant seed oil, comprising arachidonic acid comprising approximately 7 to approximately 26 percent by weight of the total fatty acid content, the ratio of the percentages by weight of arachidonic acid to gamma-linolenic acid being approximately 1:1 to approximately 5:1 and the ratio of the percentages by weight of arachidonic acid to dihomo-gamma-linolenic acid being approximately 1:1 to approximately 5:1.

BRIEF DESCRIPTION OF THE FIGURES

FIG. 7 shows the fatty acid ratios in breast milk (Reference: Yuhas et 25 al. 2006 Lipids 41:851-8).

DETAILED DESCRIPTION OF THE INVENTION

Figure 1:
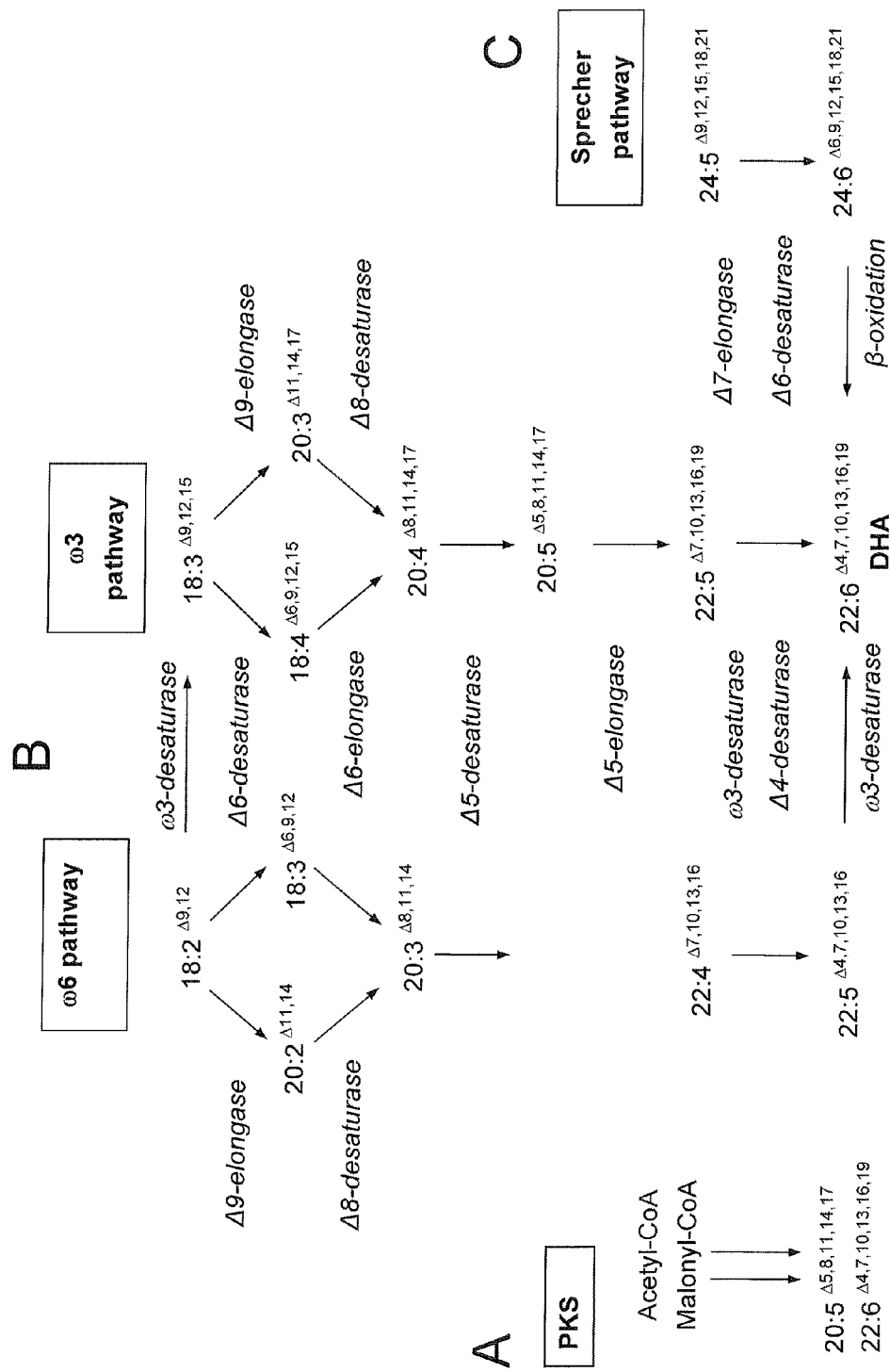
FIG. 1 shows the metabolic pathways for the synthesis of long chain polyunsaturated fatty acids.

In contrast to the experiments previously carried out for the preparation of arachidonic acids in transgenic plants, such as, for example, in WO2005/083093 or Kajikawa et al. (Biosci. Biotechno. Biochem., 72, 70549-1-10, 2008), or of oils from microorganisms, such as, for example, oils from *Mortierella alpina*, the plant seed oil according to the invention has surprising, novel properties. In particular, the plant seed oil of the invention mentioned has quantitative ratios between the fatty acids arachidonic acid (ARA) and gamma-linolenic acid (GLA) as well as arachidonic acid and dihomo-gamma-linolenic acids (DGLA)) such as are also present in breast milk. In breast milk, the ratio between arachidonic acid (ARA) and gamma-linolenic acid (GLA) is approximately 2:1 to 4:1 and between arachidonic acid and dihomo-gamma-linolenic acids (DGLA) approximately 1:1 to 2:1 (Yuhas et al. 2006 Lipids 41:851-8). FIG. 7 gives a survey on this point about the fatty acid ratios in breast milk.

In the plant seed oil according to the invention, the ratio of the percentages by weight of arachidonic acid to gamma-linolenic acid is approximately 1:1 to approximately 5:1 and the ratio of the percentages by weight of arachidonic acid to dihomo-gamma-linolenic acid is approximately 1:1 to approximately 5:1.

If not stated otherwise, the ratios mentioned herein relate to the ratios of the percentages by weight of the respective fatty acids.

Thus the plant seed oil according to the invention also offers a favorable ratio of arachidonic acid to GLA and arachidonic acid to DGLA in addition to a high content of arachidonic acid with its physiologically positive action. GLA and DGLA are, in addition to arachidonic acid, important components of the fat fraction of breast milk (Wang et al. Pediatrics International 2000, 42(1):14-20; Yuhas et al. 2006 Lipids 41:851-8). The most recent research moreover shows that the n-6 fatty acids of the infant compete with one another in the physiological integration into the human tissue lipids (Geppert et al. 2008, Br. J. Nutrition 99: 360-9). Therefore only a balanced ratio of the fatty acids in the infant food makes possible optimum growth and optimum development of the infant. With the plant seed oil according to the invention, it was thus possible to obtain a composition that is very close to the fatty acid composition in breast milk. It was possible to achieve this ratio of arachidonic acid to GLA and arachidonic acid to DGLA that comes very close to breast milk by the production of transgenic plants that express an acyl-CoA-dependent delta-6 desaturase. This delta-6 desaturase originates from *Ostreococcus tauri*. Only the use of this enzyme in the specific promoter gene combination as is present in the nucleic acid constructs according to the invention made possible the production of a plant seed oil that is distinguished for the first time by low contents of gamma-linolenic acid and dihomo-gamma-linolenic acid in comparison to the oils described in the prior art. Known delta 6-desaturases, such as used and described, for example, in WO2005/083093, use linoleic acid esterified in the sn-2 position with phospholipids, such as, for example, phosphatidylcholine, phosphatidylethanolamine, phosphatidylinositol, or phosphatidylglycol, as a substrate. For the delta 6-desaturase from *Ostreococcus tauri*, it was possible to show a different substrate utilization in yeast model studies, as described in WO2006/069710. The nucleic acid constructs according to the invention described further below and in the examples were now prepared for the transformation of rape (*Brassica napus*) and transgenic rape plants were produced with this property. Surprisingly, seed oils of these plants show low contents of GLA and DGLA (FIG. 3B and Table 3), from which the following synthesis sequence can be derived: the delta 6-desaturase uses linolate-CoA as a substrate. The product gamma-linolate-CoA is reacted directly by the A6-elongase as a substrate to give dihomo-gamma-linolenate-CoA. The product of the elongation reaction is converted by acyl transferases in the sn2 position of phospholipids and reacted by the delta 5-desaturase to give arachidonic acid-phosphatidylcholine, or other phospholipids described above. By means of acyltransferases, arachidonic acid is converted to triacylglycerides (i.e. oil) and is thus a component of the seed oil.

In particular, it was possible to show that the intermediate products of the synthesis corresponding to the promoter and gene activity could be influenced in their concentration. In the nucleic acid constructs according to the invention described here, the invention identifies promoter-gene combinations for the production of plant seed oils with a fatty acid composition that is similar to breast milk and therefore advantageously suitable for the production of baby food. It was only possible to achieve this with the specific promoter-gene combinations present in the nucleic acid constructs according to the invention of SEQ ID NOs. 15, 16 and 17.

The plant seed oil according to the invention can be used in various concentrations for infant milk or other food products for infants. In the concentrations and formulations specified herein, the plant seed oil according to the invention has a fatty acid profile that comes closest to that of breast milk than all of the products used earlier. Thus the plant seed oil according to the invention allows a direct integration of the high-grade unsaturated fatty acids into the lipid fraction of the infant food, in order to match the substitute food as well as possible with breast milk. As a result of its favorable content of ARA, GLA and DGLA, the plant seed oil according to the invention is particularly suitable for the food of newborn infants and babys up to the age of approximately 2 years in order to guarantee healthy development, particularly of the nervous system and eyes and also of the immune system, of the newborn infant or baby. By mixing or formulation of the plant seed oil according to the invention with a limited number of vegetable and non-vegetable oils, such as microbial oils or fish oils, an even better match of the substitute food with the fatty acid pattern of the breast milk can be achieved. The plant seed oil according to the invention moreover has a background fatty acid profile that is similar to that of rape or canola oil, which is used, inter alia, for infant food. The plant seed oil according to the invention is thereby better suited as an ARA source than the ARA source ARASCO® most used at present.

For example, ARASCO® comprises fatty acids largely foreign to human breast milk such as, for example, C22:0, C24:0 and C22:5 n-6 in concentrations up to 3% (Australia New Zeland Food Authority 2002, Proposal P93—Review Of Infant Formula, Supplementary Final Assessment (Inquiry—S.24), Report, 08/02). The plant seed oil according to the invention is clearly below ARASCO® in these fatty acids and moreover comprises large amounts of C18:1 n-9, which is the most frequent fatty acid in breast milk (Innis & King, Am J Clin Nutr 1999, 70:383-90).

The plant seed oil according to the invention is distinguished in contrast to the conventional oils described in the prior art, such as microbial oils from *Mortierella alpina* or *Crypthecodinium cohnii* or fish oils from salmon, whale or egg yolk, in that arachidonic acid and gamma-linolenic acid and also arachidonic acid and dihomo-gamma-linolenic acid are present for the first time in a more balanced ratio that comes closest to that of breast milk. Table 4 in the following examples gives an exemplary survey of the mentioned quantitative ratios of the fatty acids in the plant seed oil according to the invention in comparison to oils from various organisms that either produce arachidonic acid naturally or were transferred in the genes for the metabolic pathway. Thus in the seed oil from *Brassica juncea* described in WO2005/083093 the ratio between the fatty acids arachidonic acid (ARA) and gamma-linolenic acid (GLA) is approximately 1:1 and greater than 1:1 (i.e. more GLA als ARA), and between arachidonic acid and dihomo-gamma-linolenic acids (DGLA) approximately 1:5 and less (i.e. even less DGLA than ARA than in the ratio 1:5). In the oil from *Marchantia polymorpha*, the ratio between the fatty acid arachidonic acid (ARA) and gamma-linolenic acid (GLA) is approximately 1:4 to 1:5 and between arachidonic acid and dihomo-gamma-linolenic acids (DGLA) approximately 1:10 and more (i.e. even less DGLA than ARA than in the ratio 1:10). In the oil from *Glycine max*, the ratio between the fatty acid arachidonic acid (ARA) and gamma-linolenic acid (GLA) is approximately 0.1:1 to 0.15:1 and between arachidonic acid and dihomo-gamma-linolenic acids (DGLA) approximately 0.18:1 to 0.2:1. The content of arachidonic acid in the oil from Glycine was 2-3%, since the previous processes were not able to yield any commercially utilizable arachidonic acid contents. In the oil from *Mortierella alpina* (Suntory TGA40), the ratio between the fatty acid arachidonic acid (ARA) and gamma-linolenic acid (GLA) is more than 10:1 and between arachidonic acid and dihomo-gamma-linolenic acids (DGLA) likewise more than 10:1. In breast milk, however, the ratio between arachidonic acid (ARA) and gamma-linolenic acid (GLA) is approximately 2:1 to approximately 4:1 and between arachidonic acid and dihomo-gamma-linolenic acids (DGLA) approximately 1:1 to approximately 2:1 (Yuhas et al. 2006 Lipids 41:851-8).

In the plant seed oil according to the invention, the ratio of the percentages by weight of arachidonic acid to gamma-linolenic acid is approximately 1:1 to approximately 5:1 and the ratio of the percentages by weight of arachidonic acid to dihomo-gamma-linolenic acid is approximately 1:1 to approximately 5:1 and thus for the first time in the ranges that are also present in breast milk.

The invention thus relates in particular to a plant seed oil comprising arachidonic acid with a content of approximately 7 to approximately 26 or 7 to 26 percent by weight of the total fatty acid content, the ratio of the percentages by weight of arachidonic acid to gamma-linolenic acid being approximately 1:1 to approximately 5:1 or 1:1 to 5:1 and the ratio of the percentages by weight of arachidonic acid to dihomo-gamma-linolenic acid being approximately 1:1 to approximately 5:1 or 1:1 to 5:1.

The arachidonic acid content in the plant seed oil according to the invention is between approximately 7 and approximately 26 percent by weight or between 7 and 26 percent by weight, preferably between approximately 10 and approximately 26 percent by weight or between 10 and 26 percent by weight, even more preferably between approximately 12 and approximately 26 percent by weight or between 12 and 26 percent by weight, or between approximately 15 and approximately 26 percent by weight or between 15 and 26 percent by weight, in the total fatty acid content. Particularly preferably, the arachidonic acid content in the plant seed oil according to the invention is 15 percent by weight of the total fatty acid content. The composition of such an oil is described further below and in the examples.

In a preferred embodiment of the plant seed oil of the invention, the ratio of the percentages by weight of linoleic acid to alpha-linolenic acid is approximately 3:1 to approximately 12:1 or 3:1 to 12:1, preferably approximately 4:1 to approximately 12:1 or 4:1 to 12:1, even more preferably approximately 5:1 to approximately 12:1 or 5:1 to 12:1 or approximately 6:1 to approximately 12:1 or 6:1 to 12:1.

The plant seed oil according to the invention, like breast milk, comprises the essential fatty acids linoleic acid and alpha-linolenic acid. With regard to the ratio of linoleic acid to alpha-linolenic acid, the plant seed oil according to the invention supplements the oils mainly used in infant food products, such as soybean oil or sunflower oil. The infant nutrition products supplemented by the plant seed oil according to the invention come very close to the linoleic acid to alpha-linolenic acid ratios that are present in breast milk. The ratio here is about 7:1 to 18:1 (Yuhas et al. 2006 Lipids 41: 851-8).

In a further preferred embodiment of the plant seed oil of the invention, the ratio of the percentages by weight of arachidonic acid to eicosapentaenoic acid is approximately 3:1 to approximately 7:1 or 3:1 to 7:1, preferably approximately 4:1 to approximately 7:1 or 4:1 to 7:1 and even more preferably approximately 5:1 to approximately 7:1 or 5:1 to 7:1, and also reflects here the ratio ARA:EPA present in breast milk of about 2:1 to about 7:1 (Yuhas et al. 2006 Lipids 41: 851-8).

In a further embodiment, the plant seed oil of the invention also comprises the fatty acid stearidonic acid. Preferably, stearidonic acid is present with a content of approximately 0.1 to approximately 1 or 0.1 to 1 percent by weight in the total fatty acid content (particularly if used in the infant food), preferably of approximately 0.3 to approximately 1 or 0.3 to 1 percent by weight, or approximately 0.4 to approximately 1 or 0.4 to 1 percent by weight, particularly preferably of approximately 0.5 to approximately 1 or 0.5 to 1 percent by weight.

For the measurements of the oil specifications, variation ranges always apply that are based on the individual development of the organism, the digestion and extraction process and the apparatus measuring accuracy. The ratios mentioned herein are for this reason referred to by the terms "approximately", "about", or "for example".

Dihomo-gamma-linolenic acid, ARA and EPA are precursors of the biologically active eicosanoids (Das 2008 Lipids Health Dis. 7:9). This is of particular importance for premature and newborn infants, whose metabolism is not yet adequately developed. ARA and DHA are important components of specific membrane phospholipids and of great importance for the development of the nervous system, the retina and visual functions. SDA, ARA, EPA and DHA are comprised in breast milk and therefore essential constituents of premature infant and infant starting foods (Yuhas et al. 2006 Lipids 41:851-8). Thus the plant seed oil according to the invention not only for the first time comprises a high content of ARA and a balanced ratio of ARA to GLA and DGLA than all oils previously described in the prior art. With the essential fatty acids linoleic acid and alpha-linolenic acid and also the high-grade unsaturated fatty acids SDA and EPA, it comprises further components that also occur in the breast milk. DHA can be added, for example, by mixing with other oils, as described in more detail below. The background fatty acid profile of the oil according to the invention thus comes very close to the fatty acid composition of breast milk.

In a further preferred embodiment, the plant seed oil is obtained from a transgenic plant.

The term "transgenic" is to be understood as meaning that a heterologous polynucleotide, that is a polynucleotide not occurring naturally in the respective plant, is inserted into the plant. This can either be achieved by random insertion of the polynucleotide or by homologous recombination. Of course, instead of the polynucleotide a vector can also be inserted. Methods for the insertion of polynucleotides or vectors for the purpose of random insertion or homologous recombination are known in the prior art and also described in more detail below. Host cells that comprise the polynucleotide or the vector can likewise be inserted into a plant and thus produce a transgenic plant. Such a plant is then, however, a chimeric plant in which only the cells that are derived from the inserted cells are transgenic, i.e. comprise the heterologous polynucleotide. Preferably, a nucleic acid construct according to the invention as shown in the SEQ ID NOs. 15, 16 or 17 is inserted into the transgenic plant.

Preferably, the transgenic plants are oil-producing plants, that is those that are used for the production of oils.

The transgenic plants used can fundamentally be all plants, i.e. both dicotyledonous and monocotyledonous plants. Preferably, they are oilseed plants that comprise large amounts of lipid compounds, such as rape, canola, false saffron (safflower, *Carthamus tinctoria*), flax or else field crops such as corn.

Preferably, the plant seed oil according to the invention is produced in transgenic rape, transgenic soybeans, transgenic flax, transgenic false saffron or transgenic corn, which are transformed using a nucleic acid construct as shown in SEQ ID NOs. 15, 16 or 17.

Very particularly preferably, the transgenic plant is transgenic rape.

Table 1 in the following examples shows the genes preferably used for the synthesis of ARA having the preferred fatty acid composition.

The invention also relates to the nucleic acid constructs as shown in SEQ ID NOs. 15, 16 and 17 and transgenic plants that are transformed using these nucleic acid constructs and their descendants that have stably integrated the nucleic acid construct in the genome.

If a plant seed oil comprising DHA is to be produced, the nucleic acid constructs according to the invention comprise, additionally to the abovementioned genes, suitable promoter gene terminator cassettes that preferably comprise the DNA from *Ostreococcus tauri* coding for the delta 5-elongase as shown in SEQ ID NO. 18 and or the DNA from *Traustochytrium* ssp. coding for the delta 4-desaturase as shown in SEQ ID NO. 20. The DNAs and suitable cassettes mentioned are described, for example, in WO2005/083093.

The invention moreover relates to a plant seed oil comprising a fatty acid spectrum comprising palmitic acid, stearic acid, oleic acid, linoleic acid, gamma-linolenic acid, alpha-linolenic acid, stearidonic acid, dihomo-gamma-linolenic acid, arachidonic acid and eicosapentaenoic acid. Such a fatty acid spectrum is shown in, for example, FIG. 3B.

Even more preferably, the plant seed oil of the invention comprises approximately 3.2-5.3% of palmitic acid, approximately 2.2-5.3% of stearic acid, approximately 10-25% of oleic acid, approximately 22-36% of linoleic acid, approximately 4-12% of gamma-linolenic acid, approximately 3-8% of alpha-linolenic acid, approximately 0.2-1% of stearidonic acid, approximately 3-9% of dihomo-gamma-linolenic acid, approximately 12-25% of arachidonic acid and approximately 1-4% of eicosapentaenoic acid based on the total fatty acid content; or the plant seed oil of the invention comprises 3.2-5.3% of palmitic acid, 2.2-5.3% of stearic acid, 10-25% of oleic acid, 22-36% of linoleic acid, 4-12% of gamma-linolenic acid, 3-8% of alpha-linolenic acid, 0.2-1% of stearidonic acid, 3-9% of dihomo-gamma-linolenic acid, 12-25% of arachidonic acid and 1-4% of eicosapentaenoic acid based on the total fatty acid content.

Particularly preferably, the plant seed oil according to the invention comprises the fatty acids important for the infant food in the following percentages by weight (mass of the fatty acids in percent of the total fatty acid content)

|  | % |
|---|---|
| Target fatty acid | |
| arachidonic acid (20:4 n-6) | about 15 |
| Essential fatty acids: | |
| linoleic acid (18:2 n-6) | about 20-25 |
| alpha-linolenic acid (18:3 n-3) | about 3-7 |
| Additional fatty acids useful for the infant: | |
| gamma-linolenic acid (GLA) (18:3 n-6) | about 6-11 |
| dihomo-gamma-linolenic acid (DGLA)(20:3 n-6) | about 4-8 |
| stearidonic acid (SDA) | about 1-2 |
| eicosapentaenoic acid (EPA) | about 2-4; |
| or | |
| Target fatty acid | |
| arachidonic acid (20:4 n-6) | 15 |
| Essential fatty acids: | |
| linoleic acid (18:2 n-6) | 20-25 |
| alpha-linolenic acid (18:3 n-3) | 3-7 |
| Additional fatty acids useful for the infant: | |
| gamma-linolenic acid (GLA) (18:3 n-6) | 6-11 |
| dihomo-gamma-linolenic acid (DGLA)(20:3 n-6) | 4-8 |
| stearidonic acid (SDA) | 1-2 |
| eicosapentaenoic acid (EPA) | 2-4. |

The invention furthermore relates to a formulation or a mixed oil, comprising a plant seed oil according to the invention and at least one further oil selected from the group consisting of plant oil, microbial oil and fish oil, the plant oil, microbial oil or fish oil comprising docosahexaenoic acid.

The plant seed oil according to the invention can be mixed with one or more oils, in order, for example, to change, i.e. to increase or to reduce, the content of one or more fatty acids. The admixed oil can be, for example, a further naturally occurring or transgenic plant oil or plant seed oil. An example which may be mentioned is linseed oil, which comprises a high proportion of alpha linolenic acid. It can also be a microbial oil, for example an oil from Mortierella alpina or from *Crypthecodinium cohnii*. Particularly suitable here are DHASCO® (DHA, *Crypthecodinium cohnii*) and ARASCO® (ARA, *Mortierella alpina*) oil mixtures, that are used, for example in infant foods. By means of the admixture of DHASCO® (DHA, *Crypthecodinium cohnii*) to the plant seed oil according to the invention, it is possible, for example, to introduce the fatty acid DHA. However, fish oils are also suitable for the formulation of the plant seed oil of the invention, for example salmon oil, herring oil, mackerel oil, tuna fish oil or cod oil (United States Department of Agriculture 2005, "Nutrition and Your Health: Dietary Guidelines for Americans" EPA and DHA Content of Fish Species, Data From NDB SR 16-1; see also, for example, GRAS Notifications 94, 109 and 193), in order, for example, to change the composition of the fatty acids in the plant seed oil according to the invention. Fish oils are distinguished, inter alia, by high content of long-chain, polyunsaturated omega-3 fatty acids. The plant seed oil of the invention can be mixed with only one further oil, but also with two, three or even more oils. The one oil or the further admixed oils can originate here from the same organism or from different organisms. For example, the plant seed oil according to the invention can be formulated with a microbial oil, e.g. an oil from Mortierella alpina or from *Crypthecodinium cohnii* or *Schizochytrium* sp. (Arterburn et al. 2007_Lipids 42-1011-24), and/or a fish oil (for example salmon oil or tuna fish oil). Formulations of plant seed oils are described in the prior art. For example, the plant seed oil according to the invention can also be processed in an infant food with the BASF powder product number 30056967, "Dry n-3® 5:25 C Powder Microencapsulated fish oil rich in DHA for Infant formula". Alternatively, DHASCO® (docosahexaenoic acid-rich single-cell oil) can also be used as a source of DHA as described in the GRAS Notice No. GRN 000041. Here, the plant seed oil according to the invention can first be converted to a microencapsulated powder similarly to the abovementioned BASF product or used directly as a processed and stabilized plant seed oil. Both of these powders or oils can then be mixed or added individually to the desired amounts of the infant food product. The addition takes place toward the end of the production of the infant food product with protective measures against oxidation. Preferred concentrations at which the products are added to the infant food depend on various factors. A preferred amount for the addition of the plant seed oil according to the invention based on the end product is that amount of oil which results in a concentration of up to 1 g of ARA/100 g of the total fat in the infant food product. A preferred amount for the addition of the BASF product number 30056967 or of the DHASCO® oil based on the final product is that amount of the powder or oil which results in a concentration of up to 1 g of DHA/100 g of the total fat in the infant food product. The preferred amounts of the plant seed oil according to the invention and of the BASF product number 30056967 or of the DHASCO oil can depend, inter alia, on the national legislation of the individual countries in which the infant food product is marketed, on the manufacturer's product demands and on the customer demands.

The invention moreover makes available a foodstuff which comprises a plant seed oil according to the invention.

The plant seed oil according to the invention can be used, for example, directly as a cold-pressed oil, e.g. as salad oil. It can also be used, for example, in milk or milk products such as cheese or yogurt. It is also possible, however, to add it to margarine, or bread or bakery products. Finally, it is generally suitable as a food supplement (supplement). These are to be understood as meaning products for the increased supply of the human metabolism with certain nutrients or active ingredients in the border area between medicaments and foodstuffs.

Legally, this product group of food supplements is controlled in EU law by the guideline 2002/46/EC. In this, the permissible minerals and vitamins are specified in particular. In the food supplement directive based on this, a food supplement is: "a food that is intended to supplement the general nutrition, a food concentrate or other substances having nutrition-specific or physiological action alone or in combination and is marketed in dose form, in particular in the form of capsules, pastilles, tablets, pills, effervescent tablets and other similar administration forms, sachets, liquid ampoules, bottles with drop inserts and similar administration forms of liquids and powders for taking in measured small amounts". Since legally they belong to the foodstuffs, in Germany they come under the regulations of the Lebensmittel- and Futtergesetzbuch (LFGB; German food and feed code). The ingredients allowed are listed in Appendix 1 of the Nahrungsergänzungsmittelverordnung (NemV; Food supplement directive).

The plant seed oil according to the invention can be used here alone or in combination with one oil or further oils such as, for example, microbial oil, for example from Mortierella alpina or Crypthecodinium cohnii or fish oil for food supplementation. Tocopherols, e.g. vitamin E and tocotrienols and ascorbyl palmitate or plant extracts such as, for example, rosemary and plant sterols, or carotenoids such as, for example, lutein, zeaxanthin, astaxanthin and lycopene, or coenzymes such as, for example, coenzyme Q can also be added. Suitable administration forms here are capsules, pastilles, tablets, pills, effervescent tablets and other suitable administration forms, sachets, liquid ampoules, bottles with drop inserts and similar administration forms of liquids and powders for taking the plant seed oil according to the invention in measured small amounts. The dosage of the fatty acids for food supplementation is adequately described in the prior art.

The invention preferably relates here to a baby food which comprises the plant seed oil according to the invention.

If not breast-fed, baby food serves in the first months of life after birth as the sole food. The term "baby food" as used here comprises, for example, premature infant food, infant formula, infant food, or small child food. Premature infant food here means food for newborn children who are born before the calculated delivery date. Infant formulas are foods that are intended for the specific nourishment of infants during the first four to six months after birth (that is from birth up to the age of four to six months) and on their own meet the nutritional requirements of this group of persons. Infant food is to be understood as meaning food for infants, where small children up to approximately twelve months are meant by infants (birth up to the age of 12 months). Small child food is to be understood as meaning food that is given to small children up to the age of approximately twenty-four months (birth to 24 months). The LC-PUFA contents for such applications in the feeding of babies or small children of age about 4-6 months to 24 months are in the same area as for infant formulas based on the fat content of the food. The composition of an exemplary infant formula that comprises the plant seed oil according to the invention is shown in the following examples. The plant seed oils according to the invention can be employed, for example, in replacement mother's milk, in follow-on milk (for example after weaning the infant from the mother's breast) or as complementary food, for example as an addition of baby cereal, bottled baby food, reconstituted dry food, milk and milk substitute drinks, juice and other warm or cold drinks and dietary foodstuffs. The plant seed oils of the invention can, however, also find applications in the diet of pregnant mothers and also breast-feeding mothers, since the LC-PUFAs can reach the breast milk. Moreover, they can also be utilized for food supplement purposes for children of age up to 24 months, but also for older children and adults. Food supplements can be given in any form, for example in the form of milk, juice, purée, syrup, candy, fermented product, pills, capsules or coated tablets.

Baby food or infant food as used herein is to be understood as meaning a generic term for all foodstuffs that are particularly suitable for the nutrition of infants or small children up to 24 months. These also include breast milk. Industrial convenience baby food is generally produced without salt, spices, sugar and mostly also without colorants and preservatives. A differentiation is made here in terms of foodstuffs law between infant formula, follow-on food and complementary food (Lebensmittel-Lexikon Dr. Oetker [Dr. Oetker Foodstuff Encyclopedia], 4th ed. 2004, infant food article).

A differentiation can be made here between:

Infant Formula (0 to 6 Months)

Infant formula is designated in terms of foodstuffs law as all foodstuffs and products that are intended especially for feeding in the first six months of life and comprise all nutrients that the infant needs. For the preparation of the finished products, in some cases water is additionally added.

Follow-on Food (4 to 24 Months)

Follow-on food for infants in foodstuffs law are all foodstuffs and products that are intended especially for infants approximately from the fourth month and like the starter formula have a liquid consistency, but comprise more carbohydrates in the form of starch.

Complementary Food (4 to 24 Months)

Complementary food is designated as all foodstuffs and preparations that are used for infants as a substitute for formula in order to prepare for the change to solid food.

Special Food (0 to 24 Months)

For babys and small children of allergic people who have an increased hereditary proneness to allergy. Since the intestinal mucous membrane is still permeable in the case of babys and foreign protein, for example from cow's milk, can trigger a foodstuff allergy, "hypoallergenic infant food" is on the market. It should also be supplemented with ARA.

The plant seed oil according to the invention is also suitable as a complete food in addition to the abovementioned applications. Complete food is to be understood here as meaning a food that covers the complete food need of an animal or human individual (e.g. of a baby), such that healthy growth is optimally guaranteed. A complete food to which the plant seed oil according to the invention is added comprises arachidonic acid (ARA) in similar concentrations to breast milk. The complete food also comprises gamma-linolenic acid (GLA), dihomo-gamma-linolenic acid (DGLA), stearidonic acid (SDA) and eicosapentaenoic acid (EPA), and where appropriate DHA, in similar concentrations to breast milk. It is therefore very particularly highly suitable for the production of baby food. The abovementioned complete food can be, for example, baby milk, follow-on milk, drink for the small child, fruit juice, purée products, milk, yogurt or fermented products. It is intended for the feeding of infants and children in order to support their normal growth and their development. In the case of the complete product, it can also be solid baby food, candies, biscuits or gelatin products.

The ARA content in the infant food as shown in the examples was matched with the total amount of ARA that was found in breast milk during the first 0-12 months of lactation. An additional advantage consists in the fact that if the plant seed oil according to the invention is used in order to supplement the infant milk with ARA, the values for the GLA, DGLA and SDA are also in the range of concentrations as in breast milk. This lies in the fact that the plant seed oil according to the invention comprises the three high-grade unsaturated fatty acids almost in the proportions that were also found in breast milk. If the plant seed oil according to the invention is also used as a constituent of the baby food in order to match the ARA concentration, then the GLA and the DGLA are also supplied in the right concentrations in order to provide the appropriate nutrients for the special baby and infant foods. In this case no change in the oil like, for example, the admixture of, for example, further GLA-, DGLA- and SDA-comprising oils is necessary.

Baby foods are assigned in Europe to the dietetic foodstuffs (see, for example "Directive 91/321/EC"). The quality requirements for infant and baby food are therefore very high and strictly controlled worldwide. Europe follows the EC guideline 91/321/EC and the Codex Alimentarius Alinorm 03/26a here, which at the same time have been converted to national law within the EC. Important new European guidelines and directives that may be mentioned are the Codex Alimentarius: International Code of Hygienic Practice for Foods for Infants and Children (2004), VO 852/2004/EC Lebensmittelhygienegesetz [Foodstuffs hygiene law], Annex II (GHP,GMP)(Novellierung des Hygienerechts in Deutschland [Amendment of the hygiene law in Germany], 29.04.2004), and VO 178/2002/EC: Festlegung der allgemeinen Grundsätze and Anforderungen des Lebensmittelrechts, zur Festlegung von Verfahren zur Lebensmittelsicherheit [Definition of the general fundamentals and requirements of the foodstuffs law, for the definition of procedures for foodstuffs safety]. 28.02.2002 (Chain Control, traceability of raw materials). Eastern Europe also follows the EC guidelines here and has national, very strict legal procedures. Asia and Australia: align with the WHO/FAO Code, Codex Alimentarius and the FDA regulatory requirements of the USA. The FDA regulatory requirements of the USA largely correspond to the WHO Code and Codex Alimentarius. The national legislation in South and Central America follows the US regulation, the WHO Code and Codex Alimentarius.

Important legal regulations in Germany are mentioned in the Diät-Verordnung (VO) [Diet Ordinance], in §§14, 14b, 14c, 14d, 22a, 22b (Germany). EC Verodnung (VO; EC Ordinance) 683/2004/EC relates to aflatoxins and mycotoxins in infant and small child foods. VO 1830/2003/EC controls the traceability of genetically modified organisms (GMO) and of foodstuffs produced from GMO organisms (22.09.2003). The highest amounts VO relates here to residues of plant protection agents or pesticides (05.11.2003). VO 2377/90/EC relates to the fixing of highest amounts for veterinary pharmaceutical residues in foodstuffs of animal origin (30.12.2000). The harmful substance VO relates, for example, to the maximally permissible dioxin and PCB content.

Baby foods can be prepared, for example, in powder form. For this purpose they are, for example, spray dried, instantiated, and agglomerated. Packaging takes place in white cans (gassed with nitrogen/carbon dioxide) or aluminum composite film bags (gassed, not gassed). Baby foods, however, can also be produced in in liquid and emulsified form. For this purpose, for example, they are terminally sterilized in glass bottles or filled into cans. Aseptic filling into glass (Brikpak) or filling of the terminally sterilized concentrate into cans can further be practiced.

Raw materials used for the production of baby food can be, for example, the following components:

cow's milk, goat's milk (e.g. China, Australia), casein/caseinates, demineralized whey powder, amino acids, taurine, carnitine; plant oils (palm oil, soybean oil, sunflower oil, highly oil-comprising sunflower oil, safflower oil, coconut oil, rape oil), milk fat, fish oils (tuna fish oil, cod liver oil, krill oil), egg lipids (ovothin), ARASCO®, DHASCO®; carbohydrates (lactose, maltodextrin, starch), other types of sugar, oligosaccharides (prebiotics), bacterial cultures (probiotics); vitamins, choline, myo-inositol; minerals (Ca, Na, K, Mg, P, Cl), trace elements (Fe, Zn, Cu, Mn, Cr, Se, F, I), nucleotides.

In the most important production process, the production of the baby food is carried out by spray drying fat-comprising semifinished products and subsequent mixing of carbohydrates, vitamins and micronutrients. The production of the baby food can, however, also be carried out by the incorporation of LC-PUFAs into the fatty phase and spraying with the protein and carbohydrate components to give a semifinished product.

Figure 5:
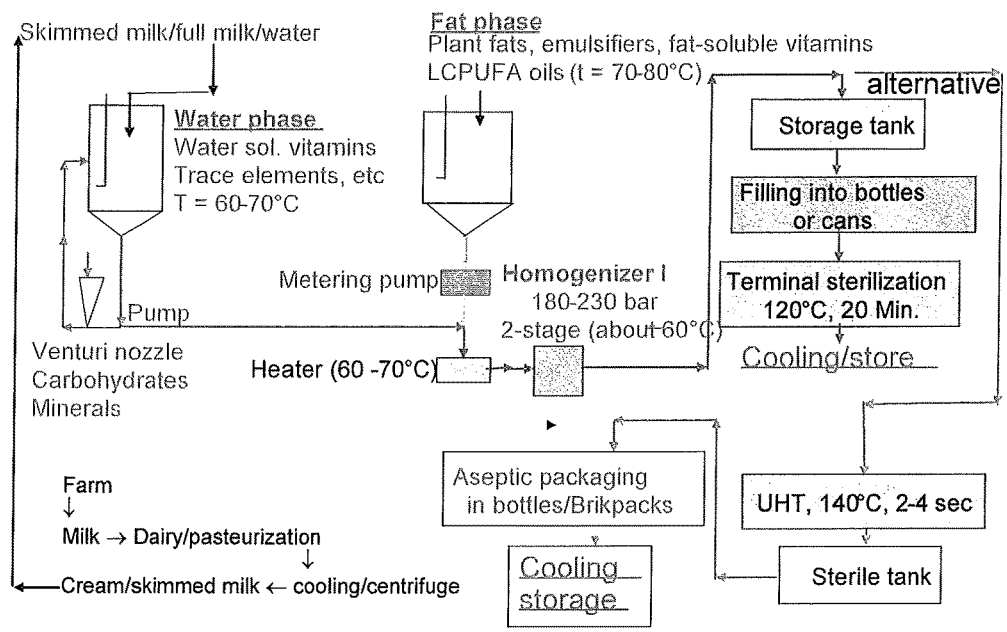
FIG. 5 shows the production of infant food in liquid form.
Figure 6:
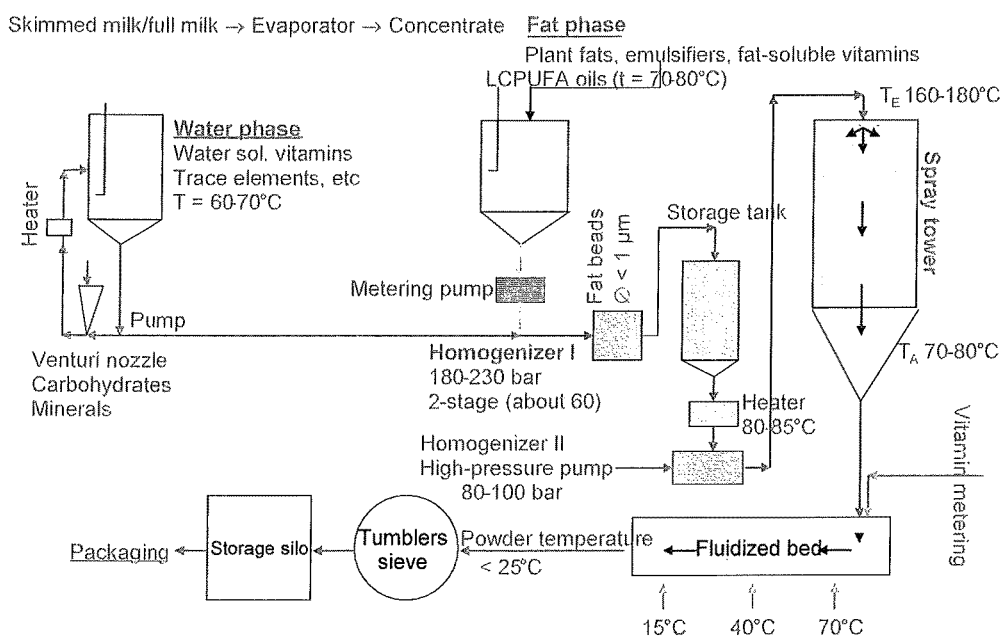
FIG. 6 shows the production of powdered infant food.

FIG. 5 exemplarily shows the production of infant food in liquid form, while FIG. 6 gives an example of the production of infant food by complete spraying.

A stabilization of the LC-PUFAs in the plant seed oil according to the invention can be achieved here, for example, by the addition of tocopherols and tocotrenols. The addition of tocopherols, ascorbyl pamitate and sodium ascorbate leads to the protection of the LC-PUFAs and to the improvement of the shelf life by increasing the product stability and reducing the risk of rancidity. Reference may be made here to the ESPGHAN recommendation, which illuminates the vitamin E content in infant foods (J. Ped. Gastroenterology and Nutrition 26, pp. 351-352, 1996). Further additives for the stabilization of the LC-PUFAs can be plant extracts such as, for example, rosemary and plant sterols, or carotenoids such as, for example, lutein, zeaxanthin, astaxanthin and lycopene, or coenzymes such as, for example, various forms of coenzyme Q. When using stabilizing additives, regional and national legal regulations are to be observed.

In order to make available the LC-PUFA comprised in the plant seed oil according to the invention in powder form or oil form for the production of baby food, the following technologies, for example, are suitable. For the powder form, simple dry mix systems (e.g. Lödige mixer) can be used for mixing with pulverulent and raw materials and semifinished products to give the final product. For the oil form (e.g. packaged in gassed containers), the incorporation is carried out into fatty mixtures together with emulsifiers and antioxidants. Production of an emulsion with the water phase and drying to give a semifinished product (spray drying) then takes place. The semifinished product is then mixed dry with the remaining formulation components to give the final product. Alternatively, the production of a special fatty mixture takes place together with LC-PUFAs and further processing as described above for the oil form.

Simple handling and safe metering favors the use of LC-PUFAs in powder form in the production of baby food. As a disadvantage, it is to be mentioned that the content of LC-PUFAs is only about 25% and the proportion of microencapsulation substances about 75%. Greater oil loadings are being worked on at present and loadings of much more than 50% of oil appear commercially possible. In the case of use of 1% of LCPUFA/100 g of product, 4% of powder (=3 g of carrier substance/100 g) are necessary. The proportion of carriers is considerable and is to be taken into consideration in the formulation (especially in premature infant foods). Carriers used can be, for example, gelatin, sucrose, starch, caseinate, lecithin, tricalcium phosphate, vitamin C, vitamin E, or sodium ascorbate. A further disadvantage is to be seen in the lack of homogenization (fatty bead size >1 μm). Free oil on the particle surface (as a result of diffusion and incomplete encapsulation) can also lead to rancidity.

The use of LCPUFAs in oil form in the production of baby food is accompanied as an advantage by simple processing together with the fatty mixture, which leads to a homogeneous distribution. Stabilizers can also display their action better in the oil form. The homogenization leads to a complete dissolution of the LCPUFA in the fatty phase of the food. A further advantage is to be seen in the absence of concomitant substances and a good shelf life of the final product.

Finally, the oil form is also not associated with microbiological problems, since the product is heated in the liquid phase before drying.

As a disadvantage, it is to be mentioned that the viscosity can lead to increased complexity during processing. The process management can also lead to increased oxidation during spray drying and subsequent processing of the powder. The spray dried semifinished product (comprising LCPUFA) should not be stored intermediately for longer than 3-4 weeks ungassed. As rapid as possible further processing to give the final product and packaging in cans under protective gas (nitrogen/carbon dioxide) is therefore desirable.

Since the plant seed oil according to the invention is already present in oil form, it is particularly suitable for the production of infant foods. The use of LCPUFA in oil form is more cost-effective and advantageous, especially in the case of products using a high production volume. FIG. 6 shows the processing of the plant seed oil according to the invention by means of an example of complete spraying, which leads to a dry final product, and FIG. 5 by an example of the production of a liquid baby food product.

Claim: The invention moreover relates to a process for the production of a plant seed oil according to the invention, comprising the steps:
a) production of a transgenic plant by transformation using the nucleic acid construct as shown in the SEQ ID NOs. 15, 16 or 17
b) culturing of the transgenic plants from step a) under conditions that allow the biosynthesis of the plant seed oil
c) harvesting of the plant seeds, extraction and refining of the plant seed oil.

After the harvesting and cleaning of the seeds, the seeds obtained are processed for the obtainment of the plant seed oil according to the invention. The processing begins with the pressing of the seeds, followed by an extraction and subsequent refining of the oil and stabilization. Preferably, the seeds are cold-pressed and subsequently vacuum-filtered. This process preferably takes place under an inert atmosphere, preferably unter nitrogen. Approximately half of the plant seed oil according to the invention is obtained by this process.

In one embodiment of the process according to the invention, the extraction of the plant seed oil in step c) comprises a hexane extraction.

The subsequent extraction of the press residue remaining from the pressing with solvent, preferably hexane, achieves a yield of the oil of over 90%. Various processes are suitable for the extraction of edible oils, such as, for example, continuous processes by means of hexane (Belitz & Grosch, 1999 "Edible Fats and Oils" In: Food Chemistry, 2nd ed. Springer Verlag). A Miscella distillation is suitable for the subsequent removal of the hexane to below the prescribed highest amounts for foodstuff products. Subsequently, the extracted oil is mixed with the press oil under an inert atmosphere. The crude oil is now ready for further processing by refining. The extraction by means of hexane is suitable for edible oils, as an addition to margarine, but also for the production of biodiesel. A disadvantage of the hexane extraction is to be seen in that the extracted oil can comprise hexane residues, so that such an extracted oil is not equally highly suitable for all applications, for example in baby food.

In a preferred embodiment of the process according to the invention, the extraction of the plant seed oil in step c) therefore comprises a supercritical $CO_2$ extraction. An oil extracted in such a way advantageously comprises no solvent residues, such as, for example, a hexane-extracted oil. Particularly preferably, the extraction of the plant seed oil in step c) of the process according to the invention comprises the following steps:
(i) comminution of the plant seeds by grinding or pressing, preferably under an inert atmosphere to a particle size of less than 0.2 mm; and
(ii) supercritical CO2 extraction, the pressure being at least 300 bar, the temperature between 40 and 60° C. and the extraction run throughput being 60 kg of CO2 per hour and being complete after 30 to 120 min.

Supercritical carbon dioxide ($CO_2$) extraction is based on the utilization of carbon dioxide in subcritical or supercritical state as an extracting agent, the extracting agent being circulated (Barthet and Daun 2002, JAOCS 79:245-51).

Here, the ground seed of the plants described herein is used directly or a press cake obtained by pressing the plant oil according to the invention is used for partial removal of the oily constituents used. This process for the obtainment of oil from plant seeds has the advantage that it can be carried out particularly gently under an inert atmosphere and at relatively low temperatures, which reduces the oxidative processes in the oil.

For obtaining the plant oil according to the invention as completely as possible, a process described in the examples was developed, in which the seeds are firstly comminuted to a defined size and subsequently nearly completely extracted. First, for this the seed was comminuted by grinding or pressing to a particle size of less than 0.2 mm. Particularly advantageous is the use of a roll press with a gap size of 0.15 mm. In the subsequent supercritical extraction, the preferred pressure is at least 300 bar, particularly preferably 350 bar. The temperature can be kept between 40 and 60° C., preferably an as low as possible temperature of 40 to 50° C. or even better 40 to 45° C. being chosen in order to reduce oxidative processes in the oil. An optimal yield is achieved after 120 min in an extraction run of 60 kg of $CO_2$ per hour. Here, the optimal $CO_2$ mass throughput is particularly preferably 80- to 100-times the mass of the substrate in order to achieve a 90% yield of the maximally achievable yield. Shorter extraction times result in a less complete extraction.

The moisture remaining in the air-dried seed (approximately 7%) passes over into the extraction oil and advantageously increases the total oil yield in the $CO_2$ extraction compared with freeze-dried substrate. Air drying of the substrate is therefore preferred. During the entire extraction process, an oil remaining largely identical with regard to its fatty acids composition and its oxidation parameters (acid number, iodine number) is obtained. The extraction efficiency in the supercritical $CO_2$ extraction under the optimized conditions specified here was comparable to the extraction efficiency of a conventional soxhlet extraction by means of hexane. The supercritical carbon dioxide ($CO_2$) extraction carried out on the pilot scale can be increased to the industrial scale needed of, for example, 800 tonnes of oil per year without significant changes.

Figure 4:
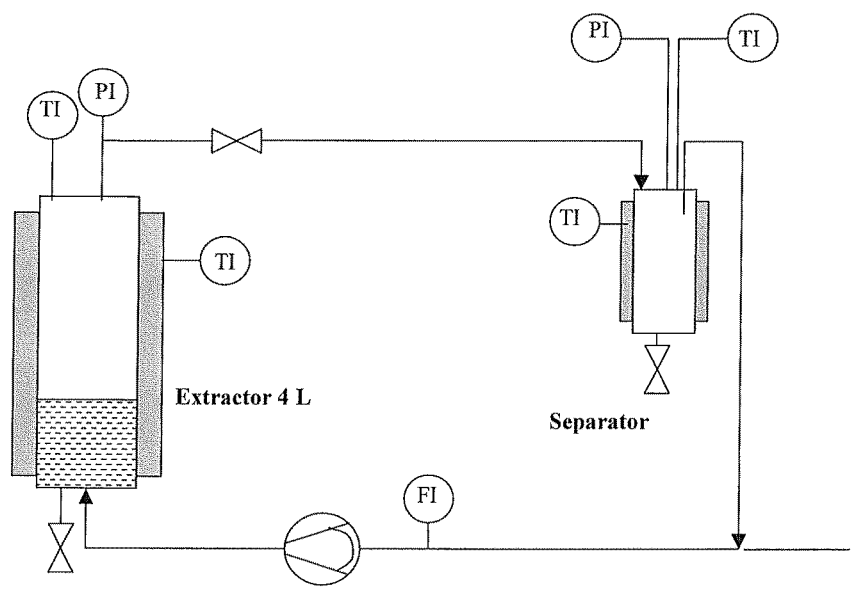
FIG. 4 is a pilot plant sketch for the supercritical CO2 extraction for oils.

The supercritical CO2 extraction by means of the process described herein is suitable in particular for the extraction of the plant seed oil according to the invention, as in contrast to the hexane extraction it comprises no residues of the solvent hexane. Thus a plant seed oil according to the invention extracted in such a way is particularly advantageously used in baby food. Preferably, the oil is obtained by means of supercritical CO$_2$ extraction according to the process mentioned in the examples. FIG. 4 exemplarily shows a pilot plant sketch for supercritical CO$_2$ extraction for the plant seed oils according to the invention.

In a preferred embodiment of the process according to the invention, the refining of the plant seed oil in step c) comprises an alkali refining technology adapted to the plant seed oil according to the invention, which is used in large plants and described in more detail below. Refining in the case of the oil obtained from the supercritical CO$_2$ extraction is not necessary in every case. For some of the applications of the plant seed oil according to the invention described, the direct use of the oil obtained by means of SLE supercritical CO2 extraction is possible, i.e. no subsequent refining is necessary for this. These products include milk, juice, purée, syrup, candies and fermented product for the baby.

For oil obtained by means of hexane extraction (where appropriate also for oil obtained by means of supercritical CO$_2$ extraction), subsequent refining is carried out. The refining of the crude plant oil (mixed oil from press and extraction oil) and filling take place completely under vacuum or under nitrogen. First, the crude oil is hydrated with 10% of water (85° C., 45 min, 300 rpm). Subsequent slime removal with 1.5% citric acid (20% strength) likewise takes place at 85° C. (45 min, 300 rpm, 10% water). Neutralization by washing with 7% strength sodium hydroxide solution (90-95° C., 20 min, 250 rpm, 10% water) and drying at 90° C. (11 min, 350 rpm to 30 mbar) follows. Bleaching takes place with 1% bleaching earth (Tonsil Optimum 214 FF, 90° C., 20 min, 350 rpm, to 20 mbar). Subsequently, the oil is filtered by means of an acetate filter under pressure and nitrogen. The deodorization is carried out at 220° C., 20 min, 1-2 mbar using deionized and degassed water.

Alternatively, a cold-pressed plant oil according to the invention can also be employed directly for the food.

The extracted plant oil according to the invention is then stabilized by exactly metered addition of a selection of stabilizing additives, which can comprise: tocopherols, e.g. vitamin E and tocotrienols, ascorbyl palmitate, plant extracts such as, for example, rosemary and plant sterols, carotenoids such as, for example, lutein, zeaxanthin, astaxanthin and lycopene, phospholipids such as, for example, phosphatidylcholine, phosphatidylethanolamine, phosphatidylinositol, phosphatidylserine and phosphatidylglycol or coenzymes such as, for example, coenzyme Q.

After a subsequent biochemical quality control, the oil is ready for use as described herein, for example in foodstuff products, dietetic products, in particular baby food and food supplements. Typical values for the biochemical quality parameters are: acid number 0.15; peroxide number below the detection limit; color AOCS 0.6 R and 22 Y.

The plant seed oil produced by the process according to the invention comprises in a preferred embodiment substances having a structure that is shown in the following general formula I

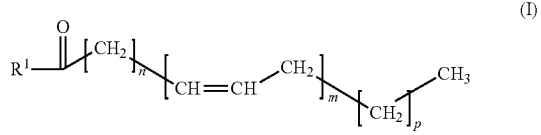

where the variables and substituents are the following

R$^1$=hydroxyl, coenzyme A (thioester), lysophosphatidylcholine, lysophosphatidylethanolamine, lysophosphatidylglycerol, lysodiphosphatidylglycerol, lysophosphatidylserine, lysophosphatidylinositol, sphingo base or a radical of the formula II

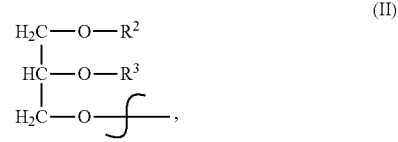

R$^2$=hydrogen, lysophosphatidylcholine, lysophosphatidylethanolamine, lysophosphatidylglycerol, lysodiphosphatidylglycerol, lysophosphatidylserine, lysophosphatidylinositol or saturated or unsaturated C$_2$-C$_{24}$-alkylcarbonyl, R$^3$=hydrogen, saturated or unsaturated C$_2$-C$_{24}$-alkylcarbonyl, or R$^2$ and R$^3$ are independently of one another a radical of the formula Ia:

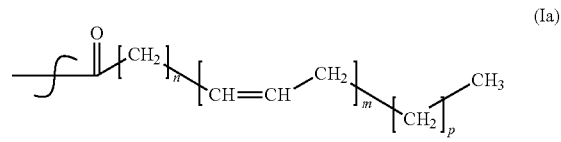

n=2, 3, 4, 5, 6, 7 or 9, m=2, 3, 4, 5 or 6 and p=0 or 3.

R$^1$ in the general formula I denotes hydroxyl-, coenzyme A-(thioester), lyso-phosphatidylcholine-, lyso-phosphatidylethanolamine-, lyso-phosphatidylglycerol-, lyso-diphosphatidylglycerol-, lyso-phosphatidylserine-, lyso-phosphatidylinositol-, sphingobase-, or a radical of the general formula II

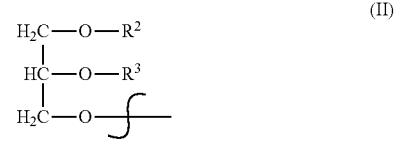

The abovementioned radicals of R$^1$ are always bonded to the compounds of the general formula I in the form of their thioesters.

R$^2$ in the general formula II denotes hydrogen-, lyso-phosphatidylcholine-, lyso-phosphatidyl-ethanolamine-, lyso-phosphatidylglycerol-, lyso-diphosphatidylglycerol-, lyso-phosphatidyl-serine-, lyso-phosphatidylinositol- or saturated or unsaturated C$_2$-C$_{24}$-alkylcarbonyl.

Alkyl radicals that may be mentioned are substituted or unsubstituted, saturated or unsaturated C$_2$-C$_{24}$-alkylcarbonyl chains such as ethylcarbonyl-, n-propylcarbonyl-, n-butylcarbonyl-, n-pentylcarbonyl-, n-hexylcarbonyl-, n-heptylcarbonyl-, n-octylcarbonyl-, n-nonylcarbonyl-, n-decylcarbonyl-, n-undecylcarbonyl-, n-dodecylcarbonyl-, n-tridecylcarbonyl-, n-tetradecylcarbonyl-, n-pentadecylcarbonyl-, n-hexadecylcarbonyl-, n-heptadecylcarbonyl-, n-octadecylcarbonyl-, n-nonadecylcarbonyl-, n-eicosylcarbonyl-, n-docosanylcarbonyl- or n-tetracosanylcarbonyl-, that comprise one or more double bond(s). Saturated or unsaturated C$_{10}$-C$_{22}$-alkylcarbonyl radicals such as n-decylcarbonyl-, n-undecylcarbonyl-, n-dodecylcarbonyl-, n-tridecylcarbonyl-, n-tetradecylcarbonyl-, n-pentadecylcarbonyl-, n-hexadecylcarbonyl-, n-heptadecylcarbonyl-, n-octadecylcarbonyl-, n-nonadecylcarbonyl-, n-eicosylcarbonyl-, n-docosanylcarbonyl- or n-tetracosanylcarbonyl-, that comprise one or more double bond(s) are preferred. Particularly preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals, that comprise one or more double bond(s). Very particularly preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals, that comprise one or more double bond(s). These advantageous radicals can comprise two, three, four, five or six double bonds. The particularly advantageous radicals having 20 or 22 carbon atoms in the fatty acid chain comprise up to six double bonds, advantageously three, four, five or six double bonds, particularly preferably five or six double bonds. All radicals mentioned are derived from the corresponding fatty acids.

$R^3$ in the general formula II denotes hydrogen-, saturated or unsaturated $C_2$-$C_{24}$-alkylcarbonyl.

Alkyl radicals that may be mentioned are substituted or unsubstituted, saturated or unsaturated $C_2$-$C_{24}$-alkylcarbonyl chains such as ethylcarbonyl-, n-propylcarbonyl-, n-butylcarbonyl-, n-pentylcarbonyl-, n-hexylcarbonyl-, n-heptylcarbonyl-, n-octylcarbonyl-, n-nonylcarbonyl-, n-decylcarbonyl-, n-undecylcarbonyl-, n-dodecylcarbonyl-, n-tridecylcarbonyl-, n-tetradecylcarbonyl-, n-pentadecylcarbonyl-, n-hexadecylcarbonyl-, n-heptadecylcarbonyl-, n-octadecylcarbonyl-, n-nonadecylcarbonyl-, n-eicosylcarbonyl-, n-docosanylcarbonyl- or n-tetracosanylcarbonyl- that comprise one or more double bonds. Saturated or unsaturated $C_{10}$-$C_{22}$-alkylcarbonyl radicals such as n-decylcarbonyl-, n-undecylcarbonyl-, n-dodecylcarbonyl-, n-tridecylcarbonyl-, n-tetradecylcarbonyl-, n-pentadecylcarbonyl-, n-hexadecylcarbonyl-, n-heptadecylcarbonyl-, n-octadecylcarbonyl-, n-nonadecylcarbonyl-, n-eicosylcarbonyl-, n-docosanylcarbonyl- or n-tetracosanylcarbonyl- that comprise one or more double bonds are preferred. Particularly preferred are saturated and/or unsaturated $C_{10}$-$C_{22}$-alkylcarbonyl radicals such as $C_{10}$-alkylcarbonyl, $C_{11}$-alkylcarbonyl, $C_{12}$-alkylcarbonyl, $C_{13}$-alkylcarbonyl, $C_{14}$-alkylcarbonyl, $C_{16}$-alkylcarbonyl, $C_{18}$-alkylcarbonyl, $C_{20}$-alkylcarbonyl or $C_{22}$-alkylcarbonyl radicals that comprise one or more double bonds. Very particularly preferred are saturated or unsaturated $C_{16}$-$C_{22}$-alkylcarbonyl radicals such as $C_{16}$-alkylcarbonyl, $C_{18}$-alkylcarbonyl, $C_{20}$-alkylcarbonyl or $C_{22}$-alkylcarbonyl radicals that comprise one or more double bonds. These advantageous radicals can comprise two, three, four, five or six double bonds. The particularly advantageous radicals having 20 or 22 carbon atoms in the fatty acid chain comprise up to six double bonds, advantageously three, four, five or six double bonds, particularly preferably five or six double bonds. All radicals mentioned are derived from the corresponding fatty acids.

The abovementioned radicals of $R^1$, $R^2$ and $R^3$ can be substituted with hydroxyl and/or epoxy groups and/or can comprise triple bonds.

Advantageously, the plant seed oil described below, prepared in the process according to the invention comprises polyunsaturated fatty acids having at least one, two, three, four, five or six double bonds. Particularly advantageously the fatty acids comprise four, five or six double bonds. The fatty acids advantageously have 18, 20 or 22 C atoms in the fatty acid chain, preferably the fatty acids comprise 20 or 22 carbon atoms in the fatty acid chain. Advantageously, saturated fatty acids comprising the nucleic acid constructs used in the process are reacted little or not at all. Little is to be understood as meaning that in comparison to polyunsaturated fatty acids the saturated fatty acids with less than 5% of the activity, advantageously less than 3%, particularly advantageously with less than 2%, very particularly preferably with less than 1; 0.9; 0.8; 0.7; 0.6; 0.5; 0.4; 0.3; 0.25 or 0.125% are reacted. These fatty acids prepared by the process according to the invention are present in the plant seed oil in a fatty acid mixture.

Advantageously, the substituents $R^2$ or $R^3$ in the general formulae I and II independently of one another denote saturated or unsaturated $C_18$-$C_{22}$-alkylcarbonyl-, particularly advantageously they denote independently of one another unsaturated $C_{18}$-, $C_{20}$- or $C_{22}$-alkylcarbonyl- having at least two double bonds.

The plant seed oil produced in the process comprises polyunsaturated fatty acids that are advantageously bound in membrane lipids and/or triacylglycerides, however they can also occur as free fatty acids or else bound in the form of other fatty acid esters in the plants. Here, they are advantageously present in the form of mixtures of various fatty acids or mixtures of different glycerides. The various fatty acids bound in the triacylglycerides can be derived here from short-chain fatty acids having 4 to 6 C atoms, medium-chain fatty acids having 8 to 12 C atoms or long-chain fatty acids having 14 to 24 C atoms, the long-chain fatty acids are preferred, the long-chain fatty acids LCPUFAs of $C_{18}$-, $C_{20}$- and/or $C_{22}$-fatty acids are particularly preferred.

In the process according to the invention, a plant seed oil is advantageously prepared using fatty acid esters with mono- or polyunsaturated $C_{18}$-, $C_{20}$- and/or $C_{22}$-fatty acid molecules having at least one or two double bonds in the fatty acid ester, advantageously having at least three, four, five or six double bonds in the fatty acid ester, particularly advantageously of at least five or six double bonds in the fatty acid ester and lead advantageously to the synthesis of linoleic acid (=LA, C18:$2^{\Delta 9,12}$), gamma-linolenic acid (=GLA, C18:$3^{\Delta 9,12}$), stearidonic acid (=SDA, C18:$4^{\Delta 9,12}$), dihomo-gamma-linolenic acid (=DGLA, 20:$3^{\Delta 8,11,14}$), ω-3-eicosatetraenoic acid (=ETA, C20:$4^{\Delta 5,8,11,14}$) arachidonic acid (ARA, C20:$4^{\Delta 5,8,11,14}$), eicosapentaenoic acid (EPA, C20.$5^{\Delta 5,8,11,14,17}$) ω-6-docosatetraenoic acid) (C22.$5^{\Delta 4,7,10,13,16}$) ω-6-docosapentaenoic acid (C22:$4^{\Delta 7,10,13,16}$) ω-3-docosapentaenoic acid (=DPA, C22: $56^{\Delta 7,10,13,16,19}$) docosahexaenoic acid (=DHA, C22:$6^{\Delta 4,7,10,13,16,19}$) or their mixtures. The plant seed oil produced preferably comprises a fatty acid spectrum comprising palmitic acid, stearic acid, oleic acid, linoleic acid, gamma-linolenic acid, alpha-linolenic acid, stearidonic acid, dihomo-gamma-linolenic acid, arachidonic acid and eicosapentaenoic acid, as also shown in FIG. 3B.

The fatty acid esters having polyunsaturated $C_{18}$-, $C_{20}$- and/or $C_{22}$-fatty acid molecules can be isolated from the plants that were used for the production of the fatty acid esters, in the form of an oil or lipid, for example in the form of compounds such as sphingolipids, phosphoglycerides, lipids, glycolipids such as glycosphingolipids, phospholipids such as phosphatidylethanolamine, phosphatidylcholine, phosphatidylserine, phosphatidylglycerol, phosphatidylinositol or diphosphatidylglycerol, monoacylglycerides, diacylglycerides, triacylglycerides or other fatty acid esters such as the acetylcoenzymeA esters that comprise the polyunsaturated fatty acids having at least two, three, four, five or six, preferably five or six, double bonds, advantageously they are isolated in the form of their diacylglycerides, triacylglycerides and/or in the form of phosphatidylcholine, particularly preferably in the form of the triacylglycerides. In addition to these esters, the polyunsaturated fatty acids are also comprised as free fatty acids or bound in other compounds in the plants. Generally, the various previously mentioned compounds (fatty acid esters and fatty acids) are present in the plants in an approximate distribution of 80 to 90 percent by weight (% by weight) of triglycerides, 2 to 5% by weight of diglycerides, 5 to 10% by weight of monoglycerides, 1 to 5% by weight of free fatty acids, 2 to 8% by weight of phospholipids, where the sum of the various compounds adds to give 100% by weight.

In the process according to the invention, the LCPUFAs produced with a content of at least 3% by weight, advantageously of at least 5% by weight, preferably of at least 8% by weight, particularly preferably of at least 10% by weight, very particularly preferably of at least 15% by weight based on the total fatty acids are prepared in a transgenic plant. Here, advantageously $C_{18}$- and/or $C_{20}$-fatty acids that are present in the host organisms are reacted to at least 10%, advantageously to at least 20%, particularly advantageously to at least 30%, very particularly advantageously to at least 40% to the corresponding products such as ARA, EPA, DPA or DHA, only to mention a few by way of example. Advantageously, the fatty acids are produced in bound form. With the aid of the nucleic acids used in the process according to the invention, these unsaturated fatty acids can be brought to sn1, sn2 and/or sn3 position of the advantageously produced triglycerides. Since in the process according to the invention a plurality of reaction steps are passed through by the starting compounds linoleic acid ($C_{18:2}$) or linolenic acid ($C_{18:3}$), the products of the process such as, for example, arachidonic acid (ARA), eicosapentaenoic acid (EPA), ω-6-docosapentaenoic acid or DHA are not obtained as absolutely pure products, small amounts of the precursors are always also comprised in the final product. If both linoleic acid and linolenic acid are present in the starting plant, then the final products such as ARA, EPA or DHA are present as mixtures. The precursors should advantageously amount to not more than 20% by weight, preferably not more than 15% by weight, particularly preferably not than 10% by weight, very particularly preferably not more than 5, 4, 3, 2, 1 or 0.5% by weight based on the amount of the respective final product. Advantageously, in a transgenic plant as described herein palmitic acid, stearic acid, oleic acid, linoleic acid, gamma-linolenic acid, alpha-linolenic acid, stearidonic acid, dihomo-gamma-linolenic acid, arachidonic acid and eicosapentaenoic acid, as also shown in the fatty acid spectrum in FIG. 3B, are formed as final products.

The fatty acid esters or fatty acid mixtures comprised in the plant seed oil, which were prepared by the process according to the invention, advantageously comprise approximately 3.2-5.3% of palmitic acid, approximately 2.2-5.3% of stearic acid, approximately 10-25% of oleic acid, approximately 22-36% of linoleic acid, approximately 4-12% of gamma-linolenic acid, approximately 3-8% of alpha-linolenic acid, approximately 0.2-1% of stearidonic acid, approximately 3-9% of dihomo-gamma-linolenic acid, approximately 12-25% of arachidonic acid and approximately 1-4% of eicosapentaenoic acid, based on the total fatty acid content. Furthermore, the fatty acid esters or fatty acid mixtures comprised in the plant seed oil, which were prepared by the process according to the invention, can advantageously comprise fatty acids selected from the group consisting of the fatty acids erucic acid (13-docosaenoic acid), sterculic acid (9,10-methyleneoctadec-9-enoic acid), malvalic acid (8,9-methyleneheptadec-8-enonic acid), chaulmoogric acid (cyclopentenedodecanoic acid), furan fatty acid (9,12-epoxyoctadeca-9,11-dienoic acid), vernon acid (9,10-epoxyoctadec-12-enoic acid), tarinic acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenyninic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienic acid, calendula acid (8t10t12c-octadecatrienic acid), catalpinic acid (9t11t13c-octadecatrienic acid), eleosteric acid (9c11t13t-octadecatrienic acid), jacaric acid (8c10t12c-octadecatrienic acid), punicic acid (9c11t13c-octadecatrienic acid), parinaric acid (9c11t13t15c-octadecatetraenic acid), pinolenic acid (all-cis-5,9,12-octadecatrienic acid), laballenic acid (5,6-octadecadienallenic acid), ricinoleic acid (12-hydroxy oil acid) and/or coriolinic acid (13-hydroxy-9c,11t-octadecadienoic acid). The aforementioned fatty acids generally advantageously occur in the fatty acid esters or fatty acid mixtures prepared by the process according to the invention only in traces, that is they occur, based on the total fatty acids, to less than 30%, preferably to less than 25%, 24%, 23%, 22% or 21%, particularly preferably to less than 20%, 15%, 10%, 9%, 8%, 7%, 6% or 5%, very particularly preferably to less than 4%, 3%, 2% or 1%. Advantageously, the fatty acid esters or fatty acid mixtures prepared by the process according to the invention comprise less than 0.1% based on the total fatty acids in one of the following fatty acids, or better no clupanodoic acid (=docosapentaenoic acid, $C22:5^{\Delta4,8,12,15,21}$) and no nisic acid (tetracosahexaenoic acid, $C23:6^{\Delta3,8,12,15,18,21}$).

By means of the nucleic acid constructs according to the invention or the nucleic acid constructs used in the process according to the invention, an increase in the yield of polyunsaturated fatty acids of at least 50%, advantageously of at least 80%, particularly advantageously of at least 100%, very particularly advantageously of at least 150% compared to the non-transgenic starting plant, for example rape, flax, safflower or soybean, can be achieved by comparison in the GC analysis.

Chemically pure polyunsaturated fatty acid compositions can also be prepared by the previously described process. For this, the fatty acid compositions are isolated from the plants in a known manner, for example by means of extraction, distillation, crystallization, chromatography or combinations of these methods. These chemically pure fatty acid compositions are advantageous for applications in the field of the foodstuffs industry for the preparation of foodstuffs, in particular baby food, but also in the cosmetics industry and the pharmaceutical industry.

The nucleic acid constructs according to the invention are shown in the SEQ ID NOs. 15, 16 and 17 and described in detail above and in Tables 1 and 2. In principle, all genes of the fatty acid or lipid metabolism can advantageously be used in combination with the inventive nucleic acid constructs (within the meaning of this application the plural is intended to comprise the singular and conversely) in the process for the production of plant seed oil using polyunsaturated fatty acids. For example, a transgenic plant that is transformed with the nucleic acid construct according to the invention can be expressed with a further expression vector, by means of which one or more genes of the fatty acid or lipid metabolism can be expressed, and additionally incorporated by means of suitable transformation processes into the transgenic plant. Advantageously, genes of the fatty acid or lipid metabolism selected from the group consisting of acyl-CoA dehydrogenase(s), acyl-ACP[=acyl carrier protein] desaturase(s), acyl-ACP thioesterase(s), fatty acid acyl transferase(s), acyl-CoA:lysophospholipid acyltransferases, fatty acid synthase(s), fatty acid hydroxylase(s), acetyl coenzyme A carboxylase(s), acyl-coenzyme A oxidase(s), fatty acid desaturase(s), fatty acid acetylenases, lipoxygenases, triacylglycerol lipases, allene oxide synthases, hydroperoxide lyases or fatty acid elongase(s) are used. Particularly preferably, genes selected from the group consisting of the Δ-5-desaturases, Δ-6-desaturases, Δ-8-desaturases, Δ-12-desaturases, omega-3-desaturases in combination with the nucleic acid constructs according to the invention are used, where individual genes or several genes can be used in combination. Particularly preferably, as already mentioned, in this connection the Δ-6-desaturase with SEQ ID Nos. 5 and 7, the Δ-5-desaturase with SEQ ID No. 9, the Δ-12-desaturase with SEQ ID Nos. 11 and 13, the Δ-6-elongase with SEQ ID Nos. 1 and 3, the Δ-5-elongase with the SEQ ID No. 18, and/or the Δ-4-desaturase with the SEQ ID NO. 20 can be employed.

Advantageously, the desaturases used in the nucleic acid construct according to the invention convert their respective substrates in the form of the CoA-fatty acid esters. This advantageously leads, if an elongation step has taken place beforehand, to an increased product yield. The respective desaturation products are thereby synthesized in higher amounts, since the elongation step generally takes place on the CoA-fatty acid esters, while the desaturation step mainly takes place on the phospholipids or on the triglycerides. An exchange reaction that would make necessary a further possibly limiting enzyme reaction between the CoA-fatty acid esters and the phospholipids or triglycerides is thus not necessary.

As a result of the enzymatic activity of the polypeptides encoded by the nucleic acid construct according to the invention, the most different polyunsaturated fatty acids can be prepared in the process according to the invention. Depending on the choice of the plants used for the process according to the invention, mixtures of the various fatty acids such as palmitic acid, stearic acid, oleic acid, linoleic acid, gamma-linolenic acid, alpha-linolenic acid, stearidonic acid, dihomo-gamma-linolenic acid, arachidonic acid, eicosapentaenoic acid and/or DHA can be prepared in free or bound form. Depending on which fatty acid composition predominates in the starting plant ($C_{18:2}$- or $C_{18:3}$-fatty acids), fatty acids thus result that are derived from $C_{18:2}$-fatty acids, such as GLA, DGLA or ARA or those that are derived from $C_{18:3}$-fatty acids, such as SDA, ETA or EPA. If only linoleic acid (=LA, $C18:2^{\Delta9,12}$) is present as an unsaturated fatty acid in the plant used for the process, only GLA, DGLA and ARA, which can be present as free fatty acids or bound, can result as products of the process. If only alpha-linolenic acid (=ALA, $C_{18:3}^{\Delta9,12,15}$) is present as an unsaturated fatty acid in the plant used in the process, such as, for example in flax, only SDA, ETA, EPA and/or DHA can result as products of the process, which as described above can be present as free fatty acids or bound. By modification of the activity of the enzymes Δ-5-desaturase, Δ-6-desaturase, Δ-4-desaturase, Δ-12-desaturase, elongase and/or Δ-6-elongase involved in the synthesis, plant seed oils having a desired fatty acid composition can be specifically produced in the aforementioned plants. Owing to the activity of the Δ-6-desaturase and Δ-6-elongase, oils, for example, result comprising GLA and DGLA or SDA and ETA, depending on starting plant and unsaturated fatty acid. If the Δ-5-desaturase, the Δ-5-elongase and the Δ-4-desaturase are additionally incorporated into the plant, then ARA, EPA and/or DHA additionally result. Since these are biosynthesis chains, the respective final products are not present in the plants as pure substances. Small amounts of the precursor compounds are always also comprised in the final products. These small amounts are less than 20% by weight, advantageously less than 15% by weight, particularly advantageously less than 10% by weight, very particularly advantageously less than 5, 4, 3, 2 or 1% by weight based on the desired final products, for example palmitic acid, stearic acid, oleic acid, linoleic acid, gamma-linolenic acid, alpha-linolenic acid, stearidonic acid, dihomo-gamma-linolenic acid, arachidonic acid, eicosapentaenoic acid and/or DHA or their mixtures.

To increase the yield in the described process for the production of plant seed oils having an advantageously increased content of polyunsaturated fatty acids, it is advantageous to increase the amount of starting material for the fatty acid synthesis; this can be achieved, for example, by the introduction of a nucleic acid into the plant, which codes for a polypeptide with Δ-12-desaturase. This is particularly advantageous in oil-producing plants, for example of the family of the Brassicaceae such as the genus Brassica, e.g. rapeseed, that have a high oleic acid content. Since these organisms only have a small content of linoleic acid (Mikoklajczak et al., Journal of the American Oil Chemical Society, 38, 1961, 678-681), the use of the Δ-12-desaturases mentioned for the preparation of the starting material linoleic acid is advantageous.

Advantageously, the aforementioned nucleic acid constructs are employed in the process according to the invention.

In a preferred embodiment, the process furthermore comprises the step of obtaining a plant cell or a whole plant that comprises the nucleic acid constructs used in the process, the cell and/or the plant being transformed using a nucleic acid construct according to the invention, as described, alone or in combination with further nucleic acid sequences that code for proteins of the fatty acid or lipid metabolism. In a further preferred embodiment, this process furthermore comprises the step of obtaining the oils, lipids or free fatty acids from the plant or from the culture. The culture can involve, for example, a greenhouse or field culture of a plant. The cell or plant thus produced is advantageously a cell of an oil-producing organism, such as an oil fruit plant, such as, for example, rape, canola, flax, soybean, safflower or a field crop plant such as corn.

Growing is to be understood, for example, as culturing in the case of plant cells, tissue or organs on or in a nutrient medium or of the whole plant on or in a substrate, for example in hydroculture, earth in a container used for growing plants, or in a soil.

Suitable organisms or host cells for the process according to the invention are those that are able to synthesize fatty acids, especially unsaturated fatty acids or are suitable for the expression of recombinant genes. The plants rape, canola, flax, soybean, safflower or corn are preferred.

Transgenic plants that comprise the polyunsaturated fatty acids synthesized in the process according to the invention can advantageously be marketed directly without the synthesized oils, lipids or fatty acids having to be isolated. Plants in the process according to the invention are to be understood as meaning whole plants and all plant parts, plant organs or plant parts such as leaf, stalk, seed, root, tubers, anthers, fibers, root hairs, stem, embryos, calli, cotyledons, petioles, crops, plant tissue, reproductive tissue, cell cultures, which are derived from the transgenic plant and/or can further be used for producing the transgenic plant. The seed here comprises all seed parts like the seed coats, epidermal and seed cells, endosperm or embryo tissue. The compounds produced in the process according to the invention can, however, also be isolated from the plants or plant parts such as, for example, the seeds in the form of their oils, fat, lipids and/or free fatty acids. Polyunsaturated fatty acids produced by this process can be harvested by harvesting the plants either from the culture in which they are growing, or from the field. This can take place by means of pressing or extraction of the plant parts, preferably the plant seeds. Here, the oils, fats, lipids and/or free fatty acids can be obtained by pressing without supply of heat by "cold beating" or "cold pressing". In order that plant parts, especially the seeds, can be crushed more easily, they are comminuted, steamed or roasted beforehand. The seeds pretreated in this way can subsequently be pressed or extracted with solvent such as warm hexane. Subsequently, the solvent is removed again. In the case of plant cells, these are extracted directly after harvesting, for example, without further working steps or else after crushing by means of various methods known to the person skilled in the art. In this way, more than 96% of the compounds produced in the process can be isolated.

Subsequently, the products thus obtained are processed further, that is refined. Here, firstly, for example, the mucilages and suspended matter are removed. The "degumming" can take place enzymatically or, for example, chemically/physically by addition of acid such as phosphoric acid. Subsequently, the free fatty acids are removed by treatment with a base, for example sodium hydroxide solution. The product obtained is washed thoroughly with water and dried for the removal of the base remaining in the product. In order to remove the colorants still comprised in the product, the products are subjected to bleaching with, for example, bleaching earth or activated charcoal. Finally, the product is additionally deodorized, for example with steam.

Preferably, the plant seed oil produced by the process according to the invention comprises PUFAs and LCPUFAs, i.e. $C_{18}$-, $C_{20}$- or $C_{22}$-fatty acid molecules, advantageously $C_{18}$-, $C_{20}$- or $C_{22}$-fatty acid molecules having at least one double bond in the fatty acid molecule, preferably two, three, four, five or six double bonds. These $C_{18}$-, $C_{20}$- or $C_{22}$-fatty acid molecules can be isolated from the plant, especially plant seeds, in the form of an oil or lipids.

An embodiment of the invention is therefore plant seed oils, lipids or fatty acids or fractions thereof that comprise arachidonic acid with a content of approximately 7 to approximately 26 percent by weight in the total fatty acid content, the ratio of the percentages by weight of arachidonic acid to gamma-linolenic acid being approximately 1:1 to approximately 5:1 and the ratio of the percentages by weight of arachidonic acid to dihomo-gamma-linolenic acid being approximately 1:1 to approximately 5:1. These plant seed oils, lipids or fatty acids or fractions thereof can be prepared by the process described above using transgenic plants that can have the nucleic acid constructs according to the invention as shown in the SEQ ID NOs. 15, 16 or 17 integrated into their genome.

The plant seed oil according to the invention here preferably comprises a fatty acid spectrum comprising the fatty acids palmitic acid, stearic acid, oleic acid, linoleic acid, gamma-linolenic acid, alpha-linolenic acid, stearidonic acid, dihomo-gamma-linolenic acid, arachidonic acid and eicosapentaenoic acid, as also shown in the fatty acid spectrum in FIG. 3B.

The fatty acid esters or fatty acid mixtures present in the plant seed oil advantageously comprise approximately 3.2-5.3% of palmitic acid, approximately 2.2-5.3% of stearic acid, approximately 10-25% of oleic acid, approximately 22-36% of linoleic acid, approximately 4-12% of gamma-linolenic acid, approximately 3-8% of alpha-linolenic acid, approximately 0.2-1% of stearidonic acid, approximately 3-9% of dihomo-gamma-linolenic acid, approximately 12-25% of arachidonic acid and approximately 1-4% of eicosapentaenoic acid, based on the total fatty acid content. Furthermore, the fatty acid esters or fatty acid mixtures mentioned can advantageously comprise fatty acids selected from the group consisting of the fatty acids erucic acid (13-docosaenoic acid), sterculic acid (9,10-methyleneoctadec-9-enoic acid), malvalic acid (8,9-methyleneheptadec-8-enoic acid), chaulmoogric acid (cyclopentenedodecanoic acid), furan fatty acid (9,12-epoxyoctadeca-9,11-dienoic acid), vernonic acid (9,10-epoxyoctadec-12-enoic acid), tarinic acid (6-octadecynoic acid), 6-nonadecynoic acid, santalbic acid (t11-octadecen-9-ynoic acid), 6,9-octadecenynoic acid, pyrulic acid (t10-heptadecen-8-ynoic acid), crepenynic acid (9-octadecen-12-ynoic acid), 13,14-dihydrooropheic acid, octadecen-13-ene-9,11-diynoic acid, petroselenic acid (cis-6-octadecenoic acid), 9c,12t-octadecadienoic acid, calendula acid (8t10t12c-octadecatrienoic acid), catalpinic acid (9t11t13c-octadecatrienoic acid), eleosteric acid (9c11t13t-octadecatrienoic acid), jacaric acid (8c10t12c-octadecatrienoic acid), punicic acid (9c11t13c-octadecatrienoic acid), parinaric acid (9c11t13t15c-octadecatetraenoic acid), pinolenic acid (all-cis-5,9,12-octadecatrienoic acid), laballenic acid (5,6-octadecadienallenic acid), ricinolec acid (12-hydroxy oil acid) and/or coriolic acid (13-hydroxy-9c,11t-octadecadienoic acid). The aforementioned fatty acids generally occur advantageously only in traces in the fatty acid esters or fatty acid mixtures prepared by the process according to the invention, that is they occur, based on the total fatty acids, to less than 30%, preferably to less than 25%, 24%, 23%, 22% or 21%, particularly preferably to less than 20%, 15%, 10%, 9%, 8%, 7%, 6% or 5%, very particularly preferably to less than 4%, 3%, 2%, 1%, 0.5% or 0.1%. Advantageously, the abovementioned fatty acid esters or fatty acid mixtures comprise less than 0.1% based on the total fatty acids in one of the following fatty acids, or better no clupanodonic acid (=docosapentaenoic acid, $C_{22:5}^{\Delta 4,8,12,15,21}$) and no nisic acid (tetracosahexaenoic acid, $C23:6^{\Delta 3,8,12,15,18,21}$).

Preferably, the plant seed oils according to the invention comprise approximately 7 to approximately 26 percent by weight of ARA and at least 1%, 1.5%, 2%, 3%, 4% or 5%, advantageously at least 6%, or 7%, particularly advantageously at least 8%, 9% or 10% of EPA based on the total fatty acid content of the production organism, advantageously a transgenic plant, particularly advantageously an oil fruit plant such as soybean, rape, safflower, flax or the field crop corn. Additionally, the abovementioned plant seed oil can comprise DHA in the amounts specified for EPA.

A further embodiment according to the invention is the use of the plant seed oil of the invention or of LC-PUFAs extracted therefrom in feedstuffs, foodstuffs, preferably baby food, cosmetics or pharmaceuticals. The plant seed oils according to the invention or LC-PUFAs extracted therefrom can be used in the manner known to the person skilled in the art for blending with other oils, lipids, fatty acids or fatty acid mixtures, for example vegetable (as described above) or microbial (e.g. from Mortierella alpina or *Crythecodinium cohnii*) or animal origin (such as fish oils). These mixtures of oils, lipids, fatty acids or fatty acid mixtures, which consist of (i) vegetable and microbial or (ii) vegetable and animal or (iii) of vegetable and microbial and animal constituents, can also be used for the production of feedstuffs, foodstuffs, preferably baby food, cosmetics or pharmaceuticals.

The term "oil", "lipid" or "fat" is understood as meaning a fatty acid mixture that comprises unsaturated, saturated, preferably esterified, fatty acid(s). It is preferred that the oil, lipid or fat has a high proportion of mono- and polyunsaturated, advantageously esterified fatty acid(s). Preferably, the proportion of unsaturated esterified fatty acids is approximately 30%, more preferred is a proportion of 50%, even more preferred is a proportion of 60%, 70%, 80%, 90%, 95%, 99% or 99.5%. For determination, it is possible, for example, to determine the proportion of fatty acid by gas chromatography after conversion of the fatty acids to the methyl esters by transesterification. The oil, lipid or fat can comprise various other saturated or unsaturated fatty acids, e.g. calendula acid, palmitic, palmitoleic, stearic, oleic acid etc. In particular, it is possible, depending on the starting plant, for the proportion of the various fatty acids in the oil or fat to vary.

The polyunsaturated fatty acids produced in the process, advantageously having at least two double bonds, are as described above, for example, sphingolipids, phosphoglycerides, lipids, glycolipids, phospholipids, monoacylglycerol, diacylglycerol, triacylglycerol or other fatty acid esters.

From the plant seed oil comprising polyunsaturated fatty acids advantageously having at least one, two, three, four, five or six double bonds produced in the process according to the invention, the polyunsaturated fatty acids can be released, for example by means of an alkali treatment, for example aqueous KOH or NaOH or acidic hydrolysis, advantageously in the presence of an alcohol such as methanol or ethanol or by means of an enzymatic cleavage and isolated by means of, for example, phase separation and subsequent acidification by means of, for example, $H_2SO_4$. The release of the fatty acids can also take place directly without the work-up described beforehand.

After introduction into a plant cell or plant, the nucleic acid constructs used in the process can advantageously be integrated either on a separate plasmid or into the genome of the host cell. In integration into the genome, the integration can be random or take place by such recombination that the native gene is replaced by the introduced copy, whereby the production of the desired compound is modulated by the cell, or by use of a gene in "trans", so that the gene is functionally associated with a functional expression unit which comprises at least one sequence guaranteeing the expression of a gene and at least one sequence guaranteeing the polyadenylation of a functionally transcribed gene. Advantageously, the nucleic acids are brought by means of multiexpression cassettes or constructs to multiparallel expression in the plant advantageously to the multiparallel seed-specific expression of genes in the plants.

Mosses and algae are the only known plant systems that produce considerable amounts of polyunsaturated fatty acids, such as arachidonic acid (ARA) and/or eicosapentaenoic acid (EPA) and/or docosahexaenoic acid (DHA). Mosses comprise PUFAs in membrane lipids while algae, algae-related organisms and some fungi also accumulate noticeable amounts of PUFAs in the triacylglycerol fraction. Therefore nucleic acid molecules that are isolated from such strains also accumulate the PUFAs in the triacylglycerol fraction, particularly advantageously for the process according to the invention and thus for the modification of the lipid and PUFA production system in a host, in particular plants, such as oil fruit plants, for example rape, canola, flax, soybean, safflower. They can therefore be used advantageously in the process according to the invention.

For the production of the plant seed oil comprising the long-chain PUFAs in the process according to the invention with preferred use of the nucleic acid constructs having the SEQ ID NOs. 15, 16 or 17, the polyunsaturated $C_{18}$-fatty acids must first be desaturated by the enzymatic activity of a desaturase and subsequently elongated by at least two carbon atoms by means of an elongase. After an elongation round, this enzyme activity leads to $C_{20}$-fatty acids, and after two elongation rounds to $C_{22}$-fatty acids. The activity of the desaturases and elongases used process according to the invention preferably leads to $C_{18}$-, $C_{20}$- and/or $C_{22}$-fatty acids advantageously having at least one double bond in the fatty acid molecule, preferably having two, three, four, five or six double bonds, particularly preferably leads to $C_{18}$-, $C_{20}$- and/or $C_{22}$-fatty acids having at least two double bonds in the fatty acid molecule, preferably having three, four, five or six double bonds, very particularly preferably having five or six double bonds in the molecule. After a first desaturation and the elongation have taken place, further desaturation and elongation steps such as, for example, such a desaturation in the Δ-5 and Δ-4 position can follow. Particularly preferred as products of the process according to the invention are palmitic acid, stearic acid, oleic acid, linoleic acid, gamma-linolenic acid, alpha-linolenic acid, stearidonic acid, dihomo-gamma-linolenic acid, arachidonic acid and eicosapentaenoic acid.

The preferred biosynthesis sites of fatty acids, oils, lipids or fats in the transgenic plants advantageously used is, for example, in general the seeds or cell layers of the seed, such that a seed-specific expression of the nucleic acids used in the process is expedient. The biosynthesis of fatty acids, oils or lipids must not be restricted to the seed tissue, but can also take place tissue-specifically in all other parts of the plant—for example in epidermal cells or in the tubers.

By the use of the nucleic acid constructs according to the invention, which code, inter alia, for an elongase, the polyunsaturated fatty acids produced can be increased at least by 5%, preferably at least by 10%, particularly preferably at least by 20%, very particularly preferably by at least 50% in the process compared to the wild-type of the plants, which comprise the nucleic acids non-recombinantly.

By the process according to the invention, the polyunsaturated fatty acids in the plant seed oil produced in the process can in principle be increased to two types. Advantageously, the pool of free polyunsaturated fatty acids and/or the proportion of the esterified polyunsaturated fatty acids produced by means of the process can be increased. Advantageously, the pool of esterified polyunsaturated fatty acids in the transgenic plants is increased by the process according to the invention.

The nucleic acid constructs of the present invention, which are involved in the metabolism of lipids and fatty acids, PUFA cofactors and enzymes or in the transport of lipophilic compounds by means of membranes, are used in the process according to the invention for the modulation of the production of PUFAs in transgenic plants, such as corn, soybean, Linum species such as flax, oil or fiber flax, Brassica species, such as rape, canola and rapeseed, safflowers either directly (e.g. if the overexpression or optimization of a fatty acid biosynthesis protein has a direct influence on the yield, production and/or efficiency of production of the fatty acid from modified plants) and/or can have an indirect action, which nevertheless leads to an increase in the yield, production and/or efficiency of production of the PUFAs or a decrease in undesired compounds (e.g. if the modulation of the metabolism of lipids and fatty acids, cofactors and enzymes leads to changes in the yield, production and/or efficiency of production or of the composition of the desired compounds within the cells, which in turn can influence the production of one or more fatty acids).

The combination of various precursor molecules and biosynthesis enzymes leads to the production of various fatty acid molecules, which has a decisive effect on the composition of the lipids. Since polyunsaturated fatty acids (=PUFAs) are not only simply incorporated in triacylglycerol but also in membrane lipids.

Lipid synthesis can be divided into two sections: the synthesis of fatty acids and their binding to sn-glycerol 3-phosphate and the addition or modification of a polar headgroup. Customary lipids that are used in membranes comprise phospholipids, glycolipids, sphingolipids and phosphoglycerides. The fatty acid synthesis begins with the conversion of acetyl-CoA to malonyl-CoA by acetyl-CoA carboxylase or to acetyl-ACP by acetyltransacylase. After condensation reaction, these two product molecules together form acetoacetyl-ACP, which is converted by means of a number of condensation, reduction and dehydration reactions such that a saturated fatty acid molecule having the desired chain length is obtained. The production of the unsaturated fatty acids from these molecules is catalyzed by specific desaturases, and to be specific either aerobically by means of molecular oxygen or anaerobically (with regard to fatty acid synthesis in microorganisms see F. C. Neidhardt et al. (1996) E. coli and Salmonella. ASM Press: Washington, D.C., pp. 612-636 and citations comprised therein; Lengeler et al. (eds.) (1999) Biology of Procaryotes. Thieme: Stuttgart, New York, and the comprised citations, and Magnuson, K., et al. (1993) Microbiological Reviews 57:522-542 and the comprised citations). The fatty acids bound to phospholipids thus prepared must subsequently be converted again for the further elongations of the phospholipids in the fatty acid CoA ester pool. Acyl-CoA: lysophospholipid acyltransferases make this possible. Furthermore, these enzymes can transfer the elongated fatty acids again from the CoA esters to the phospholipids. This reaction sequence can be carried out where appropriate several times.

Precursors for the PUFA biosynthesis are, for example, oleic acid, linoleic acid and linolenic acid. These $C_{18}$-carbon fatty acids must be elongated to $C_{20}$ and $C_{22}$ in order that fatty acids of the eicosa and docosa chain type are obtained. With the aid of the nucleic acid constructs used in the process, the desaturases (such as the Δ-12- and Δ-15, omega-3-, Δ-12, Δ-4-, Δ-5- and Δ-6-desaturases) and/or elongases (Δ-5- and Δ-6-elongases), for example, arachidonic acid, eicosapentaenoic acid, docosapentaenoic acid or docosahexaenoic acid can be prepared and subsequently used for various purposes in foodstuffs, feed, cosmetic or pharmaceutical applications. Using the enzymes mentioned, $C_{20}$- and/or $C_{22}$-fatty acids having at least one, advantageously at least two, three, four, five or six double bonds in the fatty acid molecule, preferably $C_{20}$- or $C_{22}$-fatty acids advantageously having four, five or six double bonds in the fatty acid molecule, can be prepared. The desaturation can take place before or after elongation of the corresponding fatty acid. The products of the desaturase activities and the possible further desaturation and elongation therefore lead to preferred PUFAs having a higher degree of desaturation, including a further elongation of $C_{20}$ to $C_{22}$-fatty acids, to fatty acids such as gamma-linolenic acid, dihomo-gamma-linolenic acid, arachidonic acid, stearidonic acid, eicosatetraenoic acid or eicosapentaenoic acid. Substrates of the desaturases and elongases used in the process according to the invention are $C_{16}$-, $C_{18}$- or $C_{20}$-fatty acids such as, for example, linoleic acid, gamma-linolenic acid, alpha-linolenic acid, dihomo-gamma-linolenic acid, eicosatetraenoic acid or stearidonic acid. Preferred substrates are linoleic acid, gamma-linolenic acid and/or alpha-linolenic acid, dihomo-gamma-linolenic acid or arachidonic acid, eicosatetraenoic acid or eicosapentaenoic acid. The synthesized $C_{20}$- or $C_{22}$-fatty acids having at least one, two, three, four, five or six double bonds in the fatty acid are obtained in the process according to the invention in the form of free fatty acid or in the form of their esters, for example in the form of their glycerides.

The term "glyceride" is understood as meaning a glycerol esterified with one, two or three carboxylic acid radicals (mono-, di- or triglyceride). "Glyceride" is also understood as meaning a mixture of various glycerides. The glyceride or the glyceride mixture can comprise further additives, e.g. free fatty acids, antioxidants, proteins, carbohydrates, vitamins and/or other substances. A "glyceride" within the meaning of the process according to the invention is understood as meaning further derivatives derived from the glycerol. These also include, in addition to the fatty acid glycerides described above, glycerophospholipids and glyceroglycolipids. Preferably, mention may be made by way of example here of the glycerophospholipids such as lecithin (phosphatidylcholine), cardiolipin, phosphatidylglycerol, phosphatidylserine and alkylacylglycerophospholipids.

Furthermore, fatty acids must subsequently be transported to various modification sites and incorporated into the triacylglycerol storage lipid. A further important step in lipid synthesis is the transfer of fatty acids to the polar headgroups, for example by glycerol fatty acid acyltransferase (see Frentzen, 1998, Lipid, 100(4-5):161-166).

See publications about the plant fatty acid biosynthesis, desaturation, the lipid metabolism and membrane transport of fat-comprising compounds, the beta oxidation, fatty acid modification and cofactors, triacylglycerol storage and assembling including the citations therein in the following articles: Kinney, 1997, Genetic Engeneering, ed.: J K Setlow, 19:149-166; Ohlrogge and Browse, 1995, Plant Cell 7:957-970; Shanklin and Cahoon, 1998, Annu. Rev. Plant Physiol. Plant Mol. Biol. 49:611-641; Voelker, 1996, Genetic Engeneering, ed.: J K Setlow, 18:111-13; Gerhardt, 1992, Prog. Lipid R. 31:397-417; Gühnemann-Schäfer & Kindl, 1995, Biochim. Biophys Acta 1256:181-186; Kunau et al., 1995, Prog. Lipid Res. 34:267-342; Stymne et al., 1993, in: Biochemistry and Molecular Biology of Membrane and Storage Lipids of Plants, ed.: Murata and Somerville, Rockville, American Society of Plant Physiologists, 150-158, Murphy & Ross 1998, Plant Journal. 13(1):1-16.

The plant seed oil produced in the process comprises PUFAs, a group of molecules that higher animals can no longer synthesize and must thus assimilate or that higher animals can no longer adequately produce themselves and thus must additionally assimilate, although they are easily synthesized by other organisms, such as bacteria. For example, cats can no longer synthesize arachidonic acid.

"Phospholipids" within the meaning of the invention are to be understood as meaning phosphatidylcholine, phosphatidylethanolamine, phosphatidylserine, phosphatidylglycerol and/or phosphatidylinositol more advantageously phosphatidylcholine. The terms "production or productivity" are known in the specialist field and include the concentration of the product (compounds of the formula I) that is formed in a certain time span and a certain volume (e.g. kg of product per hour per liter). It also comprises the productivity within a plant cell or a plant, that is the content of the desired fatty acids produced in the process based on the content of all fatty acids in this cell or plant. The term "efficiency of production" comprises the time that is necessary for the obtainment of a certain production quantity (e.g. how long the cell needs for the erection of a certain throughput rate of a fine chemical). The term "yield or product/carbon yield" is known in the specialist field and comprises the efficiency of the conversion of the carbon source in the product (i.e. the fine chemical). This is usually expressed, for example, as kg of product per kg of carbon source. By increasing the yield or production of the compound, the amount of molecules obtained or the suitable molecules of this compound obtained in a certain culture quantity over a fixed period of time is increased. The terms "biosynthesis or biosynthesis pathway" are known in the specialist field and comprise the synthesis of a compound, preferably an organic compound, by a cell from intermediate compounds, for example in a multistep and highly regulated process. The terms "degradation or degradation pathway" are known in the specialist field and comprise the cleavage of a compound, preferably an organic compound, by a cell to degradation products (more generally, smaller or less complex molecules), for example in a multistep and highly regulated process. The term "metabolism" is known in the specialist field and comprises the entirety of the biochemical reactions that take place in an organism. The metabolism of a certain compound (e.g. the metabolism of a fatty acid) then comprises the entirety of the biosynthesis, modification and degradation pathways of this compound in the cell, which relate to this compound.

By the use of the nucleic acid constructs according to the invention and where appropriate further polynucleotides that code for enzymes of the lipid or fatty acid metabolism, various advantageous effects can be achieved in the process according to the invention. Thus, the yield, production and/or efficiency of the production of the polyunsaturated fatty acids in a plant, preferably in an oil fruit plant, can be influenced. The number or activity of the polypeptides or polynucleotides can be increased such that greater amounts of the gene products and thus finally greater amounts of the compounds of the general formula I can be produced. A de novo synthesis in an organism, in which the activity and the ability for the biosynthesis of the compounds before the incorporation of the corresponding gene/genes was absent, is also possible. This applies accordingly for the combination with further desaturases or elongases or further enzymes from the fatty acid and lipid metabolism. The use of various divergent sequences, i.e. different at the DNA sequence level, can also be advantageous here, or the use of promoters for gene expression, which makes possible a different temporal gene expression e.g. dependent on the degree of maturity of a seed or oil-storing tissue.

By the introduction of a nucleic acid construct according to the invention into a plant, alone or in combination with other genes, not only can the biosynthesis flow to the final products be increased, but also the corresponding triacylglycerol composition can be increased or created de novo. Likewise, the number or activity of other genes that are increased in the import of nutrients that are necessary for the biosynthesis of one or more fatty acids, oils, polar and/or neutral lipids, such that the concentration of these precursors, cofactors or intermediate compounds within the cells or within the storage compartment can be increased, whereby the ability of the cells for the production of PUFAs is raised further. By optimization of the activity or increase in the number of one or more polynucleotides or polypeptides that are involved in the biosynthesis of these compounds, or by destroying the activity of one or more genes that are involved in the degradation of these compounds, it can be possible to raise the yield, production and/or efficiency of the production of fatty acid and lipid molecules from plants. The plant seed oil obtained in the process is suitable as a starting material for the chemical synthesis of further valuable products. They can be used, for example, in combination with one another or alone for the production of pharmaceuticals, foodstuffs, in particular infant or baby food, animal feed or cosmetics.

Preferably, the process according to the invention comprises a further step d) of the formulation of the plant seed oil as an oil, lipid or fatty acid composition.

Even more preferably, the oil, lipid or fatty acid composition is further formulated in the process according to the invention to give a foodstuff, preferably to give baby food.

In a preferred embodiment of this process, the oil, lipid or fatty acid composition is further formulated to give a medicament, to give cosmetics, to give a foodstuff, to give a food supplement, to give a feed, preferably fish food or feed for laying hens, or to give a food supplement.

Finally, the invention fundamentally relates to the use of the nucleic acid construct according to the invention, a transgenic plant cell or a transgenic plant that comprises these nucleic acid constructs, for the production of an oil, lipid or fatty acid composition. This is then preferably to be employed as a pharmaceutical, cosmetic, foodstuff, particularly baby food, feed, preferably fish food or food for laying hens, or food supplement.

For example, the plant seed oil according to the invention can be used, in addition to the applications described above, for the feeding of animals, in particular as a food supplement for feed applications for the improvement of the breeding result. A feed additive for the improvement of stock breeding results, for example of Salmonidae, cattle, sheep, pigs, hens, and for the health of domestic animals, for example of cats and dogs, comprises arachidonic acid (ARA) in concentrations that are suitable for improving the reproduction rates if the food of the young animal or of the mother animal is supplemented with ARA. In addition to ARA, the feed product here also comprises gamma-linolenic acid (GLA), dihomo-gamma-linolenic acid (DGLA), stearidonic acid (SDA) and eicosapentaenoic acid (EPA) in order to obtain a high-quality feed additive. The supplementation of food and feedstuff products leads to higher reproduction rates, better chances of survival for the young animals, and to improved neurological and visual development.

Furthermore, the plant seed oil according to the invention can also be employed for technical purposes, for example in the form of a technical oil. Such an oil comprises a uniquely high concentration of unsaturated fatty acids having double bonds as a polymerization component. The plant seed oil according to the invention can be employed alone or in combination with a polymerizing agent for the following technical applications:

1. Lacquers and coatings (use as an oxidative drying oil)

2. Polymers for floor coverings or plastics (use as an oxidative drying oil)

3. Other chemical applications

4. Cosmetic applications

5. Applications in the field of electronics and semiconductor technology

The advantage of the plant seed oil according to the invention described above lies in its unique polymerization properties. The oil polymerizes more rapidly and uniformly and forms a stronger three-dimensional structure, which is expedient where strength, durability and elasticity of the network are necessary (coatings and floor coverings or plastics). As a result of its uniform distribution of the double bonds in most fatty acids in the oil, the product moreover has a high elasticity.

The content of all citations, patent applications, patents and published patent applications cited in this patent application is hereby included by reference to the respective specific disclosure content.

FIGURES

FIG. 1: Metabolic pathways for the synthesis of LC-PUFA.

Figure 2A:
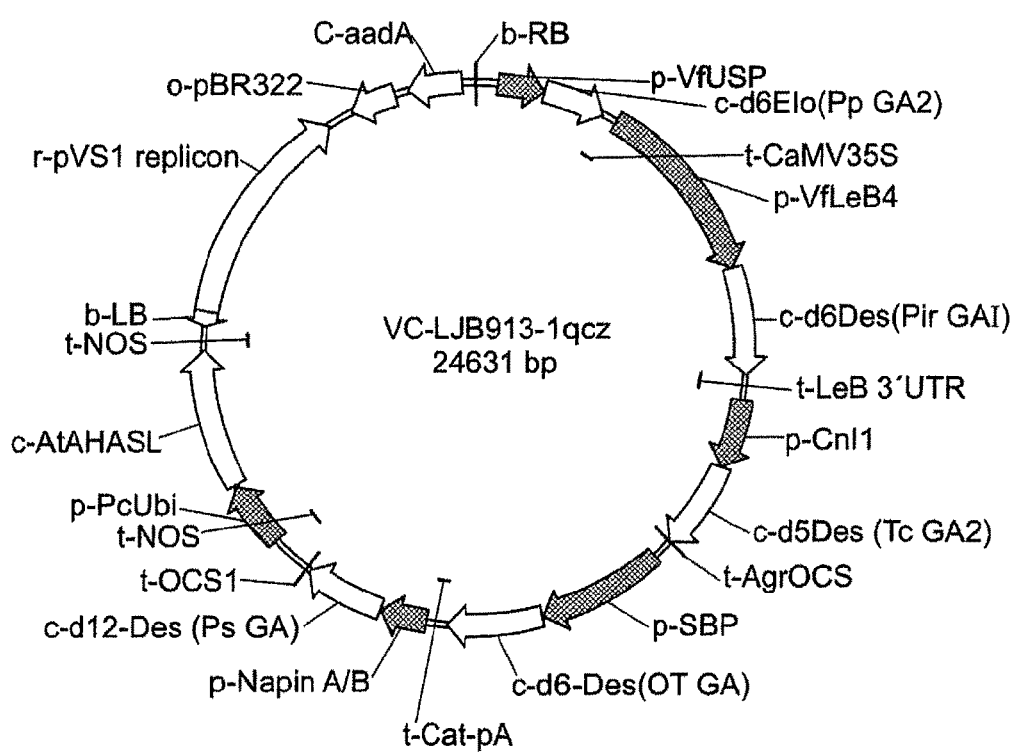
FIG. 2A is a plasmid map of T plasmids constructed for transformation in *Brassica napus*. The assigned sequence is shown in the SEQ ID NO 15.
Figure 2B:
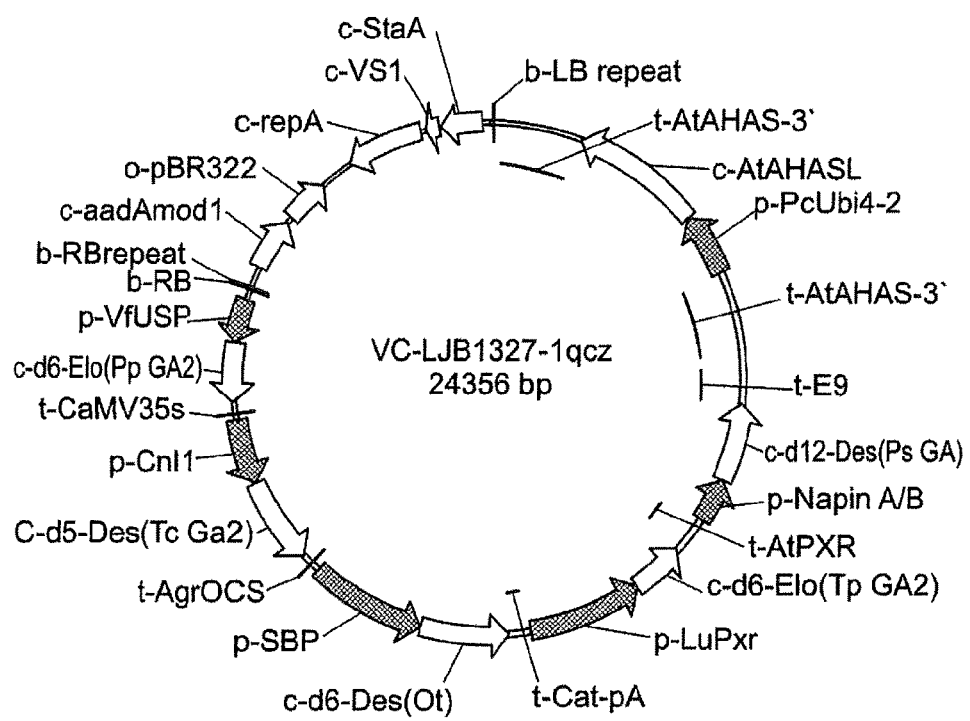
FIG. 2B is a plasmid map of T plasmids constructed for transformation in *Brassica napus*. The assigned sequence is shown in the SEQ ID NO 16.
Figure 2C:
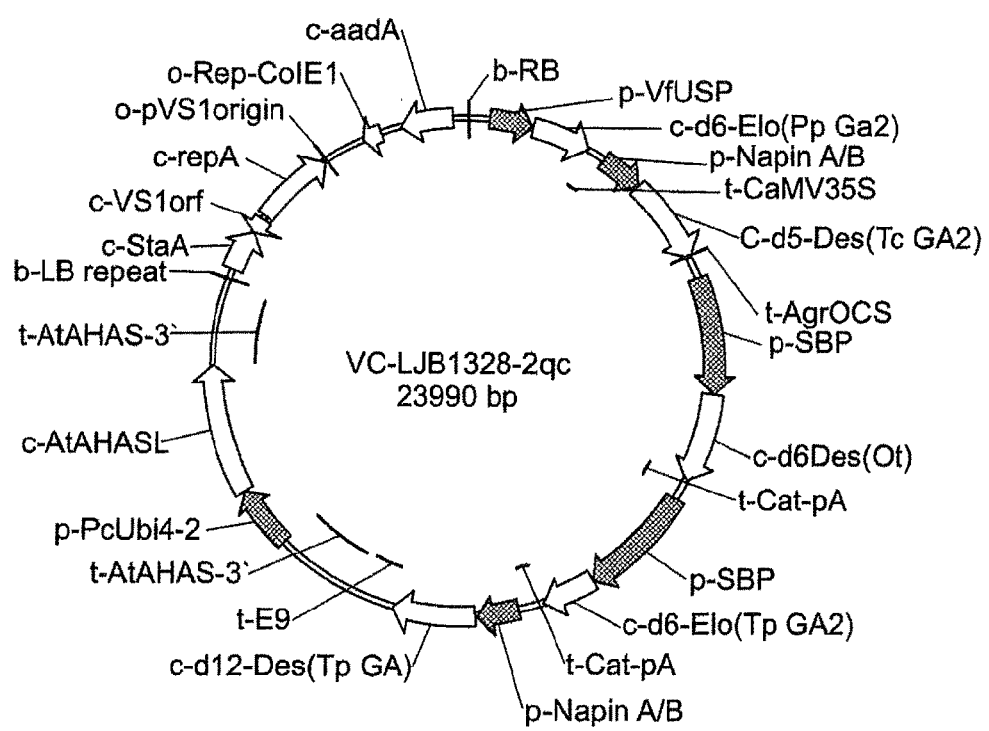
FIG. 2C is a plasmid map of T plasmids constructed for transformation in *Brassica napus*. The assigned sequence is shown in the SEQ ID NO 17.

FIG. 2A-C: Plasmid maps of the T plasmids constructed for transformation in *Brassica napus*. The assigned sequences are shown in the SEQ ID NOs. 15 (FIG. 2A), 16 (FIG. 2B) and 17 (FIG. 2C).

Figure 3A:
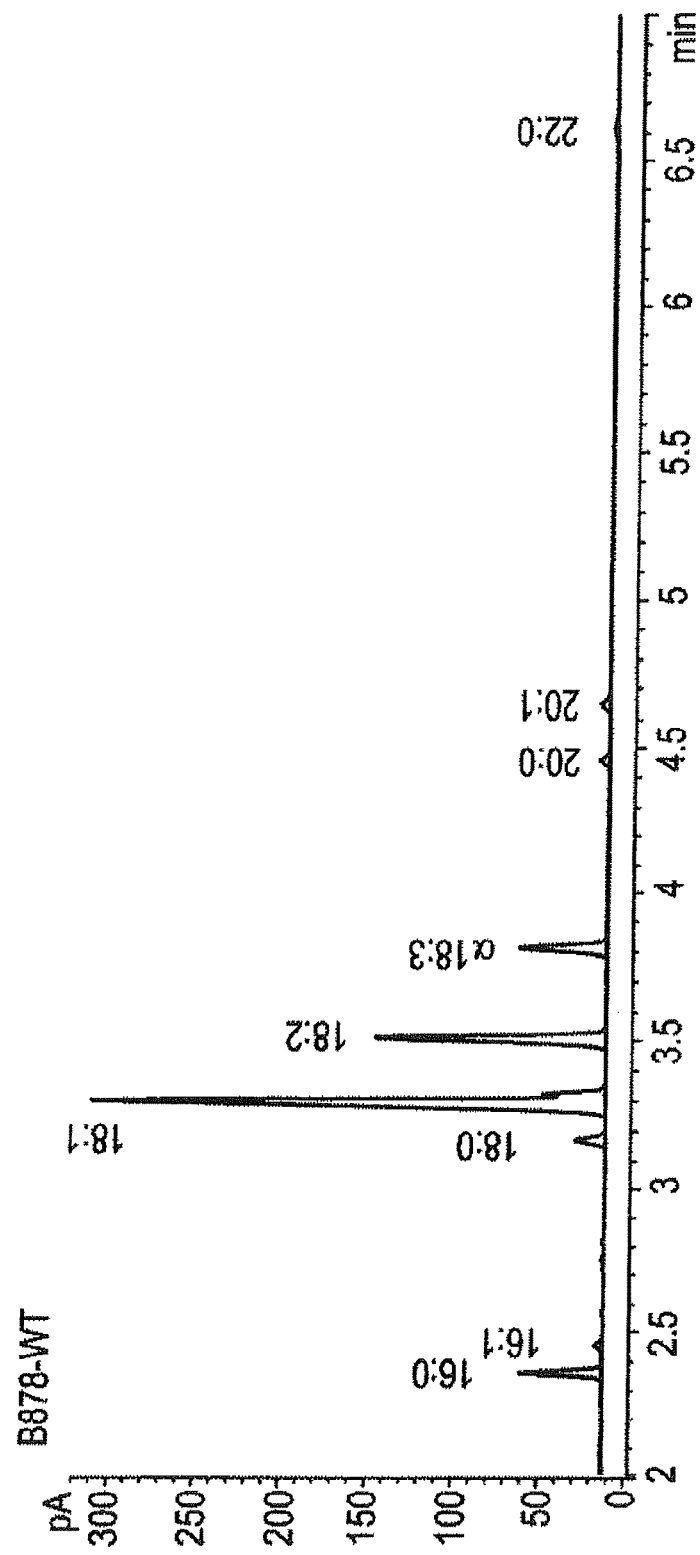
FIG. 3A is a chromatogram of the gas-chromatographic fatty acid analysis of non-transgenic rape (*Brassica napus*).
Figure 3B:
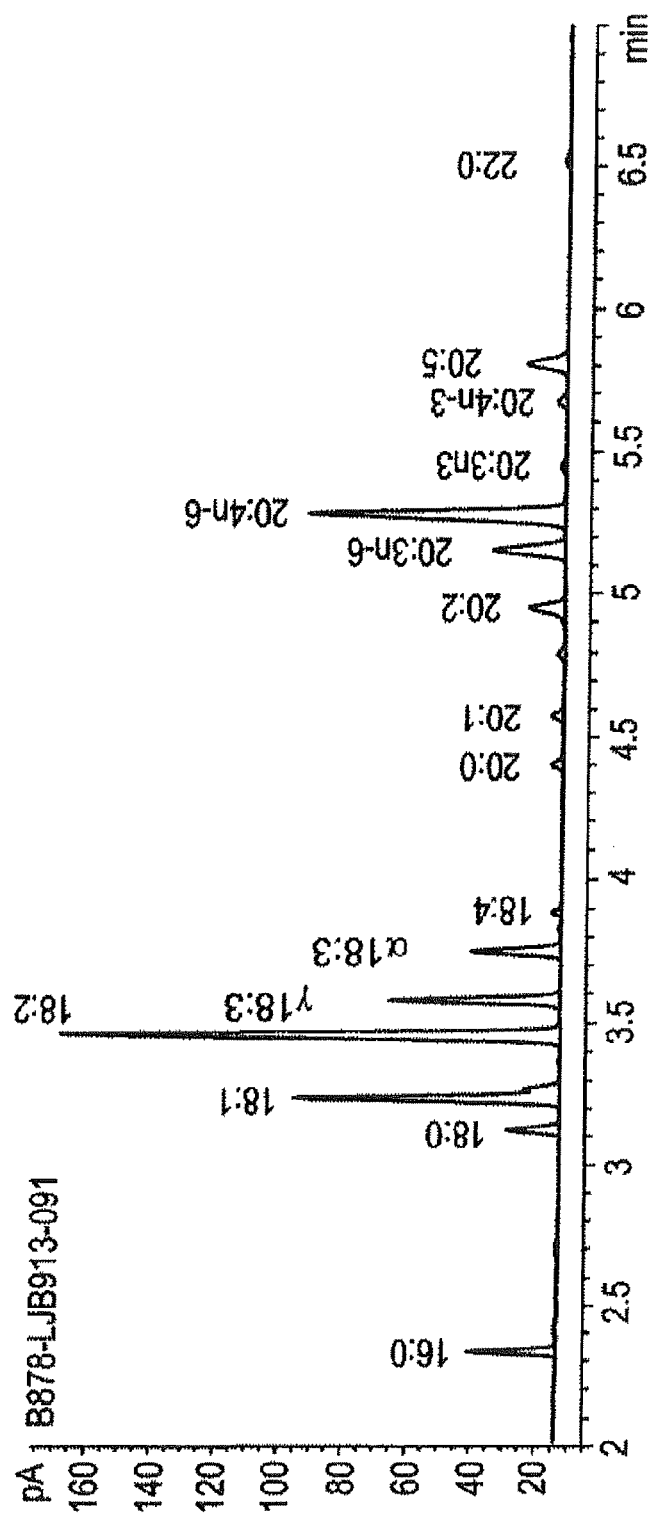
FIG. 3B is a chromatogram of the gas-chromatographic fatty acid analysis of transgenic rape (*Brassica napus*), transformed with the construct VC-LJB913-1qcz (SEQ ID NO. 15).

FIG. 3A: Chromatogram of the gas-chromatographic fatty acid analysis of non-transgenic rape (*Brassica napus*). The peaks are annotated with the assigned fatty acids, the nomenclature is explained in Table 5.

FIG. 3B: Chromatogram of the gas-chromatographic fatty acid analysis of transgenic rape (*Brassica napus*), transformed with the construct VC-LJB913-1qcz (SEQ ID NO. 15). The peaks are annotated with the assigned fatty acids, the nomenclature is explained in Table 5.

FIG. 4: Pilot plant sketch for the supercritical CO2 extraction for oils.

FIG. 5: Production of infant food in liquid form.

FIG. 6: Production of infant food by complete spraying (total product).

FIG. 7: Fatty acid ratios in breast milk: The values were averaged for the individual countries and the respective maximum or minimum of the ratios shown in the country averages (Yuhas et al. 2006 Lipids 41:851-8).

The invention is illustrated further by the examples below, which should not be construed as restrictive.

Example 1

General Cloning Procedures

The cloning procedures such as, for example, restriction cleavages, agarose gel electrophoresis, purification of DNA fragments, transfer of nucleic acids to nitrocellulose and nylon membranes, linkage of DNA fragments, transformation of *Escherichia coli* cells, growth of bacteria and the sequence analysis of recombinant DNA were carried out as described in Sambrook et al. (1989) (Cold Spring Harbor Laboratory Press).

Example 2

Lipid Extraction and Analysis of Plant Seed Oils

The effect of genetic modification in plants or on the production of a desired compound (such as a fatty acid) can be determined by culturing the modified plant under suitable conditions (like those described above) and investigating the medium and/or the cellular components for the increased production of the desired product (i.e. of lipids or a fatty acid). These analysis techniques are known to the person skilled in the art and comprise spectroscopy, thin-layer chromatography, staining procedures of various type, enzymatic and microbiological processes and analytical chromatography, such as high-performance liquid chromatography (see, for example, Ullman, Encyclopedia of Industrial Chemistry, Vol. A2, pp. 89-90 and pp. 443-613, VCH: Weinheim (1985); Fallon, A., et al., (1987) "Applications of HPLC in Biochemistry" in: Laboratory Techniques in Biochemistry and Molecular Biology, Vol. 17; Rehm et al. (1993) Biotechnology, Vol. 3, Chapter III: "Product recovery and purification", pp. 469-714, VCH: Weinheim; Belter, P. A., et al. (1988) Bioseparations: downstream processing for Biotechnology, John Wiley and Sons; Kennedy, J. F., and Cabral, J. M. S. (1992) Recovery processes for biological Materials, John Wiley and Sons; Shaeiwitz, J. A., and Henry, J. D. (1988) Biochemical Separations, in: Ullmann's Encyclopedia of Industrial Chemistry, Vol. B3; Chapter 11, pp. 1-27, VCH: Weinheim; and Dechow, F. J. (1989) Separation and purification techniques in biotechnology, Noyes Publications).

In addition to the abovementioned process, plant lipids are extracted from plant material as described by Cahoon et al. (1999) Proc. Natl. Acad. Sci. USA 96 (22):12935-12940, and Browse et al. (1986) Analytic Biochemistry 152:141-145. Qualitative and quantitative lipid or fatty acid analysis is described in Christie, William W., Advances in Lipid Methodology, Ayr/Scotland: Oily Press (Oily Press Lipid Library; 2); Christie, William W., Gas Chromatography and Lipids. A Practical Guide—Ayr, Scotland: Oily Press, 1989, Repr. 1992, IX, 307 S. (Oily Press Lipid Library; 1); "Progress in Lipid Research, Oxford: Pergamon Press, 1 (1952)-16 (1977) under the title: Progress in the Chemistry of Fats and Other Lipids CODEN.

An example is the analysis of fatty acids (abbreviations: FAME, fatty acid methyl ester; GC-MS, gas-liquid chromatography-mass spectrometry; TAG, triacylglycerol; TLC, thin-layer chromatography).

The material to be analyzed was broken up by grinding with a steel ball (Retsch mill, 1 min). The material was centrifuged after breaking up and the sediment was resuspended in distilled water, heated at 100° C. for 10 min, cooled on ice and centrifuged again, followed by extraction in 0.5 M sulfuric acid in methanol with 2% dimethoxypropane for 1 h at 90° C., which leads to hydrolyzed oil and lipid compounds that yield transmethylated lipids. These fatty acid methyl esters were extracted in petroleum ether and finally subjected to a GC analysis using a capillary column (Chrompack, WCOT Fused Silica, CP-Wax-52 CB, 25 microm, 0.32 mm) with a temperature gradient between 170° C. and 240° C. for 20 min and 5 min at 240° C. The identity of the fatty acid methyl esters obtained was defined using standards that are obtainable from commercial sources (e.g. Sigma).

Example 3

Combination of the Genes Involved in the Metabolic Pathway and their Assembly in a T Plasmid For the synthesis of LC-PUFA in the seeds of rape, the genes necessary in the metabolic pathway (Table 1), combined with expression elements (promoters, terminators, Table 2), were transferred to transformation vectors.

TABLE 1

Genes used for the production of arachidonic acid in rape seeds.

| Genes | Organism | Activity | SEQ ID No. |
|---|---|---|---|
| D6Des(Pir) | *Pythium irregulare* | Δ6-desaturase | 5 |
| D6Des(Ot) | *Ostreococcus tauri* | Δ6-desaturase | 7 |
| D6Elo(Pp) | *Physcomitrella patens* | Δ6-elongase | 1 |
| D6Elo(Tp) | *Thalassiosira pseudonana* | Δ6-elongase | 3 |
| D5Des(Tc) | *Thraustochytrium* ssp. | Δ5-desaturase | 9 |
| D12Des(Ps) | *Phytophtora sojae* | Δ12-desaturase | 11 |
| D12Des(Tp) | *Thalassiosira pseudonana* | Δ12-desaturase | 13 |

TABLE 2

Expression elements used for the production of arachidonic acid in rape seeds.

| Element | Organism | Function | SEQ ID No. |
|---|---|---|---|
| p-VfUSP | Vicia faba | Promoter | 22 |
| t-CaMV35S | CaMV | Terminator | 23 |
| p-VfLeB4 | Vicia faba | Promoter | 24 |
| t-Le3'UTR | Vicia faba | Terminator | 25 |
| p-Cnl1 | Linum usitatissimum | Promoter | 26 |
| t-AgrOCS | Agrobacterium tumefaciens | Terminator | 27 |
| p-SBP | Vicia faba | Promoter | 28 |
| t-Cat-pA | Brassica napus | Terminator | 29 |
| p-NapinA/B | Brassica napus | Promoter | 30 |
| t-OCS1 | Agrobacterium tumefaciens | Terminator | 31 |
| t-E9 | Pisum sativum | Terminator | 32 |
| p-LuPXR | Linum usitatissimum | Promoter | 33 |
| t-AtPXR | Arabidopsis thaliana | Terminator | 34 |

Starting from the genes and the expression elements, the gateway cloning procedure (Invitrogen) was used according to the manufacturer's instructions, in order to combine multiple cassettes in pENTR vectors into the binary T is plasmid pSUN. Hellens et al, Trends in Plant Science (2000) 5: 446-451 gives a survey of binary vectors and their use. The binary T plasmids VC-LJB913-1qcz (SEQ ID 15), VC-LJB1327-1qcz (SEQ ID 16) and VC-LJB1328-1qcz (SEQ ID 17) were obtained by the recombination reaction of the pENTR vectors. The sequence of the functional expression cassettes (promoter, gene, terminator) are shown for the vectors obtained in the FIGS. 2A, 2B and 2C.

In a similar manner, functional expression cassettes for the synthesis of a plant seed oil which comprises the polyunsaturated, long-chain fatty acid docosahexaenoic acid (DHA) can also be produced. DHA is a further important component of breast milk. For the synthesis of DHA in plants, constructs in rape can be transformed, as were described in WO2005/083093. If a plant seed oil comprising DHA is to be prepared, the nucleic acid constructs according to the invention additionally to the abovementioned genes preferably comprise genes that encode the delta 5-elongase from Ostreococcus tauri as shown in SEQ ID NO. 18 and the delta 4-desaturase from Traustochytrium ssp. as shown in SEQ ID NO. 20. Suitable promoters here are SEQ ID No. 22, 24, 26, 28, 30 and 33g as terminators SEQ ID No. 23, 25, 27, 29, 31, 32 and 34 can be employed.

Example 4

Production of Transgenic Rape Plants (Modified According to Moloney et al., 1992, Plant Cell Reports, 8:238-242)

For the production of transgenic rape plants (Brassica napus), binary vectors such as the pSUN plasmids described further above were transformed with the appropriately combined genes in Agrobacterium tumefaciens C58C1:pGV2260 (Deblaere et al, 1984, Nucl. Acids. Res. 13, 4777-4788). For the transformation of rape plants, a 1:50 dilution of an overnight culture of a positively transformed Agrobacteria colony in Murashige-Skoog medium (Murashige and Skoog 1962 Physiol. Plant. 15, 473) comprising 3% sucrose (3MS medium) was used. Petioles or hypocotyledons of freshly germinated sterile rape plants (each to about 1 cm$^2$) were incubated in a petri dish with a 1:50 Agrobacteria dilution for 5-10 minutes. A 3-day co-incubation in darkness at 25° C. in 3MS medium comprising 0.8% Bacto agar followed. The culturing was continued after 3 days with 16 hours of light/8 hours of darkness and continued in a weekly rhythm on MS medium with 500 mg/l of Claforan (cefotaxime sodium), 50 mg/l of kanamycin, 20 mM of benzylaminopurine (BAP) and 1.6 g/l of glucose. Growing shoots were transferred to MS medium comprising 2% sucrose, 250 mg/l of Claforan and 0.8% Bacto agar. If no roots formed after three weeks, 2-indolebutyric acid was added to the medium as a growth hormone for rooting.

Regenerated shoots were obtained on 2MS medium with kanamycin and Claforan, transferred to earth after rooting and after cultivation for two weeks raised in a climatic chamber or in the greenhouse, brought to flowering, ripe seeds were harvested and, on expression of the desaturase or elongase genes, investigated by means of lipid analyses as described by way of example in Qiu et al. 2001, J. Biol. Chem. 276, 31561-31566.

B) Production of Transgenic Flax Plants

The production of transgenic flax plants can be generated, for example, according to the method of Bell et al., 1999, In Vitro Cell. Dev. Biol.-Plant. 35(6):456-465 by means of particle bombardment. Agrobacteria-mediated transformations can be produced, for example, according to Mlynarova et al. (1994), Plant Cell Report 13: 282-285.

Example 5

Lipid Analysis of Transgenic Rape Plants, Transformed with the Prepared T Plasmids The plasmids that were prepared in Example 3 were transformed in rape (Brassica napus) as described in Example 4. After selection of the transgenic plants by means of PCR, these were raised to seed maturation (day/night cycle: 16 h, 200mE, 21° C., 8 h dark, 19° C.) and the seeds were harvested.

Harvested seeds were extracted as described in Example 2 and subjected to gas-chromatographic analysis. Table 3 shows the results of various lines of these constructs. Table 5 shows the nomenclature used for the fatty acids. Table 6 shows the ratios of ARA to the mean values of all measured fatty acids.

Surprisingly, it was possible to find here that in contrast to experiments previously carried out for the production of arachidonic acids in transgenic plants (e.g. WO2005/083093 or Kajikawa et al. Biosci. Biotechno. Biochem., 72, 70549-1-10, 2008) or from oils of microorganisms (e.g. Mortierella alpina), it was possible to achieve new properties. In particular, new ratios between the fatty acids gamma-linolenic acid (GLA) and arachidonic acid (ARA) and dihomo-gamma-linolenic acids (DGLA) and arachidonic acid were obtained. Table 4 gives a survey of the ratios in comparison to different organisms that either produce arachidonic acid naturally or were transferred to the genes for the corresponding metabolic pathway.

In addition to the physiologically positive effect of arachidonic acid, mention may again also be made at this point of the favorable ratio for GLA and DGLA obtained in the plants. In addition to arachidonic acid, GLA and DGLA are important components of the fatty fraction of breast milk. The ratios present in the plant seed oil according to the invention are very close to those in breast milk. Moreover, the fatty acid composition in the plant seed oil according to the invention is very similar to that present in breast milk; compare FIG. 7.

TABLE 3

Gas-chromatographic determination of the fatty acid pattern of seed oil transgenic rape plants.

| Plants | 16:0 | 18:0 | 18:1n-9 | 18:2n-6 LA | 18:3n-6 GLA | 18:3n-3 ALA | 18:4n-3 | 20:0 | 20:1n-9 | 20:2n-6 | 20:3n-6 DGLA | 20:3n-3 | 20:4n-6 ARA | 20:5n-3 | 22:0 | Ratio ARA:GLA | Ratio ARA:DGLA | Ratio LA:ALA | Ratio ARA:EPA |
|---|---|---|---|---|---|---|---|---|---|---|---|---|---|---|---|---|---|---|---|
| LJB913 64-13a | 4.4 | 3.9 | 11.3 | 21.7 | 11.7 | 3.7 | 0.7 | 1.1 | 0.9 | 3.7 | 6.7 | 0.0 | 25.6 | 3.8 | 0.0 | 2.2 | 3.8 | 5.9 | 6.7 |
| LJB913 64 9 | 3.8 | 2.7 | 9.8 | 21.8 | 12.7 | 4.3 | 0.8 | 0.9 | 1.0 | 4.5 | 8.7 | 0.6 | 23.6 | 3.8 | 0.0 | 1.8 | 2.7 | 5.1 | 6.1 |
| LJB913_64_3 | 4.2 | 3.6 | 12.0 | 22.4 | 11.7 | 3.5 | 0.7 | 1.0 | 1.2 | 5.7 | 6.5 | 0.7 | 22.0 | 3.5 | 0.5 | 1.9 | 3.4 | 6.5 | 6.4 |
| LJB913 64 20 | 3.5 | 3.3 | 14.1 | 25.9 | 8.7 | 3.0 | 0.5 | 0.9 | 1.2 | 5.0 | 7.4 | 0.5 | 21.2 | 3.2 | 0.4 | 2.4 | 2.9 | 8.5 | 6.6 |
| LJB913 91 5 | 3.5 | 2.8 | 15.7 | 27.1 | 9.0 | 4.9 | 0.5 | 0.8 | 0.9 | 3.1 | 6.0 | 0.4 | 20.3 | 3.5 | 0.4 | 2.2 | 3.4 | 5.5 | 5.8 |
| LJB913 64 22 | 4.8 | 4.0 | 13.4 | 25.9 | 9.3 | 3.9 | 0.7 | 1.2 | 1.0 | 4.3 | 6.0 | 0.6 | 19.8 | 3.3 | 0.7 | 2.1 | 3.3 | 6.6 | 6.0 |
| LJB913 64 23 | 4.5 | 3.9 | 13.4 | 25.0 | 9.9 | 3.9 | 0.7 | 1.1 | 1.1 | 5.2 | 6.1 | 0.7 | 19.5 | 3.4 | 0.5 | 2.0 | 3.2 | 6.4 | 5.8 |
| LJB913 91 4 | 4.1 | 3.7 | 16.2 | 32.4 | 5.2 | 6.1 | 0.4 | 1.0 | 0.7 | 1.7 | 4.7 | 0.0 | 19.4 | 3.4 | 0.0 | 3.7 | 4.1 | 5.3 | 5.7 |
| LJB913 64 10 | 3.9 | 4.6 | 15.0 | 27.3 | 6.0 | 4.5 | 0.3 | 1.2 | 1.3 | 6.2 | 6.4 | 0.7 | 18.9 | 2.5 | 0.5 | 3.2 | 3.0 | 6.0 | 7.6 |
| LJB913 64 13b | 3.9 | 3.5 | 15.0 | 25.1 | 9.4 | 4.5 | 0.5 | 0.9 | 1.1 | 4.5 | 7.8 | 0.6 | 18.7 | 3.1 | 0.0 | 2.0 | 2.4 | 5.6 | 6.0 |
| LJB913 91 14 | 3.6 | 3.5 | 17.0 | 26.6 | 9.3 | 5.1 | 0.5 | 0.9 | 0.9 | 2.8 | 6.5 | 0.4 | 18.7 | 3.1 | 0.0 | 2.0 | 2.9 | 5.2 | 6.0 |
| LJB913 64-12a | 4.8 | 4.8 | 13.9 | 24.1 | 7.1 | 5.0 | 0.0 | 1.4 | 1.3 | 7.7 | 6.5 | 1.2 | 18.5 | 3.5 | 0.0 | 2.6 | 2.8 | 4.8 | 5.2 |
| LJB913 91 28 | 4.2 | 4.0 | 17.1 | 27.4 | 7.5 | 5.9 | 0.4 | 1.1 | 0.9 | 2.9 | 6.5 | 0.0 | 18.4 | 2.9 | 0.0 | 2.4 | 2.8 | 4.7 | 6.3 |
| LJB913 91 20 | 3.2 | 3.0 | 18.7 | 28.9 | 7.2 | 4.7 | 0.3 | 0.7 | 0.9 | 2.5 | 7.1 | 0.3 | 18.3 | 2.9 | 0.0 | 2.5 | 2.6 | 6.1 | 6.3 |
| LJB913 64 17 | 4.7 | 4.3 | 14.3 | 27.0 | 9.6 | 3.8 | 0.5 | 1.1 | 1.0 | 4.0 | 6.5 | 0.5 | 18.2 | 2.9 | 0.6 | 1.9 | 2.8 | 7.1 | 6.2 |
| LJB913 91 18 | 3.6 | 4.0 | 17.8 | 31.0 | 6.1 | 4.6 | 0.3 | 1.0 | 0.9 | 2.5 | 5.6 | 0.3 | 18.2 | 2.8 | 0.5 | 3.0 | 3.2 | 6.8 | 6.6 |
| LJB913 64 14b | 4.0 | 4.2 | 14.9 | 26.2 | 8.9 | 5.5 | 0.7 | 1.1 | 1.0 | 3.9 | 6.5 | 0.6 | 17.8 | 3.5 | 0.0 | 2.0 | 2.7 | 4.7 | 5.1 |
| LJB913 91 3 | 3.8 | 3.1 | 18.1 | 29.7 | 6.5 | 6.8 | 0.5 | 0.9 | 0.8 | 1.9 | 5.3 | 0.0 | 17.7 | 3.7 | 0.0 | 2.7 | 3.3 | 4.4 | 4.8 |
| LJB913_64-14a | 5.3 | 4.6 | 14.7 | 28.7 | 6.4 | 4.3 | 0.0 | 1.4 | 1.1 | 6.1 | 7.1 | 0.0 | 17.6 | 2.7 | 0.0 | 2.8 | 2.5 | 6.6 | 6.4 |
| LJB913 64 11 | 4.1 | 3.3 | 16.1 | 27.3 | 9.2 | 4.5 | 0.7 | 1.0 | 1.0 | 3.1 | 6.4 | 0.5 | 17.5 | 3.5 | 0.5 | 1.9 | 2.8 | 6.0 | 5.0 |
| LJB913 64 15 | 4.4 | 4.4 | 15.6 | 26.1 | 6.9 | 4.7 | 0.6 | 1.2 | 1.4 | 7.5 | 5.3 | 1.0 | 16.5 | 3.1 | 0.6 | 2.4 | 3.1 | 5.6 | 5.3 |
| LJB913 64 21 | 4.2 | 4.9 | 17.4 | 28.8 | 7.2 | 3.6 | 0.4 | 1.2 | 1.3 | 5.0 | 5.2 | 0.5 | 16.5 | 2.3 | 0.6 | 2.3 | 3.2 | 7.9 | 7.1 |
| LJB913 91 12 | 3.8 | 3.4 | 19.5 | 29.2 | 5.4 | 7.2 | 0.5 | 1.0 | 0.9 | 2.3 | 4.9 | 0.4 | 16.4 | 4.0 | 0.0 | 3.0 | 3.4 | 4.1 | 4.1 |
| LJB913 91 19 | 4.1 | 3.5 | 19.0 | 35.0 | 4.3 | 5.1 | 0.3 | 1.1 | 0.8 | 2.2 | 5.0 | 0.0 | 15.8 | 2.5 | 0.5 | 3.7 | 3.1 | 6.9 | 6.2 |
| LJB913 64 6 | 3.3 | 3.1 | 19.2 | 29.3 | 7.3 | 4.7 | 0.4 | 0.8 | 1.2 | 4.4 | 5.9 | 0.6 | 15.6 | 2.6 | 0.4 | 2.1 | 2.6 | 6.2 | 6.0 |
| LJB913 64 4 | 3.5 | 3.8 | 17.1 | 27.6 | 5.7 | 6.7 | 0.3 | 1.1 | 1.3 | 5.1 | 7.2 | 0.8 | 15.6 | 3.0 | 0.0 | 2.7 | 2.2 | 4.1 | 5.2 |
| LJB913 91 13 | 4.5 | 5.3 | 19.1 | 33.9 | 4.0 | 5.5 | 0.3 | 1.3 | 1.0 | 2.1 | 3.6 | 0.0 | 15.4 | 2.6 | 0.5 | 3.8 | 4.3 | 6.2 | 5.9 |
| LJB913 91 22 | 3.9 | 4.4 | 20.4 | 28.0 | 7.2 | 4.8 | 0.5 | 1.1 | 1.1 | 3.7 | 5.0 | 0.6 | 15.3 | 2.8 | 0.4 | 2.1 | 3.0 | 5.9 | 5.5 |
| LJB913 64 19 | 4.7 | 4.4 | 17.1 | 27.1 | 7.7 | 5.2 | 0.6 | 1.2 | 1.3 | 5.2 | 5.6 | | | | | | | | |
| LJB913 91 10 | 4.1 | 2.2 | 20.3 | 36.3 | 3.6 | 6.0 | 0.3 | 0.7 | 0.8 | 2.1 | 4.3 | | | | | | | | |
| LJB913 64 5 | 4.6 | 3.1 | 16.9 | 27.7 | 7.4 | 5.4 | 0.8 | 1.0 | 1.1 | 5.9 | 5.2 | | | | | | | | |
| LJB913 64 7 | 3.5 | 3.3 | 20.3 | 29.0 | 7.3 | 5.3 | 0.4 | 0.9 | 1.0 | 2.1 | 8.2 | | | | | | | | |
| LJB913 64 18 | 4.4 | 3.6 | 17.5 | 29.0 | 8.7 | 6.3 | 0.8 | 1.0 | 0.9 | 3.0 | 6.1 | | | | | | | | |
| LJB913 91 23 | 4.4 | 5.1 | 19.4 | 31.5 | 4.2 | 5.9 | 0.2 | 1.1 | 1.1 | 4.2 | 4.3 | | | | | | | | |
| LJB913_91_8 | 4.4 | 4.0 | 19.6 | 31.3 | 5.9 | 6.8 | 0.6 | 1.1 | 0.9 | 2.2 | 4.6 | | | | | | | | |
| LJB913_91_31 | 4.0 | 3.5 | 22.2 | 31.2 | 5.7 | 7.0 | 0.5 | 0.9 | 0.9 | 2.0 | 4.7 | | | | | | | | |
| LJB913_91_2 | 4.4 | 4.5 | 19.8 | 33.1 | 6.2 | 5.2 | 0.5 | 1.2 | 0.9 | 2.4 | 4.0 | | | | | | | | |
| LJB913_64_12b | 4.7 | 4.6 | 20.2 | 31.5 | 5.9 | 5.5 | 0.4 | 1.3 | 1.0 | 2.9 | 5.7 | | | | | | | | |
| LJB913_91_16 | 4.4 | 4.3 | 21.3 | 34.4 | 4.8 | 5.2 | 0.3 | 1.1 | 0.8 | 1.9 | 6.2 | | | | | | | | |
| LJB913_91_9 | 4.2 | 4.1 | 21.7 | 33.4 | 4.0 | 7.0 | 0.3 | 1.0 | 0.9 | 2.3 | 4.4 | | | | | | | | |
| LJB913_91_15 | 4.0 | 3.9 | 21.6 | 32.6 | 4.7 | 7.7 | 0.4 | 0.9 | 0.9 | 1.6 | 5.3 | | | | | | | | |
| LJB913_91_11 | 3.8 | 3.8 | 22.3 | 35.9 | 4.4 | 5.2 | 0.3 | 1.0 | 0.8 | 1.6 | 5.1 | | | | | | | | |
| LJB913_91_6 | 4.0 | 4.2 | 27.2 | 32.6 | 4.2 | 6.6 | 0.3 | 1.3 | 1.0 | 2.3 | 6.3 | | | | | | | | |

TABLE 3-continued

Gas-chromatographic determination of the fatty acid pattern of seed oil transgenic rape plants.

| | | | | | | | | |
|---|---|---|---|---|---|---|---|---|
| LJB913 64 19 | 0.8 | 14.9 | 2.9 | 0.0 | 1.9 | 2.6 | 5.2 | 5.1 |
| LJB913 91 10 | 0.2 | 14.8 | 3.0 | 0.4 | 4.1 | 3.4 | 6.1 | 4.9 |
| LJB913 64 5 | 1.0 | 14.4 | 3.5 | 0.5 | 2.0 | 2.8 | 5.1 | 4.1 |
| LJB913 64 7 | 0.3 | 14.4 | 2.4 | 0.0 | 2.0 | 1.8 | 5.5 | 6.1 |
| LJB913 64 18 | 0.0 | 14.3 | 2.9 | 0.0 | 1.7 | 2.3 | 4.6 | 5.0 |
| LJB913 91 23 | 0.6 | 14.0 | 2.6 | 0.5 | 3.3 | 3.2 | 5.3 | 5.4 |
| LJB913_91_8 | 0.4 | 13.7 | 3.3 | 0.0 | 2.3 | 3.0 | 4.6 | 4.1 |
| LJB913_91_31 | 0.0 | 13.1 | 3.2 | 0.0 | 2.3 | 2.8 | 4.4 | 4.1 |
| LJB913_91_2 | 0.4 | 13.1 | 2.7 | 0.5 | 2.1 | 3.2 | 6.4 | 4.9 |
| LJB913_64_12b | 0.0 | 12.7 | 2.1 | 0.6 | 2.2 | 2.2 | 5.7 | 5.9 |
| LJB913_91_16 | 0.0 | 12.5 | 2.1 | 0.0 | 2.6 | 2.0 | 6.7 | 6.0 |
| LJB913_91_9 | 0.3 | 12.3 | 2.6 | 0.4 | 3.1 | 2.8 | 4.8 | 4.7 |
| LJB913_91_15 | 0.0 | 12.3 | 3.1 | 0.0 | 2.6 | 2.3 | 4.2 | 4.0 |
| LJB913_91_11 | 0.0 | 12.3 | 1.9 | 0.5 | 2.8 | 2.4 | 6.9 | 6.3 |
| LJB913_91_6 | 0.0 | 7.3 | 1.2 | 0.7 | 1.7 | 1.2 | 5.0 | 6.0 |

TABLE 4

Ratios of ARA:GLA, ARA:DGLA and LA:ALA in various organisms.

| Source | ARA:GLA | ARA:DGLA | LA:ALA |
|---|---|---|---|
| WO2005/083093: production of ARA in seed oils of *Brassica juncea* | >1 | <0.2 | n.a. |
| *Marchantia polymorpha* (Biosc. Biotechnol. Biochem. 2000, 72, 70549 ff) | 4.0-4.6 | <15.0-16.0 | 0.15-0.20 |
| *Marchantia polymorpha*, transgene (Biosc. Biotechnol. Biochem. 2000, 72, 70549 ff) | 9.5-10.5 | >10 | 0.15-0.20 |
| *Glycine max*, transgene (Biosc. Biotechnol. Biochem. 2000, 72, 70549 ff) | 0.10-0.15 | 0.18-0.20 | 6.25-6.50 |
| *Mortierella alpina* (Suntory TGA40) | >10 | >10 | 15-18 |
| This application, Table 3 | 1.7-3.8 | 1.2-4.3 | 4.1-7.9 |

TABLE 5

Nomenclature used

| Fatty acid | Nomenclature | |
|---|---|---|
| Oleic acid | 18:1Δ9 | 18:1n-9 |
| Linoleic acid | 18:2Δ6, 12 | 18:2n-6 |
| α-Linoleic acid | 18:3Δ9, 12, 15 | α18:3n-3 |
| γ-Linoleic acid | 18:3Δ6, 9, 12 | γ18:3n-6 |
| Stearidonic acid | 18:4Δ6, 9, 12, 15 | 18:4n-3 |
| Dihomo-γ-linolenic acid | 20:3Δ8, 11, 14 | 20:3n-6 |
| Eicosatrienoic acid | 20:3Δ11, 14, 17 | 20:3n-3 |
| Iso-arachidonic acid | 20:4Δ8, 11, 14, 17 | 20:4n-3 |
| Arachidonic acid | 20:4Δ5, 8, 11, 14 | 20:4n-6 |
| Eicosapentaenoic acid | 20:5 Δ 5, 8, 11, 14, 17 | 20:5n-3 |

Example 6

Processing of the Plant Seed Oil

After harvesting, cleaning and air-drying of the seeds (approximately 7% residual moisture) of the transgenic rape plants produced in Example 4 and of wild-type rape plants, the seeds obtained were processed for the obtainment of the plant seed oil according to the invention and of the wild-type oil. The processing began with the comminution and pressing of the seeds followed by an extraction. Extraction was carried out once by means of hexane and on the other hand by means of supercritical $CO_2$ extraction. Subsequently, refining of the hexane-extracted oil and stabilization was carried out.

The extraction processes and the refining process are described in detail below.

TABLE 6

Ratios of ARA to the mean values of all fatty acids measured.

| | 16:0 | 18:0 | 18:1n-9 | 18:2n-6 LA | 18:3n-6 GLA | 18:3n-3 ALA | 18:4n-3 | 20:0 | 20:1n-9 | 20:2n-6 | 20:3n-6 DGLA | 20:3n-3 | 20:4n-6 ARA | 20:5n-3 | 22:0 |
|---|---|---|---|---|---|---|---|---|---|---|---|---|---|---|---|
| Mean values of all measurements | 4.1 | 3.9 | 17.5 | 29.0 | 7.1 | 5.2 | 0.5 | 1.1 | 1.0 | 3.6 | 5.9 | 0.4 | 16.6 | 3.0 | 0.3 |
| Ratio of ARA to the fatty acids listed | 4.0 | 4.3 | 0.9 | 0.6 | 2.3 | 3.2 | 36.2 | 15.8 | 16.4 | 4.6 | 2.8 | 43.0 | 1.0 | 5.6 | 60.2 |

The supercritical carbon dioxide ($CO_2$) extraction is based on the use of carbon dioxide in sub-critical or supercritical state as an extracting agent, the extracting agent being circulated (Barthet and Daun 2002, JAOCS 79:245-51). For extraction by means of supercritical liquid extraction (SLE), the seed of transgenic rape plants as described in Example 4 and the seed of a *Brassica napus* wild-type were used. Before extraction with SLE, the seeds were first comminuted to 0.15 mm or 0.05 mm under a nitrogen atmosphere by means of a pre-pressing (roll press).

For comparison, a classical soxhlet extraction by means of hexane was carried out. For this organic extraction, largely standard conditions were chosen. 10 g of a pre-pressed seed were placed in a cellulose filter. A distillation flask comprising 200 ml of the organic solvent (hexane) was heated. Evaporated solvent condensed in the condenser attached above the flask. The condensate dripped into the filter equipped with the pre-pressed seed and dissolved the fat-soluble constituents. As soon as the liquid level had reached the limit of the aspirator tube, the solvent flowed back into the distillation flask under pressure. The soxhlet extraction was considered as complete and was stopped as soon as the color transparency of the extraction solvent in the filter unit remained constant. The extract was thereupon removed from the solvent by evaporation of the solvent in vacuo and the mass of the extract was determined.

For the SLE, $CO_2$ having a purity of 99.95% was used (Sigma Aldrich). The batchwise SLE was carried out on the one hand on the laboratory scale by means of "Spe-ed SLE" (25-50 ml, dimension 15.8 cm×1.4 cm i.d., manufacturer: Applied Chemistry, Allntown, US), on the other hand a pilot plant (manufacturer: Nova, Switzerland, capacity 4 l, dimension of the extraction cylinder 22 cm high×7.5 cm i.d.) was used (see FIG. 4).

The experiments were first carried out on the laboratory scale on the "Spe-ed SLE" test unit, in order to be able to vary parameters such as pressure, temperature, extraction time, $CO_2$ throughput (flow rate) and degree of comminution of the seed in a flexible manner. The best experimentally determined parameters were then transferred to the pilot scale.

The extraction cylinder of the pilot plant, whose bottom was lined with glass wool, was equipped with pre-pressed seed. Before closure of the cylinder, glass wool was placed on the pre-pressed seed. The cylinder unit was thereupon connected with inflow and outflow valves and placed in a pre-heated oven (4 l autoclaving oven). It was then possible to pump the compressed $CO_2$ through the pre-pressed seed fixed with glass wool. Behind the outflow of the extraction cylinder, the pressure of the $CO_2$ loaded with extract was removed by means of an expansion valve and let off into a separator. Sample material was collected here. The expansion valve let off the pressure in the laboratory system to 1 bar, in the pilot plant to 50-70 bar. It was not possible to collect $CO_2$ in the laboratory system. In the pilot plant, the $CO_2$ was fed to the high-pressure pump again by means of a return from the separator (FIG. 4) and therefore formed a closed system.

The stepwise approach showed the following optimized parameters for the as complete as possible and gentle extraction of a Brassica seed oil. Pre-press particle size of less than 0.2 mm by means of roll press with gap size 0.15 mm, SLE with preferred pressure of at least 300 bar, better 350 bar. It was possible to keep the temperature between 40 and 60° C. An as low as possible temperature of 40° C. is to be preferred here, in order to reduce oxidative processes in the oil. An optimal yield was achieved with an extraction run of 60 kg $CO_2$ per hour after 120 min. The optimal $CO_2$ mass throughput here was 80 to 100 times the mass of the substrate in order to achieve a 90% yield of the maximally achievable yield. Shorter extraction times resulted in a less complete extraction, but could offer advantages for the extraction costs.

The advantages of the SLE technology developed further here for the extraction of Brassica seeds can be summarized as follows. The extraction efficiency is clearly optimized in the process developed here on the pilot scale, compared to the prior art. By means of $CO_2$ SLE, a comparable extraction efficiency to conventional soxhlet extraction by means of hexane was surprisingly achieved under the conditions shown here. The $CO_2$ SLE carried out on the pilot scale can thus be scaled up to the required industrial scale of, for example, 800 tonnes of oil per year without significant changes. A plant seed oil according to the invention extracted in such a way comprises no solvent residues at all and is therefore suitable in particular for foodstuff production, preferably for the production of baby food.

For the plant seed oil obtained by means of the hexane extraction, subsequent refining was carried out. Refining of the crude plant oil (mixed oil from press oil and extraction oil) and filling took place completely under vacuum or under nitrogen. The crude oil was first hydrated with 10% water (85° C., 45 min, 300 rpm). Subsequent degumming with 1.5% citric acid (20% strength) likewise took place at 85° C. (45 min, 300 rpm, 10% water). Neutralization by washing with 7% strength sodium hydroxide solution followed (90-95° C., 20 min, 250 rpm, 10% water) and drying at 90° C. (11 min, 350 rpm to 30 mbar). Bleaching took place with 1% bleaching earth (Tonsil Optimum 214 FF, 90° C., 20 min, 350 rpm, to 20 mbar). The mixture was subsequently filtered under pressure and nitrogen by means of an acetate filter. Deodorization is carried out at 220° C., 20 min, 1-2 mbar with deionized and degassed water.

Refining is not necessary in every case with the plant seed oil obtained from the supercritical $CO_2$ extraction. For some of the applications of the plant seed oil according to the invention described, the direct use of the oil obtained by means of SLE supercritical CO2 extraction is possible, i.e. no subsequent refining is necessary for this. These products include milk, juice, purée, syrup, candies and fermented product for the small child. Refining of the plant seed oil obtained by means of supercritical $CO_2$ extraction is recommended, however, for the abovementioned reasons for use in baby food.

Example 7

Composition of the Plant Seed Oil According to the Invention

The plant seed oil according to the invention comprises the fatty acids important for infant food in the following percentages by weight (mass of the fatty acids in percent of the total fatty acid content)

| Target fatty acid | % |
| --- | --- |
| arachidonic acid (20:4 n-6) | 15 |
| Essential fatty acids: | |
| linoleic acid (18:2 n-6) | 20-25 |
| alpha-linolenic acid (18:3 n-3) | 3-7 |

-continued

| | % |
|---|---|
| Additional fatty acids valuable for the infant: | |
| gamma-linolenic acid (GLA) (18:3 n-6) | 6-11 |
| dihomo-gamma-linolenic acid (DGLA)(20:3 n-6) | 4-8 |
| stearidonic acid (SDA) | 1-2 |
| eicosapentaenoic acid (EPA) | 2-4 |

Example 8

Infant Food that Comprises the Plant Seed Oil According to the Invention

The ARA content in the exemplary infant food described herein was matched to the total amount of ARA that was found in breast milk during the first 0-12 months of lactation. An additional advantage consists in the fact that if the plant seed oil according to the invention is used in order to supplement the infant milk with ARA, the values for the GLA, DGLA, SDA and EPA thus also lie in the range of concentrations as in the breast milk. This is due to the fact that the plant seed oil according to the invention comprises the three high-grade unsaturated fatty acids almost in the proportions that were also found in breast milk. If the plant seed oil according to the invention is also used as a constituent of infant food, in order to match the ARA concentration, then the GLA, DGLA, SDA and EPA are supplied in the correct concentrations in order to make available the corresponding nutrients for the special infant, baby and child foods. In this case, no change in the oil, such as, for example, the admixture of, for example, further GLA-, DGLA-, SDA- and EPA-comprising oils is necessary.

The ARA-comprising plant seed oil according to the invention was added to the infant food (0.5-7.5 g of ARA-comprising oil/100 g of total fat content in the infant food). This added ARA amount makes up some of the total amount of fat (total fat content of approximately 28 g per 100 g of dry matter). By the addition of the plant seed oil according to the invention, the fatty acid pattern of the infant food with regard to the LCPUFA of the breast milk is decisively approximated, as is evident from Table 7 below. Table 7 compares the average fatty acid pattern of infant food of three independent manufacturers, as documented in the nutrient database of the USA (USDA National Nutrient Database for Standard Reference, Release 20 (2007)).

TABLE 7

Average fatty acid pattern of the fat mixture of three commercial infant foods that are marketed as a dry powder for preparing a substitute breast milk and that are not supplemented with ARA (column 2, infant foods: Mead Johnson, Enfamil, with iron, powder, NDB No: 03805; Ross, Similac, Isomil, with iron, powder, NDB No: 03843; Nestle, Good Start Supreme, with iron, powder NDB No: 03802), three commercial infant foods that have been supplemented with ARA (column 3, infant foods: Mead Johnson, Enfamil, Lipil, with iron, powder (NDB No: 03808); Ross, Similac, Isomil, Advance with iron, powder (NDB No: 03954); PBM Products, Ultra Bright Beginnings, powder (NDB No: 03883)) and and exemplary infant food (column 4) that was supplemented with ARA by means of the plant seed oil according to the invention (described in column 5). Column 6 describes the average contents of the most important LCPUFA of the breast milk from various countries (Yuhas et al. 2006 Lipids 41: 851-8).

| 1<br>Fatty acids based on the total fatty acid content (mass ratios) | 2<br>Infant food without PUFA (%) | 3<br>Infant food with PUFA (ARA + DHA) (%) | 4<br>Infant food with plant seed oil according to the invention (%) | 5<br>Plant seed oil according to the invention (%) | 6<br>Human breast milk (%) |
|---|---|---|---|---|---|
| C6:0 | 0.1 | 0.1 | 0.1 | 0.0 | |
| C8:0 | 2.2 | 2.1 | 2.0 | 0.0 | |
| C10:0 | 1.6 | 1.6 | 1.5 | 0.0 | |
| C12:0 | 11.7 | 11.7 | 11.1 | 0.0 | |
| C14:0 | 4.8 | 5.4 | 4.6 | 0.0 | |
| C16:0 | 15.9 | 14.5 | 15.3 | 4.0 | |
| C18:0 | 3.8 | 5.4 | 3.8 | 3.0 | |
| C20:0 (not in NDB) | | | 0.03 | 0.5 | |
| C22:0 (not in NDB) | | | 0.03 | 0.5 | |
| C24:0 (not in NDB) | | | 0.02 | 0.4 | |
| C16:1 not differentiated | 0.0 | 0.7 | 0.1 | 0.5 | |
| C18:1 not differentiated | 37.1 | 38.0 | 36.4 | 23.0 | |
| C20:1 n-9 (not in NDB) | 0.1 | 0.1 | 0.16 | 1.0 | |
| C22:1 not differentiated | 0.0 | 0.0 | 0.0 | 0.1 | |
| C18:2 not differentiated | 20.5 | 17.5 | 20.5 | 21.0 | 12.96% |
| C18:2 n-9 (not in NDB) | | | 0.0 | 0.5 | |
| C20:2 n-6 (not in NDB) | | | 0.2 | 4.0 | |
| C16:3 (not in NDB) | | | 0.1 | 1.0 | |
| C18:3 not differentiated | 2.2 | 1.9 | 2.3 | 5.0 | 1.15% |
| C18:3 n-6 (GLA) (not in NDB) | | | 0.45 | 9.00 | 0.15% |
| C20:3 n-6 (DGLA) (not in NDB) | | | 0.30 | 6.00 | 0.33% |
| C20:3 n-3 (not in NDB) | | | 0.03 | 0.5 | |
| C18:4 n-3 (SDA) | 0.00 | 0.00 | 0.08 | 1.50 | 0.03% |
| C20:4 n-6 (ARA) | 0.00 | 0.65 | 0.75 | 15.00 | 0.41% |
| C20:3 n-4 (not in NDB) | | | 0.03 | 0.5 | |
| C20:5 n-3 (EPA) | 0.00 | 0.00 | 0.15 | 3.00 | 0.11% |

TABLE 7-continued

Average fatty acid pattern of the fat mixture of three commercial infant foods that are marketed as a dry powder for preparing a substitute breast milk and that are not supplemented with ARA (column 2, infant foods: Mead Johnson, Enfamil, with iron, powder, NDB No: 03805; Ross, Similac, Isomil, with iron, powder, NDB No: 03843; Nestle, Good Start Supreme, with iron, powder NDB No: 03802), three commercial infant foods that have been supplemented with ARA (column 3, infant foods: Mead Johnson, Enfamil, Lipil, with iron, powder (NDB No: 03808); Ross, Similac, Isomil, Advance with iron, powder (NDB No: 03954); PBM Products, Ultra Bright Beginnings, powder (NDB No: 03883)) and and exemplary infant food (column 4) that was supplemented with ARA by means of the plant seed oil according to the invention (described in column 5). Column 6 describes the average contents of the most important LCPUFA of the breast milk from various countries (Yuhas et al. 2006 Lipids 41: 851-8).

| 1<br>Fatty acids based on<br>the total fatty acid<br>content (mass ratios) | 2<br>Infant food<br>without<br>PUFA<br>(%) | 3<br>Infant food<br>with PUFA<br>(ARA +<br>DHA)<br>(%) | 4<br>Infant food with<br>plant seed oil<br>according to the<br>invention<br>(%) | 5<br>Plant seed oil<br>according to the<br>invention<br>(%) | 6<br>Human<br>breast<br>milk<br>(%) |
|---|---|---|---|---|---|
| C22:5 (DPA) | | | 0.00 | 0.00 | |
| C22:6 n-3 (DHA) | 0.0 | 0.4 | 0.00 | 0.0 | 0.40% |
| Total fatty acids | 100.00 | 100.00 | 100.00 | 100.00 | |

NDB here stands for Nutrients DataBase.

The upper limit of 0.75% ARA as part of the daily fat absorption for infants is recommended in US GRAS GRN 80 (www.cfsan.fda.gov/~rdb/opa-g080.html). In order to achieve the target concentration of 0.75% ARA in the total fatty acid content of the infant food an addition of 5% of the plant seed oil according to the invention is necessary, which comprises 15% ARA based on its total fatty acid content. A total addition of 1.36% of the plant seed oil according to the invention is thereby calculated based on infant food dry matter. A higher or a lower target concentration of ARA in the infant food can be achieved by a corresponding increase or reduction of the plant seed oil according to the invention in the total fat mixture.

The plant seed oil according to the invention can be employed not only in infant food, but also in complete food. A complete food that is added to the plant seed oil according to the invention comprises arachidonic acid (ARA) in similar concentrations to breast milk. The complete food also comprises gamma-linolenic acid (GLA), dihomo-gamma-linolenic acid (DGLA), stearidonic acid (SDA) and eicosapentaenoic acid (EPA) in similar concentrations to breast milk. The complete food mentioned can be, for example, baby milk, follow-on formula, beverage for the small child, fruit juice, cereal gruel, milk, yogurt or a fermented product. The complete product can also be solid or mashed baby food, candies, cookies or gelatin products. It is intended, for example, for the nutrition of infants, small children and children in order to support their normal growth and their healthy development.

By the addition of the plant seed oil according to the invention to the infant food or complete food, a ratio of the most important unsaturated fatty acids very similar to breast milk is achieved (Table 8).

TABLE 8

Comparison of the ratios of the most important PUFA (with the exception of DHA) in infant food and breast milk. Column 2 shows the average ratios of the most important PUFA in three commercial infant foods (dry powder for preparing a substitute breast milk) that were supplemented with ARA and DHA (infant foods: Mead Johnson, Enfamil, Lipil, with iron, powder (NDB No: 03808); Ross, Similac, Isomil, Advance with iron, powder (NDB No: 03954); PBM Products, Ultra Bright Beginnings, powder (NDB No: 03883)), the most important PUFA ratios of an exemplary infant food (column 3) that was supplemented with ARA by means of the plant seed oil according to the invention (column 4). Column 5 describes the average PUFA ratios of breast milk from various countries (Yuhas et al. 2006 Lipids 41: 851-8).

| 1<br>Mass<br>ratios | 2<br>Infant food<br>with<br>PUFA<br>(ARASCO ®) | 3<br>Infant food with<br>plant seed oil<br>according to<br>the invention | 4<br>Plant seed oil<br>according to the<br>invention | 5<br>Human<br>breast<br>milk |
|---|---|---|---|---|
| ARA/GLA | — | 1.7 | 1.7 | 2.7 |
| ARA/DGLA | — | 2.5 | 2.5 | 1.2 |
| ARA/SDA | — | 10.0 | 10.0 | 14.2 |
| ARA/EPA | — | 5.0 | 5.0 | 3.7 |
| LA/ALA | 9.1 | 8.9 | 4.2 | 11.3 |

The example chosen shows that the favorable ratios of the important PUFA ARA, GLA, DGLA, SDA and EPA of the plant seed oil according to the invention (Table 8, column 4) are reflected directly in the infant food (Table 8, columns 3 and 5). In the plant seed oil according to the invention, the ratio of arachidonic acid to gamma-linolenic acid is approximately 1:1 to approximately 5:1 and the ratio of arachidonic acid to dihomo-gamma-linolenic acid is approximately 1:1 to approximately 5:1. The ratios achieved with the plant seed oil according to the invention therefore very advantageously cover the ratios present in breast milk between arachidonic acid (ARA) and gamma-linolenic acid (GLA) 2:1 to 4:1 and between arachidonic acid and dihomo-gamma-linolenic acids (DGLA) 1:1 to 2:1 (Yuhas et al. 2006_Lipids 41:851-8); see Table 8, column 5 and FIG. 7.

In the plant seed oil of the invention, the ratio of arachidonic acid to stearidonic acid is 14:1 to 38:1 and also reflects here the ratio present in breast milk (ARA:SDA about 7:1 to 45:1) (Yuhas et al. 2006 Lipids 41:851-8). Moreover, the ratio of arachidonic acid to eicosapentaenoic acid in the plant seed oil according to the invention is 3:1 to 7:1 and also reflects here the ratio present in breast milk (ARA:EPA about 2:1 to 7:1) (Yuhas et al. 2006 Lipids 41:851-8).

The plant seed oil according to the invention moreover comprises, like the breast milk, the essential fatty acids linoleic acid and alpha-linolenic acid. Also, with regard to the ratio of linoleic acid to alpha-linolenic acid, the plant seed oil according to the invention comes very close to breast milk (Table 8, columns 3 and 5). In the breast milk, the ratio is about 7:1 to 18:1 (Yuhas et al. 2006 Lipids 41:851-8).

Advantageously, infant food comprising the plant seed oil according to the invention is supplemented by the important PUFA ARA, GLA, DGLA, SDA and EPA in order to match the concentrations and ratios to those present in breast milk. Moreover, the infant food supplemented in this way can be further supplemented with a source of DHA.

For DHA, the upper limit of 0.5% DAH as part of the daily fat absorption for infants is recommended in US GRAS GRN 80 (www.cfsan.fda.gov/~rdb/opa-g080.html). In order to achieve the target concentration of 0.5% DHA in the total fatty acid content of the infant food, an addition of 1.2 g of DHASCO® per 100 g of total fat, for example, is necessary, which comprises 40% DHA based on its total fatty acid content (Arterburn et al. 2007, Lipids 42:1011-24). A total addition of 0.32% DHASCO® is thereby calculated based on infant food dry matter. A higher or a lower target concentration of DHA in the infant food can be achieved by appropriate increase or reduction of the DHA-comprising ingredient determined for the product.

The ARA-comprising plant seed oil according to the invention (0.5-7.5 g/100 g fat) and DHASCO® can therefore be added to the infant food. In the example, the added ARA amount makes up 5% and the added DHA amount makes up 1.2% of the total fatty matter (in the case of a total fat content of the infant food of approximately 28 g per 100 g of dry matter). By the addition of both oils, the fatty acid pattern of the infant food with regard to the LCPUFA of breast milk is even further approximated, as is evident from Table 9 below. Table 9 compares the average fatty acid pattern of infant food of three independent manufacturers as documented in the nutrient database of the USA (USDA National Nutrient Database for Standard Reference, Release 20 (2007))

TABLE 9

Average fatty acid pattern of the fat mixture of three commercial infant foods (dry powder for preparing a substitute breast milk) that were not supplemented with ARA and DHA (column 2, infant foods: Mead Johnson, Enfamil, with iron, powder, NDB No: 03805; Ross, Similac, Isomil, with iron, powder, NDB No: 03843; Nestle, Good Start Supreme, with iron, powder NDB No: 03802), three commercial infant foods that were supplemented with ARA (column 3, infant foods: Mead Johnson, Enfamil, Lipil, with iron, powder (NDB No: 03808); Ross, Similac, Isomil, Advance with iron, powder (NDB No: 03954); PBM Products, Ultra Bright Beginnings, powder (NDB No: 03883)) and an exemplary infant food (column 4) that was supplemented with ARA by means of the plant seed oil according to the invention described in column 5 and that was supplemented with DHA by means of DHASCO ® (Arterburn et al. 2007, Lipids 42: 1011-24) (column 6). Column 7 describes the average contents of the most important LCPUFA of breast milk in various countries (Yuhas, loc.cit).

| 1 Fatty acids based on the total fatty acid content (mass ratios) | 2 Infant food without PUFA (%) | 3 Infant food with PUFA (ARA + DHA) (%) | 4 Infant food with plant seed oil according to the invention (%) | 5 Plant seed oil according to the invention (%) | 6 DHASCO ® oil (%) | 7 Human breast milk |
|---|---|---|---|---|---|---|
| C6:0 | 0.1 | 0.1 | 0.1 | 0.0 | 0.0 | |
| C8:0 | 2.2 | 2.1 | 2.0 | 0.0 | 0.9 | |
| C10:0 | 1.6 | 1.6 | 1.5 | 0.0 | 1.0 | |
| C12:0 | 11.7 | 11.7 | 11.0 | 0.0 | 2.8 | |
| C14:0 | 4.8 | 5.4 | 4.7 | 0.0 | 12.9 | |
| C16:0 | 15.9 | 14.5 | 15.3 | 4.0 | 13.4 | |
| C18:0 | 3.8 | 5.4 | 3.8 | 3.0 | 0.1 | |
| C20:0 (not in NDB) | | | 0.0 | 0.5 | 0.1 | |
| C22:0 (not in NDB) | | | 0.0 | 0.5 | 0.2 | |
| C24:0 (not in NDB) | | | 0.0 | 0.4 | 0.1 | |
| C16:1 not differentiated | 0.0 | 0.7 | 0.1 | 0.5 | 1.4 | |
| C18:1 not differentiated | 37.1 | 38.0 | 36.2 | 23.0 | 22.6 | |
| C20:1 n-9 (not in NDB) | 0.1 | 0.1 | 0.2 | 1.0 | 0.1 | |
| C22:1 not differentiated | 0.0 | 0.0 | 0.0 | 0.1 | 0.0 | |
| C18:2 not differentiated | 20.5 | 17.5 | 20.3 | 21.0 | 1.3 | 12.96% |
| C18:2 n-9 (not in NDB) | | | 0.0 | 0.5 | 0.0 | |
| C20:2 n-6 (not in NDB) | | | 0.2 | 4.0 | 0.0 | |
| C16:3 (not in NDB) | | | 0.1 | 1.0 | 0.0 | |
| C18:3 not differentiated | 2.2 | 1.9 | 2.3 | 5.0 | 0.1 | 1.15% |
| C18:3 n-6 (GLA) (not in NDB) | | | 0.5 | 9.00 | 0.1 | 0.15% |
| C20:3 n-6 (DGLA) (not in NDB) | | | 0.3 | 6.00 | 0.0 | 0.33% |

TABLE 9-continued

Average fatty acid pattern of the fat mixture of three commercial infant foods (dry powder for preparing a substitute breast milk) that were not supplemented with ARA and DHA (column 2, infant foods: Mead Johnson, Enfamil, with iron, powder, NDB No: 03805; Ross, Similac, Isomil, with iron, powder, NDB No: 03843; Nestle, Good Start Supreme, with iron, powder NDB No: 03802), three commercial infant foods that were supplemented with ARA (column 3, infant foods: Mead Johnson, Enfamil, Lipil, with iron, powder (NDB No: 03808); Ross, Similac, Isomil, Advance with iron, powder (NDB No: 03954); PBM Products, Ultra Bright Beginnings, powder (NDB No: 03883)) and an exemplary infant food (column 4) that was supplemented with ARA by means of the plant seed oil according to the invention described in column 5 and that was supplemented with DHA by means of DHASCO ® (Arterburn et al. 2007, Lipids 42: 1011-24) (column 6). Column 7 describes the average contents of the most important LCPUFA of breast milk in various countries (Yuhas, loc.cit).

| 1 Fatty acids based on the total fatty acid content (mass ratios) | 2 Infant food without PUFA (%) | 3 Infant food with PUFA (ARA + DHA) (%) | 4 Infant food with plant seed oil according to the invention (%) | 5 Plant seed oil according to the invention (%) | 6 DHASCO ® oil (%) | 7 Human breast milk |
|---|---|---|---|---|---|---|
| C20:3 n-3 (not in NDB) |  |  | 0.0 | 0.5 | 0.0 |  |
| C18:4 n-3 (SDA) | 0.00 | 0.00 | 0.1 | 1.50 | 0.1 | 0.03% |
| C20:4 n-6 (ARA) | 0.00 | 0.65 | 0.75 | 15.00 | 0.1 | 0.41% |
| C20:3 n-4 (not in NDB) |  |  | 0.0 | 0.5 | 0.1 |  |
| C20:5 n-3 (EPA) | 0.00 | 0.00 | 0.15 | 3.00 | 0.1 | 0.11% |
| C22:5 (DPA) |  |  | 0.0 | 0.00 | 0.0 |  |
| C22:6 n-3 (DHA) | 0.0 | 0.4 | 0.50 | 0.0 | 42.3 | 0.40% |
| Total fatty acids | 100.00 | 100.00 | 100.00 | 100.00 | 100.00 |  |

By the addition of the plant seed oil according to the invention and the simultaneous supplementation with DHASCO®, a ratio of the most important unsaturated fatty acids even more similar to that of breast milk is achieved (Table 9) than by the sole supplementation with the plant seed oil according to the invention. This further matching of the infant food to the breast milk by the addition of DHA can also be achieved with other high-DHA comprising oils, such as, for example the BASF powder product number 30056967 (Dry n-3® 5:25 C Powder Microencapsulated fish oil rich in DHA for Infant formula).

In the infant food which was supplemented with the plant seed oil according to the invention and with DHASCO®, the ratio of ARA to DHA is 1.5:1 and reflects here the ratio present in the breast milk (ARA:DHA about 0.6:1 to 7.2:1) (Yuhas et al. 2006 Lipids 41:851-8). Moreover, in a preferred embodiment of the plant seed oil of the invention the ratio of DHA to EPA is 3.3:1 and also reflects here the ratio present in the breast milk (DHA:EPA about 2.1:1 to 5.0:1) (Yuhas et al. 2006_Lipids 41:851-8)

The plant seed oil according to the invention was developed in order to support the optimal growth, visual and cognitive development and development of an improved immunity of newborn infants, babys and small children. It is preferable as an additive in the baby food for prematurely born infants and for babys or small children at an age of: 0-6 months (infant formula), 0-12 months (infant food), and 12-24 months (small children).

TABLE 10

Comparison of the ratios of the most important PUFA in infant foods and breast milk. Column 2 shows the average ratios of the most important PUFA in three commercial infant foods that were supplemented with ARA and DHA (infant foods: Mead Johnson, Enfamil, Lipil, with iron, powder (NDB No: 03808); Ross, Similac, Isomil, Advance with iron, powder (NDB No: 03954); PBM Products, Ultra Bright Beginnings, powder (NDB No: 03883)), the most important PUFA ratios of an exemplary infant food (column 3) that was supplemented with ARA by means of the plant seed oil according to the invention (column 4) and by means of DHASCO ® (column 5, Arterburn et al. 2007, Lipids 42: 1011-24). Column 6 describes the average PUFA ratios of breast milk from various countries (Yuhas et al. 2006_Lipids 41: 851-8).

| 1 Mass ratios: | 2 Infant food with PUFA (ARASCO ®) | 3 Infant food with plant seed oil according to the invention | 4 Plant seed oil according to the invention | 5 DHASCO ® Oil | 6 Human breast milk |
|---|---|---|---|---|---|
| ARA/GLA | — | 1.7 | 1.7 | 1.0 | 2.7 |
| ARA/DGLA | — | 2.5 | 2.5 | — | 1.2 |
| ARA/SDA | — | 9.9 | 10.0 | 1.0 | 14.2 |
| ARA/EPA | — | 5.0 | 5.0 | 1.0 | 3.7 |
| LA/ALA | 9.1 | 8.9 | 4.2 | 12.7 | 11.3 |
| ARA/DHA | 1.8 | 1.5 | — | 0.0 | 1.0 |
| DHA/EPA | — | 3.3 | 0.0 | 423 | 3.6 |

Table 10 shows that the favorable ratios of the important PUFA ARA, GLA, DGLA, SDA, EPA and DHA of the plant seed oil according to the invention (Table 10, Column 4) are reflected directly in the infant food (Table 10, Column 3) and that moreover particularly favorable ratios of the fatty acids DHA and EPA are achieved.

In the following, formulations are listed by way of example which are particularly favorably supplemented by the plant seed oil according to the invention. Particularly favorably, the ingredients of the formulations are mixed in quantitative ratios, such that the infant food comprises principal nutrients in the following concentrations (details in g/100 kcal of the infant food): fats, 3-7 g; proteins, 1-5 g; carbohydrates, 6-16 g. Additionally, the infant food comprises vitamins and minerals in amounts recommended for the corresponding age of the infant or small child, and ARA and DHA to in each case 0.025 to 0.5 percent of the energy of the infant food or in a concentration of in each case 0.05 to 1.0 g/100 g of fat of the infant food. The infant food moreover comprises GLA, DGLA, SDA and EPA in ratios which are particularly similar to breast milk. The functional fatty acids ARA, GLA, DGLA, SDA and EPA originate here from the plant seed oil according to the invention.

The infant food can be composed, for example, from the following constituents: mineral-reduced whey, low-fat milk, plant oil (palmolein, soybean, coconut, oleic acid-rich sunflower and erucic acid-low rape oils), lactose, the plant seed oil according to the invention, *Crypthecodinium cohnii* oil or fish oil, vitamin A palmitate, vitamin D3, vitamin E acetate, vitamin K1, thiamine hydrochloride, vitamin B6 hydrochloride, vitamin B12, niacinamide, folic acid, calcium pantothenate, biotin, sodium ascorbate, inositol, calcium chloride, calcium phosphate, iron sulfate, zinc sulfate, manganese sulfate, copper sulfate, sodium chloride, sodium citrate, potassium citrate, potassium hydroxide, sodium selenite, taurine, nucleotides (adenosine 5-monophosphate, cytidine 5-monophosphate, disodium guanosine 5-monophosphate, disodium uridine 5-monophosphate), a source of carotenoids, a source of prebiotics and a source of probiotics.

A further example of the composition of an infant food comprising the plant seed oil according to the invention is an infant food comprising probiotics and comprising ARA, alternatively combined with prebiotics. ARA can be alternatively combined here with docosahexaenoic acid (DHA), as shown further above. Important constituents of this infant food here are modified intact or partly hydrolyzed sweet whey proteins, probiotics in the form of Bifidobacteria and/or Lactobacillae, alternatively prebiotics in the form of specific mono- and disaccharides, oligosaccharides or starches and the plant seed oil according to the invention. This infant food comprises (per 100 kcal): energy content (kcal) (100), protein (g) (casein/whey: 30/70) (1.83), total fat content (g) (5.3) thereof linoleic acid (g) (0.7-0.8), alpha-linolenic acid (mg) (90-110), ARA (mg) (5-60), GLA (mg) (3-40), DGLA (mg) (2-30), SDA (mg) (1-6), EPA (mg) (1-12), DHA (mg) (5-60), lactose (g) (11.2), and minerals (g) (0.37), Na (mg) (23), K (mg) (89), Cl (mg) (64), Ca (mg) (62), P (mg) (31), Mg (mg) (7), Mn (µg) (8), Se (µg) (2), vitamin A (pg RE) (105), vitamin D (µg) (1.5), vitamin E (mg TE) (0.8), vitamin K1 (µg)(8), vitamin C (mg) (10), vitamin B1 (mg) (0.07), vitamin B2 (mg) (0.15), niacin (mg) (16.7), vitamin B6 (mg) (0.075), folic acid (µg) (9), pantothenic acid (mg) (0.45), vitamin B12 (µg) (0.3), biotin (µg) (2.2), choline (mg) (10), Fe (mg) (1.2), I (µg) (15), Cu (mg) (0.06), Zn (mg) (0.75) as nutrients.

Moreover, a further example is an infant food comprising the plant seed oil according to the invention and the carotenoids beta-carotene, lycopene, lutein and zeaxanthin. The combination of lutein, lycopene and beta-carotene makes up 0.05-0.8 mg/100 g of the total fat content or of the nutrient formulation. The mass proportions of the total amount of oil in the infant food are: 0.01-0.6 mg of beta-carotene, 0.01-0.8 mg of lycopene and 0.01-0.5 mg of lutein plus zeaxanthin. The proportion of polyunsaturated fatty acids is 0.05-20% by weight in the total solid of the infant food. The polyunsaturated fatty acids are arachidonic acid (preferably), GLA, DGLA, SDA, eicosapentaenoic acid, docosahexaenoic acid, linoleic acid and/or alpha linolenic acid. The amount of ARA comprised in the infant food is 0.1 to 1.0 g/100 g of the total fat or 0.05 to 0.5 percent of the total energy. The amounts of GLA, DGLA, SDA and EPA comprised are in each case 0.06-0.7, 0.04-0.5, 0.01-0.1 and 0.02-0.2 g/100 g of the total fat.

A liquid infant food was also prepared. Water was processed for this with the following dry constituents: lactose 44.5%, plant seed oil according to the invention (15% ARA) 0.1 to 1.5%, DHA-comprising oil (40% DHA) 0.1%, fatless dried milk 18.7%, oleic acid-rich safflower oil 10.7%, mono- and diglycerides 0.27%, soybean oil 8.2%, whey protein 4.6%, calcium carbonate 0.35%, coconut oil 7.58%, citric acid 0.02%, potassium citrate 0.40%, ascorbic acid 0.29%, lecithin 0.27%, magnesium chloride 0.04%, potassium chloride 0.14%, iron sulfate 0.04%, carrageenan 0.22%, choline chloride 0.04%, nucleotide and choline pre-mixture 0.22%, riboflavin 0.002%, L-carnitine 0.002%, potassium hydroxide 1.65%, lutein solution (5% active) 0.64%, water-soluble vitamin pre-mixture 0.27%, vitamin-ADEK pre-mixture 20%, vitamin A 0.0007%, beta-carotene solution (30%) 0.0001%, lutein (1.2 ppm), lycopene (0.48 ppm).

TABLE 11

Ranges of the nutrient composition in infant food comprising the plant seed oil according to the invention (source: USDA National Nutrient Database for Standard Reference, publication 20 (2007)

| | | Value per 100 grams Nutrient and calorific values | |
|---|---|---|---|
| | Units | min | max |
| Nutrient | | | |
| Water | g | 2 | 3 |
| Energy | kcal | 511 | 524 |
| Energy | kj | 2138 | 2192 |
| Protein | g | 11 | 13 |
| Total lipid (fat) | g | 27 | 28 |
| Ash | g | 2 | 3 |
| Carbohydrates (by difference) | g | 54 | 56 |
| Roughage, total | g | 0 | 0 |
| Sugar, total | g | 53 | 56 |
| Lactose | g | 56 | 56 |
| Minerals | | | |
| Calcium, Ca | mg | 331 | 540 |
| Iron, Fe | mg | 9 | 10 |
| Magnesium, Mg | mg | 36 | 41 |
| Phosphorus, P | mg | 221 | 386 |
| Potassium, K | mg | 441 | 560 |
| Sodium, Na | mg | 118 | 226 |
| Zinc, Zn | mg | 4 | 5 |
| Copper, Cu | mg | 0.4 | 0.4 |
| Selenium, Se | µg | 11 | 15 |
| Vitamins | | | |
| Vitamin C, total ascorbic acid | mg | 43 | 62 |
| Thiamine | mg | 0 | 1 |
| Riboflavin | mg. | 0 | 1 |
| Niacin | mg | 4 | 7 |
| Vitamin B6 | mg | 0.31 | 0.33 |
| Folate, total | µg | 39 | 83 |
| Folic acid | µg | 39 | 83 |
| Folate, food | µg | 0 | 0 |
| Folate, DFE | µg _DFE | 66 | 141 |
| Choline, total | mg | 60 | 82 |
| Vitamin B12 | µg | 1 | 2 |
| Vitamin B12, added | µg | 1 | 2 |

TABLE 11-continued

Ranges of the nutrient composition in infant food comprising the plant seed oil according to the invention (source: USDA National Nutrient Database for Standard Reference, publication 20 (2007)

| | | Value per 100 grams Nutrient and calorific values | |
|---|---|---|---|
| | Units | min | max |
| Vitamin A, IU | IU | 1543 | 1577 |
| Vitamin A, RAE | μg_RAE | 462 | 473 |
| Retinol | μg | 463 | 473 |
| Vitamin E (alpha-tocopherol) | mg | 3 | 7 |
| Vitamin E, added | mg | 3 | 7 |
| Vitamin D | IU | 309 | 310 |
| Vitamin K (phylloquinone) | μg | 41 | 57 |
| Total fatty acid content | g | 21.4 | 32.9 |
| Other lipids | | | |
| Cholesterol | mg | 0 | 32 |
| Carotene, beta- | mg | 0 | 0.16 |
| Lycopene | mg | 0 | 0.22 |
| Lutein + zeaxanthin | mg | 0 | 0.14 |

Example 9

Use of the Plant Seed Oil According to the Invention for the Feeding of Animals

The plant seed oil according to the invention is also suitable as a food supplement product for feed applications for the improvement of breeding results. It can be used as a feed additive for the improvement of stock breeding results (for example of Salmonidae, cattle, pigs, hens) and for the health of domestic animals (for example of cats and dogs). For this, the plant seed oil according to the invention comprises arachidonic acid (ARA) in concentrations that are suitable in order to improve the reproduction rates if the nutrition of the young animal or of the mother animal is supplemented with ARA.

As a result of the addition of the plant seed oil according to the invention, in addition to ARA the feed receives gamma-linolenic acid (GLA), dihomo-gamma-linolenic acid (DGLA), stearidonic acid (SDA) and eicosapentaenoic acid (EPA). The supplementation of nutritional products with the plant seed oil of the invention leads to higher reproduction rates, better chances of survival for the young animals, and to improved neurological and visual development.

Example 10

Technical Applications of the Plant Seed Oil According to the Invention

The addition of the plant seed oil of the invention yields a technical oil having a uniquely high concentration of unsaturated fatty acids comprising double bonds as a polymerization component for technical applications.

The oil can be employed for the following applications alone or in combination with a polymerizing agent:
1. Lacquers and coatings (use as an oxidative drying oil)
2. Polymers for floor coverings or plastics (use as an oxidative drying oil)
3. Other chemical applications
4. Cosmetic applications
5. Applications in the field of electronics and semiconductor technology The advantage of the oil described above lies in its unique polymerization properties. The oil polymerizes more rapidly and uniformly and forms a stronger three-dimensional structure, which is expedient where strength, durability and elasticity of the network are necessary (as, for example, in coatings and floor coverings or plastics).

The invention claimed is:

1. A plant seed oil, comprising arachidonic acid comprising approximately 7 to approximately 26 percent by weight of the total fatty acid content, the ratio of the percentages by weight of arachidonic acid to gamma-linolenic acid being approximately 1:1 to approximately 5:1, the ratio of the percentages by weight of arachidonic to dihomo-gamma-linolenic acid being approximately 1:1 to approximately 5:1, and the ratio of the percentages by weight of linoleic acid to alpha-linolenic acid being approximately 3:1 to approximately 12:1.

2. The plant seed oil of claim 1, the ratio of the percentages by weight of arachidonic acid to eicosapentaenoic acid being approximately 3:1 to approximately 7:1.

3. The plant seed oil of claim 1, further comprising stearidonic acid.

4. The plant seed oil of claim 3, wherein the stearidonic acid comprises approximately 0.1 to approximately 1 percent by weight of the total fatty acid content being present.

5. The plant seed oil of claim 1, obtained from a transgenic plant, the transgenic plant being transformed using a nucleic acid construct comprising SEQ ID NOs. 15, 16 or 17.

6. A formulation or mixed oil, comprising the plant seed oil of claim 1 and at least one further oil selected from the group consisting of plant oil, microbial oil and fish oil, the plant oil, microbial oil or fish oil comprising docosahexaenoic acid.

7. A foodstuff, comprising:
  (a) the plant seed oil of claim 1; or
  (b) a formulation or mixed oil, comprising the plant seed oil of claim 1 and at least one further oil selected from the group consisting of plant oil, microbial oil and fish oil, the plant oil, microbial oil or fish oil comprising docosahexaenoic acid.

8. A baby food, comprising:
  (a) the plant seed oil of claim 1; or
  (b) a formulation or mixed oil, comprising a plant seed oil of claim 1 and at least one further oil selected from the group consisting of plant oil, microbial oil and fish oil, the plant oil, microbial oil or fish oil comprising docosahexaenoic acid.

9. A process for the production of the plant seed oil of claim 1, comprising:
  a) producing a transgenic plant by transformation using a nucleic acid construct comprising SEQ ID NOs. 15, 16 or 17;
  b) culturing of the transgenic plants from step a) under conditions that allow the biosynthesis of the plant seed oil; and
  c) harvesting of the plant seeds, extraction and refining of the plant seed oil.

10. The process of claim 9, further comprising the step d) of formulating the plant seed oil as an oil, lipid or fatty acid composition.

11. The process of claim 10, the oil, lipid or fatty acid composition further being formulated to give a foodstuff.

12. The process of claim 11, wherein the foodstuff is baby food.

13. A process for the production of the plant seed oil of claim 1, comprising:
  a) providing a transgenic plant or transgenic seed which comprises a nucleic acid construct comprising SEQ ID NOs. 15, 16 or 17;
  b) culturing of the transgenic plant or transgenic seed from step a) under conditions that allow the biosynthesis of the plant seed oil; and
  c) harvesting of the plant seeds, extraction and refining of the plant seed oil.

14. A plant seed oil comprising approximately 3.2-5.3% of palmitic acid, approximately 2.2-5.3% of stearic acid, approximately 10-25% of oleic acid, approximately 22-36% of linoleic acid, approximately 4-12% of gamma-linolenic acid, approximately 3-8% of alpha-linolenic acid, approximately 0.2-1% of stearidonic acid, approximately 3-9% of dihomo-gamma-linolenic acid, approximately 12-25% of arachidonic acid and approximately 1-4% of eicosapentaenoic acid, based on the total fatty acid content.

* * * * *